(12) United States Patent
Fotouhi et al.

(10) Patent No.: US 6,515,124 B2
(45) Date of Patent: Feb. 4, 2003

(54) DEHYDROAMINO ACIDS

(75) Inventors: Nader Fotouhi, Chatham, NJ (US); Paul Gillespie, Westfield, NJ (US); Robert William Guthrie, Saddle Brook, NJ (US); Sherrie Lynn Pietranico-Cole, Montclair, NJ (US); Weiya Yun, Warren, NJ (US)

(73) Assignee: Hoffman-La Roche Inc., Nutley, NJ (US)

(*) Notice: Subject to any disclaimer, the term of this patent is extended or adjusted under 35 U.S.C. 154(b) by 0 days.

(21) Appl. No.: 09/754,888

(22) Filed: Jan. 5, 2001

(65) Prior Publication Data

US 2002/0161237 A1 Oct. 31, 2002

Related U.S. Application Data

(60) Provisional application No. 60/181,182, filed on Feb. 9, 2000.

(51) Int. Cl.$^7$ ................ C07C 235/84; C07D 215/14; C07D 333/24; A61K 31/167; A61P 17/06
(52) U.S. Cl. ............. 544/133; 548/251; 548/187; 548/338.1; 548/180; 548/125; 548/127; 548/375.1; 548/261; 548/495; 546/175; 546/247; 546/337; 544/236; 544/367; 544/311; 562/444; 549/441; 549/493; 549/126; 549/58
(58) Field of Search ................ 548/251, 187, 548/338.1, 180, 125, 127, 375.1, 261, 495, 126; 546/175, 247, 337; 544/236, 367, 133, 311; 562/444; 549/441, 493, 58

(56) References Cited

U.S. PATENT DOCUMENTS

| | | | |
|---|---|---|---|
| 3,984,428 A | 10/1976 | Saucy et al. | ................ 260/307 |
| 5,457,124 A | 10/1995 | Cohen et al. | |
| 5,559,109 A | 9/1996 | Nakamura et al. | |

FOREIGN PATENT DOCUMENTS

| | | |
|---|---|---|
| EP | 0 410 742 | 1/1991 |
| WO | 9949856 | 10/1999 |
| WO | WO 99/49856 | * 10/1999 |
| WO | 0021920 | 4/2000 |

OTHER PUBLICATIONS

A.S. Shaw and M.L. Dustin, Immunity vol. 6: 361 (1997).
Dustin, M.L., Shaw, A.S., Science vol. 283: pp. 649–650 (1999).
Springer, T.A., Nature vol. 346, pp. 425–434 (1990).
Kuypers et al., Res. Immunol., vol. 140: p. 461 (1989).
Davignon et al., J. Immunol. vol. 127 p. 590 (1981).
Katritzky, A.R.: Ji, F.B.; Fan, W.Q.: Delprato, I. Synth. Commun. 1993 vol. 23 pp. 2019–2025.
Brown, F.J.; Cronk, L.A.; Aharony, D.; Snyder, D.W.J. Med. Chem. 1992 vol. 35, pp. 2419–2439.
Robba, M., LeGuen, Y., Bull. Soc. Chim. Fr. 1969(5) p. 1762.
I. Sawhney and J.R.H. Wilson, J. Chem. Soc. Perkin Trans I, 1990, pp. 329–331.
V. Ganapathi. Indian Academy of Science Section A, 1945, pp. 362–378.
Frigerio, M.; Santagostino, M. Tetrahedron Lett. 1994, vol. 35, pp. 8019–8022.
Batcho, A. D.; Leimgruber, W. Organic Synthesis 1985, vol. 63, pp. 214–225.
Keuning, K.J.; Evenhuis, N. Recueil Trav. Chim. Pays–Bas 1935, vol. 54, pp. 73–75.
Schmidt, U.; Wild, J. Liebigs. Ann. Chem. 1985, pp. 1882–1894.
Van Es, T.; Staskun, B. Organic Synthesis 1971, vol. 51 pp. 20–23.
Buu–Hol, et al, J. Chem. Soc. 1969, pp. 339–340.

* cited by examiner

*Primary Examiner*—Mukund J. Shah
*Assistant Examiner*—Hong Liu
(74) *Attorney, Agent, or Firm*—George W. Johnston; Dennis P. Tramaloni

(57) ABSTRACT

Aromatic dehydroamino acids are disclosed that are active as LFA-1 arnagonists This activity enables these compounds to prevent inflammation which is a consequence of T cell activation and accordingly reduce or eliminate inflammatory skin disease psoriasis.

118 Claims, No Drawings

DEHYDROAMINO ACIDS

This application claims the benefit of U.S. Provisional Application No. 60/181,182, filed on Feb. 9, 2000.

BACKGROUND OF THE INVENTION

Cell-mediated immune reactions are the basis of autoimmune diseases, and inflammation of tissue plays a part in such diseases. Activation of T cells is a causitive factor in numerous inflammatory diseases, particularly psoriasis (and including: graft rejection, dermatitis, asthma, and rheumatoid arthritis).

T cell activation is the central event in the inflammatory response, which is accompanied by a recruitment of peripheral blood leukocytes to the site of inflammation or injury, leukocyte adhesion to vascular endothelium, and migration from the circulation to sites of inflammation.

T-cell activation is mediated by the T cell receptor (TCR) (A. S. Shaw and M. L. Dustin, *Immunity* 6: 361 (1997)), whose activation in turn requires engagement of at least two types of T cell surface receptors. A key T cell surface receptor in this process is a member of the CD-11 integrin family—lymphocyte function associated antigen-1 or LFA-1, (also known as CD11a/CD18), which mediates lymphocyte adhesion and activation leading to normal immune response, as well as to several pathological states (Dustin, M. L., Shaw, A. S., *Science* 283: 649–650 (1999), Springer, T. A., *Nature* 346:425–434 (1990)).

LFA-1 binds to certain specific intercellular adhesion molecules (ICAMs) found on endothelium, leukocytes and other cell types. These ICAMs, known as ICAM-1, -2, and -3 are members of the immunoglobulin superfamily. Blocking the binding of ICAM ligands to CD11integrin receptors has been found to inhibit various undesired T-cell dependent immune responses, such as skin graft and bone marrow rejection, and development of diabetes mellitus. For example, anti-CD11a Mabs inhibit T-cell activation (Kuypers et al., *Res. Immunol.*, 140: 461 (1989)), T-cell dependant B-cell proliferation and differentiation (Davignon et al., *J. Immunol.*, 127: 590 (1981)). Such blocking has up till now been performed by antibodies. Thus, antagonists of LFA-1, that is antibodies or other molecules which prevent ICAMs from binding to the LFA-1 receptor but do not themselves activate the receptor, are useful in preventing diseases related to unwanted T-cell activation, such as psoriasis, graft rejection, dermatitis, asthma, and rheumatoid arthritis.

Small molecules are preferable to antibodies for treatment purposes for numerous reasons including increased tissue penetration, reduced immunogenicity, and in general lower risk. This is especially important in treatment of psoriasis. Thus developing small molecule compounds which are LFA-1 antagonists is an important step in combatting psoriasis.

SUMMARY OF THE INVENTION

The compounds of this invention are active as LFA-1 antagonists. This activity enables these compounds to prevent the inflammation which is a consequence of T cell activation, and accordingly reduce or eliminate the inflammatory skin disease psoriasis.

This invention is directed to compounds of formulae 1, 1a–1g, 1-1, 1-1a–1-1c, and prodrugs of formulae 2 and 2-1, pharmaceutical compositions containing these compounds, and methods of treating psoriasis with these compounds.

DETAILED DESCRIPTION OF THE INVENTION

This invention is directed to compounds of formula 1 and formula 1-1:

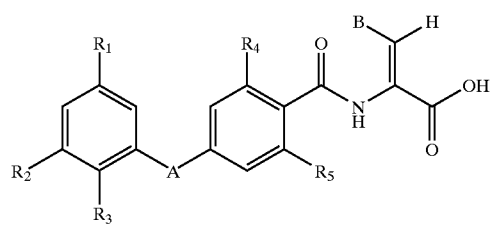

$R_1$ is hydrogen, hydroxy, amino or halogen, $R_2$ is hydrogen, hydroxy, or halogen and $R_3$ is hydrogen

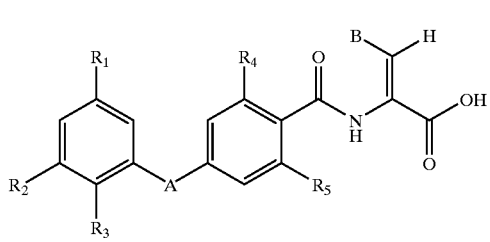

where $R_1$ is hydrogen and $R_2$ and $R_3$ taken together with the ethenylene group connecting them form phenyl, pyrrole, pyrroline, oxopyrroline, pyrazole, triazole, or imidazole. In both formula 1 and formula 1-1, A is one of the following groups,

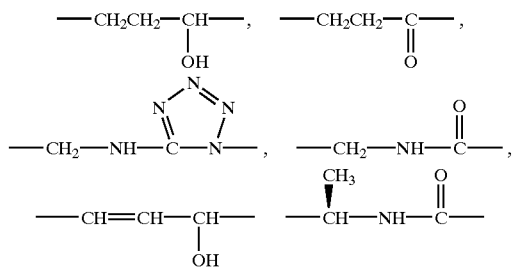

$R_4$ and $R_5$ are hydrogen, methyl, ethyl or halogen (except that $R_4$ and $R_5$ cannot both be hydrogen), and B can be selected from any one of the following 7 groups, namely:
1) B is hydrogen, or lower alkyl; or
2) B is

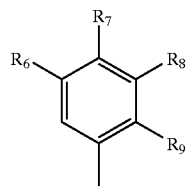

Here, $R_6$ $R_7$ $R_8$ and $R_9$ are independently hydrogen, hydroxy, aminosulfonyl, halogen, lower alkoxy, cyano, amino, lower alkyl, lower alkyl amino, or nitro; or 3) B is

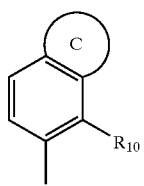

Here, $R_{10}$ is hydrogen, hydroxy, halogen, or lower alkyl and C is a five- or six-membered ring with 0 to 3 heteroatoms which are selected from nitrogen, oxygen, and sulfur. The ring may have no heteroatoms, or up to 3 heteroatoms which can be N, O, and S in any chemically appropriate combination. This ring may be unsubstituted or mono- or di-substituted with lower alkyl, cycloalkyl, amino, or substituted amino; or 4B is

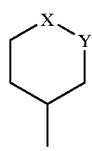

where X and Y are independently methylene or nitrogen; or

5) B is

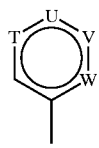

Here, at least one of T, U, V, or W is nitrogen, and any of T, U, V or W which is carbon may be substituted with lower alkyl, lower alkyl amino, lower alkoxy, hydroxy, aminosulfonyl, halogen, cyano, amino, or nitro, i.e. for any compound of this invention where B is (5), any position (from among T, U, V or W) which is carbon and not nitrogen, may have one of the substituents listed; or

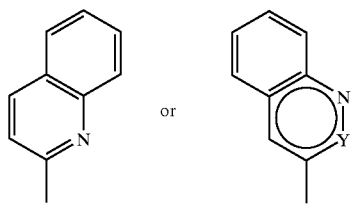

wherein Y is carbon or nitrogen; or

7) B is a five-membered aromatic ring. The ring may have 1 to 3 heteroatoms which are selected from nitrogen, oxygen, and sulfur (in any chemically appropriate combination). The ring may be unsubstituted or mono- or di- substituted at any position with lower alkyl, cycloalkyl, trifluoroloweralkyl, amino, halogen, substituted amino. The ring may also be fused with a 5 or 6 membered aromatic ring. The fused ring may contain 0 to 3 heteroatoms which heteroatoms are selected from nitrogen, oxygen, and sulfur (i.e. the fused ring may have no heteroatoms, or up to 3 heteroatoms which can be N, O, and S in any chemically appropriate combination). The ring may in particular be fused with phenyl.

Hereinafter, the groups from which B may be selected will be referred to (for convenience) by number, e.g. (1), (2), (3), (4), (5), (6), and (7)

In any compound of this invention (such as compounds of formulae 1, 1a–1g, 1-1, 1-1a–1-1c, 2, 2-1, and particularly those in the paragraph below) where B is (5), it is preferred that V be nitrogen, i.e. B is

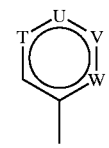

and T, U, or W are nitrogen or carbon. Any of T, U, or W which is carbon may be substituted with lower alkyl, lower alkyl amino, lower alkoxy, hydroxy, aminosulfonyl, halogen, cyano, amino, or nitro.

In any compound of this invention where B is the five-membered aromatic ring (7), it is preferred that one of the 1 to 3 heteroatoms of the ring be located at a position which is two positions from the attachment point (of the ring to the rest of the molecule depicted for example in formula 1 or 1-1). It is also preferred for any compound of this invention (such as compounds of formulae 1, 1a–1g, 1-1, 1-1a–1-1c, 2, 2-1, and particularly the compound described in this paragraph and those of the above paragraphs) where B is the five-membered aromatic ring (7) and is fused with a five or six membered aromatic ring with 0 to 3 heteroatoms, such as phenyl, that the positions of fusion are not adjacent to the attachment point.

Especially preferred compounds of this invention are compounds of formula 1 where $R_1$ is hydroxy or amino and $R_2$ and $R_3$ are hydrogen and compounds of formula 1-1 where $R_2$ and $R_3$ together with the ethenylene to which they are attached form phenyl, pyrazole or pyrrole. In these compounds, A is

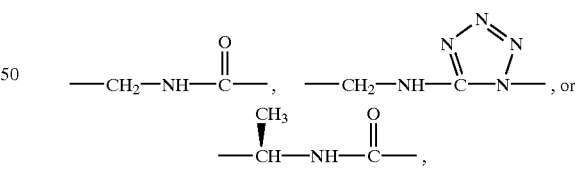

$R_4$ and $R_5$ are lower alkyl or halogen;

and B is

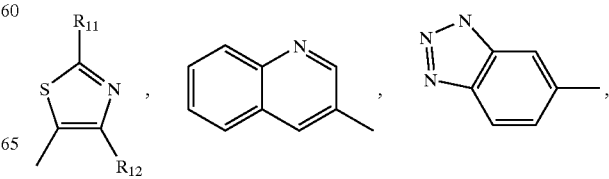

-continued

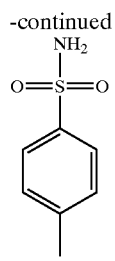

where $R_{11}$ is hydrogen, lower alkyl, substituted amino, or amino and $R_{12}$ is hydrogen, trifluoroloweralkyl or lower alkyl. All variants of these compounds are specifically contemplated by this invention. For example, compounds of formula 1 where $R_1$ is hydroxy or amino or compounds of formula 1-1 where $R_2$ and $R_3$ together with the ethenylene to which they are attached form phenyl, pyrazole or pyrrole and A is

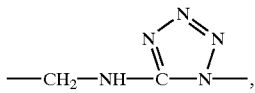

and B is the benzotriazole, or the same compounds where B is the thiazole, or the quinoline, or the aminosulfonylphenyl, are included.

Similarly compounds of formula 1 or formula 1-1 as above where A is

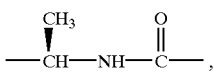

and B is the benzotriazole, or the same compound where B is the thiazole, or the quinoline, or the aminosulfonylphenyl, are included. Also part of this invention are such compounds where A is

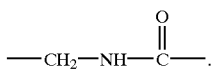

It is preferred that $R_4$ and $R_5$ are methyl or halogen. In compounds where B is the thiazole, it is preferred that $R_{11}$ is hydrogen, methyl, piperazinyl, trifluoromethyl, methyl, or cyclopropyl.

In compounds of formula 1-1 where $R_2$ and $R_3$ together with the ethenylene to which they are attached form phenyl, pyrazole or pyrrole, it is preferred that $R_2$ and $R_3$ together with the ethenylene to which they are attached form pyrazole or pyrrole.

In preferred compounds, $R_2$ and $R_3$ together with the ethenylene to which they are attached form pyrazole or pyrrole, A is

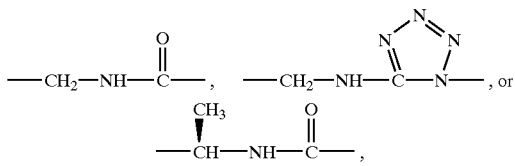

$R_4$ and $R_5$ are methyl or halogen; and B is

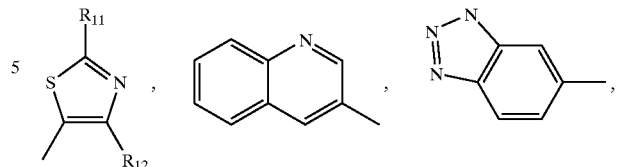

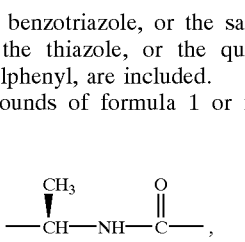

where $R_{11}$ is hydrogen, methyl, piperazinyl, isopropyl, or amino and $R_{12}$ is hydrogen, trifluoromethyl, methyl. Any variant of this compound is contemplated by this invention, as described in the two paragraphs immediately above. In an especially preferred compound, $R_2$ and $R_3$ together with the ethenylene to which they are attached form pyrazole or pyrrole, A is

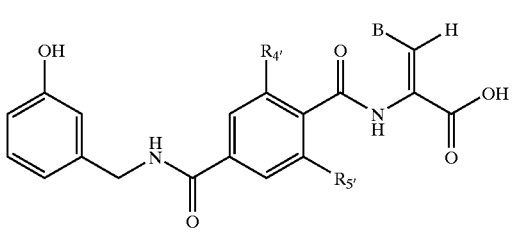

and $R_{11}$ and $R_{12}$ are methyl.

Certain compounds of formula 1 have the formula

1a wherein $R_4$ and $R_5$ are hydrogen, methyl, ethyl or halogen except that they cannot both be hydrogen, and B is selected from options (1), (2), (3), (4), (5), (6), and (7).

In some of these compounds, B is (1). Examples of such compounds are (Z)-2-[[2-bromo-4-[[(3-hydroxybenzyl)amino]carbonyl]benzoyl]amino]pent-2-enoic acid, 2-[[2-bromo-4-[[(3-hydroxybenzyl)amino]carbonyl]benzoyl]amino]propenoic acid, or 2-[[2-chloro-4-[[(3-hydroxybenzyl)amino]carbonyl]benzoyl]amino]propenoic acid.

In other compounds of formula 1a, B is (2) (i.e.

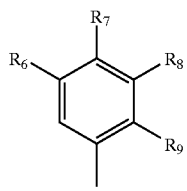

where $R_6$, $R_7$, $R_8$ and $R_9$ are independently hydrogen, hydroxy, aminosulfonyl, halogen, alkoxy, cyano, lower alkyl, lower alkyl amino, amino, or nitro), especially hydrogen, hydroxy, aminosulfonyl, or halogen, preferably hydrogen. Examples of such compounds are (Z)-2-[[2-bromo-4-[[(3-hydroxybenzyl)amino]carbonyl]benzoyl]amino]-3-(2-hydroxyphenyl)propenoic acid, (Z)-2-[[2-chloro-4-[[-(3-hydroxybenzyl)amino]carbonyl]benzoyl]amino]-3-(4-sulfamoylphenyl)propenoic acid, and (Z)-3-(4-bromophenyl)-2-[[2-chloro-4-[[(3-hydroxybenzyl)amino]carbonyl]benzoyl]amino] propenoic acid.

Compounds where $R_6$, $R_7$, $R_8$ and $R_9$ are hydrogen include (Z)-2-[[2-chloro-4-[[(3-hydroxybenzyl)amino]carbonyl]-6-methylbenzoyl]amino]-3-phenylpropenoic acid, (Z)-2-[[2-bromo-4-[[(3-hydroxybenzyl)amino]carbonyl]benzoyl]amino]-3-phenylpropenoic acid, (Z)-2-[[2-chloro-4-[[(3-hydroxybenzyl)amino]carbonyl]benzoyl]amino]-3-phenylpropenoic acid, and (Z)-2-[[4-[[(3-hydroxybenzyl)amino]carbonyl]-2-methylbenzoyl]amino]-3-phenylpropenoic acid.

Also part of this invention is a compound of formula 1a wherein B is (3) (i.e.

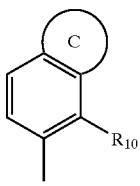

where $R_{10}$ is hydrogen, hydroxy, halogen, or lower alkyl and C is a five- or six- membered ring with 0 to 3 heteroatoms, which heteroatoms are selected from nitrogen, oxygen, and sulfur, which ring may be unsubstituted or mono- or di-substituted with lower alkyl, cycloalkyl, or substituted amino). In preferred such compounds, C is a six-membered ring, especially a six-membered ring with 0 heteroatoms (e.g. phenyl). An example of the latter compound is (Z)-2-[[2-bromo-4-[[(3-hydroxybenzyl) amino]carbonyl]benzoyl]amino]-3-(naphthalen-2-yl)propenoic acid. (A related compound of this invention is (Z)-2-[[2-bromo-4-[[(3-hydroxybenzyl) amino]carbonyl]benzoyl]amino]-3-(naphthalen-1-yl)propenoic acid).

In other preferred compounds of formula 1a where B is (3), C is a five-membered heterocyclic ring. Examples of such compounds are (Z)-3-(6-chlorobenzo[1,3]dioxol-5-yl)-2-[[2-chloro-4-[[(3-hydroxybenzyl)amino]carbonyl]benzoyl]amino]propenoic acid, (Z)-3-(benzothiazol-6-yl)-2-[[2-chloro-4-[[(3 hydroxybenzyl) amino]carbonyl]benzoyl]amino] propenoic acid, (Z)-3-(2,1,3-benzoxadiazol-5-yl)-2-[[2-chloro-4-[[(3-hydroxybenzyl) amino]carbonyl]benzoyl]amino] propenoic acid, and (Z)-3-(2,1,3-benzothiadiazol-5-yl)-2-[[2-chloro-4-[[(3-hydroxybenzyl) amino]carbonyl]benzoyl]amino] propenoic acid.

In yet other preferred compounds of formula 1a where B is (3), C is a heterocyclic ring with 1 to 3 nitrogens. Examples of such compounds are (Z)-3-(1H-benzotriazol-5-yl)-2-[[2-chloro-4-[[(3-hydroxybenzyl) amino]carbonyl]-6-methylbenzoyl]amino]propenoic acid, (Z)-3-(1H-benzotriazol-5-yl)-2-[[2-bromo-4-[[(3-hydroxybenzyl) amino]carbonyl]benzoyl]amino] propenoic acid, (Z)-3-(1H-benzotriazol-5-yl)-2-[[2,6-dimethyl-4-[[(3-hydroxybenzyl]amino]carbonyl]benzoyl]amino] propenoic acid, (Z)-2-[[2-chloro-4-[[(3-hydroxybenzyl)amino]carbonyl]benzoyl]amino]-3-(1-methyl-1H-indol-6-yl)propenoic acid and (Z)-2-[[4-[[(3-hydroxybenzyl)amino]carbonyl]-2-methylbenzoyl]amino]-3-(1H-indol-6-yl)propenoic acid.

Also part of this invention are compounds of formula 1a where B is (4), (i.e. B is

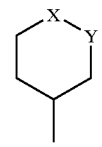

where X and Y are independently methylene or nitrogen). An example of such a compound is (Z)-2-[[bromo-4-[[(3-hydroxybenzyl) amino]carbonyl]benzoyl]amino]-3-(piperidin-4-yl)propenoic acid.

In other compounds of formula 1a, B is (5) (i.e

where at least one of T, U, V, or W is nitrogen, and any of T, U, V or W which is carbon may be substituted with lower alkyl, lower alkyl amino, lower alkoxy, hydroxy, aminosulfonyl, halogen, cyano, amino, or nitro). In preferred such compounds, the carbon is unsubstituted or substituted with lower alkoxy. Examples of such compounds are (Z)-2-[[2-bromo-4-[[(3-hydroxybenzyl) amino]carbonyl]benzoyl]amino]-3-(pyridin-2-yl)propenoic acid, (Z)-2-[[2-bromo-4-[[(3-hydroxybenzyl)amino]carbonyl]benzoyl]amino]-3-(2,4-dimethoxypyrimidin-5-yl) propenoic acid, (Z)-2-[[2-bromo-4-[[(3-hydroxybenzy)amino]carbonyl]benzoyl]]-3-(pyridin-3-yl)propenoic acid, and (Z)-2-[[2-bromo-4-[[(3-hydroxybenzyl)amino]carbonyl]benzoyl]amino]-3-(pyridin-4-yl)propenoic acid.

This invention includes compounds of formula 1a where B is (6) (i.e. B is

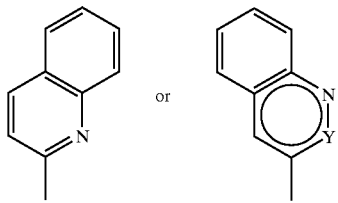

and Y is carbon or nitrogen). Examples of such compounds are (Z)-2-[[2-bromo-4-[[(3-hydroxybenzyl)amino]carbonyl]benzoyl]amino]-3-(quinolin-3-yl)propenoic acid, (Z)-2-[[2-chloro-4-[[(3-hydroxybenzyl)amino]carbonyl]benzoyl]amino]-3-(quinolin-3-yl)propenoic acid, (Z)-2-[[2-chloro-4-[[(3-hydroxybenzyl)amino]carbonyl]-6-methylbenzoyl]amino]-3-(quinolin-3-yl)propenoic acid, (Z)-2-[[4-[[(3-hydroxybenzyl) amino]carbonyl]-2-methylbenzoyl]amino]-3-(quinolin-3-yl)propenoic acid, and (Z)-2-[[2-bromo-4-[[(3-hydroxybenzyl)amino]carbonyl]benzoyl]amino]-3-(quinolin-2-yl)propenoic acid.

Also part of this invention are compounds of formula 1a where B is (7) (i.e. B is a five-membered aromatic ring with 1 to 3 heteroatoms selected from nitrogen, oxygen, and sulfur which ring may be unsubstituted or mono- or di-substituted with lower alkyl, cycloalkyl, trifluoroloweralkyl, amino, halogen, substituted amino, or which ring may be fused with a 5 or 6 membered aromatic ring containing 0 to 3 heteroatoms which heteroatoms are selected from nitrogen, oxygen, and sulfur).

In preferred compounds of formula 1a where B is (7), B is thiadiazole. An example of such a compound is (Z)-2-[[2-bromo-4-[[(3-hydroxybenzyl) amino]carbonyl]benzoyl] amino]-3-(4-methyl-[1,2,3]thiadiazol-5-yl)propenoic acid.

In other preferred compounds of formula 1a where B is (7), B is an unsubstituted five-membered aromatic ring with 1 heteroatom selected from nitrogen, oxygen, and sulfur or with 1 to 3 nitrogen heteroatoms. Examples of such compounds are (Z)-2-[[2-bromo-4-[[(3-hydroxybenzyl) amino]carbonyl]benzoyl]amino]-3-(thien-2-yl)propenoic acid, (Z)-2-[[2-bromo-4-[[(3-hydroxybenzyl)amino]carbonyl]benzoyl]amino]-3-(thien-3-yl)propenoic acid, (Z)-2-[[2-bromo-4-[[(3-hydroxybenzyl)amino]carbonyl]benzoyl]amino]-3-(furan-3-yl)propenoic acid, (Z)-2-[[2-bromo-4-[[(3-hydroxybenzyl)amino]carbonyl]benzoyl]amino]-3-(1H-imidazol-4-yl)propenoic acid, and (Z)-2-[[2-bromo-4-[[(3-hydroxybenzyl)amino]carbonyl]benzoyl]amino]-3-(1H-[1,2,4]triazol-3-yl)propenoic acid.

In yet other preferred compounds of formula 1a where B is (7),B is a five-membered aromatic ring fused with phenyl. Examples of such compounds are (Z)-3-(benzo[b]thiophen-3-yl)-2-[[2-bromo-4-[[(3-hydroxybenzyl) amino]carbonyl]benzoyl]amino] propenoic acid, (Z)-3-(benzothiazol-2-yl)-2-[[2-bromo-4-[[(3-hydroxybenzyl) amino]carbonyl]benzoyl]amino] propenoic acid, and (Z)-2-[[2-bromo-4-[[(3-hydroxybenzyl)amino] carbonyl]benzoyl]amino]-3-(1-methyl-1H-benzodiazol-2-yl)propenoic acid.

In other preferred compounds of formula 1a where B is (7), B is thiazole which is unsubstituted or is mono or di-substituted with amino, lower alkyl, trifluoromethyl, substituted amino or halogen. Examples of such compounds are (Z)-2-[[2-bromo-4-[[(3- hydroxy-benzyl)amino]carbonyl]benzoyl]amino]-3-(thiazol-2-yl)propenoic acid, (Z)-3-(2-aminothiazol-5-yl)-2-[[2-bromo-4-[[(3-hydroxybenzyl)amino]carbonyl]benzoyl]amino] propenoic acid, (Z)-2-[[2-bromo-4-[[(3-hydroxybenzyl)amino]carbonyl]benzoyl]amino]-3-(2,4-dimethylthiazol-5-yl)propenoic acid, (Z)-2-[[2-chloro-4-[[(3-hydroxybenzyl) amino]carbonyl]benzoyl]amino]-3-(2-ethyl-4-methylthiazol-5-yl) propenoic acid, (Z)-2-[[2-bromo-4-[[(3-hydroxybenzyl)amino]carbonyl]benzoyl]amino]-3-(2-dimethylamino-thiazol-5-yl) propenoic acid, (Z)-2-[[2-bromo-4-[[(3-hydroxybenzyl)amino]carbonyl]benzoyl]amino]-3-(2-methylthiazol-4-yl)propenoic acid, (Z)-2-[[2-chloro-4-[[(3-hydroxybenzyl)amino]carbonyl]benzoyl]amino]-3-[4-methyl-2-(1-methylethyl)thiazol-5-yl]propenoic acid, (Z)-2-[[2-bromo-4-[[(3-hydroxybenzyl)amino]carbonyl]benzoyl]amino]-3-[2-(morpholin-4-yl)thiazol-5-yl] propenoic acid, (Z)-2-[[2-bromo-4-[[(3-hydroxybenzyl)amino]carbonyl]benzoyl]amino]-3-[2-(piperazin-1-yl)thiazol-5-yl] propenoic acid, (Z)-2-[[2-bromo-4-[[(3-hydroxybenzyl)amino]carbonyl]benzoyl]amino]-3-(2,4-dimethylthiazol-5-yl)propenoic acid sodium salt, (Z)-3-(2-amino-4-trifluoromethylthiazol-5-yl)-2-[[2-chloro-4-[[(3-hydroxybenzyl)amino]carbonyl]benzoyl]amino]propenoic acid, (Z)-2-[[2-chloro-4-[[(3-hydroxybenzyl)amino]carbonyl]benzoyl]amino]-3-(2-chlorothiazol-5-yl)propenoic acid, (Z)-2-[[2-chloro-4-[[(3-hydroxybenzyl)amino]carbonyl]benzoyl]amino]-3-(2,4-dimethylthiazol-5-yl)propenoic acid, (Z)-2-[[2-chloro-4-[[(3-hydroxybenzyl)amino]carbonyl]benzoyl]amino]-3-(2-methylamino-4-trifluoromethylthiazol-5-yl)propenoic acid, (Z)-2-[[2,6-dimethyl-4-[[(3-hydroxybenzyl]amino]carbonyl]benzoyl]amino]-3-(2,4-dimethylthiazol-5-yl) propenoic acid, (Z)-2-[[2-chloro-4-[[(3-hydroxybenzyl)amino]carbonyl]benzoyl]amino]-3-[4-(1-methylethyl)thiazol-5-yl] propenoic acid and (Z)-2-[[2-bromo-4-[[(3-hydroxybenzyl)amino]carbonyl]benzoyl]amino]-3-[2-methyl-4-(1-methylethyl)thiazol-5-yl]propenoic acid;

(Z)-2-[[2-bromo-4-[[3-hydroxybenzyl)amino]carbonyl]benzoyl]amino]-3-[4-(trifluoromethyl)thiazol-2-yl] propenoic acid; and (Z)-2-[[2-bromo-4-[[3-hydroxybenzyl)amino]carbonyl]benzoyl]amino]-3-[4-(1-methylethyl)thiazol-2-yl] propenoic acid.

This invention is directed to compounds of formula 1 having the formula

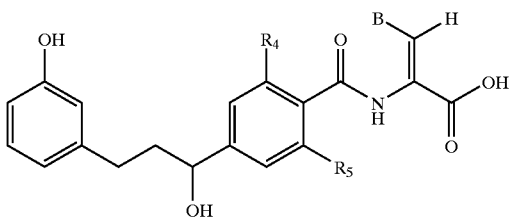

where $R_4$ and $R_5$ are hydrogen, methyl, ethyl or halogen, except that $R_4$ and $R_5$ cannot both be hydrogen, and B is selected from options (1), (2), (3), (4), (5), (6), and (7). It is preferred that $R_4$ be halogen and $R_5$ be hydrogen.

In some compounds of formula 1b (especially where $R_4$ is halogen and $R_5$ is hydrogen), B is (7) (i.e. B is a five-membered aromatic ring with 1 to 3 heteroatoms selected from nitrogen, oxygen, and sulfur which ring may be unsubstituted or mono- or di-substituted with lower alkyl, cycloalkyl, trifluoroloweralkyl, amino, halogen, substituted amino, or which ring may be fused with a 5 or 6 membered aromatic ring containing 0 to 3 heteroatoms which heteroatoms are selected from nitrogen, oxygen, and sulfur).

In preferred compounds of formula 1b where B is (7) (especially where $R_4$ is halogen and $R_5$ is hydrogen), B is thiazole. An example of such a compound rac.-(Z)-2-[[2-chloro-4-[1-hydroxy-3-(3-hydroxyphenyl)propan-1-yl]benzoyl]amino]-3-(2,4-dimethylthiazol-5-yl)propenoic acid.

In other preferred compounds of formula 1b (especially where $R_4$ is halogen and $R_5$ is hydrogen), B is (6) (i.e. B is

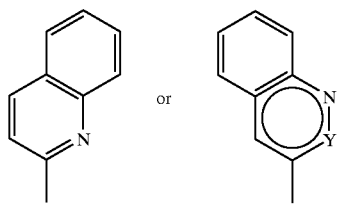

and Y is carbon or nitrogen). An example of such a compound is rac.-(Z)-2-[[2-chloro-4-[1-hydroxy-3-(3-hydroxyphenyl)propan-1-yl]benzoyl]amino]-3-(quinolin-3-yl)propenoic acid.

This invention is also directed to compounds of formula 1 having the formula

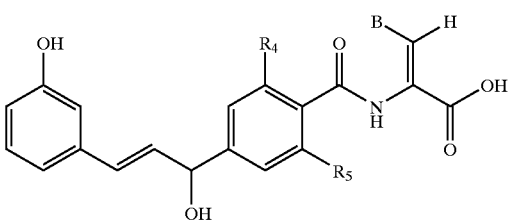

where $R_4$ and $R_5$ are hydrogen, methyl, ethyl or halogen but not both hydrogen; and B is selected from options (1), (2), (3), (4), (5), (6), and (7). In preferred compounds $R_4$ is halogen and $R_5$ is hydrogen.

In compounds of formula 1c (especially where $R_4$ is halogen and $R_5$ is hydrogen), B is (7) (i.e. B is a five-membered aromatic ring with 1 to 3 heteroatoms selected from nitrogen, oxygen, and sulfur which ring may be unsubstituted or mono- or di- substituted with lower alkyl, cycloalkyl, trifluoroloweralkyl, amino, halogen, substituted amino, or which ring may be fused with a 5 or 6 membered aromatic ring containing 0 to 3 heteroatoms which heteroatoms are selected from nitrogen, oxygen, and sulfur). In preferred such compounds, B is thiazole. An example of such a compound is rac.-(Z)-2-[[2-chloro-4-[(E)-1-hydroxy-3-(3-hydroxyphenyl)prop-2-en-1-yl]benzoyl]amino]-3-dimethylthiazol-5-yl)propenoic acid.

In other compounds of formula 1c (especially where $R_4$ is halogen and $R_5$ is hydrogen), B is (6) (i.e. B is

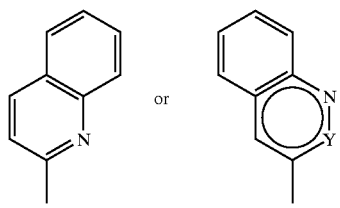

wherein Y is carbon or nitrogen). An example of such a compound is rac.-(Z)-2-[[2-chloro-4-[(E)-1-hydroxy-3-(3-hydroxyphenyl)prop-2-en-1-yl]benzoyl]amino]-3-(quinolin-3-yl)propenoic acid.

This invention includes compounds of formula 1 having the formula

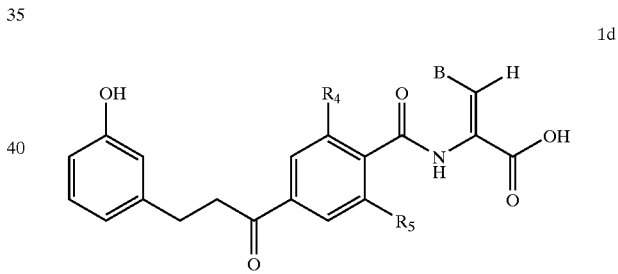

where $R_4$ and $R_5$ are hydrogen, methyl, ethyl or halogen, but not both hydrogen; and B is selected from options (1), (2), (3), (4), (5), (6), and (7). In preferred compounds, $R_4$ is halogen and $R_5$ is hydrogen. In preferred such compounds B is (7), (i.e. where B is a five-membered aromatic ring with 1 to 3 heteroatoms selected from nitrogen, oxygen, and sulfur which ring may be unsubstituted or mono- or di-substituted with lower alkyl, cycloalkyl, trifluoroloweralkyl, amino, halogen, substituted amino, or which ring may be fused with a 5 or 6 membered aromatic ring containing 0 to 3 heteroatoms which heteroatoms are selected from nitrogen, oxygen, and sulfur), especially where $R_4$ is halogen and $R_5$ is hydrogen. An example of such a compound is (Z)-2-[[2-chloro-4-[3-(3-hydroxyphenyl)-1-oxopropan-1-yl]benzoyl]amino]-3-(2,4-dimethylthiazol-5-yl)propenoic acid.

In other preferred compounds of formula 1d (especially where $R_4$ is halogen and $R_5$ is hydrogen), B is

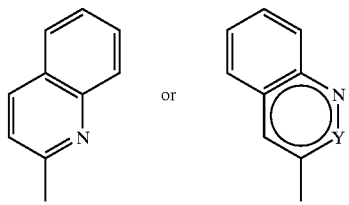

wherein Y is carbon or nitrogen). An example of such a compound is (Z)-2-[[2-chloro-4-[3-(3-hydroxyphenyl)-1-oxopropan-1-yl]benzoyl]amino]-3-(quinolin-3-yl)propenoic acid.

This invention is also directed to compounds of formula 1 having formula

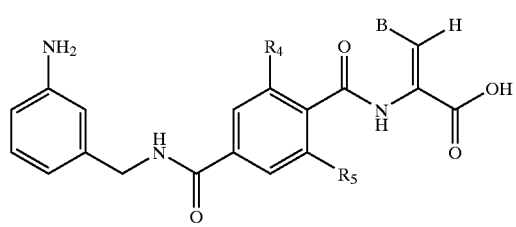

1e where $R_4$ and $R_5$ are hydrogen, methyl, ethyl or halogen but not both hydrogen, and B is selected from options (1), (2), (3), (4), (5), (6), and (7). In preferred such compounds, $R_4$ is hydrogen and $R_5$ is halogen.

In preferred compounds of formula 1e (especially where $R_4$ is halogen and $R_5$ is hydrogen), B is (6) (i.e. B is

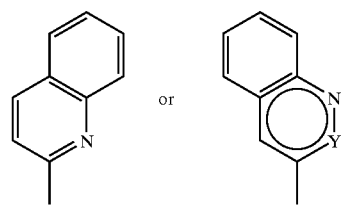

wherein Y is carbon or nitrogen). An example is (Z)-2-[[4-[[(3-aminobenzyl)amino]carbonyl]-2-bromobenzoyl]amino]-3-(quinolin-3-yl)propenoic acid.

In preferred compounds of formula 1e (especially where $R_4$ is halogen and $R_5$ is hydrogen), B is (7) (i.e. B is a five-membered aromatic ring with 1 to 3 heteroatoms selected from nitrogen, oxygen, and sulfur which ring may be unsubstituted or mono- or di- substituted with lower alkyl, cycloalkyl, trifluoroloweralkyl, amino, halogen, substituted amino, or which ring may be fused with a 5 or 6 membered aromatic ring containing 0 to 3 heteroatoms which heteroatoms are selected from nitrogen, oxygen, and sulfur). An example of such a compound is (Z)-2-[[4-[[(3-aminobenzyl)amino]carbonyl]-2-bromobenzoyl]amino]-3-(2,4-dimethylthiazol-5-yl)propenoic acid.

This invention is also directed to compounds of formula 1 having the formula

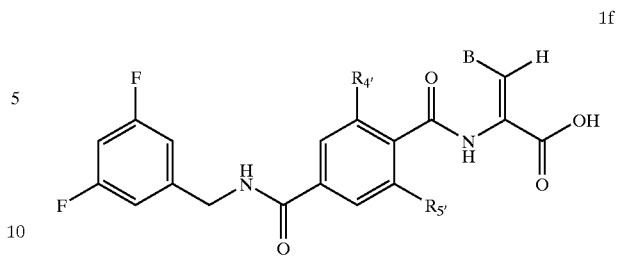

1f where $R_4$ and $R_5$ are hydrogen, methyl, ethyl or halogen but not both hydrogen; and B is selected from options (1), (2), (3), (4), (5), (6), and (7). In preferred such compounds, $R^4$ and RW are methyl. It is also preferred that B is (7) (i.e. B is a five-membered aromatic ring with 1 to 3 heteroatoms selected from nitrogen, oxygen, and sulfur which ring may be unsubstituted or mono- or di-substituted with lower alkyl, cycloalkyl, trifluoroloweralkyl, amino, halogen, substituted amino, or which ring may be fused with a 5 or 6 membered aromatic ring containing 0 to 3 heteroatoms which heteroatoms are selected from nitrogen, oxygen, and sulfur). Examples of such compounds are (Z)-2-[[4-[[(3,5-difluorobenzyl)amino]carbonyl]-2,6-dimethylbenzoyl]amino]-3-(4-methyl-1H-imidazol-5-yl)propenoic acid, and (Z)-2-[[4-[[(3,5-difluorobenzyl)amino]carbonyl]-2,6-dimethylbenzoyl]amino]-3-(2,4-dimethylthiazol-5-yl)propenoic acid.

Also preferred are compounds of formula 1f where B is (6) (i.e. B is

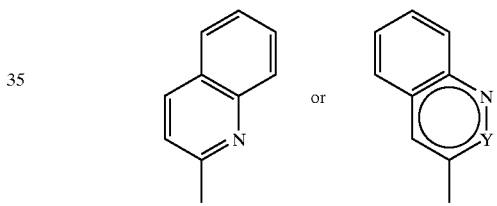

and Y is carbon or nitrogen), especially where $R^4$ and $R_5$ are methyl. An example of such a compound is (Z)-2-[[4-[[(3,5-difluorobenzyl)amino]carbonyl]-2,6-dimethylbenzoyl]amino]-3-(quinolin-3-yl)propenoic acid.

This invention is directed to compounds of formula 1-1 having the formula

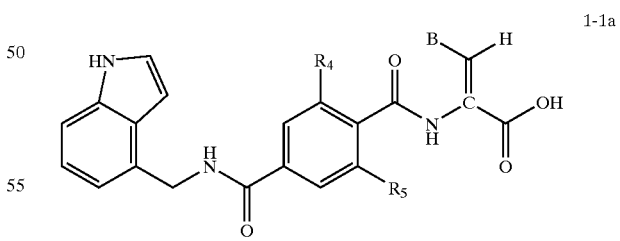

1-1a where $R_4$ and $R_5$ are hydrogen, methyl, ethyl or halogen, but not both hydrogen; and B is selected from options (1), (2), (3), (4), (5), (6), and (7), preferably (7). In preferred such compounds B is a five-membered aromatic ring with 1 to 2 heteroatoms selected from nitrogen and sulfur, which ring may be unsubstituted, or mono- or di- substituted with lower alkyl, cycloalkyl, trifluoroloweralkyl, amino, halogen, or substituted amino, especially where B may be unsubstituted or disubstituted with lower alkyl. Examples of such compounds are (Z)-2-[[2-bromo-4-[[[(1H-indol-4-yl) methyl]amino]carbonyl]benzoyl]amino]-3-(2,4-dimethylthiazol-5-yl)propenoic acid and (Z)-2-[[2-chloro-4-[[[(1H-indol-4-yl)methyl]amino]carbonyl]benzoyl]amino]-3-(thien-2-yl)propenoic acid.

Also preferred are compounds of formula 1-1a where B is (3) (i.e.

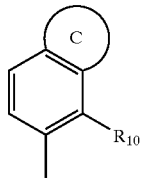

where $R_{10}$ is hydrogen, hydroxy, halogen, or lower alkyl and C is a five- or six-membered ring with 0 to 3 heteroatoms, which heteroatoms are selected from nitrogen, oxygen, and sulfur, which ring may be unsubstituted or mono- or di- substituted with lower alkyl, cycloalkyl, or substituted amino). Examples of such compounds are (Z)-3-(3H-benzotriazol-5-yl)-2-[[2-bromo-4-[[[(1H-indol-4-yl)methyllamino]carbonyl]benzoyl]amino]propenoic acid, (Z)-3-(benzothiazol-6-yl)-2-[[2-bromo-4-[[[(1H-indol-4-yl)methyl]amino]carbonyl]benzoyl]amino]propenoic acid, and (Z)-2-[[2-chloro-4-[[[(1H-indol-4-yl)methyl]amino]carbonyl]benzoyl]amino]-3-(naphthalen-2-yl)propenoic acid.

Also preferred are compounds of formula 1-1a where B is (2) (i.e. B is

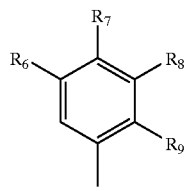

where $R_6$ $R_7$ $R_8$ and $R_9$ are independently hydrogen, hydroxy, aminosulfonyl, halogen, lower alkoxy, cyano, amino, or nitro). Examples are (Z)-2-[[2-chloro-4-[[[(1H-indol-4-yl)methyl]amino]carbonyl]benzoyl]amino]-3-phenylpropenoic acid and (Z)-2-[[2-chloro-4-[[[(1H-indol-4-yl)methyl]aminol]carbonyl]benzoyl]amino]-3-(2-hydroxyphenyl)propenoic acid.

In other preferred compounds of formula 1-1a, B is (6) (i.e. B is

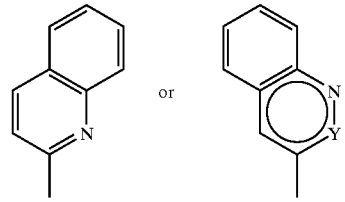

and Y is carbon or nitrogen). An example of such a compound is (Z)-2-[[2-bromo-4-[[[(1H-indol-4-yl)methyl]amino]carbonyl]benzoyl]amino]-3-(quinolin-3-yl)propenoic acid. Related compounds of this invention are (Z)-2-[[2-bromo-4-[[[(1H-indol-6-yl)methylano]carbonyl]benzoyl]amino]-3-(quinolin-3-yl)propenoic acid, and (Z)-2-[[2-chloro-4-[[[(1H-indol-6-yl)methyl]amino]carbonyl]benzoyl]amino]3-(quinolin-3-yl)propenoic acid.

In other preferred compounds of formula 1-1a, B is (5) (i.e.

where at least one of T, U, V, or W is nitrogen, and any of T, U, V, or W which are carbon may be substituted with lower alkyl, lower alkyl amino, lower alkoxy, hydroxy, aminosulfonyl, halogen, cyano, amino, or nitro). An example of such a compound is (Z)-2-[[2-chloro-4-[[[(1H-indol-4-yl)methyl]amino]carbonyl]benzoyl]amino]-3-(pyridin-2-yl)propenoic acid.

Also part of this invention are compounds of formula 1-1 having the formula 1-1b

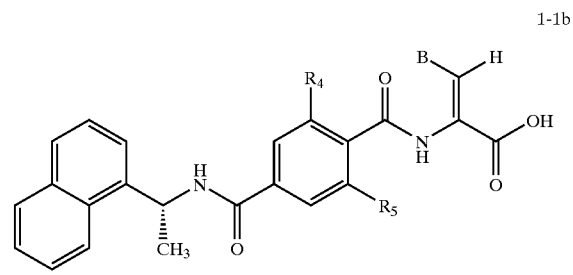

where $R_4$ and $R_5$ are hydrogen, methyl, ethyl or halogen, but not both hydrogen; and B is selected from options (1), (2), (3), (4), (5), (6), and (7).

Compounds of formula 1-1b include compounds where B is (2), especially where B is

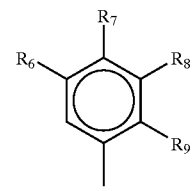

$R_6$, $R_7$, $R_8$, and $R_9$ are hydrogen. An example is [Z, (R)]-2-[2,6-dimethyl-4-[[[1-naphthalen-1-yl)ethyl]amino]carbonyl]benzoyl]amino]-3-phenylpropenoic acid.

In other compounds of formula 1-1b, B is (3), especially where B is

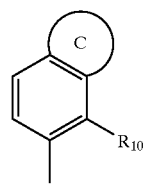

and $R_{10}$ is hydrogen and C is triazole. Examples of such compounds are [Z, (R)]-3-(1H-benzotriazol-5-yl)-2-[[2,6-dimethyl-4-[[[1-naphthalen-1-yl)ethyl]amino]carbonyl]benzoyl]amino]propenoic acid and [Z, (R)]-3-(1H- benzotriazol-5-yl)-2-[[2,6-dichloro-4-[[[1-naphthalen-1-yl)
ethyl]amino]carbonyl]benzoyl]amino]propenoic acid.

In other compounds of formula 1-1b, B is

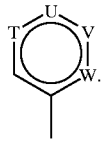

An example of such a compound is [Z,(R)]-2-[[2,6-dimethyl-4-[[[(1-(naphthalen-1-yl)ethyl]amino]carbonyl]
benzoyl]amino]-3-(pyridin-4-yl)propenoic acid.

Preferred compounds of formula 1-1b include compounds where B is (7), especially where B is a five-membered aromatic ring with one to two heteroatoms selected from N and S which ring may be mono or di substituted with lower alkyl. Examples are [Z, (R)]-2-[[2,6-dimethyl-4-[[[1-naphthalen-1-yl)ethyl]amino]carbonyl]benzoyl]amino]-3-(4-methyl-1H-imidazol-5-yl)propenoic acid,

[Z, (R)]-2-[[2-chloro-4-[[[1-naphthalen-1-yl) ethyl]
  amino]carbonyl]benzoyl]amino]-3-(thien-2-yl)
  propenoic acid,

[Z, (R)]-2-[[2,6-dimethyl-4-[[[1-naphthalen-1-yl)ethyl]
  amino]carbonyl]benzoyl]amino]-3-(2,4-
  dimethylthiazol-5-yl)propenoic acid and [Z, (R)]-2-[[2,6-dimethyl-4-[[[1-naphthalen-1-yl)
  ethyl]amino]carbonyl]benzoyl]amino]-3-(1H-
  imidazol-2-yl)propenoic acid.

Formula 1-1b includes compounds where B is (6). Examples of such compounds are [Z,(R)]-2-[[2,6-dichloro-4-[[[(1-(naphthalen-4-yl)ethyl]amino]carbonyl]benzoyl]
amino]-3-(quinolin-3-yl)propenoic acid and [Z, (R)]-2-[[2,6-dimethyl-4-[[[(1-naphthalen-1 yl)ethyl]amino]carbonyl]
benzoyl]amino]-3-(quinolin-3-yl)propenoic acid.

This invention is also directed to compounds of formula 1, which compounds have the formula

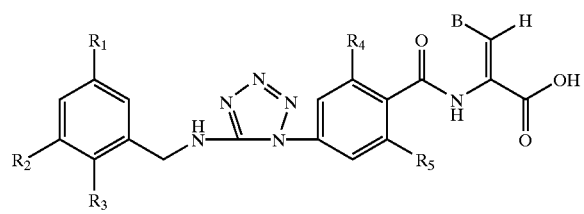

1g where $R_1$ is hydrogen, hydroxy, amino or halogen, $R_2$ is hydrogen, hydroxy, or halogen and $R_3$ is hydrogen; $R_4$ and $R_5$ are hydrogen, methyl, ethyl, or halogen but not both hydrogen, and B is selected from options (1), (2), (3), (4), (5), (6), and (7).

This invention is also directed to compounds of formula 1-1 having the formula

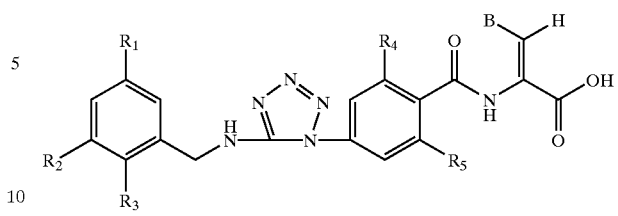

1-1c where $R_1$ is hydrogen and $R_2$ and $R_3$ taken together with the ethenylene group connecting them form phenyl, pyrrole, pyrroline, oxopyrroline, pyrazole, triazole, or imidazole; $R_4$ and $R_5$ are hydrogen, methyl, ethyl, or halogen but not both hydrogen, and B is selected from options (1), (2), (3), (4), (5), (6), and (7).

Also part of this invention are prodrug compounds (and their pharmaceutically acceptable salts). Any compound of this invention is also contemplated in prodrug form. By prodrug is meant a metabolic precursor of a drug which when administered to a patient breaks down into the drug and acceptable by-products. In the prodrugs of this invention, the carboxy group found in the formulae above is replaced by other groups, which groups come off when administered to the patient, leaving a hydrogen and reconstituting the carboxy group. Any individual compound of this invention may be iobtained as a prodrug described below.

Prodrugs of this invention include a compound of formula

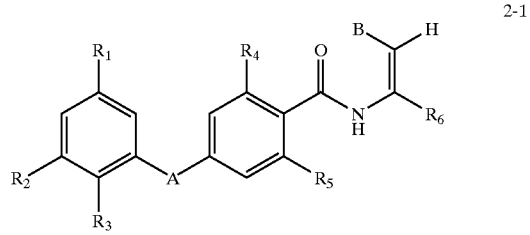

2-1 wherein $R_2$ and $R_3$ taken together with the ethenylene group connecting them form phenyl, pyrrole, pyrroline, oxopyrroline, pyrazole, triazole, or imidazole; $R_4$ and $R_5$ are hydrogen, methyl, ethyl, or halogen but not both hydrogen, and $R^6$ is one of the following groups:

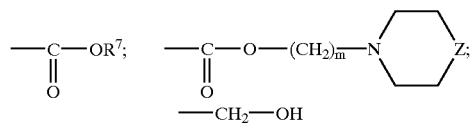

where $R^7$ is lower alkyl, $-(CH_2)_r-N(CH_3)_2$,

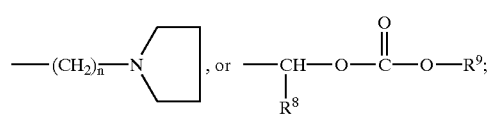

Z is oxygen or NH, $R^8$ is hydrogen or methyl and $R^9$ is lower alkyl or cycloalkyl and m, n, and r are 1 to 5 (each of m, n, and r is preferably 2).

A is one of the following groups:

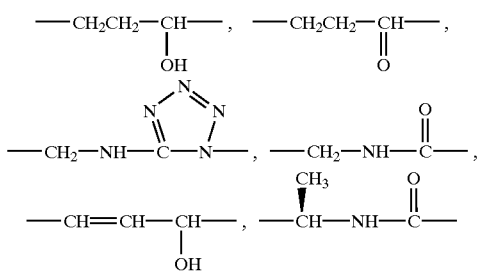

B is selected from options (1), (2), (3), (4), (5), (6), and (7). When $R^6$ is

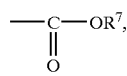

it is preferred that $R^7$ is unbranched lower alkyl, especially ethyl. It is also preferred that n is 2, especially when $R^6$ is $-C(O)-O-(CH_2)_r-N(CH_2)_2$,

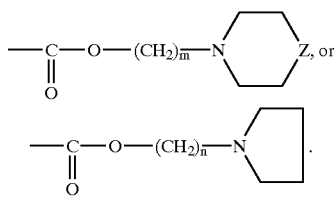

It is also preferred that $R^6$ is

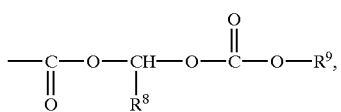

especially when $R^8$ is hydrogen or methyl and $R^9$ is ethyl or cyclohexyl. In a preferred compound, $R^6$ is

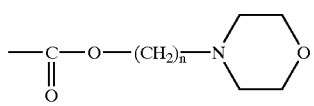

and n is 2.

Another prodrug of this invention is a compound of formula

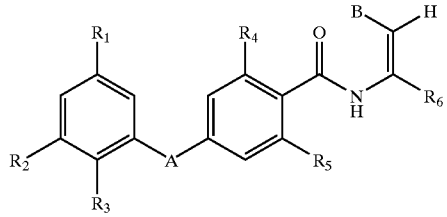

wherein $R_1$ is hydrogen, hydroxy, amino or halogen, $R_2$ is hydrogen, hydroxy or halogen and $R_3$ is hydrogen, $R_4$ and $R_5$ are hydrogen, methyl, ethyl, or halogen but not both hydrogen, and $R_6'$ is one of the following groups

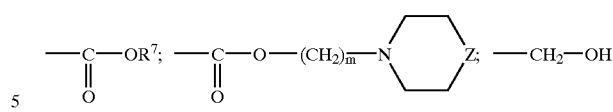

where $R^7$ is lower alkyl $-(CH_2)_r-N(CH_3)_2$,

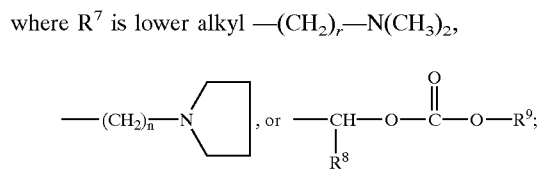

Z is oxygen or NH, $R^8$ is hydrogen or methyl and $R^9$ is lower alkyl or cycloalkyl and m, n, and r are 1 to 5 (each of m, n, and r is preferably 2). A is one of the following groups:

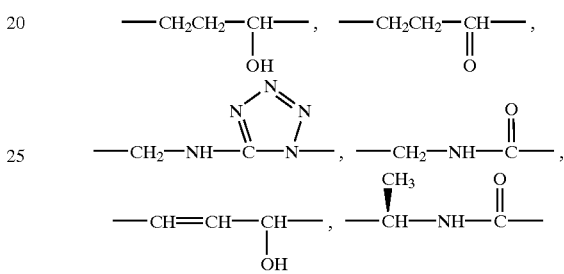

B is selected from options (1), (2), (3), (4), (5), (6), and (7). When $R^6$ is

it is preferred that $R^7$ is unbranched lower alkyl, especially ethyl. It is also preferred that n is 2, especially when $R^6$ is $-C(O)-O-(CH2)_r-N(CH3)2$,

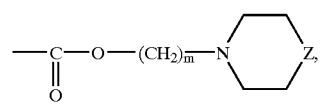

or

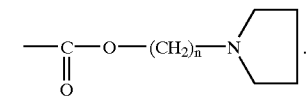

It is also preferred that $R^6$ is

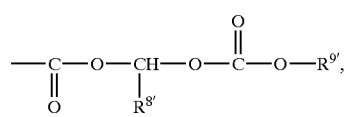

especially when $R^8$ is hydrogen or methyl and $R^{9'}$ is ethyl or cyclohexyl. In a preferred compound, $R^6$ is

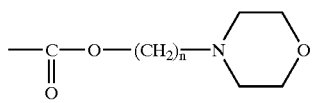

and n is 2. An example of such a compound is (Z)-2-[[2-bromo-4-[[(3-hydroxy-benzyl]amino]carbonyl]benzoyl]amino]-3-(2,4-dimethylthiazol-5-yl)propenoic acid 2-(morpholin-4-yl)ethyl ester.

Other prodrugs of this invention can be obtained from any compound of this invention by known modifications at the R. or $R_2$ position of formula 1 or formula 1-1 using known methods.

By halogen in general is meant bromine, chlorine, fluorine and iodine. For any compound of this invention, the preferred halogens are bromine, chlorine, and fluorine.

By lower alkyl is meant saturated hydrocarbon chains such as methyl, ethyl, propyl. butyl and the like. The length of the chains is preferably from 1 to 10 carbons, more preferably from 1 to 4 carbons, inclusive of any branching carbons as defmed in this paragraph. A lower alkyl group of this invention may be branched, which means a lower alkyl group that contains a carbon which is bonded to at least three other carbons, such as isopropyl or 2-ethyl-4-methylpentyl. A lower alkyl substituent may also be unbranched, which means that it does not contain any carbons bonded to more than two other carbons. Examples of various lower alkyl groups are methyl, ethyl, n-propyl, isopropyl, n-butyl, sec.butyl, isobutyl, tert.butyl, n-pentyl, n-hexyl. Preferred lower alkyl groups are methyl, ethyl, propyl (n or iso), and butyl (n, iso, sec, or tert). Lower alkyl groups may be substituted with another group, preferably halogen, such as fluorine. Such substitution may be in one or more positions. A preferred such group is trifluoroalkyl, where three of the carbons of the lower alkyl group are substituted with fluorine. A particularly preferred group is trifluoromethyl.

By cycloalkyl is meant a saturated hydrocarbon ring which is from 3 to 10 carbons in size, preferably 3 to 6 carbons, most preferably 5 or 6 carbons.

By lower alkoxy is meant a lower alkyl as defined above which may be branched or unbranched as also defmed above and which is bonded by an oxygen to another group (i.e. alkyl ethers). Examples are methoxy, ethoxy, n-propoxy, isopropoxy, n-butoxy, tert-butoxy and the like. Methoxy is preferred.

By substituted amino is meant an amino group which is mono- or di-substituted with another group, preferably a lower alkyl (e.g., methyl) or a lower acyl group (e.g., acetyl). Examples of such groups include piperazinyl, morpholino, and lower alkylamino. By lower alkylamino is meant an amino group which is substituted by one or more lower alkyl group. Examples are methylamino, ethylamino, dimethylamino, and the like. Preferred are piperazinyl, morpholino, and dimethylamino, especially piperazinyl and morpholino.

Rings of this invention may include one or more heteroatoms (e.g. heterocycles). The heteroatoms are nitrogen, oxygen, and sulfur. Unless otherwise specified, any such ring may include one, two, or three heteroatoms in any chemically acceptable combination, such as pyrroline, oxazole, dioxolane, triazine, dithiazole, pyridine, dithiane, thiomorpholine, and the like. Substituted rings of this invention are generally understood to be substituted only on those atoms which are chemically able to accept substituents. For example, substitution would not occur on the N of a pyridine or at a position of fusion between two aromatic rings.

Multiple substitution means substitution with multiple substituents (which may be the same or different) at the same number of positions, i.e. with no more than one substituent per position. For example, "disubstituted" means substitution with two substituents at two different positions, one substituent per position.

Taking $R_2$ and $R_3$ together with the ethenylene group connecting them to form phenyl, pyrroline, pyrrole, oxopyrroline, pyrazole, triazole, or imidazole means that the group formed by $R_2$ and $R_3$, and the ethenylene group connecting them, when fused with the phenyl of formula 1 to which $R_2$ and $R_3$ are attached, results in a bicyclic ring. Accordingly, when $R_2$ and $R_3$, and the ethenylene group, form phenyl, the bicyclic ring resulting from fusion with the phenyl of formula 1 is naphthyl. With regard to the remaining bicyclic rings, it is preferred that the point of attachment be at the 4-position of the heterocyclic ring system. Accordingly, $R_2$ and $R_3$ and the ethenylene group form triazole to provide benzotriazole on fusion with the phenyl, and form imidazole to provide benzimidazole, on fusion with phenyl. $R_2$ and $R_3$ and the ethenylene group form pyrroline, to provide indoline on infusion with the phenyl. $R_2$ and $R_3$ and the ethenylene group form pyrazole, to provide indazole on fusion with the phenyl. $R_2$ and $R_3$ form oxopyrroline to provide oxindole on fusion with the phenyl. $R_2$ and $R_3$ and the ethenylene group form pyrrole to provide indole on fusion with the phenyl.

A five- or six-membered ring with 0 to 3 heteroatoms is understood to include aromatic and nonaromatic rings. Examples of five-membered rings with 0 heteroatoms are cyclopentyl or cyclopentadienyl, while examples of six-membered rings with 0 heteroatoms are cyclohexyl or phenyl. Preferred rings are phenyl, triazole, thiazole, imidazole, dioxolane, and oxadiazole. The ring may be unsubstituted, or substituted with one or more groups. Preferred substituents are lower alkyl, cycloalkyl, amino, and substituted amino. Lower alkyl is especially preferred.

With regard to the ring of this invention where at least one of positions T, U, V, or W is nitrogen, and any of positions T, U, V or W which is carbon may be substituted with hydroxy, aminosulfonyl, halogen, lower alkoxy, cyano, amino, or nitro, the preferred ring substituent is lower alkoxy. Preferably either T, U, V, or W are nitrogen. Any two or more of these positions may also be nitrogen, for example T and V, or U and V and W, or U and V, etc. In any of these rings, the positions which are not nitrogen are carbon. Thus in a ring where W is nitrogen and positions T, U, and V are not specified, positions T, U, and V are carbon. The rings may be substituted as described only at carbon positions.

The five-membered aromatic ring of this invention has one to three heteroatoms selected from nitrogen, oxygen, and sulfur. This ring may be unsubstituted or mono- or di-substituted as described above at any chemically acceptable position(s). Preferred substituents are lower alkyl, trifluoroloweralkyl, amino, halogen, substituted amino. This ring may also be fused with a 5 or 6 membered aromatic ring containing 0 to 3 heteroatoms selected from nitrogen, oxygen, and sulfur. The ring may also be fused with phenyl preferably at positions not adjacent to the attachment point. Preferred rings are thiazole and triazole. By attachment point is meant the position on the ring where it is attached to the remainder of the molecule. Positions adjacent to the attachment point are the positions flanking the attachment point, one going clockwise and the other going counterclockwise from the attachment point. The preferred position for a ring heteroatom is two positions from the attachment point.

$R_4$ and $R_5$ are symmetric in that they occupy equivalent positions. Therefore for purposes of this application, a compound where $R_4$ is a first substituent while $R_5$ is a second substituent, is effectively equivalent to the compound where $R_5$ is identified as the first substituent and $R_4$ is identified as the second substituent (all other groups being identical). For example a compound where $R_4$ is chlorine and $R_5$ is methyl is equivalent to a compound where $R_5$ is chlorine and $R_4$ is methyl. Therefore description of one such compound also describes its equivalent. This does not mean in general that $R_4$ and $R_5$ must be the same. In any compound of this invention, $R_4$ and $R_5$ are independent of each other and accordingly may be the same or different. Thus in the context of this application, the phrase "$R_4$ is chlorine or bromine and $R_5$ is hydrogen" describes a compound which is equivalent to the compound described by the phrase "one of $R_4$ or $R_5$ is chlorine or bromine and the other is hydrogen." (all other groups being identical).

Pharmaceutically acceptable salts of all the compounds of this invention are included. Pharmaceutically acceptable salts and esters are well known in the art and can be made by conventional methods taking into account the chemical nature of the compound. Examples of pharmaceutically acceptable salts for acidic compounds are alkali metal or alkaline earth metals such as sodium, potassium, calcium, magnesium, basic amines or basic amino acids, ammonium or alkyl ammonium salts. Particularly desirable salts for compounds of this invention are sodium salts. The sodium salt of any compound of this invention is easily obtained from the acid by treatment with sodium hydroxide. For basic compounds, examples are salts of inorganic or organic acids such as hydrochloric, hydrobromic, sulphuric, nitric, phosphoric, citric, formic, fumaric, maleic, acetic, succinic, tartaric, methanesulfonic, and p-toluenesulfonic. Examples of pharmaceutically acceptable esters include unbranched lower alkyl esters such as methyl, ethyl, n-propyl and the like.

The compounds of this invention and their pharmaceutically acceptable salts inhibit the binding of LFA-1, expressed on activated lymphocytes, and monocytes, to the immunoglobulin ICAM-1 which is expressed on activated endothelial cells, epithelial cells, synovial cells, myocytes, glial cells and neurons as well as on lymphocytes and antigen presenting cells. The compounds in this invention can therefore be used in the treatment of disorders that involve the binding of LFA-1 with ICAM-1. This pharmaceutical activity demonstrates the utility of the compounds of this invention. Specifically, the compounds of the invention are preferably used in the treatment of psoriasis. In vitro assays for determining the desired pharmaceutical activity are provided below in the Examples. An indicator of pharmaceutical activity is the ability to inhibit a biological activity associated with LFA-1, such as T lymphocyte proliferation in a mixed lymphocyte reaction. Competitive binding assays, known in the art also indicate pharmaceutical activity. In vivo assays for pharmaceutical activity are also provided. Compounds of this invention inhibit induced paw and ear swelling in mice. Activities within the ranges exemplified in the Examples are indicative of desired pharmaceutical activity.

Accordingly part of this invention are pharmaceutical compositions which comprise compounds of this invention, for example compounds of formulae 1, 1a–1g, 1-1, 1-1a–1-1-1c, 2, and 2-1, and a pharmaceutically acceptable carrier. Compositions which include particularly preferred individual compounds of this invention, are also particularly preferred.

For example, especially preferred compositions contain compounds of formula 1 described above where $R_1$ is hydroxy or amino and $R_2$ and $R_3$ are hydrogen and compounds of formula 1-1 where $R_2$ and $R_3$ together with the ethenylene to which they are attached form phenyl, pyrazole or pyrrole. In these compounds, A is

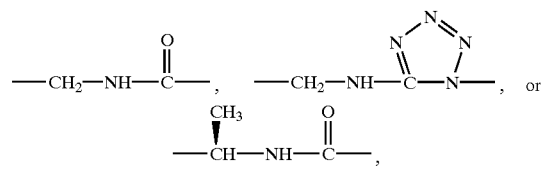

$R_4$ and $R_5$ are lower alkyl or halogen; and B is

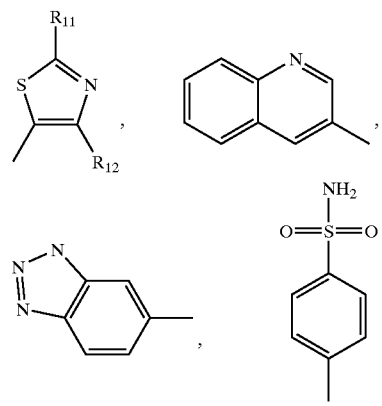

where $R_{11}$ is hydrogen, lower alkyl, substituted amino, or amino and $R_{12}$ is hydrogen, trifluoroloweralkyl, or lower alkyl in addition to other active or inactive ingredients as described below.

The pharmaceutical compositions can be made up in any conventional form, including a solid form for oral administration such as tablets, capsules, pills, powders, granules, and the like. The pharmaceutical compositions may be sterilized and/or may contain adjuvants such as preservatives, stabilizers, wetting agents, emulsifiers, salts for varying the osmotic pressure, and/or buffers. Another active compound may be added.

Typical preparations for administration by injection would be sterile aqueous solutions of the compounds of this invention including water/buffered solutions. Injection is by any conventional mode, e.g. intravenous, intramuscular, subcutaneous, or intraperitoneal. Pharmaceutically acceptable carriers or vehicles may include fluid such as water, nutrient and electrolyte replenishers, sugars such as sucrose, glucose, invert sugar. Preservatives and other additives may also be present such as antibiotics and antioxidants. Adjuvants which may be present include alcohol, polyols, glycerol, vegetable oil. Pharmaceutically acceptable excipients typically used in such preparations may be added to control such properties as pH, viscosity, sterility, stability, and dissolution rate.

Typical preparations for oral administration contain compounds of this invention in association with a compatible pharmaceutically acceptable carrier material. Any conventional pharmaceutically acceptable carrier material can be utilized. Any conventional oral dosage form such as tablets, capsules, pills, powders, granules, and the like may be used. The pharmaceutically acceptable carrier can be an organic or inorganic inert carrier material suitable for oral administration. Suitable carriers include water, gelatin, gum arabic, lactose, starch, magnesium stearate, talc, vegetable oils, polyalkylene-glycols, petroleum jelly, water, vegetable oils, fats, liquid and semisolid polyols and the like. Furthermore, the pharmaceutical composition may contain other pharmaceutically active agents. Additional additives such as flavoring agents, preservatives, stabilizers, antioxidants, emulsifying agents, masking agents, buffers and the like may be added in accordance with accepted practices of pharmaceutical compounding. Administration by suppository is also possible. Carriers for this purpose include oils, waxes, fats, polyols.

Also part of this invention is a method of treating psoriasis which comprises administering an amount of a any compound of this invention effective to reduce or eliminate the symptoms of psoriasis in a patient affected by the disease. Preferred for use in the method are those preferred compositions described in the paragraphs immmediately above.

The compounds of the invention can be administered orally, rectally, or parentally, e.g., intravenously, intramuscularly, by infusion, subcutaneously, intrathecally or transdermally; or sublingually, or as opthalmalogical preparations, or as an aerosol for the treatment of pulmonary inflammation. Capsules, tablets, suspensions or solutions for oral administration, suppositories, injection solutions, eye drops, salves or spray solutions are examples of administration forms.

The compounds of the invention are preferably administered orally. The dosages in which the compounds of the invention are administered in effective amounts depend on the nature of the specific active ingredient, the age and the requirements of the patient and the mode of administration. The dosage for any given person may be determined by a skilled person based on the information provided here. Dosages may be determined by any conventional means, however in the methods of this invention, it is preferred that the amount of compound is from about 50 mg to 2 grams administered twice daily. The compound may be administered by a skilled person to create a preselected circulatory concentration.

The compounds of this invention can be prepared by a skilled practitioner with the Synthesis provided below. The Examples which follow are illustrative and are not intended to limit the invention in any way.

Synthesis of Compounds of Structure 1

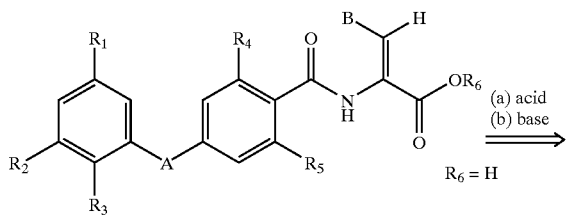

Structure 1

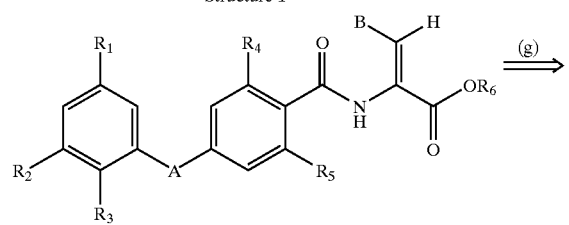

Structure 2

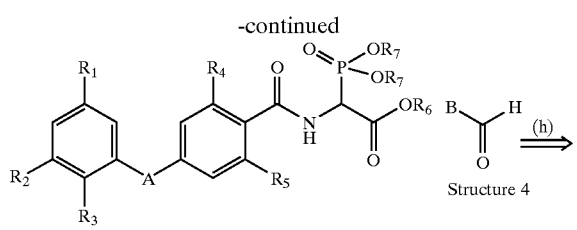

Structure 3

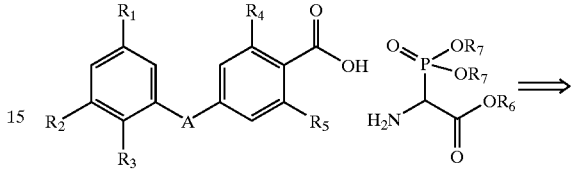

Structure 5    Structure 6

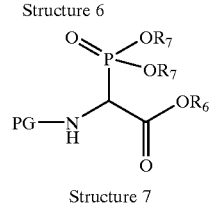

Structure 7

Synthesis of Compounds of Structure 4

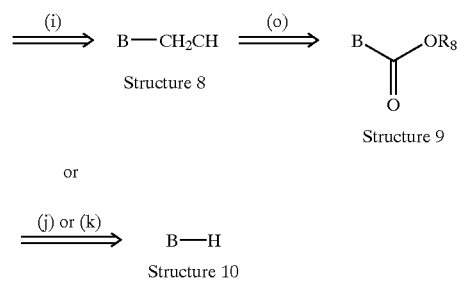

Structure 4    or

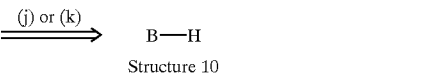

Synthesis of Compounds of Structure 5

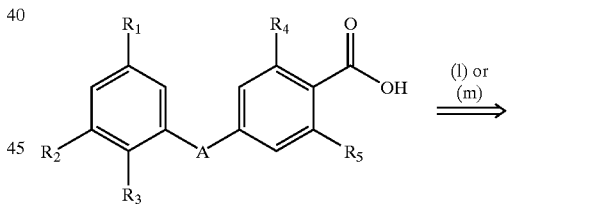

Structure 5

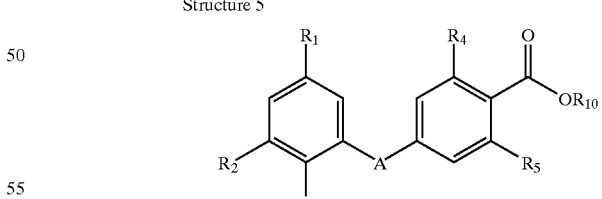

Structure 11

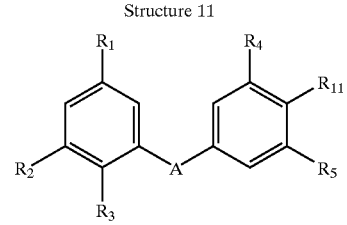

Structure 12

Synthesis of Compounds of Structure 6

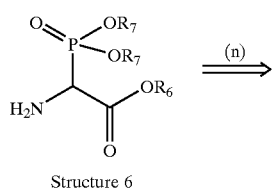

Structure 6

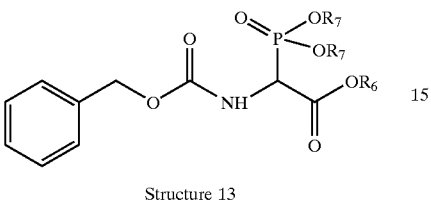

Structure 13

A compound of struture 13 ($R_6$=$R_7$=methyl) is commercially available.

Synthesis of Compounds of Structure 9

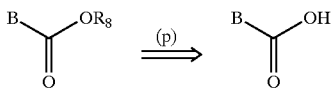

Structure 9      Structure 14

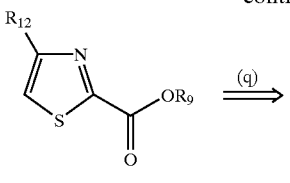

Structure 15

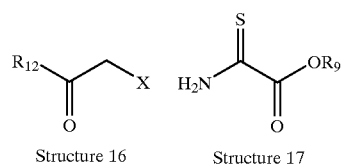

Structure 16      Structure 17

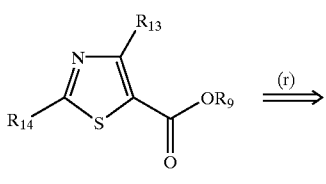

Structure 18

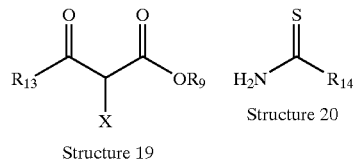

Structure 19      Structure 20

The starting materials of structure 14 are generally known compound.

Synthesis of Compounds of Structure 11

(Note: five methods are shown to make different compounds of structure 11)

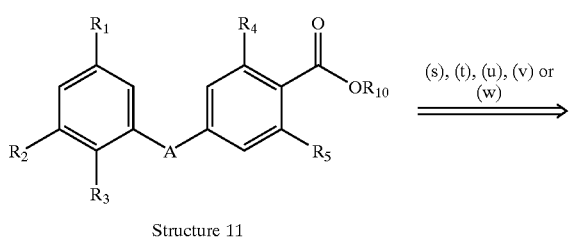

Structure 11

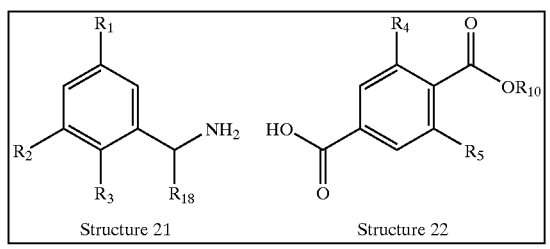

Structure 21      Structure 22

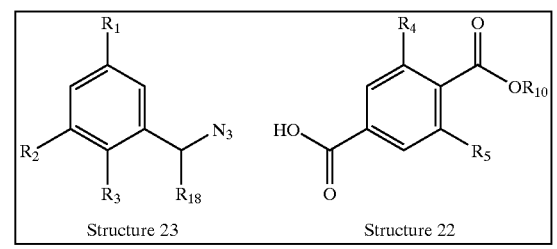

Structure 23      Structure 22

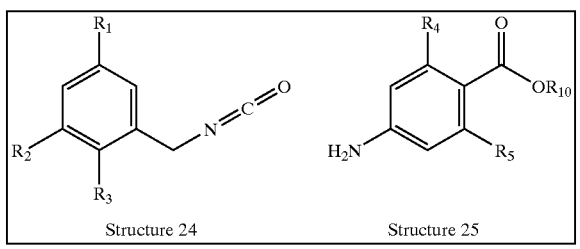

Structure 24      Structure 25

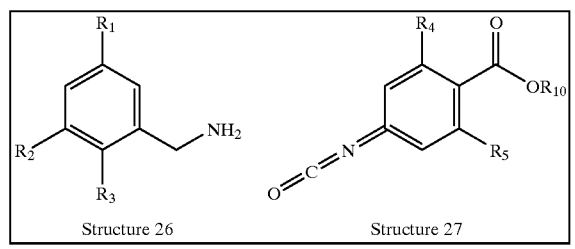

Structure 26      Structure 27

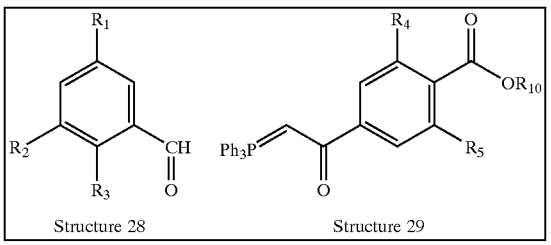
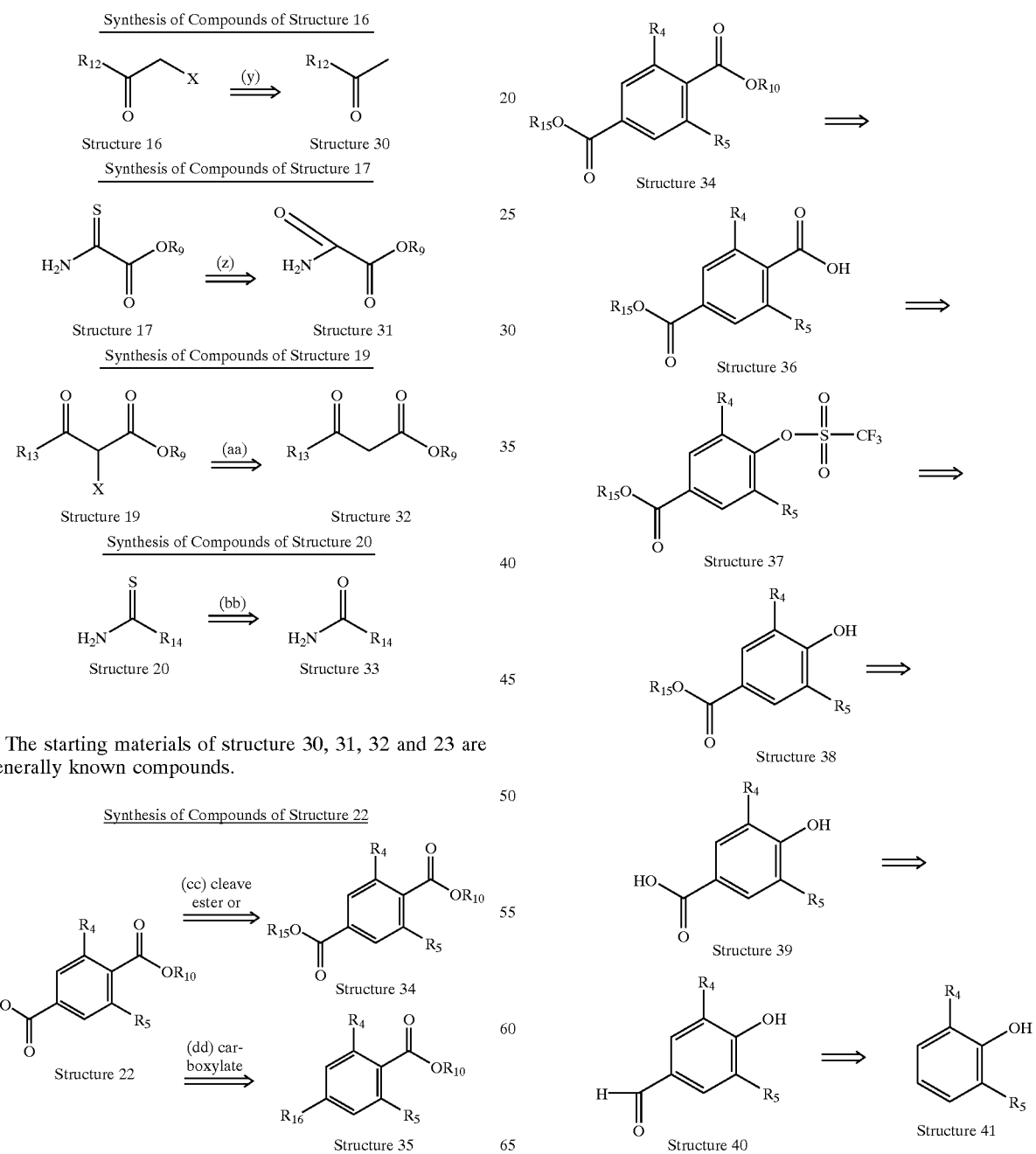
The starting materials of structure 21, 25, 26 are generally known compounds.
The starting materials of structure 30, 31, 32 and 23 are generally known compounds.
Some compounds of structure 34 are known. Others can be prepared according to the following Scheme:

Synthesis of Compounds of Structure 24

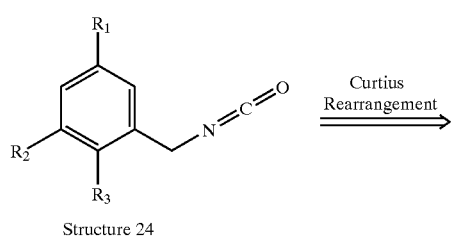

Structure 24

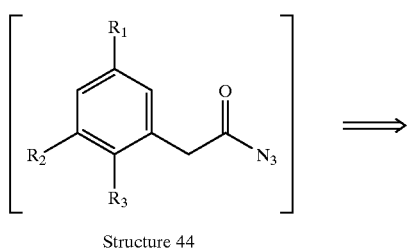

Structure 44

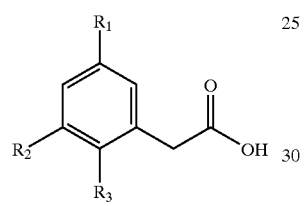

Structure 43

Synthesis of Compounds of Structure 27

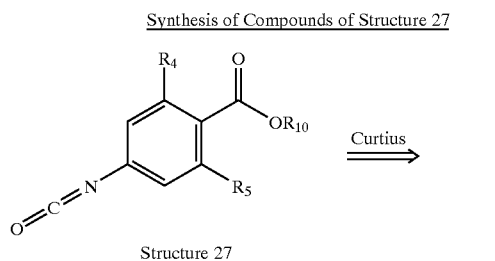

Structure 27

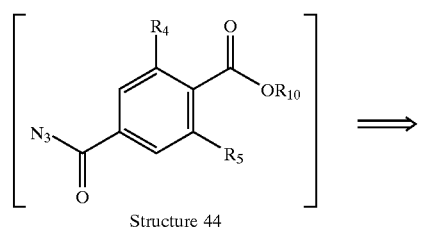

Structure 44

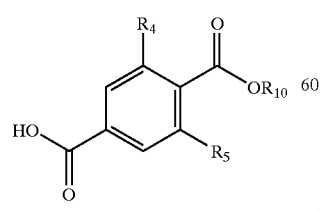

Structure 22

Synthesis of Compounds of Structure 29

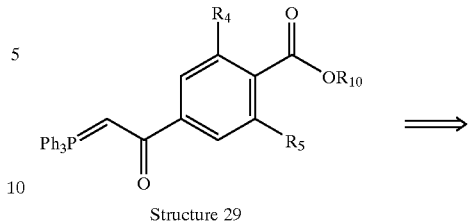

Structure 29

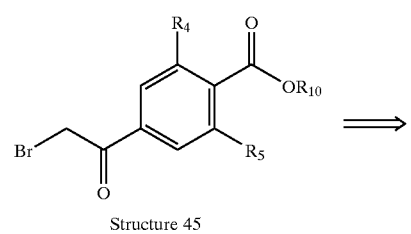

Structure 45

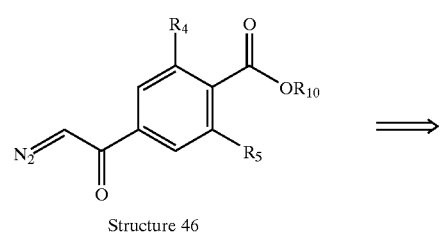

Structure 46

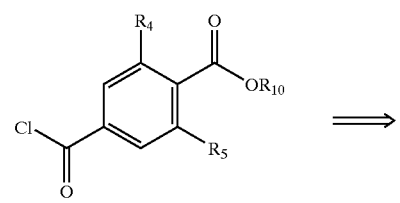

Structure 47

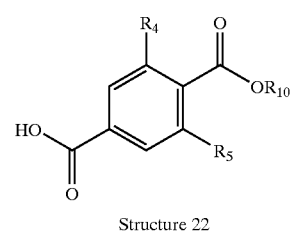

Structure 22

Structure 1

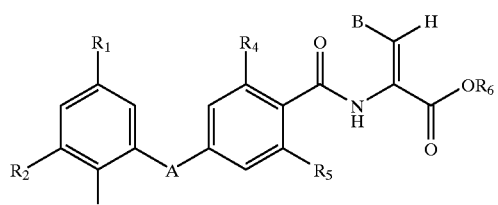

The compounds of the present invention can be prepared by any conventional means. For example, compounds of structure 1 can be manufactured by (a) for the preparation of a compound of structure 1 in which $R_6$ is hydrogen from a compound of structure 2 in which $R_6$ is an optionally substituted alkyl group that can be cleaved under acidic conditions, such as tert-butyl or aralkyl (for example Wang resin) and the like, by treatment with a strong acid, or (b) for the preparation of a compound of structure 1 in which $R_6$ is hydrogen from a compound of structure 2 in which $R_6$ is a lower alkyl or aralkyl group, unbranched on the carbon next to oxygen, for example, the methyl, ethyl, n-propyl, n-butyl, benzyl groups, and the like, by treatment with alkali metal hydroxide solution, or (c) if desired, separating a mixture of diastereomers into the optically pure diastereomers, and/or (d) if desired, converting a compound of structure 1 which bears a basic nitrogen into a pharmaceutically acceptable acid addition salt, and/or (e) if desired, converting a compound of structure 1 in which $R_6$ is hydrogen into a pharmaceutically acceptable alkali metal salt or (f) for the preparation of compounds of structure 1 where $R_6$ represents lower alkyl, dialkylaminolower alkyl, (4-morphilino)lower alkyl, (1-piperadino)lower alkyl, (1-pyrrolidino)lower alkyl and the like by esterification of a compound of structure 1 where $R_6$ is hydrogen.

The cleavage of an acid-labile ester moiety in accordance with procedure (a) can be carried out in accordance with methods that are known per se. For example, the ester may be treated with a strong inorganic acid, for example a hydrohalic acid such as hydrogen chloride or hydrogen bromide, or a strong organic acid, for example a halogenated alkane carboxylic acid such as trifluoroacetic acid and the like. The reaction is conveniently carried out in the presence of an inert organic solvent (such as dichloromethane) and at a temperature between about zero degrees and about room temperature, preferably at about room temperature.

The cleavage of an alkali-labile ester moiety in accordance with procedure (b) can be carried out according to known procedures. For example, the ester may be treated with an alkali metal hydroxide, for example lithium hydroxide, sodium hydroxide or potassium hydroxide in a suitable inert solvent system, for example a mixture of methanol and water or a mixture of methanol, tetrahydrofuran and water. The reaction is carried out at a temperature between about zero degrees and about 60 degrees, preferably between room temperature and about 50 degrees.

The optional separation in accordance with procedure (c) can be carried out according to known methods such as fractional crystallization, column chromatography, thin-layer chromatography, high pressure liquid chromatography etc.

The optional conversion of a compound of structure 1 into a pharmaceutically acceptable acid addition salt in accordance with procedure (d) can be effected by conventional means. For example, the compound can be treated with an inorganic acid, for example hydrochloric acid, hydrobromic acid, sulfuric acid, nitric acid, phosphoric acid etc., or with an appropriate organic acid such as acetic acid, trifluoroacetic acid, citric acid, tartaric acid, methanesulfonic acid, p-toluenesulfonic acid, or the like. The optional conversion of a compound of structure 1 into a pharmaceutically acceptable alkali metal salt in accordance with procedure (e) can be effected by conventional means. For example, the compound can be treated with an inorganic base such as lithium hydroxide, sodium hydroxide, potassium hydroxide, or the like. The esterification of compounds of structure 1 where $R_6$ represents hydrogen or the alkali metal salt prepared by procedure (e) can be effected by a variety of different methods, such as those conventionally used to prepare esters of carboxylic acids. In accordance with method (f) the sodium salt of structure 1 is reacted with an alcohol in the presence of a condensing agent. For example, the compounds of structure 1, in which $R_6$ represents 2-(4-morphilino)ethyl, can be prepared by treatment of the sodium salt of compounds of structure 1 with 2-(4-morphilino)ethanol in the presence of an 1,3-disubstitutedcarbodiimide, for example 1-(3-dimethylaminopropyl)-3-ethylcarbodiimide hydrochloride. The reaction is conveniently carried out in an inert solvent, for example tetrahydrofuran optionally in the presence of a catalyst, N,N-dimethylaminopyridine, at a temperature between about room temperature and about 40 degrees, preferably at about room temperature.

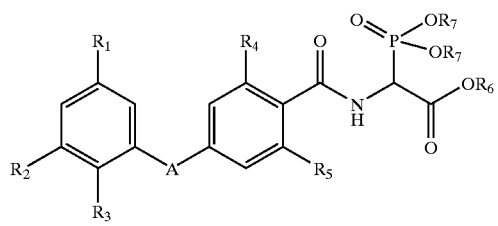

Structure 3

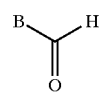

Structure 4

The compounds of structure 2 in which $R_6$ represents an optionally substituted alkyl moiety can be prepared by means which are well known to one of ordinary skill in the field. For example, they can be prepared by the reaction of compounds of structure 3, in which $R_7$ represents an optionally substituted alkyl moiety, with compounds of structure 4 in accordance with procedure (g) by using the Horner-Emmons modification of the Wittig reaction well known to one of ordinary skill in the art. For example, the transformation can be carried out by reaction of the phosphonate ester of structure 3 with a deprotonating agent, preferably 1,1,3,3-tetramethylguanidine in an inert solvent, for example, tetrahydrofuran, at a temperature of from −45 degrees to about room temperature, preferably at −45 degrees to −20 degrees. Within a short period, usually about 5 minutes, the aldehyde of structure 4 is added and the reaction is then maintained at a temperature of from −45 degrees to about room temperature.

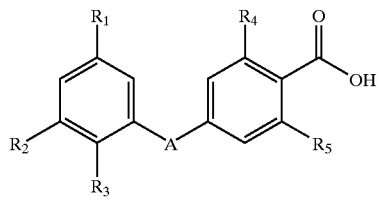

Structure 5

Structure 6

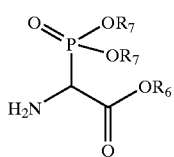

The coupling of compounds 5 with compounds of structure 6 can be carried out in accordance with procedure (h) using methods well known to one of ordinary skill in the art. For example, the transformation can be carried out by reaction of carboxylic acids of structure 5 with an amine of structure 6 in the presence, if necessary, of a coupling agent, many examples of which are well known per se in peptide chemistry. The reaction is conveniently carried out by treating the carboxylic acid of structure 5 with the amine of structure 6 in the presence a coupling agent such as O-(benzotriazol-1-yl)-1,1,3,3-tetramethyluronium hexafluorophosphate, and in the optional additional presence of a substance that increases the rate of the reaction, such as 1-hydroxybenzotriazole or 1-hydroxy-7-azabenzotriazole, in an inert solvent, such as a chlorinated hydrocarbon (e.g., dichloromethane) or N,N-dimethylformamide or N-methylpyrrolidinone, at a temperature between about zero degrees and about room temperature, preferably at about room temperature. Alternatively, activation of the carboxylic acid of structure 5 can be achieved by pretreatment of the acid with triphenylphosphine and N-chlorosuccinimide in an inert solvent, such as a chlorinated hydrocarbon (e.g., dichloromethane) at a temperature between about zero degrees and about room temperature, preferably at about zero degrees, and the formed intermediate is then allowed to couple with the amine of structure 6.

Compounds of structure 4 are generally known compounds, or if they are not known compounds, they can be prepared by methods that are well known in the field of organic chemistry. For example, they can be prepared by
  (i) oxidation of compounds of structure 8.
  (j) formylation of a compound of structure 10, where B represents represents a suitably reactive aromatic or heteroaromatic species, with a masked formylating reagent under Friedel-Crafts conditions.
  (k) reaction of a formamide with a metalated species, B-M, derived from a compound of structure 10, where B is an aryl or heteroaromatic group and M is lithium or sodium.

The oxidation of compounds of structure 8 in accordance with procedure (i) can be effected by any conventional means with the proviso that any other oxidizable functionality present in the group B is shielded by using an appropriate protecting group. The reaction may be carried out by treating a compound of structure 8 with a suitable oxidizing agent, of which among others are manganese dioxide, o-iodoxybenzene and sulfur trioxide-pyridine complex. For example, a compound of structure 8 is treated with manganese dioxide in an inert solvent, such as a chlorinated hydrocarbon (e.g., dichloromethane) or acetonitrile, at a temperature of between about zero degrees and about room temperature, preferably at about room temperature. For the alkylation of compounds of structure 10 with a masked formylating agent, in accordance with procedure (j) a variety of procedures can be used. For example a compound of structure 10, where B represents a suitably reactive aromatic or heteroaromatic species, is treated with dichloromethyl n-butyl ether in the presence of a Lewis acid, preferably titanium tetrachloride. The reaction is conveniently carried out in an inert solvent such as carbon disulfide at a temperature between about zero degrees and about room temperature, preferably at about room temperature.

The conversion of compounds of structure 10 into compounds of structure 8 in accordance with procedure (k) may be carried out by methods known per se. For example, the reaction may be conveniently carried out by treating a compound of structure 10, where B is an aryl or heteroaromatic group, with an alkyl lithium, for example n-butyl lithium, at a temperature of from zero degrees to about −78 degrees, preferably at about −78 degrees in an inert solvent such as tetrahydrofuran to form the aryl lithium or heteroaryl lithium. The metalated species is then reacted in situ with a N,N-disubstitutedformamide, e.g., N,N-dimethylformamide and the reaction is allowed to proceed at a temperature at a temperature of from room temperature to about −78 degrees, preferably at about room temperature.

The compounds of structure 5 are prepared by methods that are well known in the field of organic chemistry. For example, they can be prepared by:
  (l) by the removal of carboxylic acid protective groups from compounds of structure 11, in which $R_{10}$ represents for example an unbranched lower alkyl group (e.g., methyl or ethyl), an aralkyl group, or a tert-butyl group or the like.
  (m) by carboxylation of compounds of structure 12, where $R_{11}$ represents a group that can be carboxylated under noble metal catalysis, and where the rest of the molecule is stable to such treatment.

For the deprotection of ester protective groups in accordance with procedure (l), any conventional means can be used. For example, in the case where $R_{10}$ represents an unbranched lower alkyl group (e.g., methyl), the reaction may be carried out by treating the compound of structure 11 with an alkali methyl hydroxide, such as potassium hydroxide, sodium hydroxide or lithium hydroxide, preferably lithium hydroxide, in an appropriate solvent, such as a mixture of tetrahydrofuran, methanol and water. The reaction is conveniently carried out at a temperature between about zero degrees and about room temperature, preferably at about room temperature.

For the carboxylation of compounds of structure 12 where $R_{11}$ represents a group that can be carboxylated under noble metal catalysis, such as iodide, bromide, or trifluoromethanesulfonate, in accordance with procedure (m), a variety of procedures can be used. For example, the reaction can be carried out by reacting the compound of structure 12 with water under carbon monoxide gas at a pressure between about 14 pounds per square inch and about 50 pounds per square inch, preferably at about 40 pounds per square inch, in the presence of a noble metal catalyst such as tetrakis(triphenylphosphine)palladium(0), allylpalladium (II) chloride dimer, or dichlorobis(triphenylphosphine) palladium(II), and a base, for example a tertiary amine, such as triethylamine, in an inert solvent, such as N,N-dimethylformamide, dimethylsulfoxide, acetonitrile, or the like. The reaction can be carried out at a temperature between about 40 degrees and about 100 degrees, preferably at about 80 degrees.

Compounds of structure 12, where $R_{11}$ represents hydroxy, acetoxy, bromo, iodo or trifluoromethanesulfonyloxy can be made by methods similar to those outlined below in the procedures (s), (t), (u), (v) and (w) for the preparation of compounds of structure 11.

The compounds of structure 6, in which $R_7$ represents an lower alkyl group, can prepared by the removal of amine protective groups from compounds of structure 7, in which PG represents for example an aralkoxycarbonyl group (e.g., benzyloxycarbonyl) or the like in accordance with procedure (n). The reaction may be carried out by hydrogenation in the presence of a noble metal catalyst such as palladium-on-carbon in the presence of an inert solvent (for example, an alcohol such as methanol) at about room temperature and at a pressure between about 14 pounds per square inch and about 50 pounds per square inch, preferably about 50 pounds per square inch of hydrogen.

Compounds of structure 8 are generally known compounds, or if they are not known compounds, they can be prepared by methods that are well known to one of ordinary skill in the field. The esters of structure 9, in which $R_8$ represents an optionally branched alkyl group, may be transformed into compounds of structure 8 in accordance with procedure (o) by using a variety of reducing agents, among which are but not limited to, lithium aluminum hydride, diisobutylaluminum hydride and sodium borohydride. For example, the reaction is conducted by reacting a compound of structure 9 with diisobutylaluminum hydride in an inert solvent such as an ether (e.g., tetrahydrofuran, diethyl ether) or an aromatic hydrocarbon (e.g., toluene) at a initial temperature of from −78 degrees to −50 degrees, preferably at about −78 degrees. The reaction is allowed to proceed at a temperature of from about −78 degrees to about room temperature, preferably between zero degrees and about room temperature.

Compounds of structure 9, in which $R_8$ represents for example an unbranched lower alkyl group (e.g., methyl or ethyl) are generally known compounds, or if they are not known compounds, they can be prepared by methods that are well known in the field. For example they can be prepared by (p) esterification of a compound of structure 14 or
(q) for the preparation of a compound where B represents a thiazol-2-yl group by reacting a compound of structure 16 with a compound of structure 17 or
(r) for the preparation of a compound where B represents a thiazol-5-yl moiety by reacting a compound of structure 19 with a compound of structure 20.

The esterification of compounds of structure 14 can be accomplished by a variety of a different reactions, such as those conventionally used to prepare esters of carboxylic acids. In accordance with method (p) the acid of structure 14 is reacted with an lower unbranched alcohol in the presence of a condensing agent. For example, the compounds of structure 9, in which $R_8$ represents methyl, can be prepared by treatment of compounds of structure 14 with methanol containing an 1,3-disubstituted carbodiimide, for example 1-(3-dimethylaminopropyl)-3-ethylcarbodiimide hydrochloride. The reaction is conveniently carried out in an inert solvent, for example dichloromethane optionally in the presence of a catalyst, N,N-dimethylaminopyridine, at a temperature between about room temperature and about 40 degrees, preferably at about room temperature.

The condensation of thiooxamate of structure 17, in which $R_9$ represents for example an unbranched lower alkyl group, with an halomethylketone of structure 16, where X represents bromo or chloro and $R_{12}$ is optionally lower alkyl or trifluorolower alkyl, may be performed by methods that are well known in the field of organic chemistry to give the compounds of structure 15. For example, in accordance with procedure (q) the thiooxamate of stucture 17 was treated with the halomethylketone of structure 16 in an inert solvent such as ethanol at a temperature of from room temperature to 78 degrees, preferably at about 78 degrees.

The condensation of the thioamide of structure 20, in which $R_{14}$ represents for example amino, optionally branched lower alkyl or trifluoro lower alkyl with a 2-halo-3-oxocarboxylic acid ester of structure 19, where X represents bromo or chloro, preferably chloro and $R_{14}$ is for example optionally branched lower alkyl or trifluoro lower alkyl may be performed by methods that are well known in the field of organic chemistry to give the compounds of structure 18. For example, accordance with procedure (r) the thioamide of structure 20 was treated with a 2-halo-3-oxocarboxylic acid ester of structure 19 in an inert solvent such as ethanol at a temperature of from room temperature to 78 degrees, preferably at about 78 degrees.

The compounds of structure 11, in which $R_{10}$ represents for example an unbranched lower alkyl group (e.g., methyl or ethyl), an aralkyl group, or a tert-butyl group or the like, may be prepared by any conventional means. For example, they may be prepared by

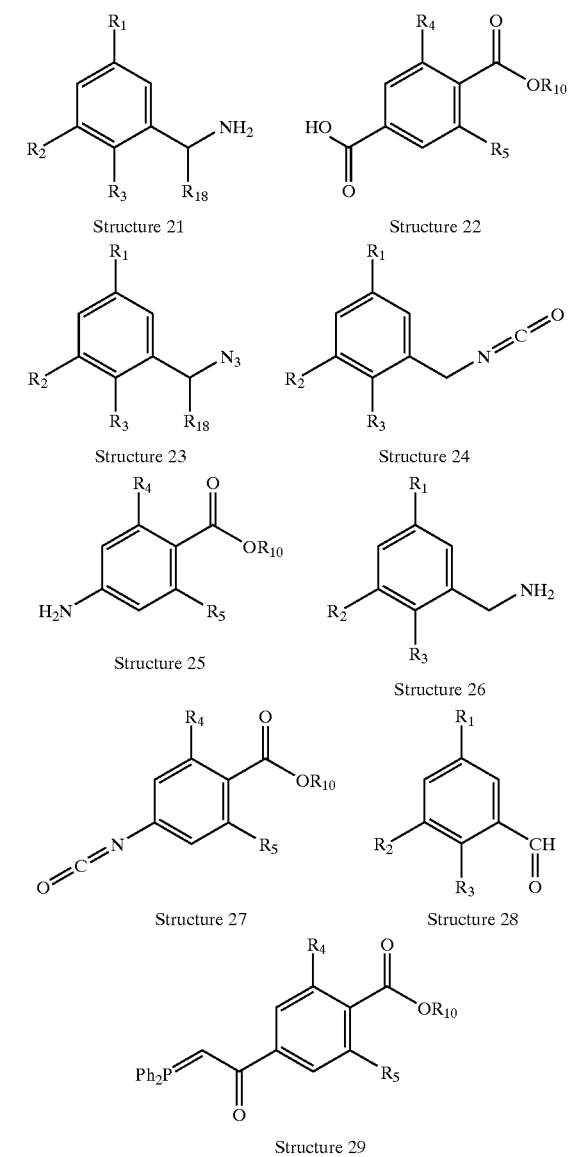

(s) for the preparation of a compound of structure 11 in which A represents

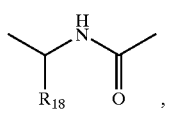

by reacting a compound of structure 21 or a salt thereof with a compound of structure 22 or a reactive derivative thereof, or (t) for the preparation of a compound of structure 11 in which A represents

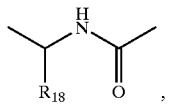

by reacting a compound of structure 23 with a reactive derivative of a compound of structure 22 under reducing conditions, or (u) for the preparation of a compound of structure 11 in which A represents

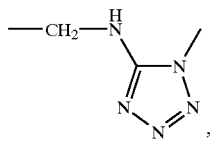

by reacting an isocyanate of structure 24 with an aniline of structure 25, and converting the resulting urea into an aminotetrazole, or (v) for the preparation of a compound of structure 11 in which A represents

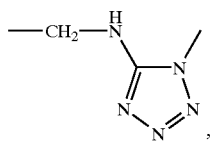

by reacting an isocyanate of structure 27 with an amine of structure 26, and converting the resulting urea into an aminotetrazole, or (w) for the preparation of a compound of structure 11 in which A represents

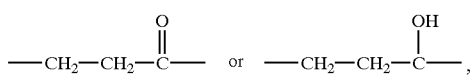

by treating an aldehyde of structure 28 with a phosphorane of structure 29, and catalytically reducing the resulting chalcone, or (x) for the preparation of a compound of structure 11 in which A represents

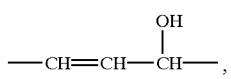

by treating an aldehyde of structure 28 with a phosphorane of structure 29, and selectively reducing the carbonyl function in the resulting chalcone, The acylation of compounds of structure 21, in which $R_{18}$ represents hydrogen or lower alkyl, to give compounds of structure 11, in which A represents

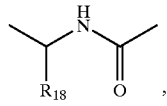

in accordance with procedure (s) can be effected in a manner analogous to that described earlier in connection with the coupling of a compound of structure 5 with a compound of structure 6.

The coupling of compounds of structure 23, in which $R_{18}$ represents hydrogen or lower alkyl, with reactive derivatives of compounds of structure 22 in accordance with procedure (t) can be carried out under conditions that are known per se. Examples of reactive derivatives of compounds of structure 22 that can be used in the reaction are acid anhydrides, mixed anhydrides, and activated esters (e.g., the N-hydroxysuccinimidyl ester), preferably activated esters. The reaction can be conveniently carried out using palladium-on-carbon as the reduction catalyst in the presence of hydrogen at a pressure between about 14 pounds per square inch and about 50 pounds per square inch, preferably about 14 pounds per square inch. The reaction may be conducted in the presence of an inert solvent such as ethyl acetate, or an aromatic hydrocarbon (e.g., benzene), or an alcohol (e.g., methanol), or in a mixture of such solvents. The reaction may be conveniently carried out at a temperature about room temperature.

The coupling of isocyanates of structure 24 with anilines of structure 25 to give ureas, in accordance with procedure (u), may be carried out by methods known per se. For example, the reaction may be carried out by reacting the isocyanate of structure 24 with the aniline of structure 25 or salt thereof in the presence of a suitable base, such as a tertiary amine (e.g., diisopropylethylamine), in an inert solvent such as an aromatic hydrocarbon (e.g., benzene). The reaction can be carried out conveniently at a temperature between about 80 degrees and about 110 degrees, preferably at about 80 degrees. Alternatively, the same urea can also be prepared by the coupling of isocyanates of structure 27 with amines of structure 26 in accordance with procedure (v). For example, the reaction may be carried out by reacting the isocyanate of structure 27 with the amine or amine salt of structure 26 in the presence of a suitable base, such as a tertiary amine (e.g., diisopropylethylamine), in an inert solvent such as an aromatic hydrocarbon (e.g., benzene). The reaction can be carried out conveniently at a temperature between about 80 degrees and about 110 degrees, preferably at about 80 degrees. The resulting urea can be converted to the aminotetrazole using any conventional means for effecting such a transformation, such as by treatment with trimethylsilylazide under dehydrating conditions. For example, the reaction can be conveniently carried out by treating the urea with trimethylsilylazide, diethylazodicarboxylate, and triphenylphosphine in an inert solvent, such as tetrahydrofuran, at a temperature between about zero degrees and about room temperature, preferably at about room temperature.

The coupling of aldehydes of structure 28 with phosphoranes of structure 29 to give chalcones, in accordance with procedure (w), may be carried out by methods that are well known in the field of organic chemistry. For example, the phosphorane may be treated with the aldehyde in an inert solvent such as an aromatic hydrocarbon (e.g., benzene) at a temperature between about 80 degrees and about 110 degrees, preferably at about 80 degrees. The resulting chalcone can be reduced by catalytic hydrogenation to give a compound of structure 11, in which A represents

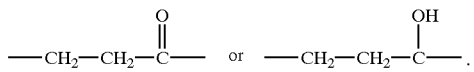

The reaction may be carried out by hydrogenation in the presence of a noble metal catalyst such as palladium-on-carbon in the presence of an inert solvent (for example, ethyl acetate or an alcohol such as ethanol) at about room temperature and under 1 atmosphere of hydrogen.

The coupling of aldehydes of structure 28 with phosphoranes of structure 29 to give chalcones, in accordance with procedure (x), may be carried out by methods that are well known in the field of organic chemistry. For example, the phosphorane may be treated is with the aldehyde in an inert solvent such as an aromatic hydrocarbon (e.g., benzene) at a temperature between about 80 degrees and about 110 degrees, preferably at about 80 degrees. The resulting chalcone can be reduced with a metal borohydride, for example sodium borohydride to give a compound of structure 11, in which A represents

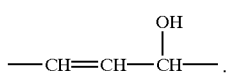

The reaction may be carried out in the presence of an inert solvent (for example, an alcohol such as methanol) at about room temperature.

The starting materials of structure 21, 25, and 26 are generally known compounds.

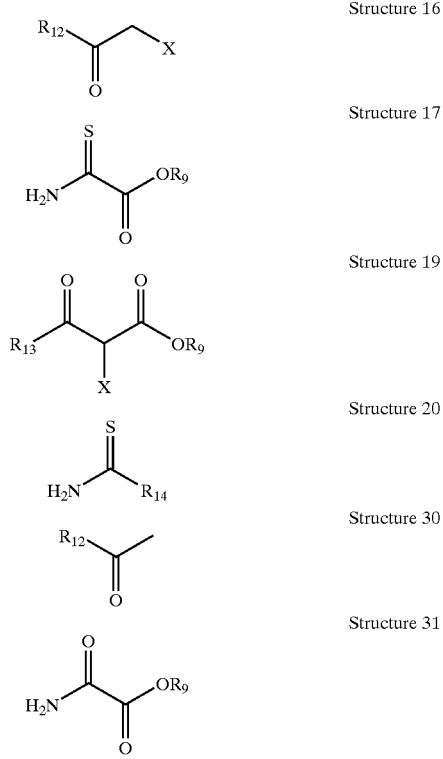

Structure 16

Structure 17

Structure 19

Structure 20

Structure 30

Structure 31

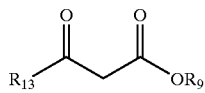

Structure 32

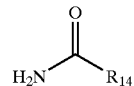

Structure 33

Compounds of structure 16 are generally known compounds, or if they are not known compounds, they can be prepared by means which are well known to one of ordinary skill in the field. For example, in accordance with procedure (y), a methyl ketone of structure 30 in a lower unbranched alcohol (e.g., methanol) is treated with bromine. The reaction is conveniently carried out at a temperature between about −5 degrees and about room temperature, preferably at zero degrees.

The thiooxamates of structure 17 are generally known compounds, or if they are not known compounds, they can be prepared by means that are well known in the field. For example, in accordance with procedure (z), an oxamic acid ester of structure 31 in an inert solvent such as an ether (e.g., tetrahydofuran) is treated with Lawesson's Reagent. The reaction is conveniently carried out at a temperature between about room temperature and about 66 degrees, preferably at about 66 degrees.

Compounds of structure 19 are generally known compounds, or if they are not known compounds, they can be prepared by methods that are well known in the field. For example, in accordance with procedure (aa), a 3-oxocarboxylic acid ester of structure 32 in an inert solvent such as a chlorinated hydrocarbon (e.g., dichloromethane) is treated with sulfuryl chloride. The reaction is conveniently carried out at a temperature between about zero degrees and about room temperature, preferably at zero degrees.

The thioamides of structure 20 are generally known compounds, or if they are not known compounds, they can be prepared by methods that are well known in the field. For example, in accordance with procedure (bb), an amide of structure 33 in an inert solvent mixture such as a mixture of an ether (e.g., diethyl ether) and an aromatic hydrocarbon (e.g., benzene) is treated with phosphorous pentasulfide. The reaction is conveniently carried out at a temperature between about zero degrees and about 35 degrees, preferably at room temperature.

The starting materials of structure 30, 31, 32, and 33 are generally known compounds. Insofar as they are not known compounds or analogues of known compounds, they can be prepared in a similar manner to the known compounds or as described in the Examples hereinafter or in analogy thereto

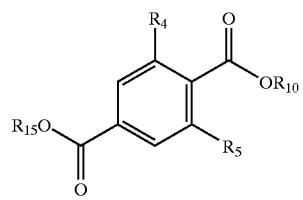

Structure 34

-continued

Structure 35

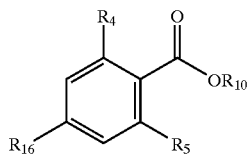

The compounds of structure 22 can be made by any conventional means. For example, they may be prepared by:
(cc) hydrolyzing a compound of structure 34 in which $R_{10}$ and $R_{15}$ separately represent an unbranched lower alkyl group (e.g., methyl or ethyl), an aralkyl group, or a tert-butyl group or the like, or
(dd) carboxylating a compound of structure 35, in which $R_{16}$ is a group that can be substituted under noble metal catalysis, such as iodide, bromide, or trifluoromethanesulfonate.

The hydrolysis of compounds of structure 34 in accordance with procedure (cc) can be effected by any conventional means. For example, in the case of a compound of structure 34 in which $R_{15}$ is a group that can be cleaved by basic hydrolysis, the reaction can be conveniently effected by treating the compound with one equivalent of an alkali metal hydroxide, such as potassium hydroxide, sodium hydroxide, or lithium hydroxide, preferably lithium hydroxide, in a suitable solvent, such as a mixture of tetrahydrofuran, methanol, and water. The reaction can be carried out at a temperature between about zero degrees and about room temperature, preferably at about room temperature.

The carboxylation of compounds of structure 35, in which $R_{16}$ is a group that can be substituted under noble metal catalysis, such as iodide, bromide, or trifluoromethanesulfonate, in accordance with procedure (dd) can be carried out using conventional methods. For example, the reaction can be carried out by reacting the compound of structure 35 with water under carbon monoxide gas at a pressure between about 14 pounds per square inch and about 50 pounds per square inch, preferably at about 40 pounds per square inch, in the presence of a noble metal catalyst such as tetrakis(triphenylphosphine)palladium(0), allylpalladium(II) chloride dimer, or dichlorobis(triphenylphosphine)palladium(II), and a base, for example a tertiary amine, such as triethylamine, in an inert solvent, such as N,N-dimethylformamide, dimethylsulfoxide, acetonitrile, or the like. The reaction can be carried out at a temperature between about 40 degrees and about 100 degrees, preferably at about 80 degrees.

Compounds of structure 23 may be prepared by any conventional means. For example, in the case where $R_{18}$ is hydrogen, they may be prepared from compounds of structure 49 by substitution of the bromine. The reaction may be carried out by treating a compound of structure 49 with an alkali metal azide salt, preferably sodium azide, in the optional additional presence of an agent that will increase the rate of the reaction, such as potassium iodide. The reaction may be carried out in the presence of an inert solvent such as acetone or N,N-dimethylformamide at a temperature of between about room temperature and about 60 degrees, preferably at about 60 degrees. In the case where $R_{18}$ is a lower alkyl group, or where compounds of structure 49 are not available due to the reactivity of the aromatic or heteroaromatic moiety, compounds of structure 23 may be prepared by reaction of an alcohol of structure 50, in which $R_{18}$ represents hydrogen or lower alkyl, with a reagent such as diphenylphosphoryl azide. The reaction is conveniently carried out in the presence of a base such as 1,8-diazabicyclo[5.4.0]undec-7-ene and an inert solvent such as tetrahydrofuran at a temperature around room temperature.

Compounds of structure 21 where $R_{18}$ is hydrogen may be made by methods that are known per se in the field of organic chemistry. For example, they may be made by the reduction of carbonitriles of structure 48. For example, in the case where the compound if of structure 21 is prepared by catalytic hydrogenation, a noble metal catalyst such as palladium-on-carbon may be used. The reaction may be carried out in the presence of a 1–2 molar ratio of a hydrohalic acid, preferably hydrochloric acid an inert solvent (for example, an alcohol such as ethanol) at about room temperature and under 1–4 atmospheres of hydrogen.

Structure 48

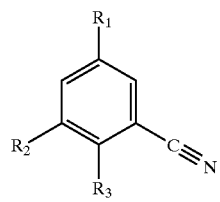

Structure 43

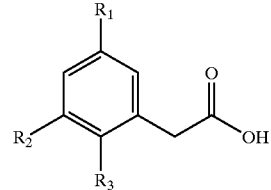

Compounds of structure 24 or 27 can be prepared by reactions that are known per se. For example, they can be prepared by an in situ Curtius rearrangement of compounds of the structure 42 and structure 44 respectively. The reaction can be conveniently carried out by initially treating the compounds of structure 43 or structure 22 with a reagent such as diphenylphosphoryl azide and a base such as a tertiary amine (e.g., diisopropylethylamine) in an inert solvent such as an aromatic hydrocarbon (e.g., benzene) at a temperature of from zero degrees to about room temperature. The rearrangement of the thus formed thermally labile intermediate acyl azides of structures 42 and 44 into the compounds of structures 24 and 27 can be carried out conveniently at a temperature of around 70 degrees.

Compounds of structure 28 are generally known compounds, or if they are not known compounds, they can be prepared by methods that are well known to one of ordinary skill in the field. For example they can be prepared by oxidation of compounds of structure 50 in which $R_{18}$ represents hydrogen by procedures analogous to those described above for the preparation of compounds of structure 4 by the oxidation of compounds of structure 8.

Compounds of structure 29 can be prepared by a variety of methods well known in the field of organic chemistry. For example, they can be prepared by deprotonation of the corresponding phosphonium salts by treatment with a base, for example sodium carbonate, in an inert solvent, such as a mixture of an aromatic hydrocarbon (e.g., benzene) and water. The reaction can conveniently be carried out at about room temperature. The phosphonium salts can be prepared by any conventional means. For example, they can be prepared by a substitution reaction of compounds of structure 45. The reaction may conveniently be carried out by treating a compound of structure 45 with triphenylphosphine in the optional presence of a catalytic amount of pyridine in an inert solvent such as acetonitrile. The reaction can be run at a temperature between about room temperature and about 80 degrees, preferably at about room temperature.

Compounds of structure 34 are generally known compounds, or if they are not known compounds, they can be prepared by any conventional means. For example, compounds of structure 34 can be prepared by esterification of compounds of structure 36. This reaction can be effected by methods that are well known to one of ordinary skill in the field. For example, a compound of structure 34, in which $R_{10}$ represents methyl, can be prepared from a compound of structure 36 by reaction with an ethereal solution of diazomethane. The reaction is conveniently carried out in an inert solvent such as an ether (e.g., diethyl ether or tetrahydrofuran) or an alcohol (e.g., methanol), at a temperature of between about zero degrees and about room temperature, preferably at about zero degrees.

Compounds of structure 34 in which $R_4$ and $R_5$ both represent chlorine can be prepared from compounds of structure 55 by reactions that are well known. For example, in the case where $R_4$ and $R_5$ both represent chlorine, compounds of structure 34 can be prepared by reaction of compounds of structure 55 with a diazotizing reagent, preferably an alkyl nitrite, most preferably isoamyl nitrite, in a suitable solvent which can also act as a hydrogen donor, for example N,N-dimethylformamide or preferably tetrahydrofuran, at a suitable temperature, for example at about 65 degrees.

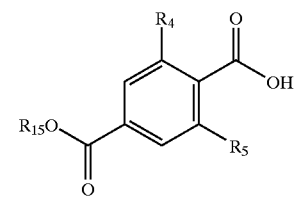

Structure 36

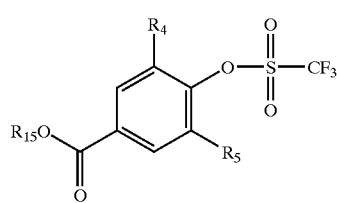

Structure 37

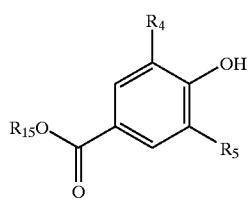

Structure 38

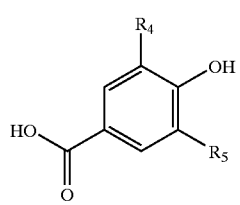

Structure 39

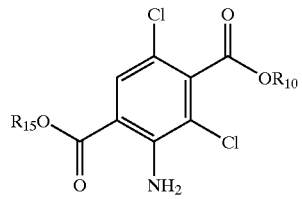

Structure 55

Compounds of structure 36 can be prepared by reactions that are well known. For example, they can be made from the trifluoromethanesulfonate derivatives, structure 37, by reaction with carbon monoxide and water under noble metal catalysis. This reaction can be carried out in a manner analogous to that described earlier in connection with the carboxylation of compounds of structure 35.

Compounds of structure 37 can be prepared by reactions that are known per se. For example, they can be prepared by reacting compounds of structure 38 with a reactive derivative of trifluoromethanesulfonic acid, such as trifluoromethanesulfonic anhydride or N-phenyltrifluoromethanesulfonimide, preferably trifluoromethanesulfonic anhydride, in the presence of a base, such as a tertiary amine (e.g., diisopropylethylamine), in an inert solvent, such as halogenated hydrocarbon (e.g., dichloromethane). The reaction can be conveniently carried out between about −78 degrees and about room temperature, preferably at about −40 degrees.

Compounds of structure 38 can be prepared by any conventional means. For example, they can be prepared by esterifying compounds of structure 39 by a number of different reactions, such as those conventionally used to prepare esters of carboxylic acids, preferably by reactions that permit the esterification of the carboxylic acid in the presence of the phenolic hydroxyl group. For example, the compounds of structure 38, in which $R_{15}$ represents methyl, can be prepared by treatment of compounds of structure 39 with a solution of methanol containing a strong inorganic acid, for example sulfuric acid or a hydrohalic acid such as hydrogen chloride. The reaction is conveniently carried out at a temperature between about room temperature and about 65 degrees, preferably at about room temperature.

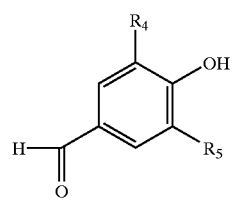

Structure 40

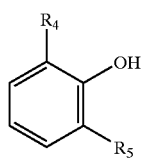

Structure 41

Compounds of structure 39 can be prepared by a variety of methods that are known in the field of organic chemistry. For example, they may be prepared by oxidation of compounds of structure 40. This oxidation can be carried out conveniently by treating the compound of structure 40 with an oxidizing agent such as sodium chlorite, in the optional presence of a scavenger of chlorine dioxide such as sulfamic acid. The reaction is conveniently carried out in an inert solvent system such as a mixture of water and tert-butanol, at a temperature between about zero degrees and about 50 degrees, preferably at about room temperature.

Compounds of structure 40 can be prepared by any conventional means. For example, they can be prepared from compounds of structure 41 by a variety of procedures, such as by treatment of the compound of structure 41 with hexamethylenetetramine under acidic conditions, for example by carrying out the reaction in an acidic solvent such as trifluoroacetic acid. The reaction is conveniently carried out at about 70 degrees.

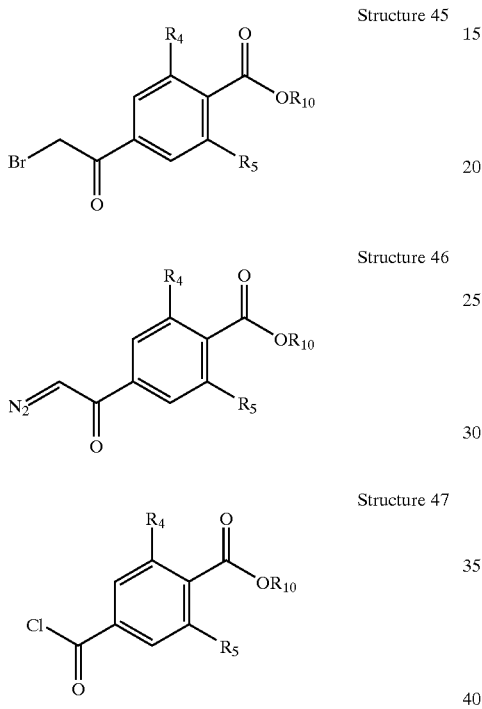

Structure 45

Structure 46

Structure 47

Compounds of structure 45 can be made by any conventional means. For example, such compounds can be made by reacting a diazoketone of structure 46 with hydrogen bromide. The reaction can be conveniently carried out by bubbling hydrogen bromide gas into a suspension of the compound of structure 46 in an inert solvent such as diethyl ether. The reaction may be carried out at a temperature between about zero degrees and about room temperature, preferably at about room temperature.

Compounds of structure 46 can be made by any conventional means. For example, they can be prepared by treating compounds of structure 47 with diazomethane. The reaction is conveniently carried out in the presence of a base, such as a tertiary amine (e.g., triethylamine) in an inert solvent such as diethyl ether at a temperature of between −10 degrees and about room temperature, preferably at about zero degrees.

Compounds of structure 47 can be made a variety of methods familiar to one of ordinary skill in the art. For example, they can be made by reaction of a compound of structure 22 with a reagent that is commonly used for the conversion of carboxylic acids to acid chlorides such as thionyl chloride or oxalyl chloride in the presence or absence of an inert solvent such as an aromatic hydrocarbon (e.g., benzene) or dichloromethane. In the case where thionyl chloride is used, the reaction can be carried out at a temperature of about 80 degrees.

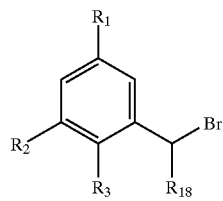

Structure 49

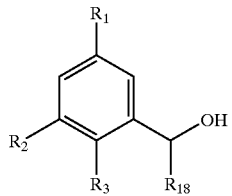

Structure 50

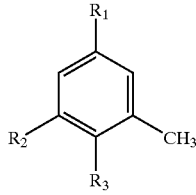

Structure 51

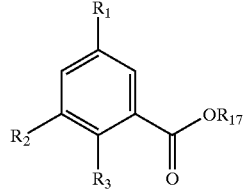

Structure 52

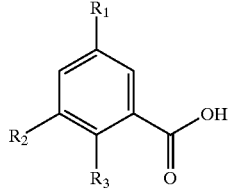

Structure 53

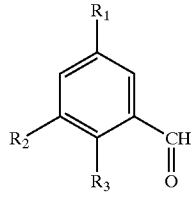

Structure 28

Compounds of structure 49, in which $R_{18}$ represents hydrogen or lower alkyl, can be made by any conventional means. For example, in the case where $R_{18}$ represents hydrogen, they may be made by bromination of compounds of structure 51 where the other functionalities in the structure may contain appropriate protective groups that will be apparent to one of ordinary skill in the art of organic synthesis. The bromination may be carried out by treatment of a compound of structure 51 with a brominating agent such as N-bromosuccinimide, 1,3-dibromo-5,5- dimethylhydantoin, or bromine, preferably N-bromosuccinimide. The reaction may be carried out in the presence of an agent that will increase the rate of the reaction such as azodiisobutyronitrile or benzoyl peroxide, and/or under irradiation from a light source such as a low pressure mercury lamp. The reaction may be carried out in the presence of an inert solvent such as carbon tetrachloride, at a suitable temperature such as about 76 degrees.

Compounds of structure 50 are generally known compounds, or can be prepared in a similar manner to the known compounds. For example, the reduction of compounds of structure 52 to give compounds of structure 50 in which $R_{18}$ represents hydrogen, in accordance with procedure (o) can be effected in a manner analogous to that described earlier in connection with the reduction of a compound of structure 9 to furnish a compound of structure 8. As a further example, compounds of structure 50 in which $R_{18}$ represents methyl can be prepared from compounds of structure 28 by reaction with an organometallic reagent. This reaction can be conveniently carried out by adding a reagent such as methyllithium or methylmagnesium bromide to the compound of structure 28 in an inert solvent such as an ether (e.g., diethyl ether or tetrahydrofuran) at a temperature between about −78 degrees and about room temperature, preferably at about −78 degrees.

Compounds of structure 51 are generally known compounds. Insofar as they are not known compounds or analogues of known compounds, they can be prepared in a similar manner to the known compounds or as described in the Examples hereinafter or in analogy thereto.

Compounds of structure 52 are generally known compounds or can be made a variety of methods familiar to one of ordinary skill in the art. For example, the esterification of compounds of structure 53 to give compounds of structure 52 in which $R_{17}$ represents lower alkyl, in accordance with procedure (p) can be done in a manner analogous to that described earlier in connection with the esterification of a compound of structure 14 to furnish a compound of structure 9.

Compounds of structure 53 are generally known compounds. Insofar as they are not known compounds or analogues of known compounds, they can be prepared in a similar manner to the known compounds or as described in the Examples hereinafter or in analogy thereto.

Structure 54

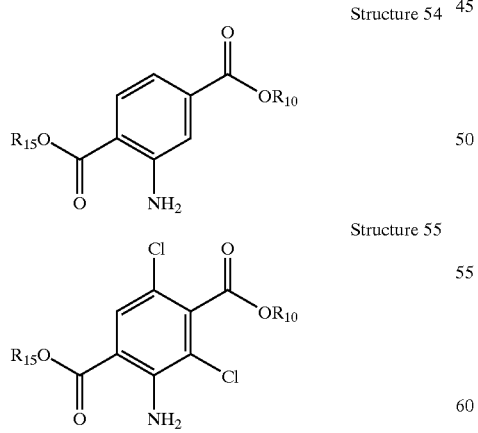

Structure 55

Compounds of structure 55 can be made by any conventional means. For example, compounds of structure 55 can be made by chlorination of compounds of structure 54, for example by treatment with a chlorinating agent such as N-chlorosuccinimide in a polar solvent such as acetonitrile at a suitable temperature, such as at around 65 degrees. Compounds of structure 54 are generally known compounds, or can be prepared in a similar manner to the known compounds.

EXAMPLES

Definitions:

BSA is bovine serum albumin,

DMF is N,N-dimethylformamide,,

ELISA is enzyme-linked immunosorbent assay,

Fc is the crystallizable fragment of an antibody,

HEPES is 4-(2-hydroxyethyl)piperazine-1-ethanesulfonic acid,

HPLC is high-pressure liquid chromatography,

HRP is horseradish peroxidase

ICAM-1 is intercellular adhesion molecule-1,

IgG is immunoglobulin G,

LFA-1 is lymphocyte function-associated antigen-1 (CD11a/CD18; αLβ2),

Mac-1 is macrophage differentiation antigen associated with type three complement receptor (CD11b/CD18; αMβ2), Nmr is nuclear magnetic resonance, PBS is phosphate-buffered saline, Tlc is thin layer chromatography, TMB is 3,3',5,5'tetramethylbenzidine TMG is 1,1,3,3-tetramethylguanidine Example 1

Preparation of 1H-Indole-4-carboxylic Acid Methyl Ester

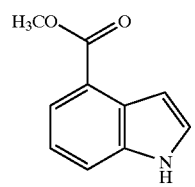

N,N-Dimethylaminopyridine (7.6 mg, 0.06 mmol) was added to a mixture of 1H-indole-6-carboxylic acid (100 mg, 0.62 mmol), 1-(3-dimethylaminopropyl)-3-ethylcarbodiimide hydrochloride (131 mg, 0.68 mmol) and methanol (1 mL, 24.7 mmol) in dichloromethane (2 mL). The mixture was allowed to stir at room temperature overnight, then the solvent was evaporated and ethyl acetate (20 mL) was added. The solution was washed with 1N hydrochloric acid solution (2×15 mL), saturated sodium bicarbonate solution (15 mL) and brine (10 mL), dried (MgSO$_4$), filtered and evaporated in vacuo to give 1H-indole-4-carboxylic acid methyl ester (85.4 mg, 79% yield) as a pale yellow solid.

Also prepared by this method were the following:

| Example | Structure | Starting Material | Comments |
|---|---|---|---|
| 2 | MeO₂C-benzothiazole | benzothiazole-6-carboxylic acid | 75% yield; off-white solid |
| 3 | MeO₂C-benzoxadiazole | 2,1,3-benzoxadiazole-5-carboxylic acid | 100% yield; colorless solid |
| 4 | cinnoline-CO₂Me | cinnoline-4-carboxylic acid | 56% yield; colorless solid |

Example 5

Preparation of 1H-Benzotriazole-1,5-dicarboxylic Acid, 1-(1,1-Dimethylethyl Ester), 5-Methyl Ester and 3H-Benzotriazole-3,5-dicarboxylic Acid, 3-(1,1-Dimethylethyl Ester), 5-Methyl Ester

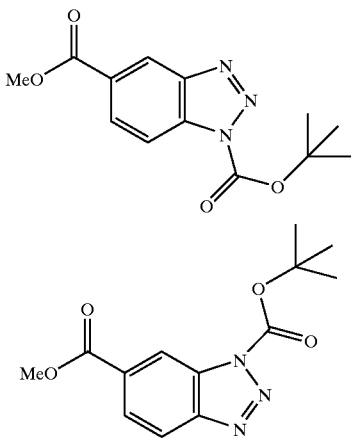

A solution of 1H-benzotriazole-5-carboxylic acid methyl ester (prepared according to the literature procedure: Katritzky, A. R.; Ji, F. B.; Fan, W. Q.; Delprato, I. *Synth. Commun.* 1993, 23, 2019–25; 5.1 g, 28.8 mmol), triethylamine (6 mL, 43.0 mmol), N,N-dimethylaminopyridine (0.35 g, 2.9 mmol) and di-tert-butyl dicarbonate (12.57 g, 57.6 mmol) in N,N-dimethylformamide (60 mL) was stirred at room temperature for 4 h. The solvent was evaporated and the residue was dissolved in ethyl acetate (50 mL). The solution was washed with 0.1N hydrochloric acid solution (2×20 mL) and brine (15 mL), dried (MgSO₄), filtered and evaporated under reduced pressure. The residue was crystallized from hot ethyl acetate to give a mixture of 1H-benzotriazole-1,5-dicarboxylic acid, 1-(1,1-dimethylethyl ester), 5-methyl ester and 3H-benzotriazole-3,5-dicarboxylic acid, 3-(1,1-dimethylethyl ester), 5-methyl ester (7.84 g, 98% yield) as a light brown solid.

Example 6

Preparation of 4-(1-Methylethyl)-2-methylthiazole-5-carboxylic Acid Ethyl Ester

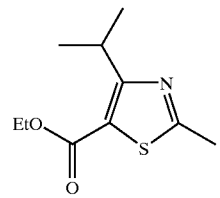

A. Ethyl 2-Chloroisobutyrylacetate

To a solution of ethyl isobutyrylacetate (2 g, 12.6 mmol) in dichloromethane (12 mL) at 0° C. was added a 1M solution of sulfuryl chloride in dichloromethane (13.9 mL, 13.9 mmol). The reaction mixture was warmed to 25° C. and stirred for 2.5 h. The reaction mixture was diluted with dichloromethane (80 mL) and washed in turn with water (2×60 mL) and brine (75 mL). The organic extract was dried (MgSO₄), filtered, concentrated to yield ethyl 2-chloroisobutyrylacetate (2.8 g, 66% product, 34% ethyl isobutyrylacetate) as a yellow oil which was used as is in the step below.

B. 4-(1-Methylethyl)-2-methylthiazole-5-carboxylic Acid Ethyl Ester.

To a solution of ethyl 2-chloroisobutyrylacetate from step A (1.58 g, 8.2 mmol, ~66% pure) in ethanol (20 mL) at 25° C. was added thioacetamide (617 mg, 8.2 mmol) and the reaction mixture was stirred at reflux for 24 h. After the solvents were removed under reduced pressure, the residual oil was diluted with ethyl acetate (100 mL), washed in turn with water (75 mL) and brine (75 mL), then was dried (MgSO₄), filtered and concentrated in vacuo. The residue was flash chromatographed over silica gel (5% diethyl ether in hexanes) to yield 4-(1-methylethyl)-2-methylthiazole-5-carboxylic acid ethyl ester (1.1 g, 63% yield) as a yellow oil.

Also prepared by this procedure was:

| Example | Structure | Reagents | Comments |
|---|---|---|---|
| 7 | 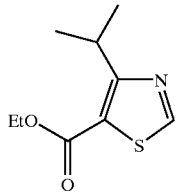 | Step A: as above<br>Step B: thiopropionamide | dichloromethane used for extraction in Step B. Colorless oil. 63% yield. |

Example 8

Preparation of 4-(1-Methylethyl)thiazole-5-carboxylic Acid Ethyl Ester

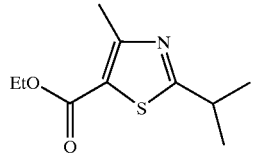

A. 2-Chloro-4-methyl-3-oxopentanoic Acid Ethyl Ester

A 1M solution of sulfuryl chloride in dichloromethane (25 mL, 25 mmol) was added to a solution of 4-methyl-3-oxopentanoic acid ethyl ester (3.95 g, 25 mmol) in dichloromethane (15 mL) cooled in a water bath. The solution was stirred at room temperature for 2 h and then the reaction mixture was washed with water (2×20 mL). Each of the aqueous layers was extracted with dichloromethane and the combined organic layers were dried (MgSO$_4$), filtered and evaporated to give 2-chloro-4-methyl-3-oxopentanoic acid ethyl ester (5.0 g, 104% of the theoretical amount). This was used directly in the next step without purification.

B. 4-(1-Methylethyl)thiazole-5-carboxylic Acid Ethyl Ester.

A solution of thioformamide (prepared according to Al-Razzar et al. U.S. Pat, No. 5,559158; 1.2 g, 20 mmol) and 2-chloro-4-methyl-3-oxopentanoic acid ethyl ester (2.0 g, 10 mmol) in ethanol (20 mL) was heated at reflux for 17 h. The reaction mixture was evaporated to dryness and the residue was chromatographed over silica gel (5–20% ethyl acetate/hexanes) to give 4-(1-methylethyl)thiazole-5-carboxylic acid ethyl ester (720 mg, 36% yield).

Example 9

Preparation of 2-(1-Methylethyl)-4-methylthiazole-5-carboxylic Acid Ethyl Ester A. 2-Methylpropanethioamide.

Phosphorus pentasulfide (3.25 g, 14.6 mmol) was added to a solution of 2-methylpropanamide (5.00 g, 57.4 mmol) in diethyl ether/benzene (2:1; 150 mL). The mixture was stirred for 2.5 h at room temperature to give a tacky yellow solid and a supernatant layer. The supernatant was filtered through Celite® and the tacky yellow solid was extracted with diethyl ether (3×25 mL) and the extracts were filtered through Celite®. The combined organic layers were evaporated to give 2-methylpropanethioamide (4.6 g, 78% yield) as a yellow oil that solidified on standing.

B. 2-(1-Methylethyl)-4-methylthiazole-5-carboxylic Acid Ethyl Ester.

A solution of 2-methylpropanethioamide (3.1 g, 30 mmol) and ethyl 2-chloroacetoacetate (3.29 g, 20 mmol) in ethanol (40 mL) was heated at reflux for 3 h. The reaction mixture was evaporated to dryness and the residue was taken up in dichloromethane (50 mL) and the solution was washed with saturated sodium bicarbonate solution (2×25 mL). The aqueous layers were back-washed with dichloromethane (25 mL), then the combined dichloromethane layers were dried (MgSO$_4$), filtered and concentrated under vacuum. The residue was purified using a Waters Prep 500 apparatus (silica gel dual column; 10% ethyl acetate/hexanes). Evaporation of the appropriate fractions afforded 2-(1-methylethyl)-4-methylthiazole-5-carboxylic acid ethyl ester (4.0 g, 93% yield).

Example 10

Preparation of (5-Ethoxycarbonyl-4-trifluoromethylthiazol-2-yl)carbamic Acid, 1,1-Dimethylethyl Ester

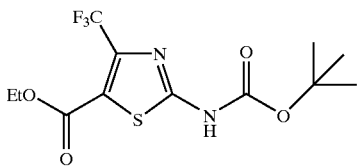

A. 2-Amino-4-trifluoromethylthiazole-5-carboxylic Acid Ethyl Ester.

A solution of thiourea (400 mg, 5.25 mmol) and ethyl 2-chloro-4,4,4-trifluoroacetoacetate (1.1 g, 5.03 mmol) in ethanol (40 mL) was heated at reflux for 4 h. The reaction mixture was evaporated to dryness and the residue was partitioned between ethyl acetate (50 mL) and saturated sodium bicarbonate solution (25 mL). The separated aqueous layer was re-extracted with ethyl acetate. The combined organic layers were washed with saturated sodium bicarbonate solution (25 mL) and brine (25 mL), dried (MgSO$_4$), filtered and evaporated in vacuo to provide a colorless solid (1.2 g). The crude material was triturated with diethyl ether and the solid was collected by filtration to give 2-amino-4-trifluoromethylthiazole-5-carboxylic acid ethyl ester (515 mg) as colorless crystals. A second crop of 250 mg was recovered from the filtrate. The total yield was 765 mg (63% yield).

B. (5-Ethoxycarbonyl-4-trifluoromethylthiazol-2-yl)carbamic Acid, 1,1-Dimethylethyl Ester.

A solution of di-tert-butyl dicarbonate (480 mg, 2.2 mmol) in acetonitrile (7.5 mL) was added to a solution of 2-amino-4-trifluoromethylthiazole-5-carboxylic acid ethyl ester (500 mg, 2.1 mmol) and N,N-dimethylaminopyridine (26 mg, 0.2 mmol) in acetonitrile (7.5 mL). The solution was stirred at room temperature for 1 h and then a further portion of di-tert-butyl dicarbonate (120 mg, 0.55 mmol) was added. After the solution was allowed to stir at room temperature for 2 h, the volatiles were evaporated under reduced pressure and the residual material was chromatographed over silica gel (0–50% ethyl acetate/hexanes) to furnish (5-ethoxycarbonyl-4-trifluoromethylthiazol-2-yl)carbamic acid, 1,1-dimethylethyl ester (554 mg, 78% yield).

Example 11

Preparation of 2-Ethyl-4-methylthiazole-5-carboxylic Acid Ethyl Ester

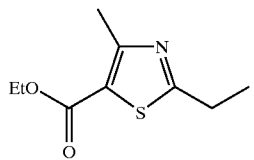

A solution of ethyl 2-chloroacetoacetate (2.00 g, 10.04 mmol) and thiopropionamide (1.00 g, 11.22 mmol) in ethanol (100 mL) was heated at reflux overnight. The solvent was evaporated and dichloromethane (100 mL) added. The solution was washed with water (2×100 mL) and brine (100 mL), dried (MgSO$_4$), filtered, evaporated and the concentrate was chromatographed over silica gel (10% ethyl acetate/hexanes) to give 2-ethyl-4-methylthiazole-5-carboxylic acid ethyl ester (1.63 g, 81% yield) as a colorless liquid.

Example 12

Preparation of 4-(1-Methylethyl)thiazole-2-carboxylic Acid Ethyl Ester

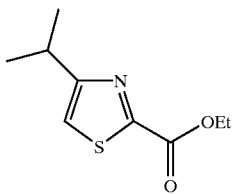

A. Ethyl Thiooxamate.

Powdered Lawesson's reagent (305 g, 0.754 mol) was added to a warm (~35° C.) solution of ethyl oxamate (200 g, 1.71 mol) in tetrahydrofuran (2.3 L). The mixture was heated to reflux for 15 min and then the orange solution was allowed to cool to room temperature over 2 h. After the solution was concentrated to constant weight in vacuo, the residual material was diluted with toluene (500 mL) and the mixture was stored at low temperature (~–20° C.) over a weekend. The resulting solids were collected by filtration, then were washed in turn with toluene and hexane and dried at room temperature in vacuo to give 155 g of ethyl thiooxamate (70% yield) as a yellow solid.

B. 1-Bromo-3-methyl-2-butanone.

A solution of 3-methyl-2-butanone (250 mL, 2.3 mol) in methanol (1.2 L) was cooled in a dry ice bath to –5° C. then bromine (128 mL, 2.5 mol) was added over 10 min while maintaining the reaction temperature at 0° C. After the addition was completed the cooling bath was changed to an ice—salt water bath and stirred reaction mixture was maintained between –5 and 0° C. After 60 min the cooling bath was removed and the reaction was allowed to equilibrate to room temperature, then was warmed briefly to 32° C. before it was re-cooled to room temperature. The solution was poured to an ice-water mixture and was extracted with pentane (3×500 mL). The organic extracts were washed in turn with saturated sodium bicarbonate solution (500 mL) and brine (500 mL), then were dried (MgSO$_4$), filtered and evaporated under reduced pressure (no heat) to furnish 1-bromo-3-methyl-2-butanone as a clear oil (378.3 g, essentially quantitative yield).

C. 4-(1-Methylethyl)thiazole-2-carboxylic Acid Ethyl Ester.

A solution of ethyl thiooxamate (155 g, 1.16 mol) and 1-bromo-3-methyl-2-butanone (203.72 g, 1.234 mol) in ethanol (1.5 L) was heated at reflux for 2 h. After the reaction mixture was evaporated to dryness in vacuo, the residual yellow oil was taken up in saturated sodium bicarbonate solution (600 mL) and extracted with dichloromethane (3×50 mL). The organic layers were washed with water and brine (25 mL), then were dried (MgSO$_4$), filtered, evaporated under reduced pressure to give 4-(1-methylethyl)thiazole-2-carboxylic acid ethyl ester as a dark oil (193.4 g, 83.7% yield).

Example 13

Preparation of 4-Trifluoromethylthiazole-2-carboxylic Acid Ethyl Ester

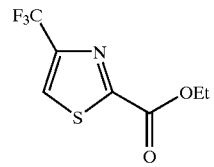

A solution of ethyl thiooxamate (Example 12, step A; 3.49 g, 26.2 mmol) and 3-bromo-1,1,1-trifluoromethyl-2-propanone (5.0 g, 26.2 mmol) in ethanol (50 mL) was heated at reflux overnight. After the reaction mixture was evaporated to dryness in vacuo, the residual semisolid was dissolved in ethyl acetate (250 mL) and the resulting solution was washed with water (2×75 mL) and with brine (75 mL). The dried (MgSO$_4$) organic layer was evaporated under reduced pressure to furnish an orange oil that was purified by chromatography over silica gel (ethyl acetate/petroleum ether; 1:9). The appropriate fractions were combined and concentrated to dryness to afford to give 4-trifluoromethylthiazole-2-carboxylic acid ethyl ester as a pale yellow oil (3.62 g, 61.4% yield).

Example 14

Preparation of 1-[(1,1-Dimethylethoxy)carbonyl]-1H-indole-6-carboxylic Acid Methyl Ester

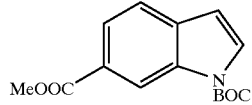

A solution of 1H-indole-6-carboxylic acid methyl ester (prepared by the literature method: Brown, F. J.; Cronk, L. A.; Aharony, D.; Snyder, D. W. *J. Med. Chem.* 1992, 35, 2419–39; 4.55 g, 26.0 mmol), di-tert-butyl dicarbonate (6.00 g, 27.5 mmol) and N,N-dimethylaminopyridine (0.50 g, 4.1 mmol) in acetonitrile (200 mL) was stirred overnight at room temperature. Silica gel was added and the solvent was evaporated. The residue was chromatographed over silica gel (10% ethyl acetate/hexanes) to give 6.33 g (89% yield) of 1-[(1,1-dimethylethoxy)carbonyl]-1H-indole-6-carboxylic acid methyl ester as a colorless liquid.

Example 15

Preparation of 1-Methyl-1H-indole-6-carboxylic Acid methyl Ester

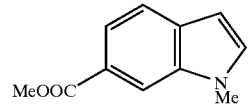

A solution of 1H-indole-6-carboxylic acid (2.60 g, 16.1 mmol) in tetrahydrofuran (100 mL) and diethyl ether (100 mL) was treated with ethereal diazomethane until tlc indicated complete consumption of the starting material. After the solution was allowed to stand overnight, the solvent was evaporated under reduced pressure and the resulting residue was dissolved in tetrahydrofuran (100 mL). The solution was cooled to ~0° C. and sodium hydride (60% suspension in mineral oil; 2.00 g, 50.0 mmol) and then iodomethane (10.00 g, 70.5 mmol) were added. and the reaction mixture was stirred at room temperature overnight. Water (200 mL) was added, carefully at first and the mixture was extracted with ethyl acetate (2×200 mL). The combined ethyl acetate layers were washed with brine (100 mL), dried (MgSO$_4$), filtered and concentrated in vacuo. The crude product was chromatographed over silica gel (30–50% ethyl acetate/hexanes) to furnish 1-methyl-1H-indole-6-carboxylic acid methyl ester (2.52 g, 83% yield) as a yellow oil that solidified on standing.

Example 16

Preparation of 5-Hydroxymethyl-1H-benzotriazole-1-carboxylic Acid, 1,1-Dimethylethyl Ester and 5-Hydroxymethyl-3H-benzotriazole-3-carboxylic Acid, 1,1-Dimethylethyl Ester

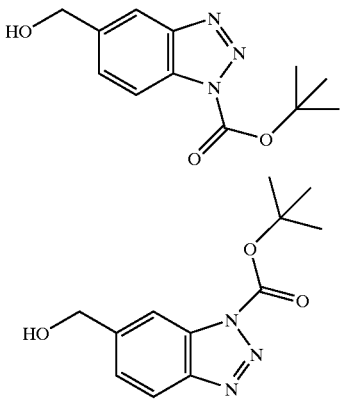

Diisobutylaluminum hydride (1.5M in toluene; 32 mL, 48 mmol) was added to a solution of a mixture of 1H-benzotriazole-1,5-dicarboxylic acid, 1-(1,1-dimethylethyl ester), 5-methyl ester and 3H-benzotriazole-3,5-dicarboxylic acid, 3-(1,1-dimethylethyl ester), 5-methyl ester (Example 5; 6.64 g, 23.97 mmol) in diethyl ether (80 mL) at −70° C. The solution was allowed to stir at −70° C. for 4 h, then ethyl acetate was added and the solution was washed with 0.1N hydrochloric acid solution (100 mL) and brine, dried (MgSO$_4$), filtered and concentrated in vacuo. The residue was chromatographed over silica gel (35–50% ethyl acetate/hexanes) to give a mixture of 5-hydroxymethyl-1H-benzotriazole-1-carboxylic acid, 1,1-dimethylethyl ester and 5-hydroxymethyl-3H-benzotriazole-3-carboxylic acid, 1,1-dimethylethyl ester (2.31 g, 39% yield) as a pale yellow oil.

Example 17

Preparation of 1H-Indole-4-methanol

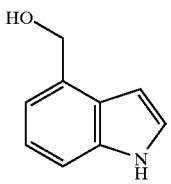

biisobutylaluminum hydride (1M in toluene; 1.3 mL, 1.3 mmol) was added to a solution of 1H-indole-4-carboxylic acid methyl ester (Example 1; 85 mg, 0.49 mmol) in diethyl ether (1.6 mL) at −70° C. The solution was allowed to stir at −70° C. for 1 h, then at room temperature for 1 h. Ethyl acetate (20 mL) was added and the solution was stirred with an aqueous solution of potassium sodium tartrate (30% w/v; 20 mL) for 30 min. The layers were separated and the aqueous layer was extracted with ethyl acetate. The combined organic layers were dried (MgSO$_4$), filtered, evaporated and dried under high vacuum to give 1H-indole-4-methanol (73.2 mg, quantitative yield) which was used in the next step without further purification.

Example 18

Preparation of 2-Methylthiazole-4-methanol

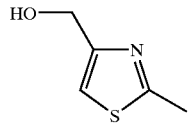

To a suspension of lithium aluminum hydride (242 mg, 6.4 mmol) in diethyl ether (5 mL) at 0° C. was added slowly dropwise a solution of ethyl-2-methylthiazole-4-carboxylate (1.0 g, 5.8 mmol) in diethyl ether (5 mL). The reaction mixture was allowed to stir at 0° C. for 10 min, then at room temperature for 24 h. Ethyl acetate (15 mL) was added very slowly dropwise at 0° C. The reaction mixture was then added slowly to an aqueous solution of potassium sodium tartrate (30% w/v; 50 mL) and stirred for 1 h. The mixture was diluted with 50 mL of ethyl acetate, the layers separated and the aqueous layer was re-extracted with ethyl acetate (3×100 mL). The combined organic layers were dried (MgSO$_4$), filtered, evaporated and dried under high vacuum to give 2-methylthiazole-4-methanol (46 mg, 92% yield) as a brown oil which was used in the next step without further purification.

Also prepared by this method were the following:

| Example | Structure | Starting Material | Comments |
|---|---|---|---|
| 19 | 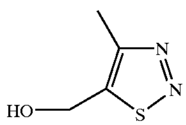 | 4-methyl-1,2,3-thiadiazole-5-carboxylic acid ethyl ester | 57% yield; yellow oil |
| 20 | 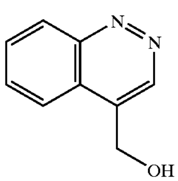 | Example 4 | 85% yield; yellow oil[a] |

[a] nmr showed the presence of a minor product in which the heteroaromatic ring had been partially reduced.

Example 21

Preparation of 2,4-Dimethylthiazole-5-methanol

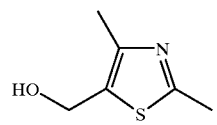

To a suspension of lithium aluminum hydride (563 mg, 14.8 mmol) in diethyl ether (25 mL) at 0° C. was added ethyl-2,4-dimethylthiazole-5-carboxylate (2.5 g, 13.5 mmol) in three portions. The reaction mixture was allowed to stir at 0° C. for 10 min, then at room temperature for 24 h. Ethyl acetate (65 mL) was added very slowly dropwise at 0° C. The reaction mixture was then added slowly to an aqueous solution of potassium sodium tartrate (30% w/v; 20 mL) and stirred for 2 h. The layers were separated and the aqueous layer was re-extracted with ethyl acetate (1×30 mL). The combined organic layers were dried (MgSO$_4$), filtered, evaporated under reduced pressure. The resulting colorless solid was dried under high vacuum to give 2,4-dimethylthiazole-5-methanol (1.7 g, 91% yield). This material was used in a subsequent step without further purification.

Example 22

Preparation of 2,1,3-Benzothiadiazole-5-methanol

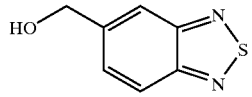

To a suspension of lithium aluminum hydride (215 mg, 5.7 mmol) in diethyl ether (15 mL) at 0° C. was added methyl 2,1,3-benzothiadiazole-5-carboxylate (1.0 g, 5.2 mmol) in one portion. The reaction mixture was allowed to stir at 0° C. for 10 min, then at room temperature for 24 h. Ethyl acetate (30 mL) was added very slowly dropwise at 0° C. The reaction mixture was then added slowly to an aqueous solution of potassium sodium tartrate (30% w/v; 100 mL) and stirred for 2 h. The reaction mixture was diluted with 100 mL of ethyl acetate and the layers were separated. The aqueous layer was re-extracted with ethyl acetate (1×100 mL). The combined organic layers were dried (MgSO$_4$), filtered and evaporated under reduced pressure. The crude product was purified by flash chromatography (silica gel, 25% ethyl acetate in petroleum ether) to give 2,1,3-benzothiadiazole-5-methanol (400 mg, 47% yield) as an orange solid.

Also prepared by this route from the corresponding methyl ester were the following:

| Example | Structure | Starting Material | Comments |
|---|---|---|---|
| 23 | 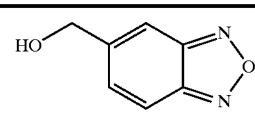 | Example 3 | Chromatographed over silica gel, (30–75% ethyl acetate in petroleum ether); off-white solid; 17% yield |
| 24 | 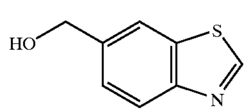 | Example 2 | 83% yield used as is |

-continued

| Example | Structure | Starting Material | Comments |
|---|---|---|---|
| 25 | 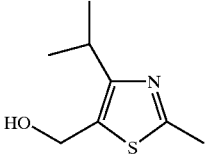 | Example 6 | Chromatographed over silica gel, (20% ethyl acetate in petroleum ether); colorless solid; 32% yield |

Example 26

Preparation of 4-(1-Methylethyl)thiazole-5-methanol

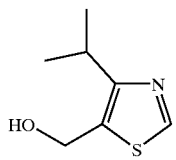

Diisobutylaluminum hydride (1.5M in toluene; 2.4 mL, 3.6 mmol) was added dropwise over 10 min to a solution of 4-(1-methylethyl)thiazole-5-carboxylic acid ethyl ester (Example 8; 650 mg, 3.26 mmol) in toluene (5 mL) at −75° C. After 80 min, a second portion of diisobutylaluminum hydride (1.5M in toluene; 1.1 mL, 1.65 mmol) was added dropwise over 5 min at −75° C. After 20 min the cold reaction mixture was treated with saturated aqueous potassium sodium tartrate (5 mL) and the reaction mixture was allowed to warm to room temperature over 15 min. The liquid phase was decanted from the colorless solids and the filter cake was washed with toluene. The combined organic layers were washed with 5% aqueous potassium sodium tartrate (20 mL) and brine, then dried (MgSO$_4$), filtered and evaporated in vacuo. The resulting residue was chromatographed over silica gel (0–25% ethyl acetate/hexanes) to give 4-(1-methylethyl)thiazole-5-methanol (350 mg, 69% yield).

Example 27

Preparation of 2-(1-Methylethyl)-4-methylthiazole-5-methanol

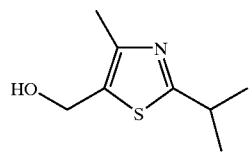

Diisobutylaluminum hydride (1.5M in toluene; 6.5 mL, 9.8 mmol) was added dropwise to a solution of 2-(1-methylethyl)-4-methylthiazole-5-carboxylic acid ethyl ester (Example 9; 1.0 g, 4.7 mmol) in toluene (8 mL) at −75° C. After 15 min, the cold reaction mixture was treated with saturated aqueous potassium sodium tartrate (15 mL) and the reaction mixture was allowed to warm to room temperature. The reaction mixture was filtered and the solids were washed thoroughly with toluene. The combined filtrates were washed with brine (50 mL) and the brine layer was back-washed with toluene (3×35 mL) and ethyl acetate (2×35 mL) to extract the product completely. The combined organic layers were dried (MgSO$_4$), filtered and evaporated under reduced pressure to give 2-(1-methylethyl)-4-methylthiazole-5-methanol (742 mg, 92% yield).

Example 28

Preparation of 2-Ethyl-4-(1-methylethyl)thiazole-5-methanol

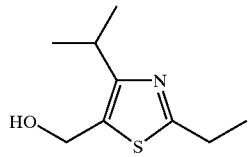

Diisobutylaluminum hydride (1M in toluene; 15 mL, 15 mmol) was added dropwise to a solution of 2-ethyl-4-(1-methylethyl)thiazole-5-carboxylic acid ethyl ester (Example 7; 1.7 g, 7.5 mmol) in toluene (20 mL) at −78° C. The solution was stirred in a dry ice-acetone bath overnight and as the dry ice dissipated the reaction temperature rose to −10° C.. Examination of the reaction by TLC showed a mixture of starting material and product. After the reaction was again cooled to −78° C., a second portion of diisobutylaluminum hydride (1M in toluene; 15 mL, 15 mmol) was added with stirring and the cooled reaction was allowed to proceed overnight. As before, the reaction temperature rose slowly from −78° C. to −10° C. The reaction temperature was re-adjusted to −50° C., then methanol was added dropwise and the mixture was stirred for 30 min. The resulting gel was filtered through Celite® and the filter cake was washed with ethyl acetate. Evaporation of the combined filtrates in vacuo yielded 1.5 g of 2-ethyl-4-(1-methylethyl)thiazole-5-methanol (108% of theory). This material was used without further purification in a subsequent reaction.

Example 29

Preparation of a Mixture of (5-Hydroxymethyl-4-trifluoromethylthiazol-2-yl)carbamic Acid, 1,1-Dimethylethyl Ester and (5-Ethoxycarbonyl-4-trifluoromethylthiazol-2-yl)carbamic Acid, 1,1-Dimethylethyl Ester

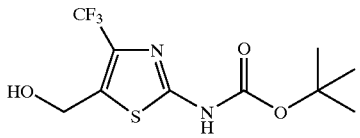

Diisobutylaluminum hydride (1.5M in toluene; 2.2 mL, 3.3 mmol) was added dropwise to a solution of (5-ethoxycarbonyl-4-trifluoromethylthiazol-2-yl)carbamic acid, 1,1-dimethylethyl ester (Example 10; 550 g, 1.6 mmol) in toluene (5 mL) at −78° C. After 30 min, the cold reaction mixture was treated with a solution of potassium sodium tartrate (1 g) in water (2 mL) and the reaction mixture was allowed to warm to room temperature. The reaction mixture was filtered and the filtrate was partitioned between ethyl acetate (25 mL) and brine. The aqueous phase was extracted twice with ethyl acetate and the combined ethyl acetate layers were dried (MgSO$_4$), filtered and evaporated to give a mixture of (5-hydroxymethyl-4-trifluoromethylthiazol-2-yl)carbamic acid, 1,1-dimethylethyl ester and (5-ethoxycarbonyl-4-trifluoromethylthiazol-2-yl)carbamic acid, 1,1-dimethylethyl ester (490 mg) as a colorless oil. This mixture was used directly in the next step without purification.

Example 30

Preparation of 2-Ethyl-4-methylthiazole-5-methanol

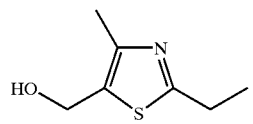

Lithium aluminum hydride (800 mg, 21.2 mmol) was added to a solution of 2-ethyl-4-methylthiazole-5-carboxylic acid ethyl ester (Example 11; 1.63 g, 8.2 mmol) in diethyl ether (100 mL). The solution was allowed to stir at room temperature for 4 h and was then poured carefully into an aqueous potassium sodium tartrate solution (30% w/v; 200 mL). After the mixture was allowed to stir at room temperature for 1 h, the layers were separated and the aqueous layer was extracted with ethyl acetate (100 mL). The combined organic layers were washed with brine (200 mL), dried (MgSO$_4$), filtered and concentrated under reduced pressure to give 2-ethyl-4-methylthiazole-5-methanol (860 mg, 67% yield) as a colorless oil.

Also prepared by this procedure was:

| Example | Structure | Starting Material | Comments |
|---|---|---|---|
| 31 | 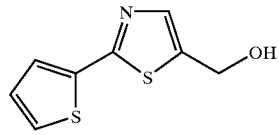 | Example 14 | 90% yield |

Example 32

Preparation of 2-(2-Thienyl)thiazole-5-methanol

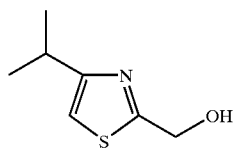

To a suspension of lithium aluminum hydride (52 mg, 1.25 mmol) in diethyl ether (2 mL) under argon was added 2-(2-thienyl)thiazole-5-carboxylic acid ethyl ester (lit: Robba, M., LeGuen, Y., *Bull. Soc. Chim. Fr.*, 1969(5)1762; 0.3 g, 1.25 mmol) at 0° C. The reaction mixture was allowed to equilibrate to room temperature and was stirred for 24 h. The reaction was re-cooled to 0° C. and was quenched by the careful addition of saturated aqueous ammonium chloride solution dropwise until no further reaction was apparent. The resulting solids were recovered by filtration, washed with diethyl ether and retained for further processing (vide infra). The filtrate was washed with brine, dried (MgSO$_4$), filtered and concentrated under reduced pressure. The solids that were recovered from the ammonium chloride quench were then slurried in ethyl acetate, filtered and washed with ethyl acetate. The resulting filtrate was washed with brine, dried (MgSO$_4$), filtered and evaporated reduced pressure. The solid residues obtained from the work up of both the diethyl ether filtrate and the ethyl acetate filtrate were combined to yield 179 mg (72% yield) of 2-(2-thienyl)thiazole-5-methanol as a yellow solid.

Example 33

Preparation of 4-(1-Methylethyl)thiazole-2-methanol

Sodium borohydride (40.4 g, 1.07 mol) was added in portions over 5–6 min to a cooled (5° C.) solution of 4-(1-methylethyl)thiazole-2-carboxylic acid ethyl ester (Example 12; 193 g, 0.97 mol) in ethanol (1.0 L). The solution was allowed then to stir at room temperature overnight. Examination of the reaction by tlc showed that a minor amount of starting ester remained. A second portion of sodium borohydride (4.0 g, 107 mmol) was added and after the mixture was stirred at ambient temperature for 40 min, the volatiles were removed under reduced pressure.

Water (1.5 L) was added and the mixture was adjusted to pH 5–6 using acetic acid, then was extracted with chloroform (3×500 mL). The organic extracts were washed with brine (500 mL), dried (MgSO$_4$), filtered and concentrated in vacuo to give 125 g of the crude alcohol as an oil. The oil was slurried in diethyl ether/hexane (1:19, 500 mL) and after the mixture was cooled, the resulting solids were collected by filtration, were washed with hexane and dried to give 4-(1-methylethyl)thiazole-2-methanol (102.6 g, 67.4% yield).

Also prepared in a similar manner was:

| Example | Structure | Starting Material | Comments |
|---|---|---|---|
| 34 | 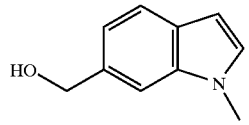 | Example 13 | Ethyl acetate used to extract product, an orange oil |

Example 35

Preparation of 1-Methyl-1H-indole-6-methanol

A solution of 1-methyl-1H-indole-6-carboxylic acid methyl ester (Example 15; 2.52 g, 13.3 mmol) in diethyl ether (50 mL) was added to a suspension of lithium aluminum hydride (0.50 g, 13.2 mmol) in diethyl ether (50 mL) and the mixture was stirred at room temperature for 5 h. Saturated Na$_2$SO$_4$ solution was added (~5 mL) and the mixture was stirred at room temperature for 30 min, then filtered and the filtrate was dried (MgSO$_4$), overnight. The mixture was filtered and evaporated to furnish 1-methyl-1H-indole-6-methanol (1.70 g, 79% yield) as a colorless oil that solidified on standing, mp 47–49° C.

Example 36

Preparation of 4-Hydroxymethylpiperidine-1-carboxylic Acid, 1,1-Dimethylethyl Ester

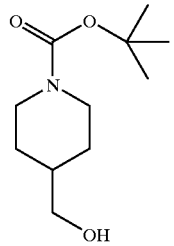

A solution of piperidine-4-methanol (0.5 g, 4.85 mmol), triethylamine (1.76 mL, 12.26 mmol) and di-tert-butyl dicarbonate (2.27 g, 5.82 mmol) in dichloromethane (25 mL) was stirred at room temperature for 4 h. The solution was washed with water (10 mL) and with brine (10 mL), dried (MgSO$_4$), filtered and evaporated to constant weight in vacuo. The residual solid was purified by chromatography over silica gel (ethyl acetate/petroleum ether, 1:1) and the appropriate fractions were combined and evaporated to yield 4-hydroxymethylpiperidine-1-carboxylic acid, 1,1-dimethylethyl ester as a colorless solid (0.826 g, 79.4%).

Also prepared in a similar manner were:

| Example | Structure | Starting Material | Comments |
|---|---|---|---|
| 37 | 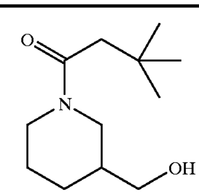 | rac-piperidine-3-methanol | chromatographed over silica gel, (50% ethyl acetate in petroleum ether); colorless solid; 94% yield |
| 38 | 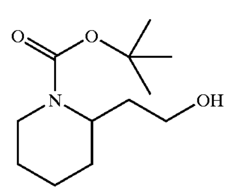 | rac-piperidine-2-ethanol | chromatographed over silica gel, (50% ethyl acetate in petroleum ether); colorless oil; 94.3% yield |

Example 39

Preparation of 3,5-Dimethylisoxazole-4-carboxaldehyde

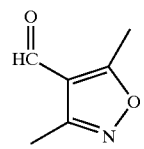

Manganese dioxide (5.48 g, 62.9 mmol) and dichloromethane (20 mL) were added to a solution of 3,5-dimethylisoxazole-4-methanol (prepared according to the literature procedure: Saucy, G.; Scott, J. W. U.S. Pat. No. 3,984,428 Oct. 5, 1976; 1.00 g, 7.9 mmol) in dichloromethane (25 mL). The mixture was stirred at room temperature overnight, then filtered through Celite®, evaporated under reduced pressure and the residual material was chromatographed over silica gel (10% ethyl acetate/hexanes) to give 3,5-dimethylisoxazole-4-carboxaldehyde (365 mg, 37% yield) as a colorless solid.

Also prepared by this route was the following:

| Example | Structure | Starting Material | Comments |
|---|---|---|---|
| 40 | 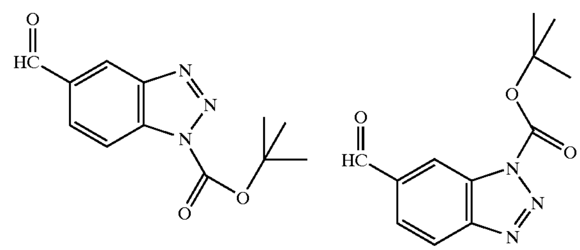 | Example 16 | 66% yield |
| 41 | 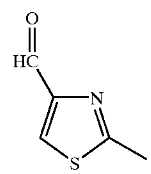 | Example 18 | 91% yield; brown oil; used as is |
| 42 | 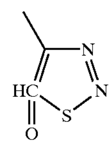 | Example 19 | 50% yield yellow oil used as is |
| 43 | 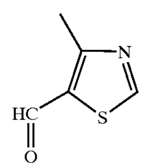 | Example 21 | 84% yield; yellow semi solid; used as is |
| 44 | 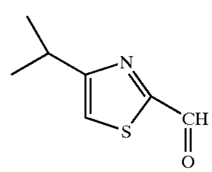 | Example 33 | 27% yield; volatile yellow oil; used as is |
| 45 | 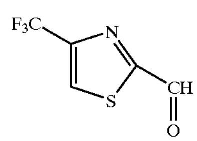 | Example 34 | 38% yield; dark oil; used as is |
| 46 | 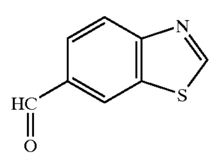 | Example 24 | 58% yield; tan solid; used as is |
| 47 | 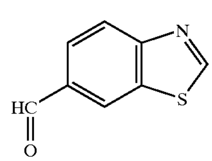 | Example 22 | 77% yield; yellow solid used as is |

-continued

| Example | Structure | Starting Material | Comments |
|---|---|---|---|
| 48 | 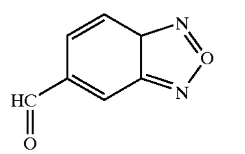 | Example 23 | 58% yield; orange solid used as is |
| 49 | 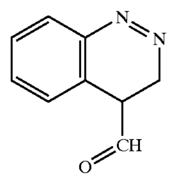 | Example 20 | 19% yield: yellow solid |
| 50 | 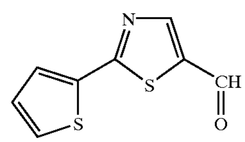 | Example 32 | 60% yield; yellow solid used as is |

Example 51

Preparation of 2-(Dimethylamino)thiazole-5-carboxaldehyde (Prepared by the Literature Procedure: I. Sawhney and J. R. H. Wilson. *J. Chem. Soc. Perkin Trans I*, 1990, 329–331).

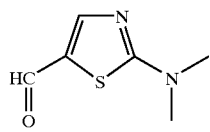

A. 2-Chlorothiazole (Prepared by the Literature Procedure: V. Genapathi. *Indian Academy of Science Section A*, 1945, 362–378).

Phosphoric acid (57 mL) was added slowly dropwise to a flask containing 2-aminothiazole (15 g, 0.15 mol). The resulting exothermic brown solution was cooled to ~5° C. and nitric acid (30 mL) was added slowly dropwise, while maintaining the temperature below 15° C. The reaction mixture was then cooled to about −5° C. and a solution of sodium nitrite (12 g) in water (40 mL) was added over 30 min. After the resulting orange solution was stirred at 0° C. for 40 min, the cold reaction mixture was then added to a solution of copper sulfate (25 g) and sodium chloride (25 g) in water (100 mL) at 10° C. The resulting mixture was stirred for 30 min in an ice bath followed by 1 h at room temperature, then was steam distilled. The product was separated from the water co-distillate, dried over $Na_2SO_4$ and filtered to yield 2-chlorothiazole (8.72 g, 49% yield).

B. 2-(Dimethylamino)thiazole-5-carboxaldehyde.

To a solution of 2-chlorothiazole (300 mg, 2.51 mmol) in distilled tetrahydrofuran (4 mL) at −78° C. was added n-butyllithium (2.5M solution in hexane, 2.58 mmol, 1.03 mL) slowly dropwise. After stirring 10 min at −78° C., N,N-dimethylformamide (2.76 mmol, 0.213 mL) was added and the reaction was warmed slowly to room temperature over 2 h. The reaction mixture was quenched with water (80 μL) and stirred for 24 h at room temperature. After the volatiles were removed under reduced pressure, the residue was diluted with water (25 mL) and extracted with ethyl acetate (2×100 mL). The combined organic layers were washed with brine (25 mL), dried ($MgSO_4$), filtered, concentrated under reduced pressure. The residue was flash chromatographed (silica gel, 50% ethyl acetate in petroleum ether) to yield 2-(dimethylamino)thiazole-5-carboxaldehyde (170 mg, 43% yield) as an orange solid.

Also prepared by this method (I. Sawhney and J. R. H. Wilson. *J. Chem. Soc. Perkin Trans I*, 1990, 329–331) from 2-chlorothiazole and the appropriate formamide was the following:

| Example | Structure | Formamide | Comments |
|---|---|---|---|
| 52 | 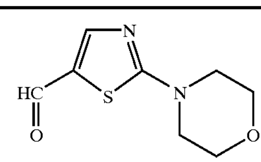 | | Chromatography over silica gel, 35–45% ethyl acetate in petroleum ether 56% yield |

Example 53

Preparation of 2-Chlorothiazole-5-carboxaldehyde (Prepared by the Literature Procedure: I. Sawhney and J. R. H. Wilson. *J. Chem. Soc. Perkin Trans I*, 1990, 329–331).

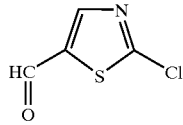

To a solution of 2-chlorothiazole (see Example 51, 500 mg, 4.2 mmol) in distilled tetrahydrofuran (7 mL) at −78° C. was added n-butyllithium (2.5M solution in hexane, 4.5 mmol, 1.78 mL) slowly dropwise. After stirring 10 min at −78° C., N,N-dimethylformamide (5.4 mmol, 0.42 mL) was added and the reaction was warmed slowly to room temperature over 2 h. The reaction mixture was then poured slowly onto 2N hydrochloric acid solution (10 mL), stirred 5 min and then was made basic with 50% ammonium hydroxide solution. The water layer was extracted with dichloromethane (2×50 mL) and the combined organic layers were washed with brine (25 mL), dried (MgSO$_4$), filtered and concentrated in vacuo. The residue was flash chromatographed (silica gel, 20% ethyl acetate in petroleum ether) to yield 2-chlorothiazole-5-carboxaldehyde (387 mg, 62% yield) as a yellow solid.

Example 54

Preparation of 2-[[4-(1,1-dimethylethoxy)carbonyl]piperazin-1-yl]thiazole-5-carboxaldehyde

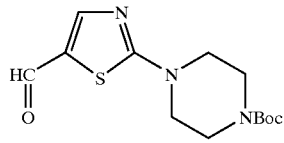

A. 2-(Piperazine-1-yl)thiazole-5-carboxaldehyde. Prepared by the Literature Procedure: I. Sawhney and J. R. H. Wilson. *J. Chem. Soc. Perkin Trans I*, 1990, 329–331.

To a solution of 2-chlorothiazole-5-carboxaldehyde (Example 53; 378 mg, 2.6 mmol) in aqueous tetrahydrofuran (9.75 mL tetrahydrofuran, 0.25 mL of water, 40:1) at 25° C. was added piperazine (0.55 g, 6.4 mmol) followed by lithium hydroxide (129 mg, 3.0 mmol). After stirring for 24 h at room temperature, the solvents were removed under reduced pressure. The residual solid was diluted with water (50 mL) and neutralized to pH 7 with 1N hydrochloric acid solution. The resulting solids were filtered, washed with water, dried under vacuum and flash chromatographed (silica gel, 10% methanol in dichloromethane) to yield 2-(piperazin-1-yl)thiazole-5-carboxaldehyde (191 mg, 38% yield) as a yellow solid.

B. 2-[[4-(1,1-Dimethylethoxy)carbonyl]piperazin-1-yl]thiazole-5-carboxaldehyde.

To a solution of 2-(piperazin-1-yl)thiazole-5-carboxaldehyde (94 mg, 0.47 mmol) in dichloromethane (2.4 mL) at 25° C. was added triethylamine (66 μL, 0.47 mmol) followed by di-tert-butyl dicarbonate (104 mg, 0.47 mmol). After stirring for 24 h at room temperature, starting material was still present. Further portions of di-tert-butyl dicarbonate (52 mg, 0.24 mmol) and triethylamine (66 μL, 0.47 mmol) were added to the reaction. After stirring 48 h, the reaction mixture was diluted with dichloromethane (25 mL) and washed with water (25 mL) followed by brine (25 mL). The organic layer was dried (MgSO$_4$), filtered, concentrated and flash chromatographed (silica gel, 5% methanol in dichloromethane) to furnish 2-[[4-(1,1-dimethylethoxy)carbonyl]piperazin-1-yl]thiazole-5-carboxaldehyde (120 mg, 85% yield) as a yellow solid.

Example 55

Preparation of Benzothiophene-3-carboxaldehyde. Prepared by the Literature Procedure: *J. Chem. Soc.*, 1969, 339–340

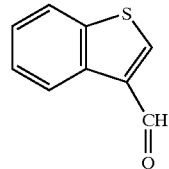

To a solution of benzothiophene (1.08 g, 8.0 mmol) in carbon disulfide (20 mL) at 0° C. was added titanium tetrachloride (3 mL, 27.3 mmol) followed by dichloromethyl n-butyl ether (1.24 g, 7.9 mmol) slowly dropwise. The reaction mixture was warmed to 25° C. and stirred for 1.5 h. The reaction was quenched with conc. hydrochloric acid solution (1 mL), diluted with chloroform (60 mL) and washed with water (50 mL), saturated sodium bicarbonate solution (2×30 mL) and brine (30 mL). The organic layer was dried (MgSO$_4$), filtered, concentrated and flash chromatographed (silica gel, 2.5–5% diethyl ether in petroleum ether) to afford benzothiophene-3-carboxaldehyde (195 mg, 15% yield) as a yellow solid.

Example 56

Preparation of 4-(1-Methylethyl)thiazole-5-carboxaldehyde

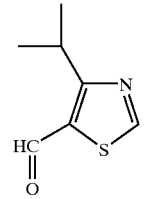

Portions of manganese dioxide (330 mg, 3.8 mmol) were added to a stirred solution of 4-(1-methylethyl)thiazole-5-methanol (Example 26; 330 mg, 2.1 mmol) in acetonitrile (10 mL) at hourly intervals for 4 h. One h after the last addition, the reaction mixture was filtered through Celite® and evaporated to dryness to give 4-(1-methylethyl)thiazole-5-carboxaldehyde (360 mg, 110% of the theoretical amount). Examination of the product by NMR indicated the presence of acetonitrile. This material was used with further purification in subsequent transformations.

The following was prepared by the same procedure:

| Example | Structure | Starting Material | Comments |
|---|---|---|---|
| 57 | 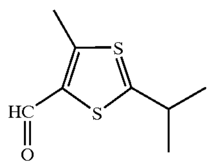 | Example 27 | Quantitative yield; used per se |
| 58 | 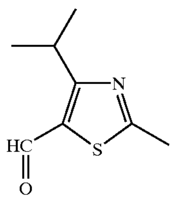 | Example 25 | Quantitative yield; used per se |

Example 59

Preparation of an Approximately 2:1 Mixture of (5-Formyl-4-trifluoromethylthiazol-2-yl)carbamic Acid, 1,1-Dimethylethyl Ester and (5-Ethoxycarbonyl-4-trifluoromethylthiazol-2-yl)carbamic Acid, 1,1-Dimethylethyl Ester

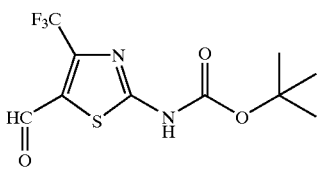

Manganese dioxide (1.0 g, 11.5 mmol) was added to a stirred solution of crude (5-hydroxymethyl-4-trifluoromethylthiazol-2-yl)carbamic acid, 1,1-dimethylethyl ester (Example 29; 480 mg, 1.6 mmol) in acetonitrile (20 mL). The mixture was allowed to stir at room temperature for 1 h and then a further portion of manganese dioxide (0.50 g, 5.75 mmol) was added. The reaction mixture was stirred at room temperature for 1 h, it then it was filtered through Celite® and the filter pad was washed with acetonitrile. The filtrate was evaporated to dryness to give (5-formyl-4-trifluoromethylthiazol-2-yl) carbamic acid, 1,1-dimethylethyl ester (480 mg). Examination of the crude product by NMR indicated the presence of approximately 33% of (5-ethoxycarbonyl-4-trifluoromethylthiazol-2-yl)carbamic acid, 1,1-dimethylethyl ester. This mixture was used without further purification in a subsequent transformation.

Example 60

Preparation of 2-Ethyl-4-methylthiazole-5-carboxaldehyde

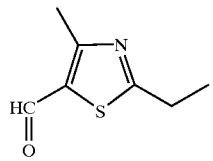

Manganese dioxide (9.50 g, 109.3 mmol) was added to a solution of 2-ethyl-4-methylthiazole-5-methanol (Example 30; 0.86 g, 5.5 mmol) in dichloromethane (200 mL). The mixture was allowed to stir at room temperature for 72 h and then was filtered through Celite®. The filter cake was washed with dichloromethane (200 mL) and the combined filtrates were concentrated to give 2-ethyl-4-methylthiazole-5-carboxaldehyde (0.48 g, 57% yield) as a colorless oil.

Also prepared by in an analogous fashion were:

| Example | Structure | Starting Material | Comments |
|---|---|---|---|
| 61 | 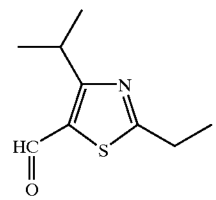 | Example 28 | 81% yield |
| 62 | 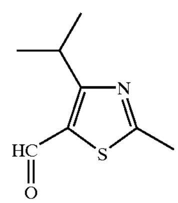 | Example 25 | |
| 63 | 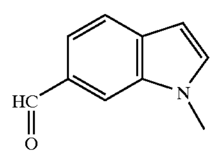 | Example 35 | 78% yield |

Example 64

Preparation of 6-Formyl-1H-indole-1-carboxylic Acid, 1,1-Dimethylethyl Ester

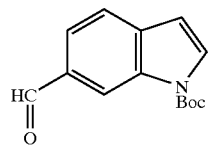

A solution of 6-hydroxymethyl-1H-indole-1-carboxylic acid, 1,1-dimethylethyl ester (Example 31; 5.10 g, 20.6 mmol) and o-iodoxybenzoic acid (prepared by the literature procedure: Frigerio, M.; Santagostino, M. *Tetrahedron Lett.*

1994, 35, 8019–8022; 8.00 g, 28.6 mmol) in dimethylsulfoxide (25 mL) was stirred at room temperature for 4 h. Water (200 mL) was added and the solution was extracted with dichloromethane (3×100 mL). The combined extracts were washed with brine (200 mL), dried (MgSO$_4$), filtered, evaporated in vacuo. The residual material was chromatographed over silica gel (20–30% ethyl acetate/hexanes) to give 6-formyl-1H-indole-1-carboxylic acid, 1,1-dimethylethyl ester (2.14 g, 42% yield) as a colorless solid.

Example 65

Preparation of 4-Formylpiperidine-1-carboxylic Acid, 1,1-Dimethylethyl Ester

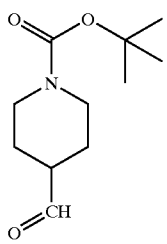

To a cooled (0° C.) solution of 4-hydroxymethyl-piperidine-1-carboxylic acid, 1,1-dimethylethyl ester (Example 36; 0.82 g, 3.8. mmol) and triethylamine (2.75 mL, 19.76 mmol) in dichloromethane (20 mL) was added sulfur trioxide pyridine complex (2.42 g, 15.2 mmol) in dimethylsulfoxide (10 mL) in three portions and the reaction was stirred at 0° C. for 3.5 h. Examination of the reaction by tlc indicated that some starting alcohol remained, so an additional quantity of sulfur trioxide pyridine complex (1.21 g, 7.6 mmol) in dimethylsulfoxide (5 mL) was added and the reaction was allowed to proceed for another 2 h at 0° C. The reaction mixture was partitioned between saturated sodium bicarbonate solution (60 mL) and diethyl ether/hexane (1:2, 125 mL) and the separated aqueous phase was re-extracted with diethyl ether/hexane (1:2, 2×50 mL). The combined organic extracts were washed with a 1M sodium dihydrogen phosphate solution (50 mL) and with brine (50 mL), then were dried (MgSO$_4$), filtered and evaporated in vacuo. The resulting residual material was chromatographed over silica gel (25% ethyl acetate/petroleum ether) to give 4-formylpiperidine-1-carboxylic acid, 1,1-dimethylethyl ester (0.492 g, 61% yield) as a colorless oil.

Also prepared in a similar manner were:

| Example | Structure | Starting Material | Comments |
|---|---|---|---|
| 66 | (structure) | Example 37 | chromatographed over silica gel, (25% ethyl acetate in petroleum ether); colorless solid; 93.3% yield |
| 67 | 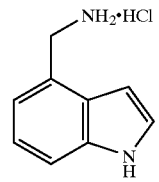 | Example 38 | chromatographed over silica gel, (20% ethyl acetate in petroleum ether); colorless oil; 77% yield |

Example 68

Preparation of 1H-Indole-4-methanamine Hydrochloride

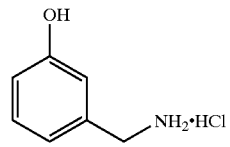

A. 4-(Azidomethyl)-1H-indole

To a solution of 1H-indole-4-methanol (Example 17; 71 mg, 0.48 mmol) in tetrahydrofuran (1 mL) at 0° C. was added diphenylphosphoryl azide (156 μL, 0.72 mmol) followed by 1,8-diazabicyclo[5.4.0]undec-7-ene (87.4 μL, 0.58 mmol). The cooling bath was removed and the solution was allowed to stir for 5 h. After the solvent was evaporated, ethyl acetate was added and the solution was washed with 1N hydrochloric acid solution and brine, dried (MgSO$_4$), filtered and concentrated. The residual material was chromatographed over silica gel (12% ethyl acetateihexanes) to give 4-(azidomethyl)-1H-indole (1.496 g, 88% yield) as an oil.

B. 1H-Indole-4-methanamine hydrochloride

A solution of 4-(azidomethyl)-1H-indole (628 mg, 3.65 mmol) in tetrahydrofuran (10 mL) at 25° C. was added triphenylphosphine (1.05 g, 3.65 mmol) and the reaction was stirred 24 h. Water (1.0 mL) was then added and after the reaction was stirred at 25° C. for a further 24 h, the solvents were evaporated under reduced pressure. The residue was diluted ethyl acetate (20 mL) and washed with 0.5N hydrochloric acid solution (1×8 mL). The acid layer was freeze dried to give 1H-indole-4-methanamine hydrochloride (510 mg, 77% yield) as an off-white solid.

Example 69

Preparation of 3-Hydroxybenzylamine Hydrochloride

To a solution of 3-cyanophenol (30 g, 0.252 mol) in ethanol (150 mL) at 25° C. under an atmosphere of nitrogen, was added 10% palladium on carbon (3 g) ) followed by concentrated hydrochloric acid solution (23 mL, 0.277 mol). The reaction mixture was hydrogenated at 50 psi in a Parr apparatus for 2.5 h and was then filtered over Celite® and washed well with ethanol (100 mL). The solvents were concentrated under reduced pressure and the resulting solid was placed under vacuum for 1 h. The solid was dissolved in 150 mL of hot ethanol, filtered and crystallized by adding diethyl ether. The solids were collected by filtration, washed well with diethyl ether and dried under vacuum 24 h to give 3-hydroxybenzylamine hydrochloride (28.88 g, 71% yield) as a colorless solid.

Example 70

Preparation of 3-[[(1,1-Dimethylethyl)dimethylsilyl] oxy]benzene Methanamine

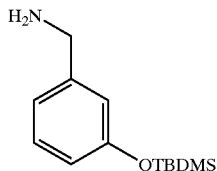

A. 3-[[(1,1-Dimethylethyl)dimethylsilyl]oxy]benzonitrile

To a solution of 3-cyanophenol (5 g, 42 mmol) and imidazole (6.3 g, 92 mmol) in N,N-dimethylformamide (85 mL) at 0° C. was added (1,1-dimethylethyl) dimethylsilylchloride (7.6 g, 50 mmol). After stirring 10 min, the reaction was warmed to room temperature and stirred for 24 h. The solvent was removed in vacuo and the residual oil was partitioned between water (100 mL) and diethyl ether (300 mL). The separated diethyl ether layer was washed with water (3×100 mL) and brine (100 mL), then was dried (MgSO$_4$) and filtered. The filtrate was evaporated under reduced pressure and the residue was flash chromatographed (silica gel, 50% ethyl acetate in petroleum ether) to yield 3-[[(1,1-dimethylethyl)dimethylsilyl]oxy] benzonitrile (9 g, 92% yield) as an oil.

B. 3-[[(1,1-Dimethylethyl)dimethylsilyl]oxy]benzenemethanamine.

Under an atmosphere of nitrogen, 10% palladium on carbon (250 mg) was added to a solution of 3-[[(1,1-dimethylethyl)dimethylsilyl]oxy]benzonitrile (1 g, 4.3 mmol) in methanol (25 mL) at 25 ° C. The reaction mixture was hydrogenated at 50 psi in a Parr apparatus for 3 h, then the reaction mixture was filtered through Celite® and the filter cake was washed well with methanol (50 mL). The combined filtrates were evaporated under reduced pressure and the residue was dried to constant weight under vacuum to give 3-[[(1,1-dimethylethyl)dimethylsilyl]oxy] benzenemethanamine (950 mg, 95% yield) as an oil.

Example 71

Preparation of 1H-Indole-6-methanamine

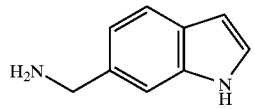

A mixture of 1H-indole-6-carbonitrile (prepared by the literature procedure: Batcho, A. D.; Leimgruber, W. *Organic Syntheses* 1985, 63, 214–225; 1.50 g, 10.6 mmol), Raney an nickel and concentrated aqueous ammonia (4 mL) in ethanol (50 mL) was hydrogenated at atmospheric pressure overnight. The mixture was filtered through Celite® and the filter cake was washed thoroughly with ethanol, while taking care not to allow the catalyst to become dry. The combined filtrates were concentrated to give 1H-indole-6-methanamine (1.50 g, 97% yield).

Example 72

Preparation of 3-Chloro-4-(methoxycarbonyl) benzoic Acid

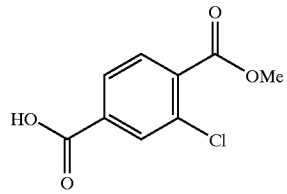

To a 2 L round-bottom flask, equipped with a mechanical stirrer, was charged 2-chloro-1,4-benzenedicarboxylic acid dimethyl ester (25.15 g, 0.11 mol), methanol (300 mL) and tetrahydrofuran (300 mL). Over 10 min, a solution of lithium hydroxide monohydrate (4.62 g, 0.11 mol) in water (200 mL) was added. After the reaction had proceeded at ambient temperature overnight, the solution was concentrated in vacuo to about 150 mL and then diluted with water (200 mL). The precipitated solid was filtered off and washed with water (2×20 mL) to give the recovered starting material, 2-chloro-1,4-benzenedicarboxylic acid dimethyl ester (1.8 g), as shiny platelets. The combined filtrates were stirred while 1N hydrochloric acid (112 mL, 0.112 mol) was added. The resulting solid was filtered off, washed with water (2×50 mL) and air dried. The solid was dissolved in methanol (300 mL) and warmed to about 45° C., then to the stirred solution, water was added to just before the cloud point. After the solution was left at room temperature overnight, the resulting colorless solid that had formed was filtered off, washed in turn with a cold mixture of methanol-water (1:2; 30 mL) and cold water (30 mL). The solid was recrystallized once more from methanol-water as described above and dried, to give 3-chloro-4-(methoxycarbonyl) benzoic acid (13.1 g, 55.5% yield) as colorless needles.

Example 73

Preparation of 2-Chloro-4-[[(2,5-dioxo-1-pyrrolidinyl)oxy]carbonyl]benzoic Acid Methyl Ester

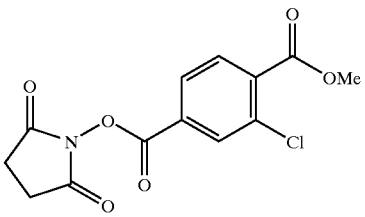

A 3-neck 1 L round-bottom flask equipped with a magnetic stirrer, ice cooling bath, thermometer and an argon inlet tube was set up and charged with 3-chloro-4-(methoxycarbonyl)benzoic acid (Example 72; 21.5 g, 0.1 mol) in tetrahydrofuran (250 mL). The solution was cooled to 10° C. under argon and was treated in succession with N-hydroxysuccinimide (12.66 g, 0.11 mol) and N,N-dicyclohexylcarbodiimide (21.66 g, 0.105 mol). These reagents were washed into the reaction flask with additional tetrahydrofuran (100 mL). A precipitate started to form immediately. The cooling bath was removed and the reaction mixture was stirred at ambient temperature overnight, then was diluted with diethyl ether (400 mL) and stirred for another 30 min. The precipitate was collected by filtration and the filter cake was washed with diethyl ether (3×50 mL). The dried solids (N,N-dicyclohexylurea) weighed 22.2 g (>99% of theory). The combined filtrates were diluted with hexane (100 mL) then were transferred to a 2 L separatory funnel and were washed in turn with cold saturated sodium bicarbonate solution (150 mL) and brine (150 mL). Each aqueous layer was back-extracted in turn with diethyl ether (200 mL), then the combined organic extracts were dried ($MgSO_4$) and evaporated to give crude 2-chloro-4-[[(2,5-dioxo-1-pyrrolidinyl)oxy]carbonyl]benzoic acid methyl ester (~35 g) as a colorless solid. This material was used directly in the next step without purification.

Example 74

Preparation of 2-Chloro-4-[[(3-hydroxybenzyl)amino]carbonyl]benzoic Acid Methyl Ester

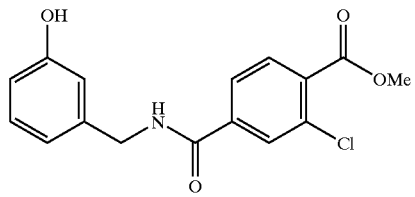

Crude 2-chloro-4-[[(2,5-dioxo-1-pyrrolidinyl)oxy]carbonyl]benzoic acid methyl ester (Example 73; ~35 g, 0.1 mol) was charged to a 1 L round bottom flask equipped with a magnetic stirrer, ice cooling bath and a argon inlet tube, using dimethylformamide (350 mL) to complete the transfer. The mixture was cooled to about 10° C., then with stirring in an argon atmosphere, 3-hydroxybenzylamine hydrochloride salt (Example 69; 18.35 g, 0.115 mol) and triethylamine (35 mL, 0.25 mol) were added in rapid succession. A precipitate began to form immediately. After the reaction was stirred at ambient temperature overnight, the volatiles were removed under reduced pressure (<0.5 mm). The oily residue was taken up in ethyl acetate (600 mL) and washed in turn with 0.5N hydrochloric acid (400 mL), brine (300 mL), saturated sodium bicarbonate solution (2×300 mL) and brine (300 mL). Each aqueous layer was back-extracted in turn with ethyl acetate (2×300 mL), then the combined organic extracts were dried ($MgSO_4$) and evaporated to give crude 2-chloro-4-[[(3-hydroxybenzyl)amino]carbonyl]benzoic acid methyl ester (~32 g) as an off-white solid.

Example 75

Preparation of 2-Chloro-4-[[(3-hydroxybenzyl)amino]carbonyl]benzoic Acid

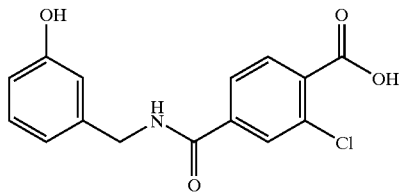

In a 2 L RB flask equipped with a magnetic stirrer, a slurry of crude 2-chloro-4-[[(3-hydroxybenzyl)amino]carbonyl] benzoic acid methyl ester (Example 74; 32 g, 0.10 mol) in water (300 mL) was treated with 1N sodium hydroxide solution (300 mL, 0.3 mol). Most of the solids quickly dissolved and the solution was stirred at room temperature overnight. The mixture was filtered through Celite® to remove undissolved solids (residual N,N-dicyclohexylurea) and the filter cake was washed with water (2×30 mL). The combined filtrates were transferred to a separatory funnel and extracted with diethyl ether (2×300 mL). Each diethyl ether extract was back-washed in turn with brine (50 mL). The combined aqueous phases were stirred as they were acidified by the addition of 6N hydrochloric acid (55 mL, 0.33 mol). The resulting mixture was stirred overnight at room temperature, then the precipitated solids were collected by filtration and the filter cake was washed with water (2×60 mL). The slightly off-white solid was dried in vacuo over $P_2O_5$ then was dissolved in warm ethyl acetate (400 mL) and the solution was treated with charcoal (4 g) and filtered through a bed of Celite®. The filter cake was washed with ethyl acetate (2×40 mL). The combined filtrates were concentrated to about 250 mL then sufficient hexane was added to the hot stirred solution to produce a permanent cloud point. The mixture was cooled to room temperature, then was stored at −20° C. overnight. The solids were collected by filtration and were washed with hexane (2×50 mL) to give 2-chloro-4-[[(3-hydroxybenzyl)amino] carbonyl]benzoic acid, mp 167–1690° C. (27.1 g, 88.6%) from 3-chloro-4-(methoxycarbonyl)benzoic acid].

Example 76

Preparation of 3-Bromo-4-(methoxycarbonyl)benzoic Acid

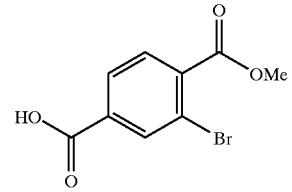

Potassium hydroxide (2.87 g, 51 mmol) was added to a solution of 2-bromo-1,4-benzenedicarboxylic acid, dimethyl ester (14 g, 51 mmol) in methanol (50 mL) at 25° C. The reaction mixture was stirred at 25° C. for 24 h and then at 50° C. for 3 h. The solvent was concentrated under reduced pressure and the residue was diluted with water (100 mL) and extracted with ethyl acetate (2×200 mL). The water layer was acidified to pH 2 with 2N hydrochloric acid solution and extracted with ethyl acetate (2×200 mL). The combined organic layers were washed with brine (100 mL), dried (MgSO$_4$), filtered and concentrated in vacuo. The resulting solid was boiled in toluene (100 mL) and the insolubles were removed by filtration. The filtrate was concentrated to dryness under reduced pressure and the resulting solid was flash chromatographed (silica gel, 50% ethyl acetate in petroleum ether with 1% acetic acid) to give 3-bromo-4-(methoxycarbonyl)benzoic acid (3.28 g, 24% yield) as a colorless solid.

Example 77

Preparation of 2-Bromo-4-[[(2,5-dioxo-1-pyrrolidinyl)oxy]carbonyl]benzoic Acid Methyl Ester

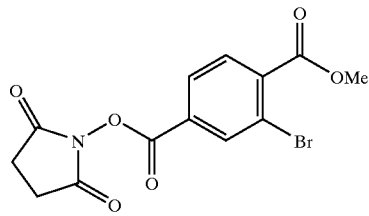

A solution of 3-bromo-4-(methoxycarbonyl)benzoic acid (Example 76; 1.60 g, 6.2 mmol) in tetrahydrofuran (30 mL) was cooled to 10° C. and N-hydroxysuccinimide (781 mg, 6.8 mmol) and 1-(3-dimethylaminopropyl)-3-ethylcarbodiimide hydrochloride (1.20 g, 6.5 mmol) were added. The solution was allowed to stir at room temperature overnight, then water was added and the solution was concentrated in vacuo to remove tetrahydrofuran. The mixture was extracted with ethyl acetate and the extracts were dried (MgSO$_4$), filtered and evaporated under reduced pressure to furnish 2-bromo-4-[[(2,5-dioxo-1-pyrrolidinyl)oxy] carbonyl]benzoic acid methyl ester (2.20 g, quantitative yield).

Example 78

Preparation of 2-Bromo-4-[[(3-hydroxybenzyl) amino]carbonyl]benzoic Acid Methyl Ester

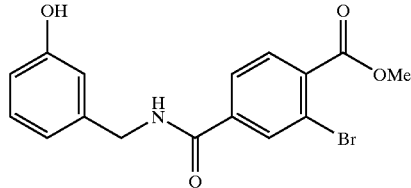

Diisopropylethylamine (8.4 mL, 48.2 mmol) was added dropwise to a cooled (~0° C.) solution of with 3-bromo-4-(methoxycarbonyl)benzoic acid (Example 76; 5.00 g, 19.3 mmol), O-(benzotriazol-1-yl)-1,1,3,3-tetramethyluronium hexafluorophosphate (7.31 g, 19.3 mmol), 3-hydroxybenzylamine hydrochloride salt (Example 69; 3.37 g, 21.2 mmol) and 1-hydroxybenzotriazole (2.6 g, 19.2 mmol) in N,N-dimethylformamide (50 mL). After the solution was allowed to stir at ~0° C. for 1 h, then at room temperature for 4 h, it was concentrated in vacuo (~1 mm) to remove most of the N,N-dimethylformamide. The residue was partitioned between ethyl acetate and 1N hydrochloric acid solution (200 mL each). The ethyl acetate layer was washed with 1N hydrochloric acid solution (2×100 mL) and the combined aqueous layers were extracted with ethyl acetate (50 mL). The combined ethyl acetate layers were washed with saturated sodium bicarbonate solution (2×100 mL) and brine, then dried (MgSO$_4$), filtered and evaporated under reduced pressure. The solid residue was crystallized from hot ethyl acetate (~60 mL) and hexanes (15 mL) to give 2-bromo-4-[[(3-hydroxybenzyl)amino]carbonyl] benzoic acid methyl ester (5.15 g, 73% yield) as colorless crystals.

Example 79

Preparation of 2-Bromo-4-[[(3-hydroxybenzyl) amino]carbonyl]benzoic Acid

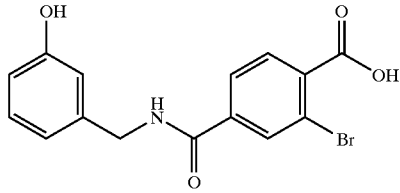

A solution of lithium hydroxide monohydrate (4.41 g, 105.1 mmol) in water (15 mL) was added to a solution of 2-bromo-4-[[(3-hydroxybenzyl)amino]carbonyl]benzoic acid methyl ester (Example 78; 15.30 g, 42.0 mmol) in tetrahydrofuran/methanol (2:1, 21 mL). The solution was concentrated under reduced pressure to remove tetrahydrofuran and methanol and the remaining aqueous solution was extracted with ethyl acetate (15 mL) and the ethyl acetate extract was discarded. The aqueous layer was acidified with 1N hydrochloric acid solution (75 mL) and extracted with ethyl acetate (2×50 mL). The combined organic layers were washed with brine (15 mL), dried (MgSO$_4$), filtered and evaporated to afford 2-bromo-4-[[(3-hydroxybenzyl)amino] carbonyl]benzoic acid (15.1 g, quantitative yield) which was used in a subsequent step without further purification.

Example 80

Preparation of 2-Chloro-4-[[[(1H-indol-6-yl)methyl] amino]carbonyl]benzoic Acid Methyl Ester

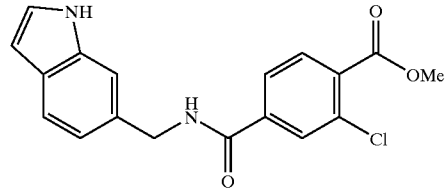

1H-Indole-6-methanamine (Example 71; 0.9 g, 6.2 mmol) was added to a cooled (~0° C.) solution of 2-chloro-4-[[(2, 5-dioxo-1-pyrrolidinyl)oxy]carbonyl]benzoic acid methyl ester (Example 73; 2.20 g, 7.1 mmol) in N,N-dimethylformamide and the solution was allowed to stir at room temperature overnight. The solvent was evaporated under high vacuum and ethyl acetate was added. The solution was washed in turn with 0.5N lo hydrochloric acid solution, saturated sodium bicarbonate solution and brine, then dried (MgSO$_4$), filtered and evaporated in vacuo to afford 2-chloro-4-[[[(1H-indol-6-yl)methyl]amino] carbonyl]benzoic acid methyl ester (2.00 g, 94% yield).

Also prepared by this route was

| Example | Structure | Starting Materials | Comments |
|---|---|---|---|
| 81 | 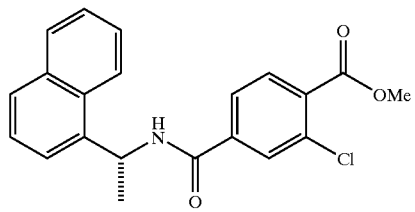 | Example 77 and Example 71 | Used equimolar amts starting materials. Product purified by chromatography, yield 79% |

Example 82

Preparation of (R)-2-Chloro-4-[[1-(naphthalen-1-yl)ethylamino]carbonyl]benzoic Acid Methyl Ester N,N-dicyclohexylcarbodiimide (5.12 g, 24.84 mmol) and 1-hydroxybenzotriazole (3.08 g, 24.84 mol) were added to a solution of 3-chloro-4-(methoxycarbonyl)benzoic acid (Example 72; 5.0 g, 23.7 mmol) and (R)-(+)-1-(naphthalen-1-yl)ethylamine (3.45 g, 20.7 mmol) in N,N-dimethylformamide (10 mL). The solution was stirred for 6 h at room temperature, then after the volatiles were removed in vacuo, the residual material was partitioned between ethyl acetate and water. The separated aqueous phase was extracted with three portions of ethyl acetate, then the combined ethyl acetate layers were washed with brine, dried (Na$_2$SO$_4$) and evaporated under reduced pressure. The resulting colorless solid was crystallized from dichloromethane/hexane to yield 8.85 g of (R)-2-chloro-4-[[1-(naphthalen-1-yl)ethylamino]carbonyl]benzoic acid methyl ester (over theory; material 94% pure by analytical HPLC).

Example 83

Preparation of 2-Bromo-4-[[[(1H-indol-4-yl)methyl]amino]carbonyl]benzoic Acid Methyl Ester Diisopropylethylamine (2.3 mL, 13.2 mmol) was added dropwise to a solution of 3-bromo-4-(methoxycarbonyl)benzoic acid (Example 76; 861 mg, 3.32 mmol), O-(benzotriazol-1-yl)-1,1,3,3-tetramethyluronium hexafluorophosphate (1.39 g, 3.65 mmol), 1H-indole-4-methanamine hydrochloride salt (Example 68; 528 mg, 3.98 mmol) and 1-hydroxybenzotriazole (493 mg, 3.65 mmol) in N,N-dimethylformamide (6.5 mL) at 0° C. The solution was allowed to warm to room temperature and then was stirred for 24 h. After the reaction mixture was concentrated under vacuum to remove most of the N,N-dimethylformamide, the residue was diluted with ethyl acetate (50 mL) and washed with 1N hydrochloric acid solution (10 mL), water (10 mL), saturated aqueous sodium bicarbonate solution (10 mL) and brine (10 mL). The organic layer was dried (MgSO$_4$), filtered, evaporated and the residue was chromatographed (silica gel, 25–35% ethyl acetate in petroleum ether) to provide 2-bromo-4-[[[(1H-indol-4-yl)methyl]amino]carbonyl]benzoic acid methyl ester (900 mg, 70% yield) as an off-white solid.

Also prepared by this method were the following:

| Example | Structure | Starting Materials | Comments |
|---|---|---|---|
| 84 | 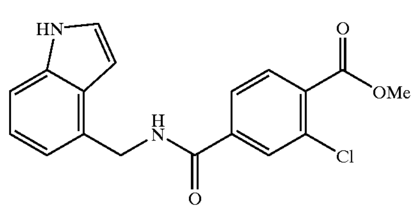 | Example 68 and Example 72 | reaction time 12 days |

-continued

| Example | Structure | Starting Materials | Comments |
|---|---|---|---|
| 85 | 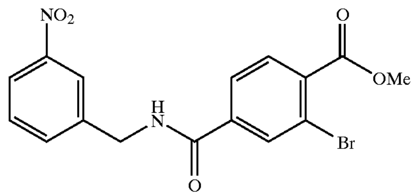 | 3-nitrobenzylamine and Example 76 | reaction time 6 h; chromatography over silica gel, 30–35% ethyl acetate in petroleum ether; Colorless solid; 82% yield |
| 86 | 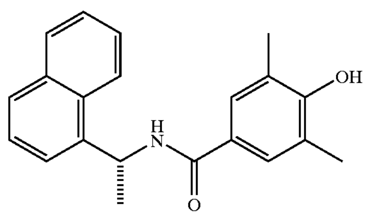 | 4-hydroxy-3,5-dimethylbenzoic acid and (R)-(+)-1-(naphthalen-1-yl)ethylamine | reaction time 24 h; chromatography over silica gel, 25% ethyl acetate in petroleum ether; colorless solid; 56% yield |

Example 87

Preparation of 2-Bromo-4-[[(3-aminobenzyl)amino]carbonyl]benzoic Acid Methyl Ester

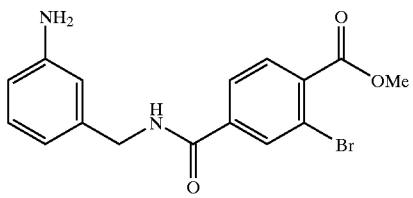

Iron powder (135 mg, 2.4 mmol) was added to a suspension of 2-bromo-4-[[(3-nitrobenzyl)amino]carbonyl]benzoic acid methyl ester (Example 85; 125 mg, 3.18 mmol) in water (530 μL) and acetic acid (111 μL) at 25° C. The reaction was heated to reflux for 30 min and then cooled to 25° C. The suspension was diluted with water (20 mL), stirred 15 min, filtered over Celite® and washed well with water (100 mL). The filtrate was washed with ethyl acetate (50 mL) followed by ethyl acetate containing 2% methanol (50 mL). The organic layers were combined, dried (MgSO$_4$), filtered and concentrated. The residue was diluted with 10% methanol in dichloromethane and stirred with Celite®. After 1 h, the suspension was filtered and washed well with 10% methanol in dichloromethane and the combined filtrates were evaporated to dryness to give 2-bromo-4-[[(3-aminobenzyl)amino]carbonyl]benzoic acid methyl ester (100 mg, 87% yield) as an off-white solid.

Example 88

Preparation of 2-Bromo-4-[[[3-[[(1,1-dimethylethoxy)carbonyl]amino]benzyl]amino]carbonyl]benzoic Acid Methyl Ester

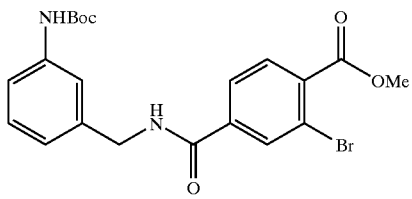

To a solution of 2-bromo-4-[[(3-aminobenzyl)amino]carbonyl]benzoic acid methyl ester (Example 87; 420 mg, 1.16 mmol) in 1,4-dioxane (6.5 mL) at 25° C. was added a solution of sodium carbonate (135 mg, 1.3 mmol) in water (2.1 mL) followed by di-tert-butyl dicarbonate (304 mg, 1.39 mmol). After stirring 24 h, the reaction mixture was diluted with water (200 mL) and washed with dichloromethane (300 mL). The organic layer was separated and washed with 10% acetic acid in water (100 mL), water (50 ML) and brine (50 mL). The organic layer was dried (MgSO$_4$), filtered, evaporated and the residue was chromatographed (silica gel, 25–35% ethyl acetate in petroleum ether) to give 2-bromo-4-[[[3-[[(1,1-dimethylethoxy)carbonyl]amino]benzyl]amino]carbonyl]benzoic acid methyl ester (499 mg, 93% yield) as a colorless foam.

Example 89

Preparation of 4-(Methoxycarbonyl)-3-methylbenzoic Acid

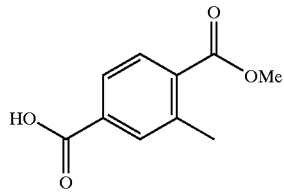

A mixture of 4-bromo-2-methylbenzoic acid methyl ester (prepared by the literature method: Keuning, K. J.; Evenhuis, N. *Recueil Trav. Chim. Pays-Bas* 1935, 54, 73–75; 12.21 g, 53.3 mmol), triethylamine (16.00 g, 158.1 mmol), palladium(II) acetate (0.28 g, 1.25 mmol), bis(diphenylphosphino)propane (0.52 g, 1.26 mmol), water (16.00 g, 888.1 mmol) and acetonitrile (40 mL) was pressurized to 40 pounds per square inch with carbon monoxide and the pressure was released. After six such cycles, the bottle was pressurized again and the contents were stirred at 83° C. for 3 h. The reaction mixture was cooled to room temperature and depressurized. Ethyl acetate (100 mL) was added and the solution was filtered and then extracted with water (5×40 mL). The combined aqueous layers were acidified with 1N hydrochloric acid solution to pH 2 and the resulting mixture was extracted with ethyl acetate (2×100 mL). The combined organic layers were washed with brine (200 mL), dried (MgSO$_4$) and evaporated under reduced pressure to give 4-(methoxycarbonyl)-3-methylbenzoic acid as a colorless solid (4.83 g, 47% yield).

Example 90

Preparation of 4-[[(3-Hydroxybenzyl)amino]carbonyl]-2-methylbenzoic Acid

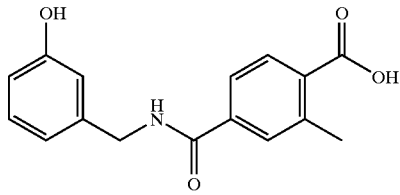

A solution of 4-(methoxycarbonyl)-3-methylbenzoic acid (Example 89; 4.83 g, 24.9 mmol) and triphenylphosphine (7.37 g, 28.1 mmol) in dichloromethane (100 mL) was cooled to ~0° C. and N-chlorosuccinimide (3.75 g, 28.1 mmol) was added portionwise. The solution was allowed to warm to room temperature and stirred for 30 min. 3-Hydroxybenzylamine (Example 69; 4.00 g, 33.0 mmol) and diisopropylethylamine (4.00 g, 30.9 mmol) were added and the solution was allowed to stir at room temperature for 72 h. The solution was washed with 1N hydrochloric acid solution, water and brine (200 mL each), dried (MgSO$_4$), filtered and evaporated to give a colorless solid (13.34 g) which contained 4-[[(3-hydroxybenzyl)amino]carbonyl]-2-methylbenzoic acid methyl ester and triphenylphosphine oxide. The solid was taken up in tetrahydrofuran/methanol (3:1; 200 mL) and a solution of lithium hydroxide monohydrate (4.00 g, 95.3 mmol) in water (50 mL) was added. The solution was stirred at room temperature for 4 h and then the solvent was evaporated under reduced pressure. The residual material was taken up in a mixture of 1N sodium hydroxide and diethyl ether (200 mL each) and the mixture was filtered to remove undissolved solids. The diethyl ether layer was discarded and the aqueous basic layer of the filtrate was acidified with conc. hydrochloric acid solution to ~pH 1. The mixture was extracted with ethyl acetate (2×100 mL) and the combined organic layers were washed with brine (200 mL), dried (MgSO$_4$), filtered and evaporated to give 4-[[(3-hydroxybenzyl)amino]carbonyl]-2-methylbenzoic acid as a colorless solid (2.40 g, 34% yield).

Example 91

Preparation of (E)-2-Chloro-4-[3-(3-hydroxyphenyl)-1-oxoprop-2-enyl]benzoic Acid, Methyl Ester

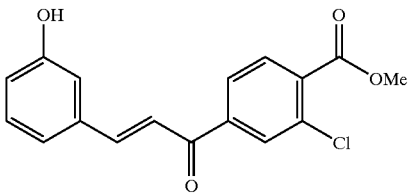

A. 2-Chloro-4-(diazoacetyl)benzoic Acid, Methyl Ester.

Oxalyl chloride (0.25 mL, 2.9 mmol) was added to a cooled (~10° C.) slurry of 3-chloro-4-(methoxycarbonyl)benzoic acid (Example 72; 430 mg, 2.0 mmol) in benzene (15 mL). A drop of N,N-dimethylformamide was added and the solution was stirred at room temperature for 3 h. The solvent was evaporated under reduced pressure and the residue was evaporated from toluene (2×25 mL) to give the acid chloride as a colorless waxy solid. A solution of the acid chloride in diethyl ether (20 mL) was treated with ethereal diazomethane until the yellow color persisted. After the reaction mixture was left overnight at room temperature, the solvents were removed in vacuo and the solid residue was triturated with hexanes, then was collected by filtration to furnish 2-chloro-4-(diazoacetyl)benzoic acid, methyl ester (410 mg, 86% yield) as bright yellow crystals.

B. 4-(Bromoacetyl)-2-chlorobenzoic Acid, Methyl Ester.

Hydrogen bromide gas was bubbled through a suspension of 2-chloro-4-(diazoacetyl)benzoic acid, methyl ester (400 mg, 1.7 mmol) in diethyl ether (30 mL) for 10 min. The solvent was evaporated and the residue was triturated with diethyl ether/hexane and filtered to give 4-(bromoacetyl)-2-chlorobenzoic acid, methyl ester (385 mg, 79% yield) as a colorless solid.

C. [2-[2-Chloro-4-(methoxycarbonyl)phenyl]-2-oxoethyl]triphenylphosphonium Bromide.

A mixture of 4-(bromoacetyl)-2-chlorobenzoic acid, methyl ester (372 mg, 1.3 mmol), triphenylphosphine (336 mg, 1.3 mmol) and pyridine (1 drop) in acetonitrile (5 mL) was stirred at room temperature for 3 h. The solvent was evaporated and the residue was triturated with tetrahydrofuran to form a granular solid. Diethyl ether was added, then the mixture was filtered and the collected solids were washed with diethyl ether to give [2-[2-chloro-4-(methoxycarbonyl)phenyl]-2-oxoethyl]triphenylphosphonium bromide (641 mg, 90% yield) as a colorless solid.

D. (E)-2-Chloro-4-[3-(3-hydroxyphenyl)-1-oxoprop-2-en-1-yl]benzoic Acid Methyl Ester.

Sodium carbonate (215 mg, 2.0 mmol) was added to [2-[2-chloro-4-(methoxycarbonyl)phenyl]-2-oxoethyl]

triphenylphosphonium bromide (620 mg, 1.1 mmol), benzene (5 mL) and water (5 mL) in a separatory funnel. The mixture was shaken until the solids dissolved (about 10 min). The aqueous layer was separated and extracted with benzene. The organic layers were washed with brine, combined, dried (MgSO$_4$) and concentrated to dryness. Benzene (4 mL) was added, followed by 3-hydroxybenzaldehyde (137 mg, 1.1 mmol) and the solution was heated at reflux for 35 h. The solution was allowed to cool, hexane (3 mL) was added and the solid was filtered off, washed with benzene/hexane and then hexane to provide (E)-2-chloro-4-[3-(3-hydroxyphenyl)-1-oxoprop-2-en-1-yl]benzoic acid methyl ester (260 mg, 73% yield) as a yellow solid.

Example 92

Preparation of rac.-(E)-2-Chloro-4-[1-hydroxy-3-(3-hydroxyphenyl)prop-2-en-1-yl]benzoic Acid Methyl Ester

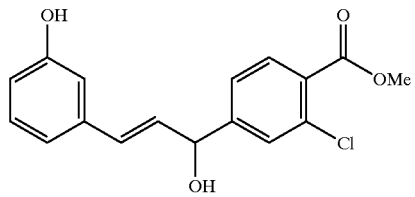

Sodium borohydride (25 mg, 0.66 mmol) was added to a solution of (E)-2-chloro-4-[3-(3-hydroxyphenyl)-1-oxoprop-2-en-1-yl]benzoic acid methyl ester (Example 91; 316 mg, 1 mmol) in methanol (3 mL). The solution was stirred at room temperature for 3 h, then acetone (1 mL) was added and the solution was stirred for a further 10 min. The solvent was evaporated, ethyl acetate (15 mL) was added and the solution was washed with 0.5N hydrochloric acid solution (10 mL) and brine. Each of the aqueous layers was extracted in turn with ethyl acetate (10 mL). The combined organic layers were dried (MgSO$_4$), filtered, evaporated and the resulting solid was triturated with diethyl ether to furnish rac.-(E)-2-chloro-4-[1-hydroxy-3-(3-hydroxyphenyl)prop-2-en-1-yl]benzoic acid methyl ester (310 mg, 97% yield) as a colorless solid.

Example 93

Preparation of rac.-2-Chloro-4-[1-hydroxy-3-(3-hydroxyphenyl)prop-2-en-1-yl]benzoic Acid

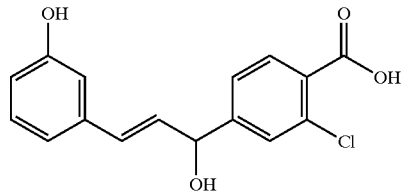

An aqueous solution of sodium hydroxide (1N, 3 mL, 3 mmol) was added to a solution of 2-chloro-4-[1-hydroxy-3-(3-hydroxyphenyl)prop-2-en-1-yl]benzoic acid methyl ester (Example 92; 310 mg, 0.97 mmol) in methanol/tetrahydrofuran (1:1; 6 mL). The solution was stirred at room temperature overnight and then evaporated to dryness. Water (4 mL) was added and the solution was acidified with 1N hydrochloric acid solution (3.3 mL). The mixture was stirred at room temperature for 1 h, then the solid was filtered off, washed with water and dried to afford 2-chloro-4-[1-hydroxy-3-(3-hydroxyphenyl)prop-2-en-1-yl]benzoic acid (243 mg, 82% yield) as an off-white solid.

Example 94

Preparation of 2-Chloro-4-[3-(3-hydroxyphenyl)-1-oxopropan-1-yl]benzoic Acid, Methyl Ester and rac.-2-Chloro-4-[1-hydroxy-3-(3-hydroxyphenyl)propan-1-yl]benzoic Acid, Methyl Ester

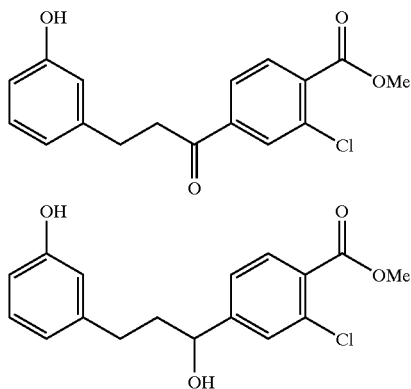

A mixture (E)-2-chloro-4-[3-(3-hydroxyphenyl)-1-oxoprop-2-en-1-yl]benzoic acid methyl ester (Example 91; 250 mg, 0.8 mmol) and 10% palladium-on-charcoal (25 mg) in ethyl acetate (5 mL) was hydrogenated at atmospheric pressure for 90 min. The reaction mixture was filtered through Celite® and the filter cake was washed with ethyl acetate. The solvent was evaporated under reduced pressure and the residue was then chromatographed over silica gel (20–50% ethyl acetate/hexanes) to give 2-chloro-4-[3-(3-hydroxyphenyl)-1-oxopropan-1-yl]benzoic acid, methyl ester (160 mg, 64% yield) and rac.-2-chloro-4-[1-hydroxy-3-(3-hydroxyphenyl)propan-1-yl]benzoic acid, methyl ester (65 mg, 26% yield). The alcohol was obtained as a racemic mixture and was not resolved.

Example 95

Preparation of 2-Chloro-4-[3-(3-hydroxyphenyl)-1-oxopropan-1-yl]benzoic Acid

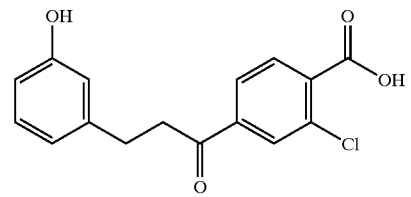

A mixture of 2-chloro-4-[3-(3-hydroxyphenyl)-1-oxopropan-1-yl]benzoic acid, methyl ester (Example 94; 2.1 g, 6.6 mmol) and 1N sodium hydroxide solution was stirred for 4 h at room temperature. The solution was filtered through Celite and the filter cake was washed with water (5 mL). 1N hydrochloric acid solution (22 mL) was added to the stirred filtrate and the resulting mixture was stirred for 2 h and then filtered. The solid was washed with water, dried and crystallized from ether/hexane to afford 2-chloro-4-[3-

(3-hydroxyphenyl)-1-oxopropan-1-yl]benzoic acid (1.59 g, 79% yield) as an off-white solid.

Example 96

Preparation of rac.-2-Chloro-4-[1-hydroxy-3-(3-hydroxyphenyl)propan-1-yl]benzoic Acid

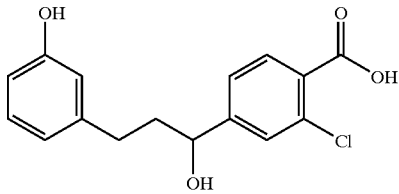

This compound was prepared in 90% yield from rac.-2-chloro-4-[1-hydroxy-3-(3-hydroxyphenyl)propan-1-yl] benzoic acid, methyl ester (Example 94) by the procedure described for 2-chloro-4-[3-(3-hydroxyphenyl)-1-oxopropan-1-yl]benzoic acid (Example 95). The product was a racemic mixture and was not resolved.

Example 97

Preparation of 3,5-Dichloro-4-(methoxycarbonyl) benzoic Acid

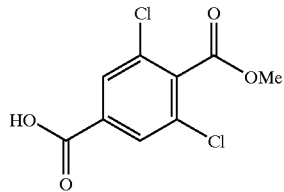

N-Chlorosuccinimide (60.00 g, 449.3 mmol) was added carefully to a solution of 2-aminoterephthalic acid dimethyl ester (50.00 g, 239 mmol) at 60° C. and the solution was then heated to 80° C. for 6 h. The reaction mixture was allowed to stand at room temperature for 4 days and then the solvent was evaporated. Diethyl ether (500 mL) was added and the mixture was washed with 1N sodium hydroxide solution (200 mL). The aqueous layer was extracted with diethyl ether (100 mL) and the combined organic layers were dried (MgSO₄), filtered and evaporated to give a red oil. This was triturated with boiling hexanes (4×300 mL) and the combined hexane extracts were evaporated to give a red oil (67.77 g). Tetrahydrofuran (300 mL) was added, followed by isoamyl nitrite (70 g, 597.5 mmol) (CAUTION: this reaction is exothermic and the isoamyl nitrite should be added cautiously) and the solution was heated at reflux for 2 h. The reaction mixture was allowed to stand at room temperature for 2 days, then the solvent was evaporated (using aspirator pressure at first, then 0.5 mm Hg). The residue was chromatographed over silica gel (3% ethyl acetate/hexanes) to yield a pale yellow liquid (27.56 g). The crude ester in tetrahydrofuran (100 mL) was treated with a solution of sodium hydroxide (4.20 g, 105 mmol) in water (100 mL) and the mixture was stirred at room temperature for 2 days. After the volatiles were removed in vacuo, water (80 mL) was added and the mixture was swirled at ~50° C. for 10 min to give a clear yellow-orange solution. 1N Hydrochloric acid solution (120 mL) was added with stirring and the mixture was swirled for another 15 min. The resulting solid was filtered off, dried and crystallized twice from methanol/water to furnish 3,5-dichloro-4-(methoxycarbonyl)benzoic acid (18.85 g, 32% yield) as a colorless solid.

Example 98

Preparation of 2,6-Dichloro-4-[[(3-hydroxybenzyl) amino]carbonyl]benzoic Acid

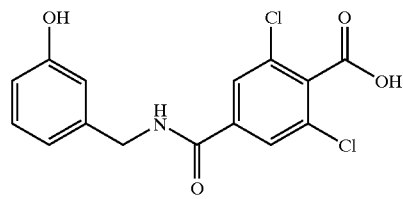

A. 2,6-Dichloro-4-[[(3-methoxybenzyl)amino]carbonyl] benzoic Acid, Methyl Ester

A solution of 3,5-dichloro-4-(methoxycarbonyl)benzoic acid (Example 97; 18.75 g, 75.3 mmol), dicyclohexylcarbodiimide (16.46 g, 79.8 mmol) and N-hydroxysuccinimide (9.59 g, 83.3 mmol) in tetrahydrofuran (200 mL) was stirred at room temperature overnight. The solid was filtered off and discarded and the filtrate was evaporated to constant weight in vacuo to give a colorless solid (29.13 g). N,N-dimethylformamide (100 mL) was added, followed by 3-methoxybenzylamine (14.20 g, 103.5 mmol) and triethylamine (14.20 g, 140.3 mmol). The solution was stirred at room temperature overnight, then the solvent was evaporated (0.5 mm Hg, ~50° C.). The residue was partitioned between 1N hydrochloric acid solution (200 mL) and dichloromethane (200 mL) and after the mixture was stirred for 10 min, the layers were allowed to separate. A colorless precipitate had formed in the dichloromethane layer. Most of the aqueous layer was decanted off and the remaining material was heated until the solid re-dissolved. Residual water was removed using a separating funnel, then after the dichloromethane solution was allowed to cool, the precipitate was filtered off and air-dried to give 2,6-dichloro-4-[[(3-methoxybenzyl)amino]carbonyl]benzoic acid, methyl ester (23.67 g, 85% yield) as a colorless solid.

B. 2,6-Dichloro-4-[[(3-hydroxybenzyl)amino]carbonyl] benzoic Acid.

A suspension of 2,6-dichloro-4-[[(3-methoxybenzyl) amino]carbonyl]benzoic acid, methyl ester (11.83 g, 32.1 mmol) in dichloromethane (400 mL) was cooled to ~−78° C. (dry ice-acetone bath) and boron tribromide (1M in dichloromethane; 100 mL, 100 mmol) was added. The mixture was stirred in the cooling bath for 3 h and then allowed to stand at room temperature for 72 h. The supernatant was decanted off and water (300 mL) was added to each of the supernatant and the residue. The mixtures were stirred at ~40° C. for 1 h and then the solids were collected by filtration, combined and air-dried to give 2,6-dichloro-4-[[(3-hydroxybenzyl) amino]carbonyl]benzoic acid (8.73 g, 80% yield) as a cream-colored solid.

Example 99

Preparation of 3-Chloro-4-hydroxy-5-methylbenzoic Acid

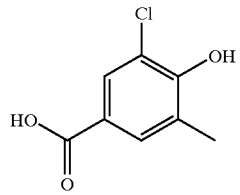

A. 3-Chloro-4-hydroxy-5-methylbenzaldehyde.

Hexamethylenetetramine (19.60 g, 139.8 mmol) was added in portions to a solution of 2-chloro-6-methylphenol (20.00 g, 117.2 mmol) in trifluoroacetic acid (200 mL). There was a slight exotherm and effervescence was noted. The reaction mixture was heated in an oil-bath at 84–86° C. for 5 h, then it was cooled and evaporated (~50° C., 0.2 mm) under reduced pressure. The residue was evaporated from hexane, then ice-water (500 mL) was added and the mixture was stirred for 20 min. Diethyl ether (100 mL) was added and the reaction was adjusted to approximately pH 5 by the careful portionwise addition of solid sodium bicarbonate (49 g). The resulting mixture was extracted with diethyl ether (2×250 mL) and the organic layers were washed with brine, dried (MgSO$_4$), filtered and concentrated to about 100 mL. The mixture was then left to crystallize over the weekend to give a solid that was collected by filtration and washed with cold diethyl ether to give 3-chloro-4-hydroxy-5-methylbenzaldehyde (6.9 g, 35% yield) as a yellow solid. The mother liquor was evaporated and dichloromethane (30 mL) was added. The yellow solid was filtered off (2.9 g, 14% yield). The remaining solution was purified by HPLC (7% ethyl acetate/hexanes) to give the aldehyde as a yellow solid (7.8 g, 39% yield). The overall yield was 17.6 g (88% yield).

B. 3-Chloro-4-hydroxy-5-methylbenzoic Acid.

A solution of sulfamic acid (11.8 g, 121.5 mmol) in water (25 mL) was added with vigorous stirring to 3-chloro-4-hydroxy-5-methylbenzaldehyde (16.00 g, 93.8 mmol) in tert-butanol (100 mL). The mixture was cooled (~12° C.) and a solution of sodium chlorite (12.00 g, 106.1 mmol) in water (25 mL) was added in 5 mL portions with vigorous stirring. The reaction was exothermic and the temperature at the end of the addition was approximately 50° C. The layers were separated and the aqueous layer was extracted with diethyl ether (2×50 mL). The organic layers were washed with brine and evaporated to dryness. Water was added and the mixture was stirred and filtered. The solid was dissolved in warm diethyl ether (250 mL) and the solution was dried, filtered, concentrated to 100 mL and cooled in the freezer (approx. −20° C.). The resulting yellow crystalline solid was filtered off and washed with cold diethyl ether to furnish 3-chloro-4-hydroxy-5-methylbenzoic acid (9.10 g, 52% yield), mp 242–244° C.

Example 100

Preparation of 3,5-Dimethyl-N-[3-[[(1,1-dimethylethyl)dimethylsilyl]oxy]benzyl]-4-hydroxybenzamide

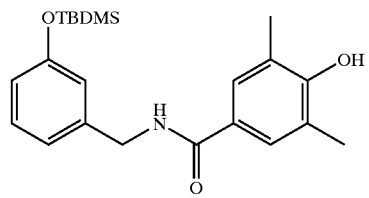

To a solution of 3,5-dimethyl-4-hydroxybenzoic acid (1.53 g, 9.2 mmol) in dichloromethane (30 mL) at 0° C. was added benzotriazol-1-yl-oxy-tris(dimethylamino) phosphonium hexafluorophosphate (4.45 g, 10 mmol), 3-[[(1,1-dimethylethyl)dimethylsilyl]oxy]benzenemethanamine (Example 70; 3.28 g, 13.8 mmol), followed by diisopropylethylamnine (4.9 mL, 27.6 mmol) slowly dropwise. After stirring 1 h, the reaction was warmed to 25° C. and stirred for 1 h. The solvent was removed under reduced pressure and the residual oil was diluted with ethyl acetate (100 mL) and washed with 1N hydrochloric acid solution (2×25 mL), saturated aqueous sodium bicarbonate solution (2×25 mL), water (25 mL) and brine (25 mL). The organic layer was dried (MgSO$_4$), filtered, evaporated and flash chromatographed (silica gel, 20–30% ethyl acetate in petroleum ether) to give 3,5-dimethyl-N-[3-[[(1,1-dimethylethyl)dimethylsilyl]oxy]benzyl]-4-hydroxybenzamide (3.1 g, 87% yield) as an off-white foam.

Also prepared by this route using the appropriate amine were the following:

| Example | Structure | Starting Materials | Purification |
|---|---|---|---|
| 101 | ![structure] | Example 99 and Example 70 | Chromatography over silica gel, 30% ethyl acetate in hexanes; pale pink solid; 59% yield |
| 102 | ![structure] | 3,5 dichloro-4-hydroxybenzoic acid and Example 70 | Chromatography over silica gel, 20–25% ethyl acetate in petroleum ether; colorless foam: 75% yield |

| Example | Structure | Starting Materials | Purification |
|---|---|---|---|
| 103 | 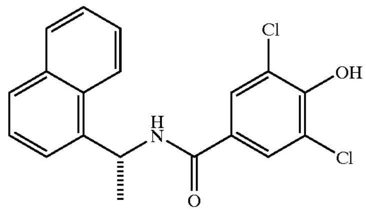 | 3,5 dichloro-4-hydroxybenzoic acid and (R)-(+)-1-(1-naphthalenyl)ethylamine | Chromatography over silica gel, 10–25% ethyl acetate in petroleum ether; colorless solid; 54% yield |
| 104 | 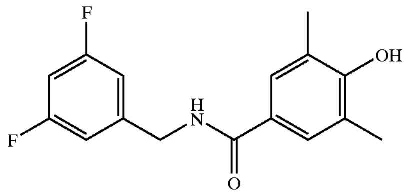 | 3,5-dimethyl-4-hydroxybenzoic acid and 3,5-difluorobenzylamine | Slurried in ethyl acetate:dichloromethane (1:9); off-white solid; 87% yield |

Example 105

Preparation of Trifluoromethanesulfonic Acid, 2,6-Dimethyl-4-[[[3-[[(1,1-dimethylethyl)dimethylsilyl]oxy]benzyl]amino]carbonyl]phenyl Ester

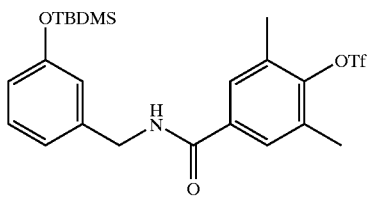

To a solution of 3,5-dimethyl-N-[3-[[(1,1-dimethylethyl)dimethylsilyl]oxy]benzyl]-4-hydroxybenzamide (Example 100; 0.5 g, 1.3 mmol) in dichloromethane (9 mL) at −78° C. was added triethylamine (0.72 mL, 5.2 mmol) followed by trifluoromethanesulfonic anhydride (0.26 mL, 1.56 mmol) slowly dropwise. After stirring 2 h, the reaction was quenched with saturated aqueous ammonium chloride (1 mL). The mixture was warmed to 25° C., diluted with ethyl acetate (70 mL) and washed with 1N hydrochloric acid solution (1×25 mL), saturated aqueous sodium bicarbonate solution (1×25 mL), water (25 mL) and brine (25 mL). The organic layer was dried (MgSO$_4$), filtered, evaporated and quickly passed over a plug of silica gel (20% ethyl acetate in petroleum ether) to give trifluoromethanesulfonic acid, 2,6-dimethyl-4-[[[3-[[(1,1-dimethylethyl)dimethylsilyl]oxy]benzyl]amino]carbonyl]phenyl ester (577 mg, 86% yield) as an oil.

Also prepared in an analogous manner were the following:

| Example | Structure | Starting Material | Comments |
|---|---|---|---|
| 106 | 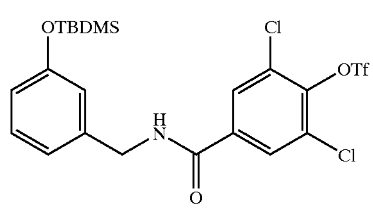 | Example 102 | Chromatography over silica gel, 10% ethyl acetate in petroleum ether; oil; 89% yield |
| 107 | 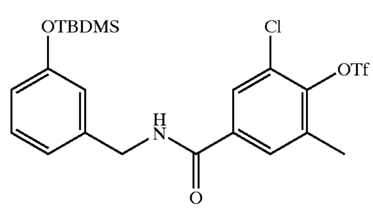 | Example 101 | Chromatography over silica gel, 20–30% ethyl acetate in hexanes; pale orange oil; 63% yield |

| Example | Structure | Starting Material | Comments |
|---|---|---|---|
| 108 | 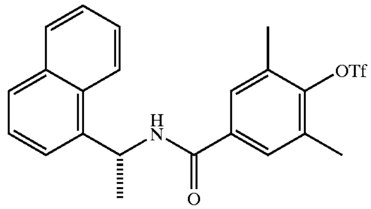 | Example 86 | Chromatography over silica gel, 10–25% ethyl acetate in petroleum ether; solid: 83% yield |
| 109 | 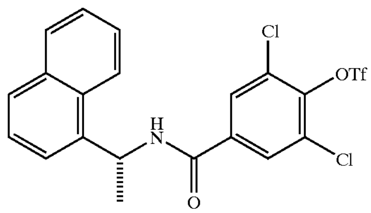 | Example 103 | Chromatography over silica gel, 10% ethyl acetate in petroleum ether; oil: 81% yield |
| 110 | 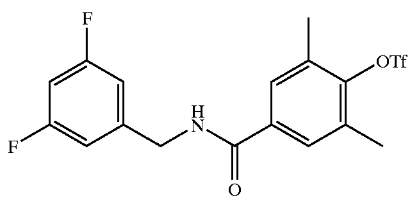 | Example 104 | Chromatography over silica gel, 10–20% ethyl acetate in petroleum ether; off-white solid; 82% yield |

Example 111

Preparation of 2,6-Dimethyl-4-[[[3-[[(1,1-dimethylethyl)dimethylsilyl]oxy]benzyl]amino]carbonyl]benzoic Acid

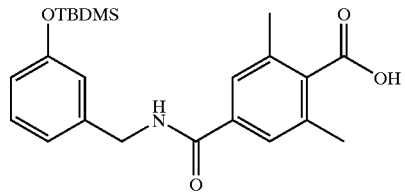

To a solution of trifluoromethanesulfonic acid, 2,6-dimethyl-4-[[[3-[[(1,1-dimethylethyl)dimethylsilyl]oxy]benzyl]amino]carbonyl]phenyl ester (Example 105, 562 mg, 1.09 mmol) in acetonitrile (7 mL) and water (1 mL) at 25° C. was added palladium (II) acetate (24 mg, 0.109 mmol), 1,3-bis(diphenylphosphino)propane (45 mg, 0.109 mmol), followed by triethylamine (2.18 mmol, 0.303 mL). The reaction was then pressurized to 40 psi with carbon monoxide and heated to 80° C. for 4 h. The mixture was diluted with ethyl acetate (100 mL) and washed with water (50 mL) containing 1 mL of triethylamine. The separated aqueous layer was re-extracted with ethyl acetate (2×50 mL) and the combined organic layers were discarded. The aqueous phase was adjusted with 1N hydrochloric acid solution to pH 2 and extracted with ethyl acetate (100 mL). The organic extract was washed with water (25 mL) and brine (25 mL), dried (MgSO$_4$), filtered and evaporated under reduced pressure to yield 2,6-dimethyl-4-[[[3-[[(1,1-dimethylethyl)dimethylsilyl]oxy]benzyl]amino]carbonyl]benzoic acid (1.7 g, 71% yield) as a colorless solid.

Also prepared by this route was the following:

| Example | Structure | Starting Material | Comments |
|---|---|---|---|
| 112 | 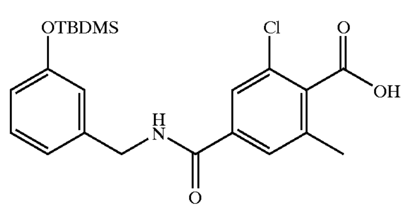 | Example 107 | 71% yield, solid |

-continued

| Example | Structure | Starting Material | Comments |
|---|---|---|---|
| 113 | 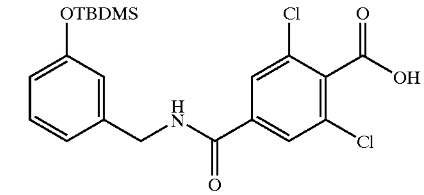 | Example 106 | |
| 114 | 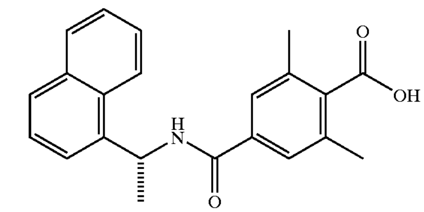 | Example 108 | 100% yield, solid |
| 115 | 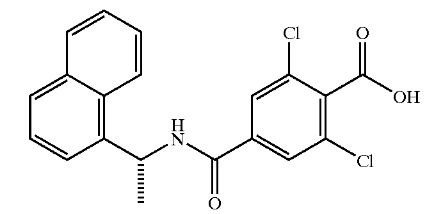 | Example 109 | 36% yield, solid |
| 116 | 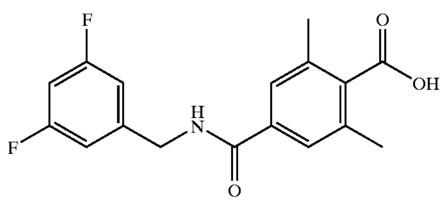 | Example 110 | 89% yield, solid |

Example 117

Preparation of 2-Chloro-4-[[[(1H-indol-6-yl)methyl]amino]carbonyl]benzoic Acid

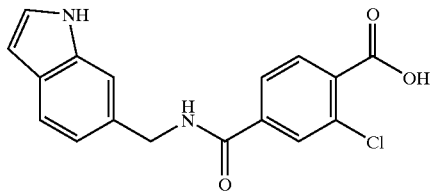

A solution of 2-chloro-4-[[[(1H-indol-6-yl)methyl]amino]carbonyl]benzoic acid methyl ester (Example 80; 2.00 g, 5.9 mmol) in tetrahydrofuran/methanol (1:1; 10 mL) was added to a solution of lithium hydroxide monohydrate (491 mg, 11.7 mmol) in water (5 mL). The solution was allowed to stir at room temperature for 72 h and then concentrated under reduced pressure to remove tetrahydrofuran and methanol. The remaining solution was diluted with water and acidified with 1N hydrochloric acid solution. The resulting mixture was extracted with ethyl acetate and the organic extracts were washed with brine, dried (MgSO₄), filtered and concentrated to afford 2-chloro-4-[[[(1H-indol-6-yl)methyl]amino]carbonyl]benzoic acid (1.90 g, 99% yield) as a colorless solid.

Also prepared by this route was:

| Example | Structure | Starting Material | Yield |
|---|---|---|---|
| 118 | 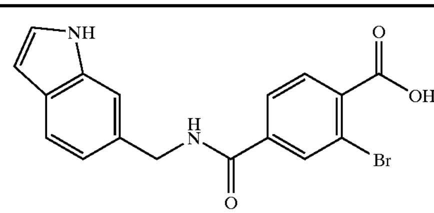 | Example 81 | 98% |

-continued

| Example | Structure | Starting Material | Yield |
|---|---|---|---|
| 119 | ![structure] | Example 84 | 100% |
| 120 | ![structure] | Example 83 | |
| 121 | ![structure] | Example 88 | |

Example 122

Preparation of (R)-2-Chloro-4-[[1-(naphthalen-1-yl)ethylamino]carbonyl]benzoic Acid

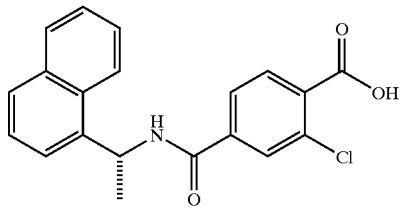

To a solution of (R)-2-chloro-4-[[1-(naphthalen-1-yl)ethylamino]carbonyl]benzoic acid methyl ester (Example 82; 3.00 g, ~8.5 mmol) in tetrahydrofuran/methanol/water (3:1:1; 20 mL) was added lithium hydroxide monohydrate (1.43 g, 34 mmol). The mixture was allowed to stir at room temperature for 4 h and then concentrated in vacuo to remove tetrahydrofuran and methanol. The concentrate was diluted with water and extracted with three portions of ethyl acetate. The organic extracts were discarded and the aqueous layer was acidified with 1N hydrochloric acid solution. Ethyl acetate was added and the resulting colorless solid was recovered by filtration and washed with ethyl acetate. The layers in the filtrate were separated and the organic phase was dried (MgSO$_4$), filtered and concentrated. The resulting residue was combined with the previously recovered solid to give (R)-2-chloro-4-[[1-(naphthalen-1-yl)ethylamino]carbonyl]benzoic acid (2.42 g, 84% yield).

Example 123

Preparation of 2-Chloro-4-[5-[(3-hydroxybenzyl)amino]tetrazol-1-yl]benzoic Acid

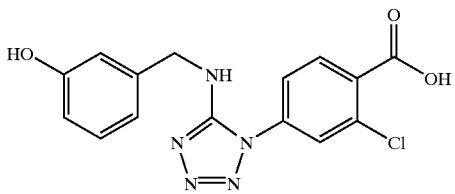

A. 4-[[(3-Acetoxybenzyl)amino]carbonyl]amino-2-chlorobenzoic Acid, Methyl Ester

A stirred suspension of 3-hydroxyphenylacetic acid (10.2 g, 67 mmol) in acetic anhydride (100 mL, 1.06 mol) under anhydrous conditions was treated with pyridine (0.5 mL). In the mildly exothermic reaction, the solids dissolved within several minutes and the mixture was maintained at 40° C. for 5 h. The reaction was concentrated in vacuo to about half volume, then water (30 g) in the form of ice chips was added at such a rate that the temperature remained <45° C. When the exotherm had subsided, a second portion of water (200 mL) was added slowly and the mixture was stirred for another 30 min. The precipitated solid was filtered, washed with water and dried to constant weight in vacuo over P$_2$O$_5$ to give 3-acetoxyphenylacetic acid (11.7 g, 90%). This material was used without further purification. In an inert atmosphere, a solution of the above 3-acetoxyphenylacetic acid (1.942 g, 10 mmol), diphenylphosphoryl azide (2.8 g, 10.17 mmol) and diisopropylethylamine (1.92 mL, 11 mmol) in benzene (25 mL) was stirred at room temperature for 1 h, then the reaction temperature was slowly raised to 70° C. Evolution of gas began to be evident as the reaction temperature reached approximately 55° C. and became much more vigorous as the reaction temperature approached 70° C. Within 30 minutes at that temperature gas evolution had stopped and the reaction solution containing 3-acetoxybenzylisocyanate was cooled to 40° C. Another portion of diisopropylethylamine (3.84 mL, 22 mmol) was added, followed by 4-amino-2-chlorobenzoic acid methyl ester hydrochloride salt (2.95 g, 13.3 mmol) and the brownish purple solution was stirred and heated at reflux under argon overnight. The reaction mixture was cooled, diluted with benzene (50 mL) and washed in turn with 1N hydrochloric acid (50 mL) and dilute brine. The aqueous layers were re-extracted with benzene and the combined extracts were dried (MgSO$_4$), evaporated and purified by HPLC (silica gel; 40% ethyl acetate/hexane). Evaporation of the appropriate fractions provided 3.24 g of the solid urea which was then crystallized from dichloromethane-ethyl acetate to afford 4-[[(3-acetoxybenzyl)amino]carbonyl]amino-2-chlorobenzoic acid, methyl ester (2.71 g, 72%) as a colorless solid, mp 113–114° C.

B. 2-Chloro-4-[5-[(3-hydroxybenzyl)amino]tetrazol-1-yl] benzoic Acid.

In a dry argon atmosphere, a solution of triphenylphosphine (1.684 g, 6.42 mmol), diethyl azodicarboxylate (1.13 g, 6.42 mmol) 4-[[(3-acetoxybenzyl)amino]carbonyl] amino-2-chlorobenzoic acid, methyl ester (1.21 g, 3.21 mmol) in dry tetrahydrofuran (30 mL) was treated with trimethylsilyl azide (0.86 mL, 6.48 mmol) and was stirred at room temperature for 24 h. Examination of the reaction mixture by tlc suggested the presence of considerable starting material, so additional amounts of triphenylphosphine (0.842 g, 3.21 mmol), diethyl azodicarboxylate (0.565 g, 3.21 mmol) and trimethylsilyl azide (0.43 mL, 3.21 mmol) were added. The reaction was stirred at room temperature for another 40 h. The solvents were removed under reduced pressure and the residue was taken up in dichloromethane (100 mL) and washed with water (2×50 mL). The aqueous layers were back-extracted in turn with dichloromethane (50 mL) and the combined organic phases were dried (MgSO$_4$), filtered and evaporated in vacuo. The residue was dissolved in a mixture of methanol (30 mL) and 1 N aqueous lithium hydroxide solution (15 mL) and the mixture was stirred at room temperature for 2 h to complete the hydrolyses of both the ester and phenolic acetate groups. Most of the volatiles were removed under reduced pressure, then the basic solution was diluted with water (20 mL) and washed with dichloromethane (2×30 mL). The aqueous layer was then acidified with 1N hydrochloric acid (16 mL) and extracted with ethyl acetate (2×50 mL). The dried (MgSO$_4$) ethyl acetate extracts were evaporated and the residual solid (810 mg), approximately a 4:1 mixture of the desired aminotetrazole and its positional isomer, was crystallized from diethyl ether to furnish 2-chloro-4-[5-[(3-hydroxybenzyl) amino]tetrazol-1-yl]benzoic acid (560 mg, 46%) as a colorless solid.

Example 124

Preparation of 2-Chloro-4-[[(3-methoxymethoxybenzyl)amino]carbonyl]benzoic Acid

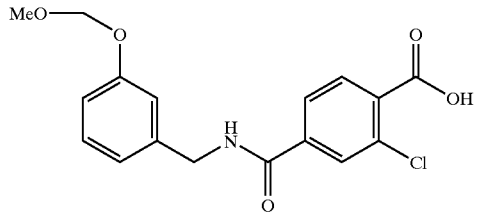

A solution of 4-[2-chloro-4-[(3-hydroxybenzyl)amino] carbonyl]benzoic acid methyl ester (Example 74; 0.304 g, 0.95 mmol) in tetrahydrofuran (10 mL) was cooled to 0° C. and sodium hydride (0.027 g, 1.13 mmol) was added followed by the addition of chloromethyl methyl ether (0.104 g, 1.3 mmol). The cooling bath was removed and the solution was stirred at room temperature under nitrogen for 13 h. Ethyl acetate was added and the solution was washed with water, dried (Na2SO$_4$) and concentrated to give 4-[2-chloro-4-[(3-methoxymethoxybenzyl)amino]carbonyl] benzoic acid methyl ester as an oil (0.356 g, 103% of the theoretical amount). A solution of lithium hydroxide monohydrate (61 mg, 1.4 mmol) in water (3 mL) was added to a solution of the ester in dioxane (3 ml). The mixture was stirred for 2 h at room temperature, acidified with 1N hydrochloric acid solution and extracted with ethyl acetate. The dried (MgSO$_4$) organic extracts were evaporated to give 2-chloro-4-[[(3-methoxymethoxybenzyl)amino]carbonyl] benzoic acid (0.34 g, 102% of the theoretical amount).

Example 125

Preparation of rac.-2-(Dimethoxyphosphinyl)glycine Methyl Ester. (Prepared According to the Literature Procedure (Schmidt, U.; Wild, J. *Liebigs Ann. Chem.* 1985, 1882–94)

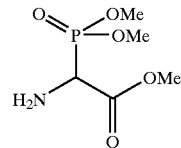

A mixture of rac.-N-(benzyloxycarbonyl)-2-(dimethoxyphosphinyl)glycine methyl ester (3.5 g, 10.56 mmol) and 10% palladium on carbon (0.5 g) in methanol (75 mL) was hydrogenated at 50 psi for 1 h. The solution was filtered through Celite® and the filtrate was concentrated and then dried under high vacuum to furnish rac.-2-(dimethoxy-phosphinyl)glycine methyl ester as an clear oil (2.0 g, 96% yield). The amine prepared in this manner was used per se in subsequent reactions.

Example 126

Preparation of rac.-N-[2,6-Dimethyl-4-[[[3-[[(1,1-dimethylethyl)dimethylsilyl]oxy]benzyl]amino] carbonyl]benzoyl]-2-(dimethoxyphosphinyl)glycine Methyl Ester.

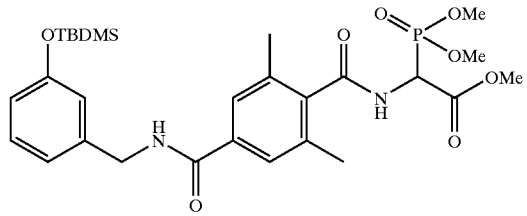

Triphenylphosphine (0.762 g, 2.9 mmol) was added to a suspension of 2,6-dimethyl-4-[[[3-[[(1,1-dimethylethyl)dimethylsilyl]oxy]benzyl]amino]carbonyl]benzoic acid (Example 111; 1 g, 2.42 mmol) in dichloromethane (12 mL) at 25° C. The mixture was cooled to 0° C. and N-chlorosuccinimide (0.387 g, 2.9 mmol) was added. After stirring 15 min at 0° C., the mixture was stirred for an additional 15 min at 25° C. and then a solution of rac.-2-(dimethoxyphosphinyl)glycine methyl ester (Example 125) freshly prepared from rac.-N-(benzyloxycarbonyl)-2-(dimethoxyphosphinyl)glycine methyl ester (1.99 g, 6 mmol) in dichloromethane (2 mL) was added in one portion. The reaction was stirred for 5 h (a precipitate formed at 2 h), then was filtered and the solids were washed with dichloromethane and discarded. The filtrate was washed with 1N hydrochloric acid solution (50 mL), saturated aqueous sodium bicarbonate solution (50 mL) and brine (50 mL), then was dried (MgSO$_4$) and concentrated under reduced pressure. The residue was flash chromatographed (silica gel, 10% ethyl acetate in petroleum ether) to yield rac.-N-[2,6-dimethyl-4-[[[3-[[(1,1-dimethylethyl)dimethylsilyl]oxy]benzyl]amino]carbonyl]benzoyl]-2-(dimethoxyphosphinyl)glycine methyl ester (1.33 g, 93% yield) as a colorless foam.

Also prepared by this route was the following:

| Example | Structure | Starting Materials | Comments |
|---|---|---|---|
| 127 | 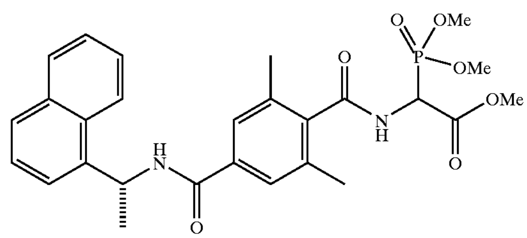 | Example 114 and Example 125 | 80% yield; colorless foam |
| 128 | 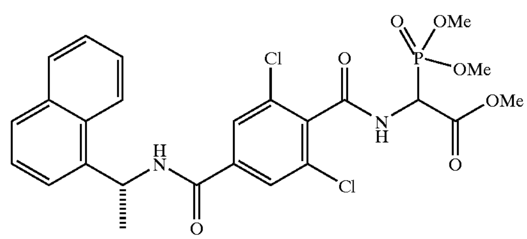 | Example 115 and Example 125 | 76% yield; colorless foam |
| 129 | 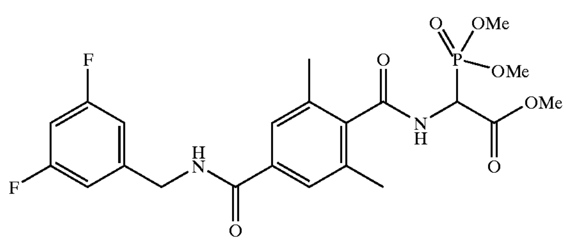 | Example 116 and Example 125 | 76% yield; solid |

Example 130

Preparation of rac.-N-[2-Bromo-4-[[(3-hydroxybenzyl)amino]carbonyl]benzoyl]-2-(dimethoxyphosphinyl)glycine Methyl Ester

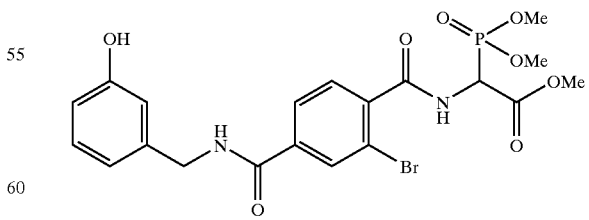

Diisopropylethylamine (1.81 g, 14 mmol) was added to a solution of rac.-2-(dimethoxyphosphinyl)glycine methyl ester (Example 125) freshly prepared from rac.-N-benzyloxycarbonyl)-2-(dimethoxyphosphinyl)glycine methyl ester (5.00 g, 15.1 mmol), O-(benzotriazol-1-yl)-1,1,3,3-tetramethyluronium hexafluorophosphate (5.20 g, 13.7 mmol), 1-hydroxybenzotriazole (1.85 g, 13.7 mmol) and 2-bromo-4-[[(3-hydroxybenzyl)amino]carbonyl]benzoic acid (Example 79; 4.80 g, 13.7 mmol) in N,N-dimethylformamide (50 mL). After the reaction was stirred for 4 h at 25° C., the volatiles were removed in vacuo. A solution of the residue in ethyl acetate (200 mL) was washed with 1N hydrochloric acid solution (100 mL), saturated aqueous sodium bicarbonate solution (100 mL), water (100 mL) and brine (100 mL). The organic layer was dried over $MgSO_4$, filtered, concentrated and the resulting residue was flash chromatographed over silica gel (ethyl acetate-3% methanol in ethyl acetate) to give rac.-N-[2-bromo-4-[[(3-hydroxybenzyl)amino]carbonyl]benzoyl]-2-(dimethoxyphosphinyl)glycine methyl ester (5.50 g, 76% yield) as a colorless foam.

Example 131

Preparation of rac.-N-[2-Bromo-4-[[[(1H-indol-4-yl)methyl]amino]carbonyl]benzoyl]-2-(dimethoxyphosphinyl)glycine Methyl Ester

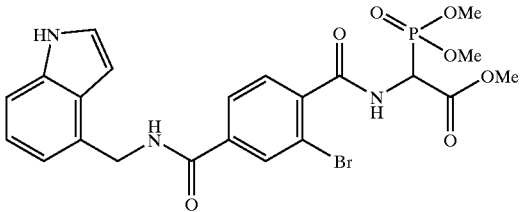

Sodium hydroxide (21.5 mg, 0.54 mmol) was added to a solution of 2-bromo-4-[[[(1H-indol-4-yl)methyl]amino]carbonyl]benzoic acid methyl ester (Example 83; 208 mg, 0.54 mmol) in tetrahydrofuran/methanol (2:1; 1.8 mL). The solution was allowed to stir at room temperature for 4 h and then more sodium hydroxide (21.5 mg, 0.54 mmol) was added. The solution was allowed to stir at room temperature overnight, then it was diluted with ethyl acetate and the solution was washed with 1N hydrochloric acid solution (10 mL), washed with brine, dried ($MgSO_4$), filtered and concentrated to give crude 2-bromo-4-[[[(1H-indol-4-yl)methyl]amino]carbonyl]benzoic acid. This was mixed with a solution of rac.-2-(dimethoxyphosphinyl)glycine methyl ester (Example 125) freshly prepared from rac.-N-(benzyloxycarbonyl)-2-(dimethoxyphosphinyl)glycine methyl ester (213.5 mg, 0.64 mmol), O-(benzotriazol-1-yl)-1,1,3,3-tetramethyluronium hexafluorophosphate (203.5 mg, 0.54 mmol), 1-hydroxybenzotriazole (72.6 mg, 0.54 mmol) and diisopropylethylamine (281 µL, 1.61 mmol) in N,N-dimethylformamide (1.5 mL). The solution was allowed to stir for 3 h, then ethyl acetate (20 mL) was added. The solution was washed with 1N hydrochloric acid solution (10 mL), saturated sodium bicarbonate solution (15 mL) and each aqueous layer was back-extracted with ethyl acetate. The combined organic layers were washed with brine (10 mL), dried ($MgSO_4$), filtered, evaporated and chromatographed over silica gel (3–5% methanol/dichloromethane) to give rac.-N-[2-bromo-4-[[[(1H-indol-4-yl)methyl]amino]carbonyl]benzoyl]-2-(dimethoxyphosphinyl)glycine methyl ester (206.8 mg, 69% yield) as a pale yellow solid.

Example 132

Preparation of rac.-N-[2-Chloro-4-[[(3-hydroxybenzyl)amino]carbonyl]-6-methylbenzoyl]-2-(dimethoxyphosphinyl)glycine Methyl Ester

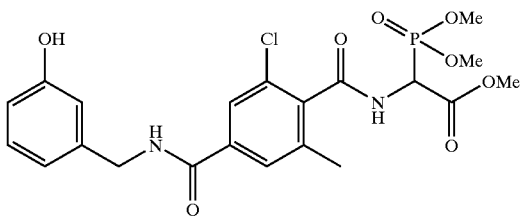

O-(Benzotriazol-1-yl)-1,1,3,3-tetramethyluronium hexafluorophosphate (645 mg, 1.7 mmol) was added to a solution of 2-chloro-4-[[(3-hydroxybenzyl)amino]carbonyl]-6-methylbenzoic acid (Example 112; 520 mg, 1.6 mmol) and rac.-2-(dimethoxyphosphinyl)glycine methyl ester (Example 125) freshly prepared from rac.-N-(benzyloxycarbonyl)-2-(dimethoxyphosphinyl)glycine methyl ester (370 mg, 1.9 mmol). 1-hydroxybenzotriazole (255 mg, 1.9 mmol) was then added, followed by diisopropylethylamine (1.25 mL, 7.2 mmol). The solution was stirred at room temperature for 65 h and then it was evaporated to dryness under high vacuum to remove N,N-dimethylformamide. The residue was partitioned between ethyl acetate (50 mL) and saturated sodium bicarbonate solution (25 mL). The ethyl acetate layer was washed with brine, 0.5N hydrochloric acid solution and brine. Each of the aqueous layers was extracted with ethyl acetate. The combined organic extracts were dried ($Na_2SO_4$), filtered, evaporated and the residue was chromatographed over silica gel (50–100% ethyl acetate/hexanes, then 5–25% methanol/ethyl acetate) to give rac.-N-[2-chloro4-[[(3-hydroxybenzyl)amino]carbonyl]-6-methylbenzoyl]-2-(dimethoxyphosphinyl)glycine methyl ester (120 mg, 15% yield).

Example 133

Preparation of rac.-N-[2-Chloro-4-[3-(3-hydroxyphenyl)-1-oxopropan-1-yl]benzoyl]-2-(dimethoxyphosphinyl)glycine Methyl Ester

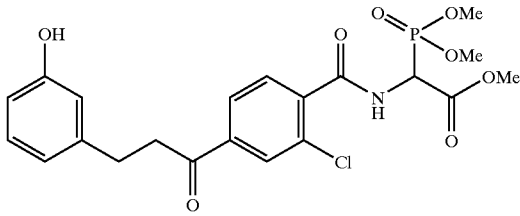

Diisopropylethylamine (1.05 mL, 6 mmol) was added to a solution of 2-chloro-4-[3-(3-hydroxyphenyl)-1-oxopropan-1-yl]benzoic acid (Example 94; 457 mg, 1.5 mmol), rac.-2-(dimethoxyphosphinyl)glycine methyl ester (Example 125) freshly prepared from rac.-N-(benzyloxycarbonyl)-2-(dimethoxyphosphinyl)glycine methyl ester (662.5 mg, 2.0 mmol), O-(benzotriazol-1-yl)-1,1,3,3-tetramethyluronium hexafluorophosphate (597 mg, 1.6 mmol) and 1-hydroxybenzotriazole (223 mg, 1.65 mmol) in N,N-dimethylformamide (12 mL). The solution was stirred at room temperature for 17 h and then it was evaporated in vacuo to remove N,N-dimethylformamide. A solution of the residue in ethyl acetate (40 mL) was washed in turn with 0.5N hydrochloric acid solution (20 mL), brine (20 mL), saturated sodium bicarbonate solution (20 mL) and brine (20 mL). Each of the aqueous layers was extracted with ethyl acetate (20 mL). The combined organic layers were dried (Na$_2$SO$_4$), filtered and evaporated under reduced pressure. The resulting oil was chromatographed over silica gel (75% ethyl acetate/hexanes, then 5% methanol/ethyl acetate) to give rac.-N-[2-chloro-4-[3-(3-hydroxyphenyl)-1-oxopropan-1-yl]benzoyl]-2-(dimethoxyphosphinyl)glycine methyl ester (450 mg, 62% yield) as an oil.

Example 134

Preparation of rac.-N-[2-Chloro-4-[1-hydroxy-3-(3-hydroxyphenyl)propan-1-yl]benzoyl]-2-(dimethoxyphosphinyl)glycine Methyl Ester

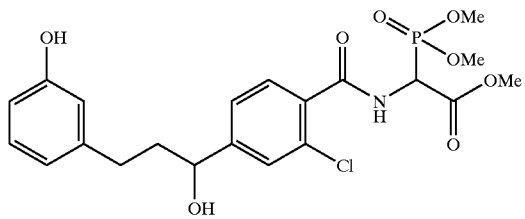

Diisopropylethylamine (0.61 mL, 3.5 mmol) was added to a solution of rac.-2-chloro-4-[1-hydroxy-3-(3-hydroxyphenyl)propan-1-yl]benzoic acid (Example 96; 270 mg, 0.88 mmol), rac.-2-(dimethoxyphosphinyl)glycine methyl ester (Example 125) freshly prepared from rac.-N-(benzyloxycarbonyl)-2-(dimethoxyphosphinyl)glycine methyl ester (397 mg, 1.2 mmol) ), O-(benzotriazol-1-yl)-1,1,3,3-tetramethyluronium hexafluorophosphate (350 mg, 0.97 mmol) and 1-hydroxybenzotriazole (131 mg, 0.97 mmol) in N,N-dimethylformamide (7 mL). The solution was stirred at room temperature for 17 h and then it was concentrated under high vacuum to remove N,N-dimethylformamide. Ethyl acetate (25 mL) was added and the solution was washed in turn with 0.5N hydrochloric acid solution (10 mL), brine (10 mL), saturated sodium bicarbonate solution (10 mL) and brine. Each of the aqueous layers was back-washed in turn with ethyl acetate (10 mL). The combined organic layers were dried (MgSO$_4$), filtered, evaporated and the resulting residue was chromatographed over silica gel (50–100% ethyl acetate/hexanes, then 5% methanol/ethyl acetate) to flirnish N-[2-chloro-4-[1-hydroxy-3-(3-hydroxyphenyl)propan-1-yl]benzoyl]-2-(dimethoxyphosphinyl)glycine methyl ester (260 mg, 61% yield) as a colorless oil.

Example 135

Preparation of rac.-(E)-N-[2-Chloro-4-[1-hydroxy-3-(3-hydroxyphenyl)-2-prop-2-en-1-yl]benzoyl]-2-(dimethoxyphosphinyl)glycine Methyl Ester

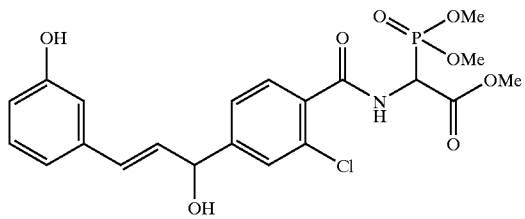

Diisopropylethylamine (0.48 mL, 2.8 mmol) was added to a solution of rac.-2-chloro-4-[1-hydroxy-3-(3-hydroxyphenyl)prop-2-en-1-yl]benzoic acid (Example 93; 225 mg, 0.69 mmol), rac.-2-(dimethoxyphosphinyl)glycine methyl ester (Example 125) freshly prepared from rac.-N-(benzyloxycarbonyl)-2-(dimethoxyphosphinyl)glycine methyl ester (331 mg, 1 mmol), O-(benzotriazol-1-yl)-1,1,3,3-tetramethyluronium hexafluorophosphate (284 mg, 0.75 mmol) and 1-hydroxybenzotriazole (102 mg, 0.76 mmol) in N,N-dimethylformamide (5 mL). The solution was stirred at room temperature for 17 h and then it was concentrated under high vacuum to remove N,N-dimethylformamide. Ethyl acetate (25 mL) was added and the resulting solution was washed in turn with 0.5N hydrochloric acid solution (10 mL), brine (10 mL), saturated sodium bicarbonate solution (10 mL) and brine (10 mL). Each of the aqueous layers was back-extracted in turn with ethyl acetate (10 mL). The combined organic layers were dried (MgSO$_4$), filtered, evaporated and chromatographed over silica gel (50–100% ethyl acetate/hexanes, then 5% methanol/ethyl acetate) to furnish rac.-N-[2-chloro-4-[1-hydroxy-3-(3-hydroxyphenyl)prop-2-en-1-yl]benzoyl]-2-(dimethoxyphosphinyl)glycine methyl ester (240 mg, 72% yield) as an oil.

Example 136

Preparation of rac.-N-[2-Chloro-4-[[[(1H-indol-6-yl)methyl]amino]carbonyl]benzoyl]-2-(dimethoxyphosphinyl)glycine Methyl Ester O-(benzotriazol-1-yl)-1,1,3,3-tetramethyluronium hexafluorophosphate (2.4 g, 6.4 mmol) was added to a solution of 2-chloro-4-[[[(1H-indol-6-yl)methyl]amino]carbonyl]benzoic acid (Example 117; 1.9 g, 5.8 mmol) and rac.-2-(dimethoxyphosphinyl)glycine methyl ester (Example 125; 2.10 g, 10.6 mmol) in N,N-dimethylformamide (20 mL). 1-hydroxybenzotriazole (861 mg, 6.4 mmol) was then added, followed by diisopropylethylamine (2 mL, 11.6 mmol). The solution was stirred overnight at room temperature and then it was concentrated under high vacuum to remove N,N-dimethylformamide. The residue was partitioned between water and ethyl acetate and the separated organic phase was washed in turn with cold 1N hydrochloric acid solution, cold saturated sodium bicarbonate solution and brine, then was dried (MgSO$_4$), filtered and evaporated in vacuo. The crude product was chromatographed over silica gel (0–4% methanol/dichloromethane) to give rac.-N-[2-chloro-4-[[[(1H-indol-6-yl)methyl]amino]carbonyl]benzoyl]-2-(dimethoxyphosphinyl)glycine methyl ester (2.1 g, 72% yield) which was used in subsequent reactions without further purification.

Also prepared by this method were:

| Example | Structure | Starting Materials | Yield |
|---|---|---|---|
| 137 | 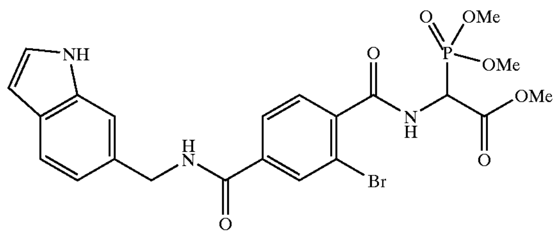 | Example 118 and Example 125 | 67% |
| 138 | 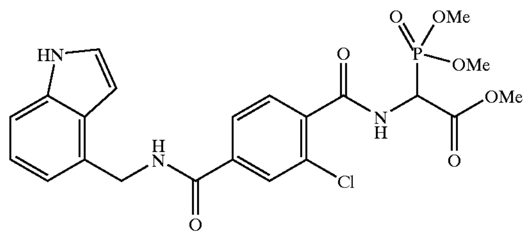 | Example 119 and Example 125 | 62% |
| 139 | 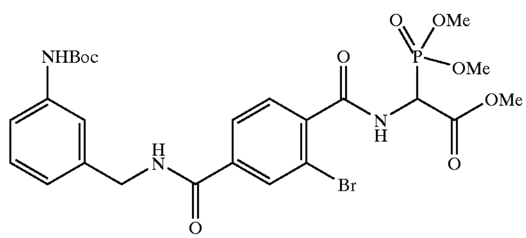 | Example 121 and Example 125 | |

Example 140

Preparation of rac.-2-(Dimethoxyphosphinyl)-N-[4-[[(3-hydroxybenzyl)amino]carbonyl]-2-methylbenzoyl]glycine Methyl Ester

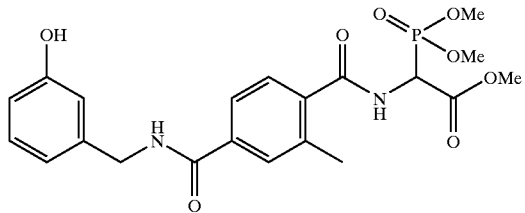

O-(benzotriazol-1-yl)-1,1,3,3-tetramethyluronium hexafluorophosphate (3.50 g, 9.2 mmol) was added to a solution of 4-[[(3-hydroxybenzyl)amino]carbonyl]-2-methylbenzoic acid (Example 90; 2.40 g, 8.4 mmol), rac.-2-(dimethoxyphosphinyl)glycine methyl ester (Example 125; 1.80 g, 9.1 mmol) and diisopropylethylamine (1.50 g, 11.6 mmol) in N,N-dimethylformamide (50 mL). The solution was stirred overnight at room temperature. Ethyl acetate (200 mL) was added and the solution was washed with 1N hydrochloric acid solution, water and brine (200 mL each), dried (MgSO$_4$), filtered and evaporated to give crude rac.-2-(dimethoxyphosphinyl)-N-[4-[[(3-hydroxybenzyl)amino]carbonyl]-2-methylbenzoyl]glycine methyl ester (2.47 g, 63% yield). This material was used in subsequent reactions without flrther purification.

Example 141

Preparation of rac.-N-[2-Chloro-4-[[(3-hydroxybenzyl)amino]carbonyl]benzoyl]-2-(dimethoxyphosphinyl)glycine Methyl Ester

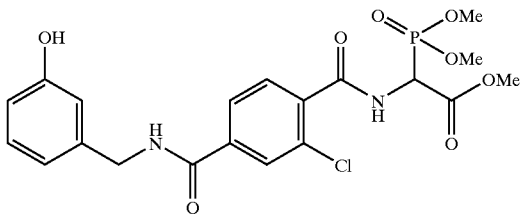

N,N-dicyclohexylcarbodiimide (0.380 g, 1.85 mmol) and 1-hydroxy-7-azabenzotriazole (0.25 g, 1.85 mol) were added to a solution of 2-chloro-4-[[(3-hydroxybenzyl)amino]carbonyl]benzoic acid (Example 75; 0.50 g, 1.85 mmol) and rac.-2-(dimethoxyphosphinyl)glycine methyl ester (Example 125; 365 mg, 1.85 mmol) in N,N-dimethylformamide (10 mL). The solution was stirred for 12 h at room temperature. Ethyl acetate was added and the solution was washed repeatedly with water. The organic layer was dried (Na$_2$SO$_4$) to give crude rac.-N-[2-chloro-N-[[(3-hydroxybenzyl)amino]carbonyl]benzoyl]-2-(dimethoxyphosphinyl)glycine methyl ester as a colorless semi-solid (0.507 g) which was used in subsequent reactions without further purification. Examination of the crude product by NMR indicated that this material was approximately 80% pure.

113

Example 142

Preparation of rac.-N-[2-Chloro-4-[[(3-methoxymethoxybenzyl)amino]carbonyl]benzoyl]-2-(dimethoxyphosphinyl)glycine Methyl Ester

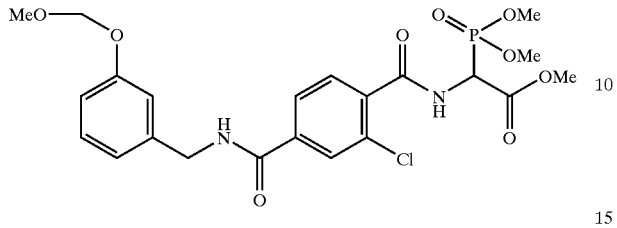

N,N-dicyclohexylcarbodiimide (0.216 g, 1.05 mmol) and 1-hydroxybenzotriazole (0.027 g, 0.2 mol) were added to a solution of 2-chloro-4-[[(3-methoxymethoxybenzyl) amino] carbonyl]benzoic acid (Example 124; 0.34 g, 1.0 mmol) and rac.-2-(dimethoxyphosphinyl)glycine methyl ester (Example 125; 197 mg, 1.0 mmol) in N,N-dimethylformamide (5 mL). The solution was stirred for 12 h, then was filtered and diluted with ethyl acetate. The resulting solution was washed with water, dried ($Na_2SO_4$), evaporated and the residual material was chromatographed (50–80% ethyl acetate/hexanes) to give rac.-N-[2-chloro-4-[[(3-methoxymethoxybenzyl) amino]carbonyl]benzoyl]-2-(dimethoxyphosphinyl)glycine methyl ester (0.24 g, 45% yield).

Example 143

Preparation of (R,S)-N-[2-Chloro-4-[[(R)-1-(naphthalen-1-yl)ethylamino]carbonyl]benzoyl]-2-(dimethoxyphosphinyl)glycine Methyl Ester

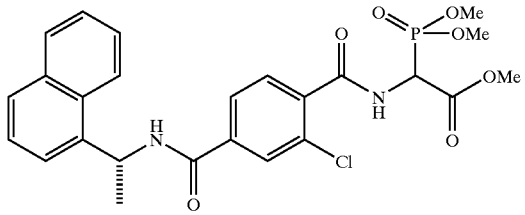

N,N-dicyclohexylcarbodiimide (1.24 g, 6.03 mmol) and 1-hydroxybenzotriazole (0.748 g, 6.03 mmol) were added to a solution of (R)-2-chloro-4-[[1-(naphthalen-1-yl) ethylamino]carbonyl]benzoic acid (Example 122; 2.13 g, 6.03 mmol) and rac.-2-(dimethoxyphosphinyl)glycine methyl ester (Example 125; 1.20 g, 6.03 mmol) in N,N-dimethylformamide (20 mL). The solution was stirred overnight at room temperature. Water was added and the mixture was extracted with three portions of ethyl acetate. The combined organic extracts were washed with a dilute sodium chloride solution and with brine, then were dried ($Na_2SO_4$) and evaporated in vacuo. The residue was chromatographed over silica gel (2–5% methanol/dichloromethane) and evaporation of the appropriate fractions furished (R,S)-N-[2-chloro-4-[[(R)-1-(naphthalen-1-yl)ethylamino]carbonyl]benzoyl]-2-(dimethoxyphosphinyl) glycine methyl ester as an off-white solid (1.23 g; 38% yield).

114

Example 144

Preparation of (R,S)-N-[2-Chloro-4-[[(R)-1-(naphthalen-1-yl)ethylamino]carbonyl]benzoyl]-2-(dimethoxyphosphinyl)glycine

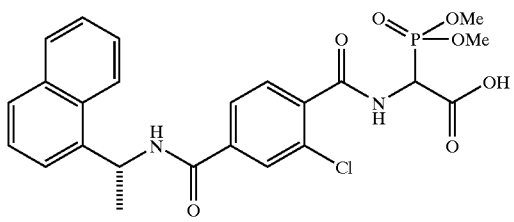

To a solution of (R,S)-N-[2-chloro-4-[[(R)-1-(naphthalen-1-yl)ethylamino]carbonyl]benzoyl]-2-(dimethoxyphosphinyl)glycine methyl ester (Example 143; 1.23 g, 2.31 mmol) in tetrahydrofuran/water/methanol (3:1:1; 10 mL) was added sodium hydroxide solution (0.1387 mL, 3.47 mmol) and the mixture was stirred at room temperature for 80 min. After the volatiles were removed under reduced pressure, the concentrate was partitioned between ethyl acetate and water. The separated aqueous phase was washed with ethyl acetate, then was acidified using 6N hydrochloric acid solution and extracted with three portions of ethyl acetate. These extracts were combined, dried ($Na_2SO_4$) and evaporated to afford 540 mg of (R,S)-N-[2-chloro4-[[(R)-1-(naphthalen-1-yl)ethylamino]carbonyl]benzoyl]-2-(dimethoxyphosphinyl)glycine as an off-white solid (45.1% yield).

Example 145

Coupling of (R,S)-N-[2-Chloro-4-[[(R)-1-(naphthalen-1-yl)ethylamino]carbonyl]benzoyl]-2-(dimethoxyphosphinyl)glycine to Wang Resin

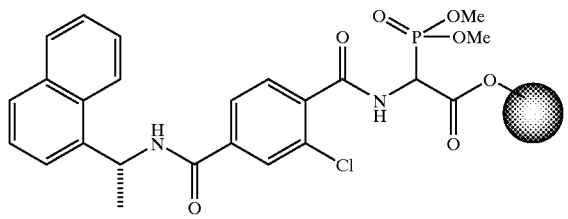

A 6 mL polyethylene vial equipped with a coarse glass frit was charged with 0.1 g of Wang resin (loading factor: 1.1 mmol/g, 300 mesh), (R,S)-N-[2-chloro-4-[[(R)-1-(naphthalen-1-yl)ethylamino]carbonyl]benzoyl]-2-(dimethoxyphosphinyl)glycine (Example 144; 86 mg, 0.166 mmol), 1-hydroxy-7-azabenzotriazole (45 mg, 0.331 mmol) and diisopropylcarbodiimide, (0.05 mL, 0.32 mmol) in N-methylpyrrolidone (1 mL) and the mixture was agitated for 1 h. The resin was filtered and washed with dimethylformamide, dichloromethane and methanol and dried to give the (R,S)-N-[2-chloro-4-[[(R)-1-(naphthalen-1-yl)ethylamino]carbonyl]benzoyl]-2-(dimethoxyphosphinyl)glycine substituted Wang resin.

Example 146

Preparation of (Z)-2-[[2-Bromo-4-[[(3-hydroxybenzyl)amino]carbonyl]benzoyl]amino]-3-(quinolin-3-yl)propenoic Acid Methyl Ester

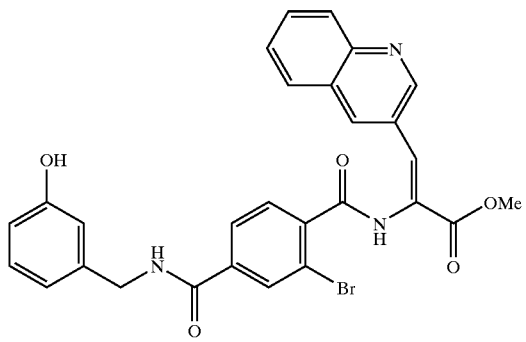

1,1,3,3-Tetramethylguanidine (0.5 mL, 4.0 mmol) was added to a solution of rac.-N-[2-bromo-4-[[(3-hydroxybenzyl)amino]carbonyl]benzoyl]-2-(dimethoxyphosphinyl)glycine methyl ester (Example 130; 1.00 g, 1.9 mmol) in tetrahydrofuran (8 mL) at −45° C. The solution was stirred at −45° C. for 5 min and then quinoline-3-carboxaldehyde (300 mg, 1.9 mmol) was added. After the reaction was allowed to proceed at −40° C. for 30 min, the mixture was warmed to room temperature and was stirred for another 2 h. Ethyl acetate and pH 6 phosphate buffer (200 mL each) were added and the resulting solid was filtered to furnish (Z)-2-[[2-bromo-4-[[(3-hydroxybenzyl)amino]carbonyl]benzoyl]amino]-3-(quinolin-3-yl)propenoic acid methyl ester (500 mg, 47% yield). The layers in the filtrate were separated and the aqueous phase was extracted with ethyl acetate (3×100 mL). The combined organic layers were dried (MgSO₄), filtered through a bed of silica gel and the filtrate was evaporated to give an additional quantity of (Z)-2-[[2-bromo-4-[[(3-hydroxybenzyl)amino]carbonyl]benzoyl]amino]-3-(quinolin-3-yl)propenoic acid methyl ester (520 mg, 49% yield) as a colorless solid.

Example 147

Preparation of (Z)-2-[[2-Bromo-4-[[(3-hydroxybenzyl)amino]carbonyl]benzoyl]amino]-3-(naphthalen-2-yl)propenoic Acid Methyl Ester

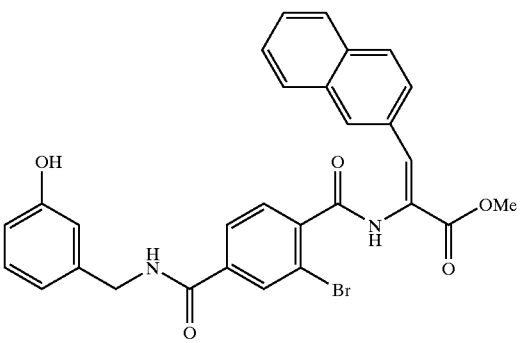

1,1,3,3-Tetramethylguanidine (50.5 µL, 0.40 mmol) was added to a solution of rac.-N-[2-bromo-4-[[(3-hydroxybenzyl)amino]carbonyl]benzoyl]-2-(dimethoxyphosphinyl)glycine methyl ester (Example 130; 106.4 mg, 0.20 mmol) in tetrahydrofuran (1 mL) at −20° C. After 5 min, a solution of naphthalene-2-carboxaldehyde (31.4 mg, 0.20 mmol) in tetrahydrofuran (0.5 mL) was added. The solution was stirred at −20° C. for 1 h and then was stirred at room temperature for 4 h. Ethyl acetate (15 mL) was added and the solution was washed with 1N hydrochloric acid solution (10 mL) and brine (10 mL). The dried (MgSO₄) organic phase was filtered, evaporated and the resulting residue was triturated with petroleum ether to furnish (Z)-2-[[2-bromo-4-[[(3-hydroxybenzyl)amino]carbonyl]benzoyl]amino]-3-(naphthalen-2-yl)propenoic acid methyl ester (88 mg, 78% yield) as a yellow solid.

Also prepared by this route were the following:

| Example | Structure | Starting Materials | Comments |
|---|---|---|---|
| 148 | 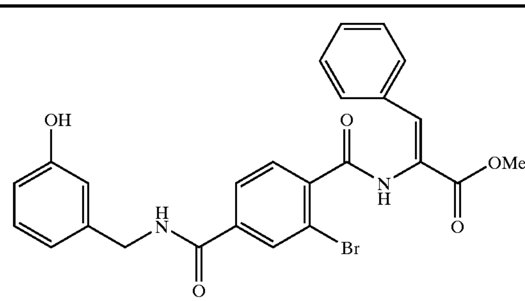 | Example 130 and benzaldehyde | 85% yield |
| 149 | 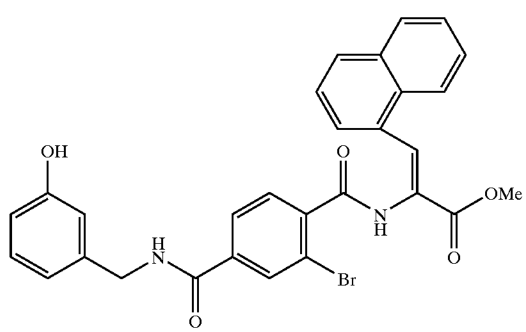 | Example 130 and naphthalene-1-carboxaldehyde | 75% yield |

-continued

| Example | Structure | Starting Materials | Comments |
|---|---|---|---|
| 150 | 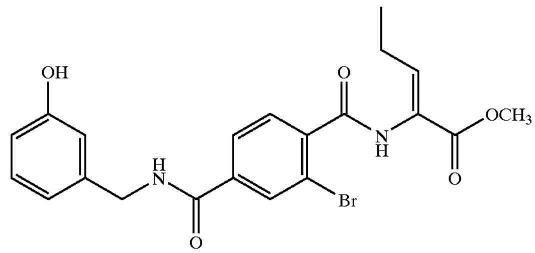 | Example 130 and propionaldehye. | |
| 151 | 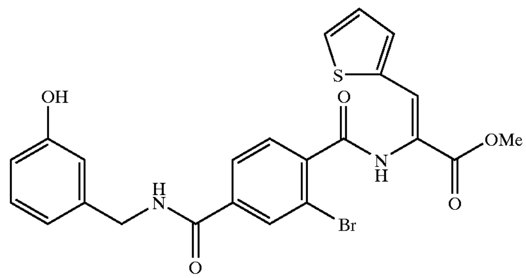 | Example 130 and thiophene-2-carboxaldehyde | 89% yield |
| 152[a] | 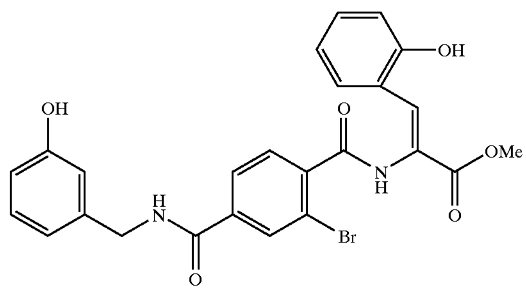 | Example 130 and salicylaldehyde | 97% yield |
| 153 | 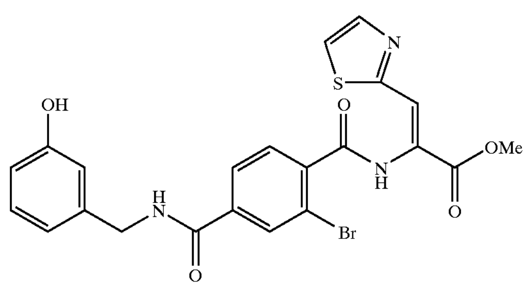 | Example 130 and thiazole-2-carboxaldehyde | 90% yield |
| 154 | 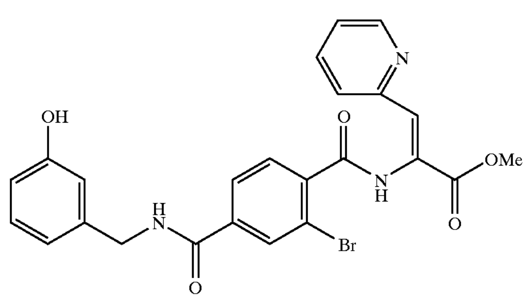 | Example 130 and pyridine-2-carboxaldehyde | 85% yield |

| Example | Structure | Starting Materials | Comments |
|---|---|---|---|
| 155 | 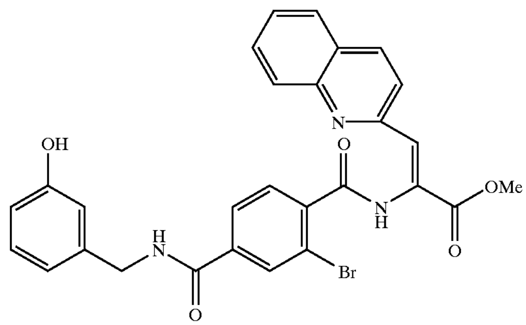 | Example 130 and quinoline-2-carboxaldehyde | 42% yield |
| 157 | 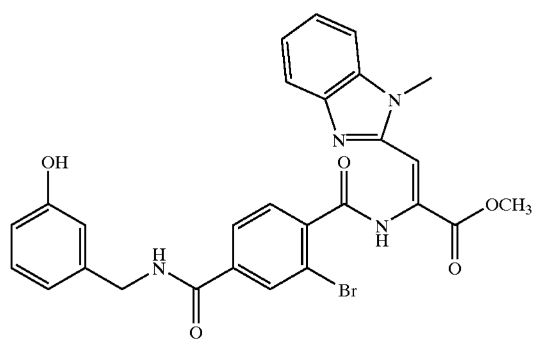 | Example 130 and 1-methyl-1H-benzimidazole-2-carboxaldehyde | |
| 158 | 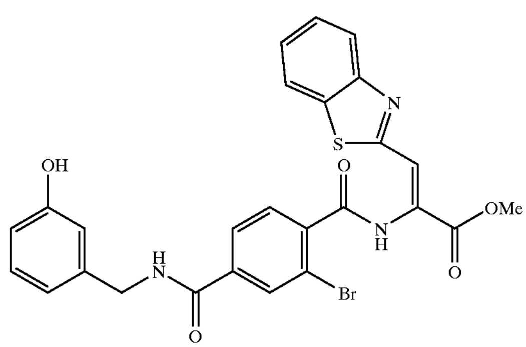 | Example 130 and benzothiazole-2-carboxaldehyde (lit.: Vetelino, M. G.; Coe, J. W. Tetrahedron Lett. 1994, 35, 219–22) | 68% yield |
| 159 | 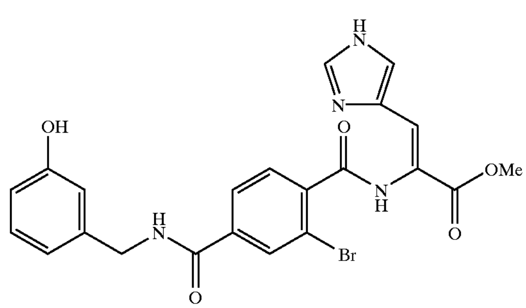 | Example 130 and imidazole-4-carboxaldehyde (lit.: Battersby, A. R.; Nicoletti, M.; Staunton, J.; Vleggaar, R. J. Chem. Soc,, Perkin Trans. 1 1980, 43–51) | 56% yield |

-continued

| Example | Structure | Starting Materials | Comments |
|---------|-----------|--------------------|----------|
| 160 | 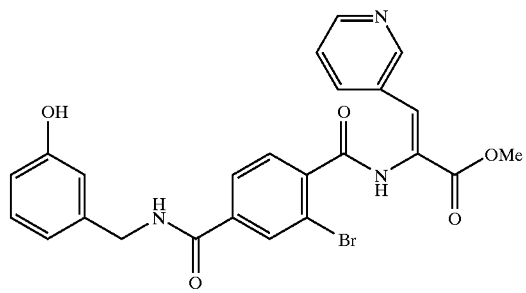 | Example 130 and pyridine-3-carboxaldehyde | 24% yield |
| 161 | 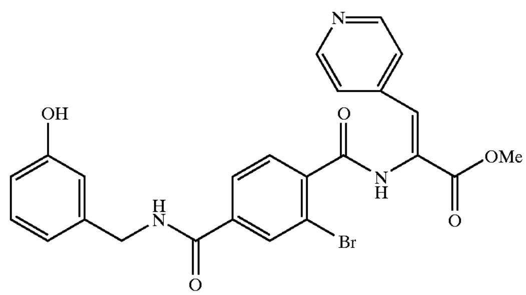 | Example 130 and pyridine-4-carboxaldehyde | 57% yield |
| 162 | 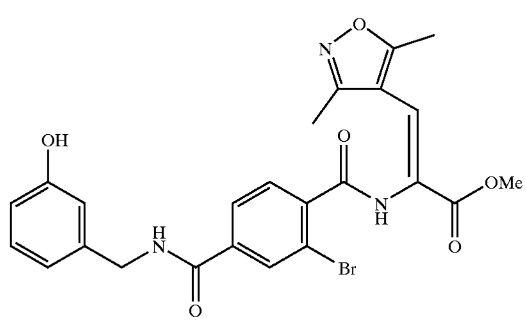 | Example 130 and Example 39 | 82% yield |
| 163 | 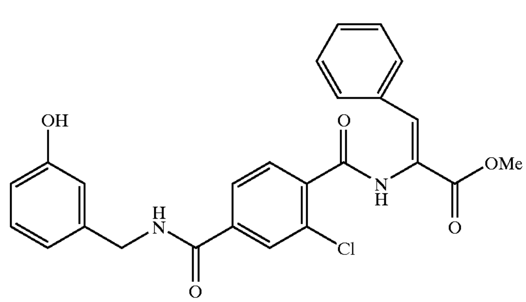 | Example 141 and benzaldehyde | 88% yield |

-continued

| Example | Structure | Starting Materials | Comments |
|---------|-----------|-------------------|----------|
| 164 | 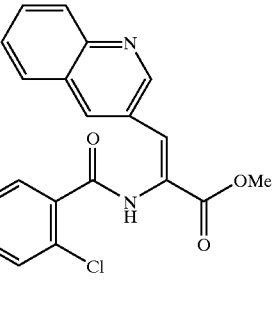 | Example 141 and quinoline-3-carboxaldehyde | 27% yield |
| 165 | 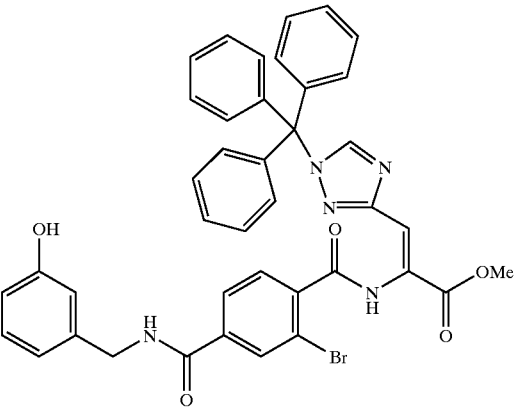 | Example 130 and 1-(triphenylmethyl)-1,2,4-triazole-3-carboxaldehyde (lit:Pirrung, M. C. et al. J. Org. Chem. 1993, 58, 5683–9 | 46% yield |
| 166 | 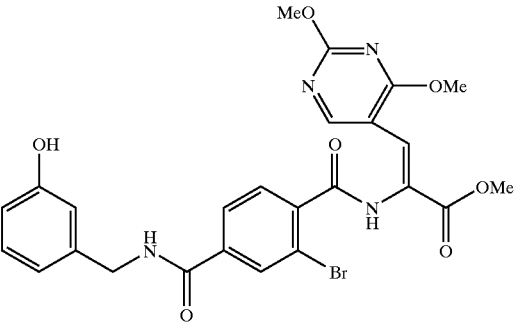 | Example 130 and 2,4-dimethoxypyrimidine-5-carboxaldehyde | 82% yield |

[a]three equivalents of 1,1,3,3-Tetramethylguanidine used.

Example 167

Preparation of (Z)-2-[[2-Bromo-4-[[(3-hydroxybenzyl)amino]carbonyl]benzoyl]amino]-3-(2-methylthiazol-4-yl)propenoic Acid Methyl Ester

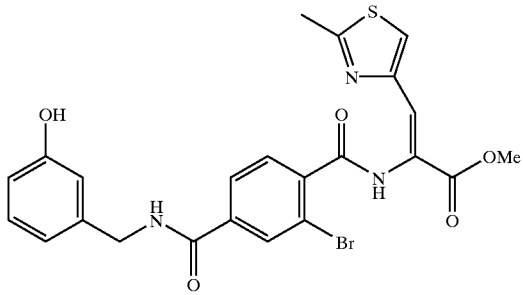

1,1,3,3-Tetramethylguanidine (50 µL, 0.397 mmol) was added to a solution of rac.-N-[2-bromo-4-[[(3-hydroxybenzyl)amino]carbonyl]benzoyl]-2-(dimethoxyphosphinyl) glycine methyl ester (Example 130; 100 mg, 0.189 mmol) in tetrahydrofuran (2 mL) at −40° C. The solution was stirred at −40° C. for 5 min and then 2-methylthiazole-4-carboxaldehyde (Example 41; 48 mg, 0.378 mmol) was added. The solution was stirred at −40° C. for 1 h and then allowed to stir at room temperature for 4 h. The solution was quenched with pH 6 phosphate buffer, diluted with ethyl acetate (15 mL) and the separated organic layer was washed with pH 6 phosphate buffer (10 mL) and brine (10 mL). The organic phase was dried (MgSO₄), filtered, evaporated and triturated with diethyl ether to give (Z)-2-[[2-bromo-4-[[(3-hydroxybenzyl)amino]carbonyl]benzoyl]amino]-3-(2-methylthiazol-4-yl)propenoic acid methyl ester (92 mg, 49% yield) as a brown solid.

Also prepared in the same manner were the following:

| Example | Structure | Starting Materials | Comments |
|---|---|---|---|
| 168 | 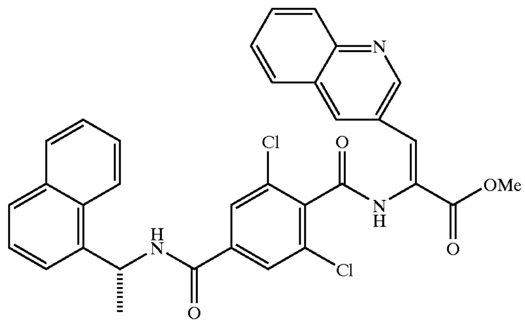 | Example 128 and quinoline-3-carboxaldehyde | 1.05 equiv. of TMG used in the reaction, product was used as is, without trituration 81% crude yield |
| 169 | 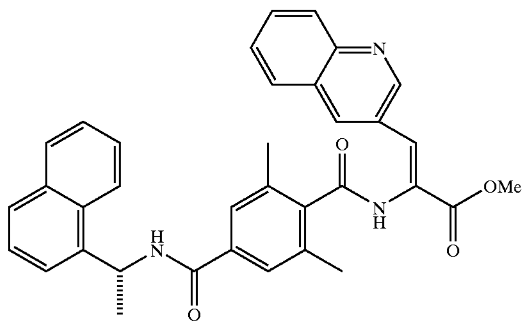 | Example 127 and quinoline-3-carboxaldehyde | 2.1 equiv. of TMG used in the reaction, product was triturated with methanol 74% yield |
| 170 | 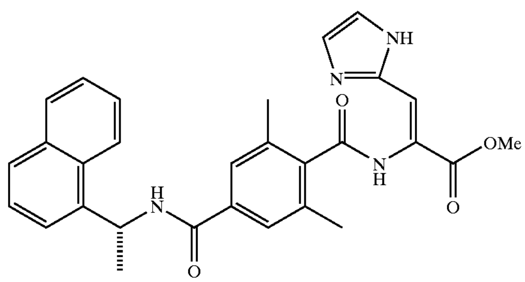 | Example 127 and 1H-imidaxole-2-carboxaldehyde | 2.1 equiv. of TMG used in the reaction, product was as is without trituration. 96% crude yield |
| 171 | 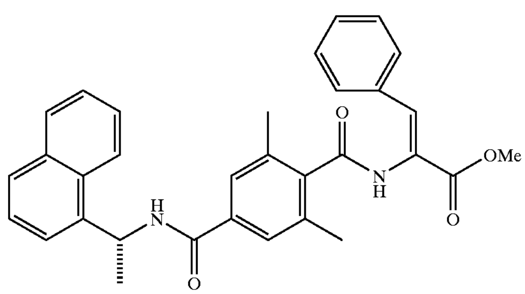 | Example 127 and benzaldehyde | 1.1 equiv. of TMG used in the reaction, product was as is without trituration; quantitative crude yield. |
| 172 | 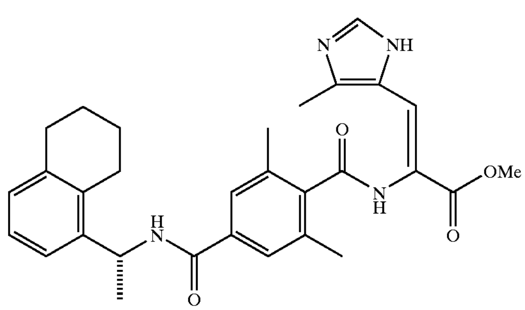 | Example 127 and 4-methyl-1H imidazole-5-carboxaldehyde | 1.3 equiv. of TMG used in the reaction, product was as is without trituration. 70% crude yield |

-continued

| Example | Structure | Starting Materials | Comments |
|---------|-----------|--------------------|----------|
| 173 | 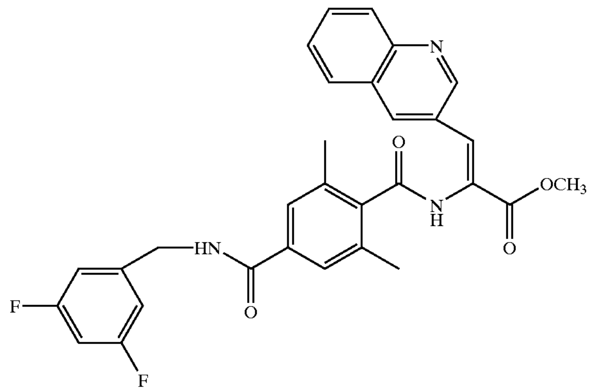 | Example 129 and quinoline-3-carboxaldehyde | 1.5 equiv. of TMG used in the reaction. The product was filtered from the reaction mixture and washed with THF, no work up required. 66% yield |
| 174 | 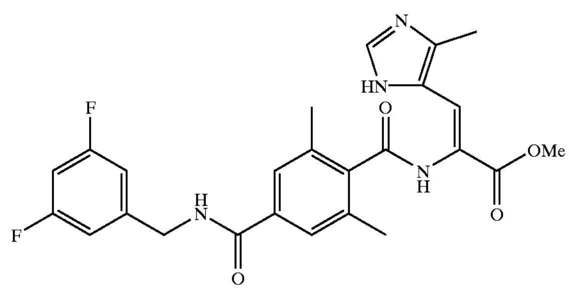 | Example 129 and 4-methyl-1H-imidazole-5-carboxaldehyde | 1.5 equiv. of TMG used; after warming, reaction stirred at room temperature overnight; used as is without trituration. |
| 175 | 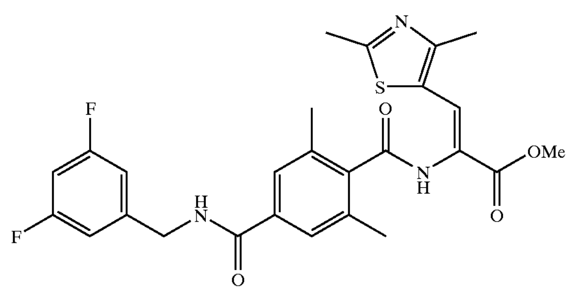 | Example 129 and Example 43 | |
| 176 | 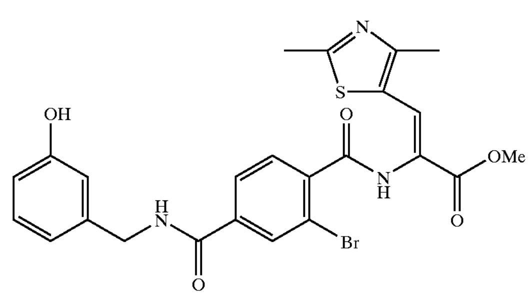 | Example 130 and Example 43 | Product was triturated with diethyl ether-petroleum ether (1:1). 81% yield. |
| 177 | 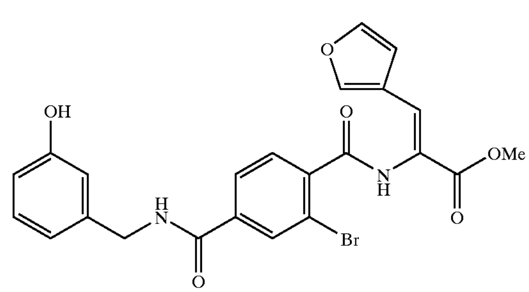 | Example 130 and furan-3-carboxaldehyde | 2.1 equiv. of TMG used in the reaction, product was as is without trituration; quantitative crude yield. |

-continued

| Example | Structure | Starting Materials | Comments |
|---------|-----------|--------------------|----------|
| 178 | 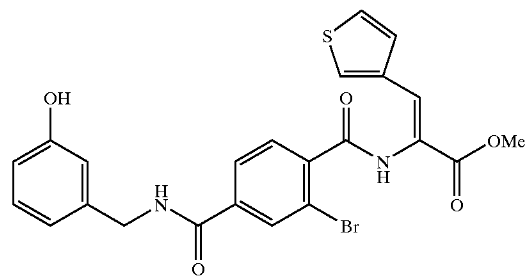 | Example 130 and thiophene-3-carboxaldehyde | 2.1 equiv. of TMG used in the reaction, product was as is without trituration. 94% crude yield. |
| 179 | 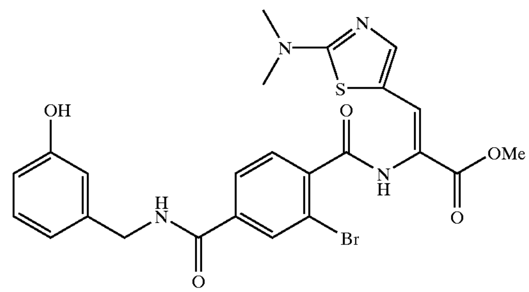 | Example 130 and Example 51 | Product was used as is, without trituration. 57% crude yield. |
| 180 | 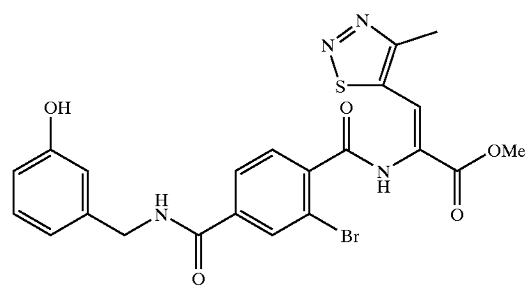 | Example 130 and Example 42 | Product was triturated with ethyl acetate. 80% yield. |
| 181 | 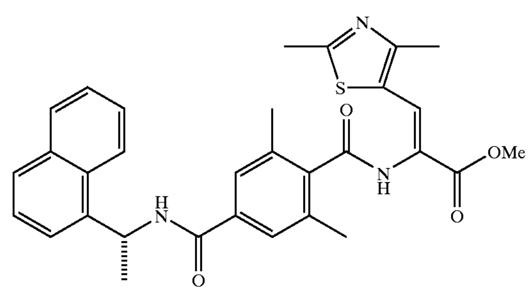 | Example 127 and Example 43 | 1.5 equiv. of TMG used in the reaction, product was triturated with diethyl ether in petroleum ether (1:1). |
| 182 | 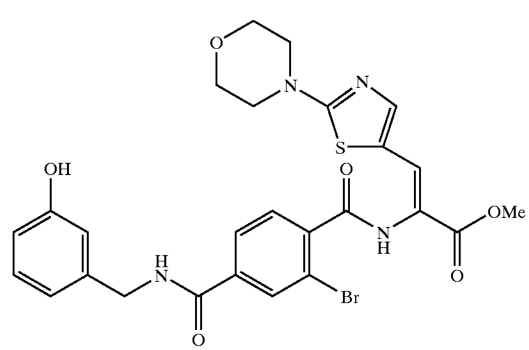 | Example 130 and Example 52 | Product was triturated with diethyl ether in petroleum ether (1:1). 96% yield |

-continued

| Example | Structure | Starting Materials | Comments |
|---|---|---|---|
| 183 | 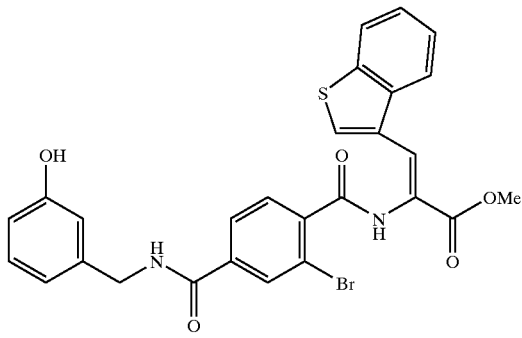 | Example 130 and benzothiopene-3-carboxaldehyde | Product was triturated with diethyl ether in petroleum ether (1:1). 82% yield |
| 184 | 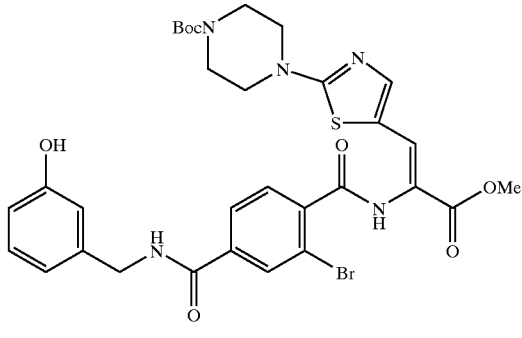 | Example 130 and Example 54 | Product was used is for the next step without trituration. 100% crude yield |
| 185 | 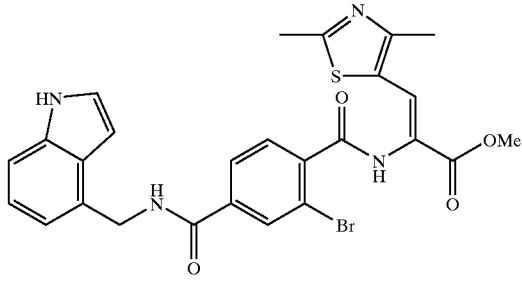 | Example 131 and Example 43 | 2 equiv. of TMG used in the reaction, product was triturated with hexane. 71% yield |
| 186 | 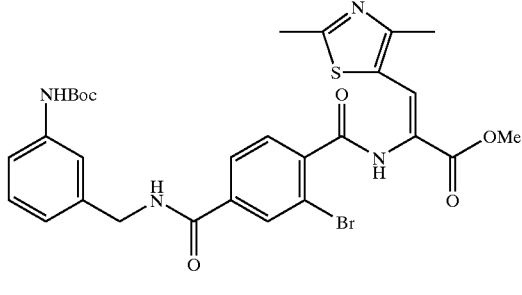 | Example 139 and Example 43 | Reaction time: 100 min at 25° C.; product chromatographed over silica gel (75% ethyl acetate in petroleum ether, then 3% methanol in ethyl acetate). 96% yield |

-continued

| Example | Structure | Starting Materials | Comments |
|---|---|---|---|
| 187 | 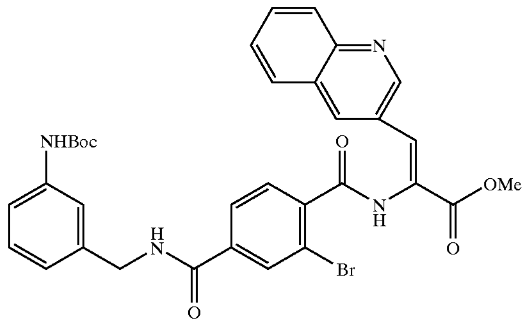 | Example 139 and quinoline-3-carboxaldehyde | Reaction time: 2 h at 25° C.; product isolated without chromatography; 87% yield, off-white solid |
| 188 | 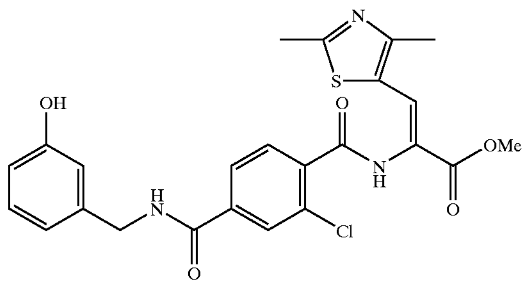 | Example 141 and Example 43 | product was used is for the next step without trituration 80% yield |
| 189 | 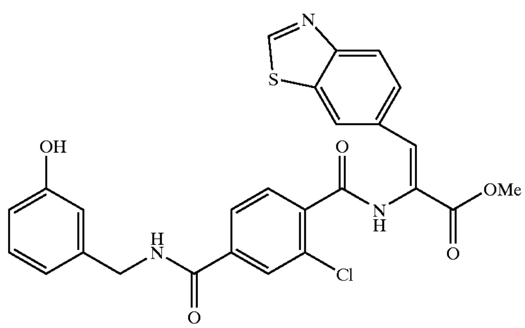 | Example 141 And Example 46 | product was triturated with 50% diethyl ether in hexane. 95% yield. |
| 190 | 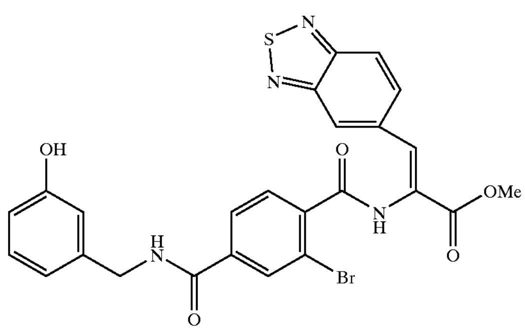 | Example 141 and Example 47 | product was triturated with 50% diethyl ether in hexane 69% yield. |
| 191 | 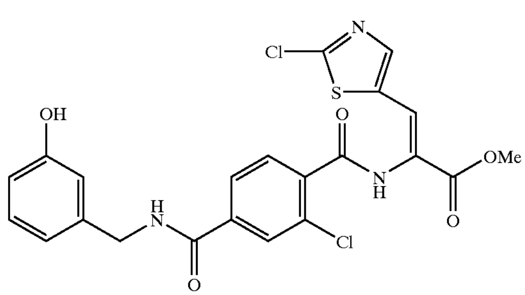 | Example 141 and Example 53 | product was triturated with diethyl ether 67% yield. |

-continued

| Example | Structure | Starting Materials | Comments |
|---|---|---|---|
| 192 | 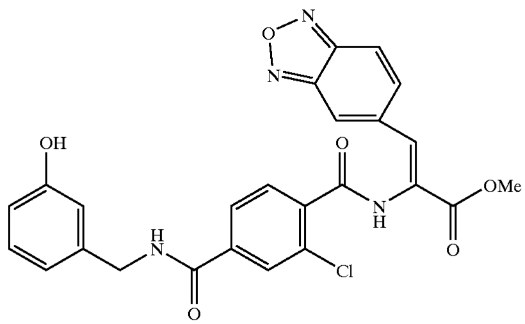 | Example 141 and Example 48 | product was triturated with diethyl ether 76% yield. |
| 193 | 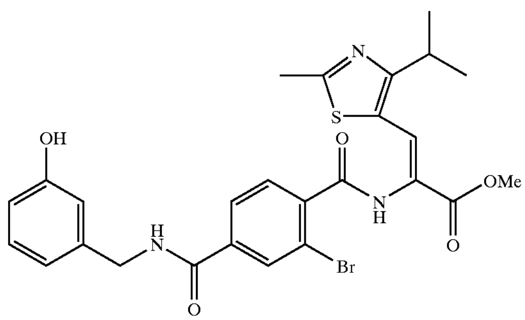 | Example 130 and Example 58 | product was triturated with diethyl ether 94% yield. |
| 194 | 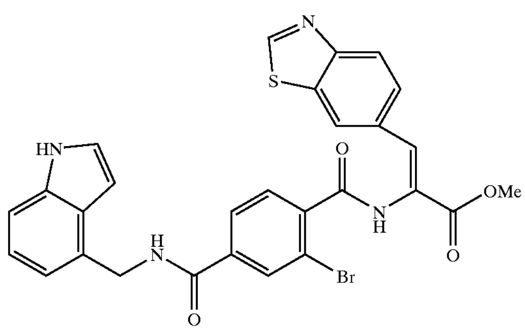 | Example 131 and Example 46 | product was triturated with diethyl ether 70% yield. |
| 195 | 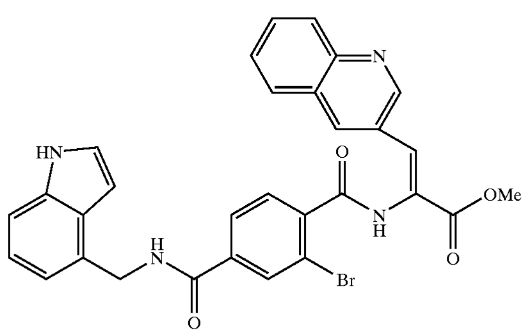 | Example 131 and quinoline-3-carboxaldehyde | product was triturated with diethyl ether. 66% yield |

-continued

| Example | Structure | Starting Materials | Comments |
|---|---|---|---|
| 196 | 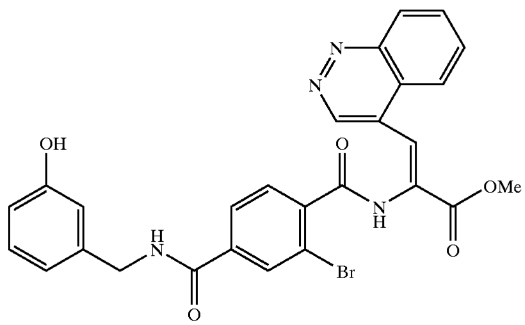 | Example 130 And Example 49 | 2.1 equiv. of TMG used; quenched with water instead of pH 6 phosphate buffer; product (yellow solid) was used as is, without trituration 78% crude yield |
| 197 | 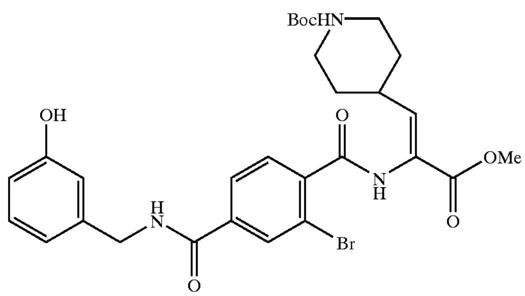 | Example 130 And Example 65 | Reaction time: 4.5 h at 25° C.; chromatographed over silica gel (40% ethyl acetate in petroleum ether). Colorless solid, 89% yield |
| 198 | 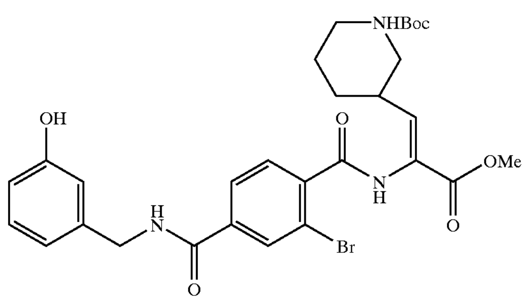 | Example 130 And Example 66 | Reaction time: 2 h at 25° C.; chromatographed over silica gel (60% ethyl acetate in petroleum ether). Colorless solid, 91% yield |
| 199 | 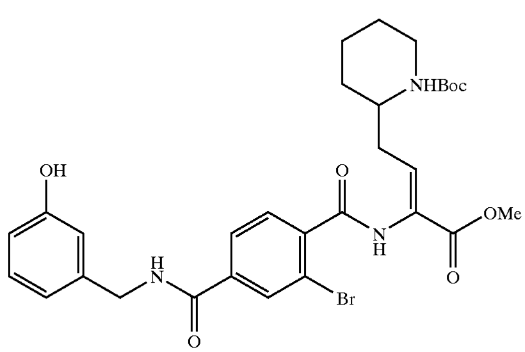 | Example 130 And Example 67 | Reaction time 2 h at 25° C.; triturated with 50% diethyl ether in petroleum ether. Colorless solid, 86% yield |

| Example | Structure | Starting Materials | Comments |
|---|---|---|---|
| 200 | 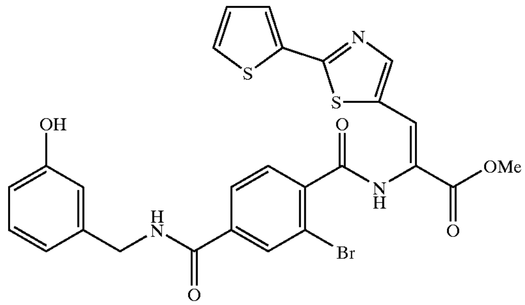 | Example 130 And Example 50 | 2.1 equiv. of TMG used in the reaction, crude product used as is. 93% yield. |
| 201 | 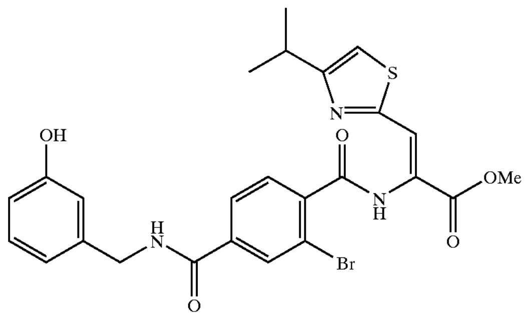 | Example 130 and Example 44 | 2.1 equiv. of TMG used in the reaction, crude product (colorless foam) used as is; quantitative recovery. |
| 202 | 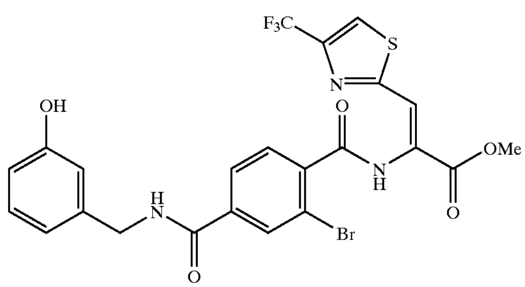 | Example 130 and Example 45 | chromatographed over silica gel (50% ethyl acetate in petroleum ether). Yellow solid, 86% yield |

Example 203

Preparation of (Z)-3-(2,4-Dimethylthiazol-5-yl)-2-[[4-[[(3-hydroxybenzyl)amino]carbonyl]-2,6-dimethylbenzoyl]amino]propenoic Acid Methyl Ester

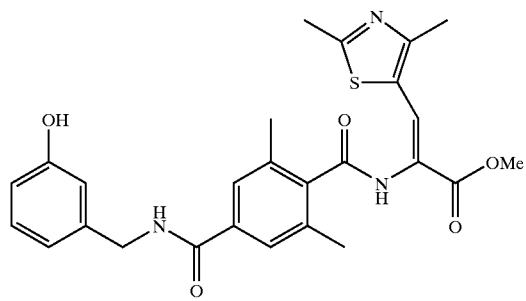

A. (Z)-2-[[4-[[[3-[[(1,1-Dimethylethyl)dimethylsilyl]oxy]benzyl]amino]carbonyl]-2,6-dimethylbenzoyl]amino]-3-(2,4-dimethylthiazol-5-yl)propenoic Acid Methyl Ester.

1,1,3,3-Tetramethylguanidine (54 μL, 0.425 mmol) was added to a solution of rac.-2-(dimethoxyphosphinyl)-N-[4-[[[3-[[(1,1-dimethylethyl)dimethylsilyl]oxy]benzyl]amino]carbonyl]-2,6-dimethylbenzoyl]glycine methyl ester (Example 126; 150 mg, 0.25 mmol) in tetrahydrofiran (2 mL) at −40° C. The solution was stirred at −40° C. for 5 min and then 2,4-dimethylthiazol-5-carboxaldehyde (Example 43; 43 mg, 0.3 mmol) was added. The reaction mixture was stirred at −40° C. for 60 min and then allowed to stir at room temperature for 4 h. A second portion of 1,1,3,3-tetramethylguanidine (27 μL, 0.213 mmol) and the reaction was allowed to stir at room temperature for 2 days. The solution was partitioned between pH 6 phosphate buffer and ethyl acetate and the organic layer was dried (MgSO$_4$), filtered and evaporated. The residue was chromatographed (silica gel, ethyl acetate in petroleum ether) to furnish 78 mg of (Z)-2-[[4-[[[3-[[(1,1-dimethylethyl)dimethylsilyl]oxy]benzyl]amino]carbonyl]-2,6-dimethylbenzoyl]amino]-3-(2,4-dimethylthiazol-5-yl)propenoic acid methyl ester as a colorless foam (50% yield).

B. (Z)-3-(2,4-Dimethylthiazol-5-yl)-2-[[4-[[(3-hydroxybenzyl)amino]carbonyl]-2,6-dimethylbenzoyl]amino]propenoic Acid Methyl Ester.

To a solution of (Z)-2-[[4-[[[3-[[(1,1-dimethylethyl)dimethylsilyl]oxy]benzyl]amino]carbonyl]-2,6-dimethylbenzoyl]amino]-3-(2,4-dimethylthiazol-5-yl)propenoic acid methyl ester (47 mg, 0.0773 mmol) in THF (1 mL) was added a 1M solution of tetrabutylammonium fluoride in tetrahydrofuran (0.085 mmol, 85 μL) and the reaction was stirred for 3 days at ambient temperature. The reaction was diluted with ethyl acetate and was then washed with in turn with water and brine. The organic layer was dried (MgSO₄), filtered and evaporated in vacuo to yield 39 mg of (Z)-2-[[4-[[(3-hydroxybenzyl)amino]carbonyl]-2,6-dimethylbenzoyl]amino]-3-(2,4-dimethylthiazol-5-yl) propenoic acid methyl ester as a yellow solid (quantitative yield).

Example 204

Preparation of [Z-(R)]-2-[[2,6-dimethyl-4-[[1-(naphthalen-1-yl)ethylamino]carbonyl]benzoyl] amino]-3-(pyridin-4-yl)propenoic Acid Methyl Ester

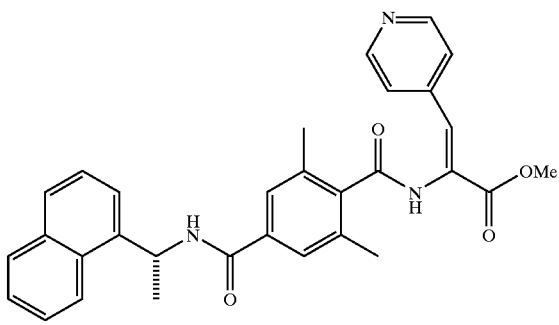

1,1,3,3-Tetramethylguanidine (31 μL, 0.26 mmol) was added to a solution of (R,S)-N-[2,6-dimethyl-4-[[(R)-1-(naphthalen-1-yl)ethylamino]carbonyl]benzoyl]-2-(dimethoxyphosphinyl)glycine methyl ester (Example 127; 100 mg, 0.2 mmol) in tetrahydrofuran (3 mL) at −40° C. The solution was stirred at −40° C. for 5 min and then pyridine-4-carboxaldehyde (18 μL, 0.2 mmol) was added. The reaction mixture was stirred at −40° C. for 1 h and then allowed to stir at 10° C. for 2 h. A second portion of 1,1,3,3-tetramethylguanidine (31 μL, 0.26 mmol) and the reaction at −40° C. and the mixture was allowed to stir at room temperature for 90 min. The solution was partitioned between pH 6 phosphate buffer and ethyl acetate and the organic layer was dried (MgSO₄), filtered and evaporated to furnish [Z-(R)]-2-[[2,6-dimethyl-4-[[1-(naphthalen-1-yl) ethylamino]carbonyl]benzoyl]amino]-3-(pyridin-4-yl) propenoic acid methyl ester as an off-white solid (89 mg, 93% yield).

Example 205

Preparation of (Z)-3-(2-Aminothiazol-5-yl)-2-[[2-chloro-4-[[(3-hydroxybenzyl)amino]carbonyl] benzoyl]amino]propenoic Acid Methyl Ester

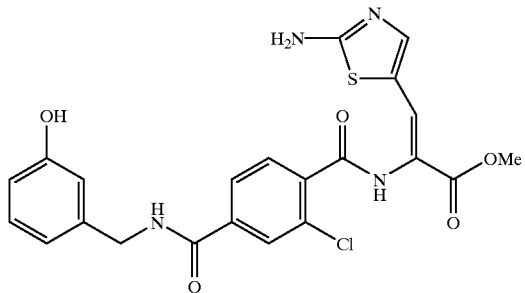

1,1,3,3-Tetramethylguanidine (79 μL, 0.63 mmol) was added to a solution of rac.-N-[2-chloro-4-[[(3-hydroxybenlzyl)amino]carbonyl]benzoyl]-2-(dimethoxyphosphinyl)glycine methyl ester (Example 141; 145 mg, 0.30 mmol) in tetrahydrofuran (1 mL) then 2-aminothiazole-5-carboxaldehyde (prepared according to the literature procedure: Frishberg, M. D. U.S. Pat. No. 4,225,719 Sep. 30, 1980; 38.3 mg, 0.30 mmol) was added. After the reaction mixture was allowed to stir overnight at room temperature, ethyl acetate (20 mL) was added and the solution was washed with pH 6 phosphate buffer (10 mL). The aqueous layer was extracted with ethyl acetate and the combined organic layers were washed with brine, dried (NgSO₄), filtered and evaporated. The residue was chromatographed over silica gel (8% methanol/dichloromethane) to give (Z)-3-(2-aminothiazol-5-yl)-2-[[2-chloro-4-[[(3-hydroxybenzyl)amino]carbonyl]benzoyl] amino]propenoic acid methyl ester (30 mg, 21% yield) as a yellow foam.

Example 206

Preparation of (Z)-3-(1H-Benzotriazol-5-yl)-2-[[2-bromo-4-[[(3-hydroxybenzyl)amino]carbonyl] benzoyl]amino]propenoic Acid Methyl Ester

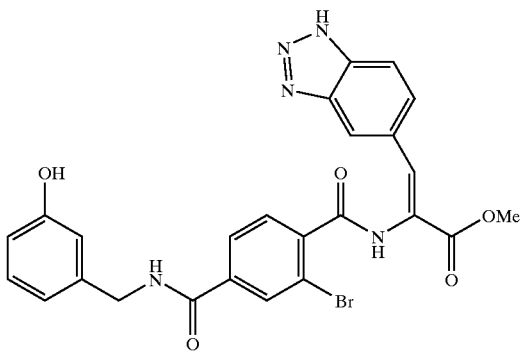

1,1,3,3-Tetramethylguanidine (0.5 mL, 3.97 mmol) was added to a solution of rac.-N-[2-bromo-4-[[(3-hydroxybenzyl)amino]carbonyl]benzoyl]-2-(dimethoxyphosphinyl) glycine methyl ester (Example 130; 1.00 g, 1.89 mmol) in tetraliydrofuran (3 mL) at −20° C. After 10 min, a solution of 1-(1,1-dimethylethoxycarbonyl)-1H-benzotriazole-5-carboxaldehyde (Example 40; 467 mg, 1.89 mmol) in tetrahydrofuran (3 mL) was added. The solution was stirred at room temperature for 1 h, then the solvent was evaporated and the residue was dissolved in a mixture of trifluoroacetic acid/dichloromethane (1:1; 4 mL). After the solution was stirred at room temperature for 2 h, the solvent was evaporated and the residue co-evaporated with toluene (2×5 mL) to remove residual trifluoroacetic acid. Ethyl acetate (20 mL) was added and the solution was washed with 5% sodium bicarbonate solution (20 mL). After the aqueous layer was back extracted with ethyl acetate, the combined organic layers were dried (MgSO₄), filtered and evaporated to dryness. The residual material was chromatographed over silica gel (5–10% methanol/dichloromethane) to give (Z)-3-(1H-benzotriazol-5-yl)-2-[[2-bromo-4-[[(3-hydroxybenzyl)amino]carbonyl]benzoyl]amino]propenoic acid methyl ester (690 mg, 66% yield) as a colorless solid.

Also prepared by this route was:

| Example | Structure | Starting Materials | Comments |
|---|---|---|---|
| 207 | 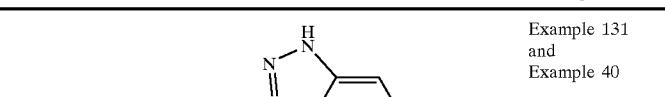 | Example 131 and Example 40 | 31% yield |

Example 208

Preparation of [Z-(R)]-3-(1H-Benzotriazol-5-yl)-2-[[2,6-dimethyl-4-[[1-(naphthalen-1-yl)ethylamino]carbonyl]benzoyl]amino]propenoic Acid Methyl Ester

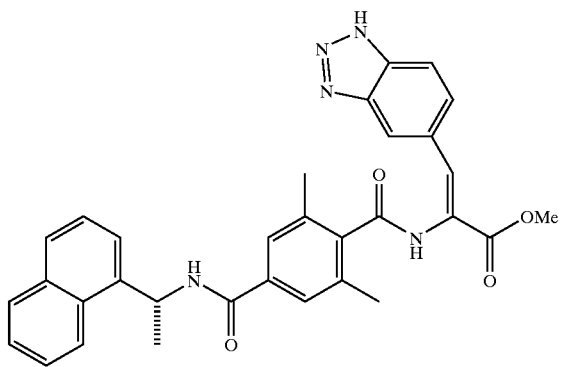

1,1,3,3-Tetramethylguanidine (36 μL, 0.28 mmol) was added to a solution of (R,S)-N-[2,6-dimethyl-4-[[(R)-1-(naphthalen-1-yl)ethylamino]carbonyl]benzoyl]-2-(dimethoxyphosphinyl)glycine methyl ester (Example 127; 100 mg, 0.19 mmol) in tetrahydrofuran (2 mL) at −40° C. After 5 min, a solution of 1-(1,1-dimethylethoxycarbonyl)-1H-benzotriazole-5-carboxaldehyde (Example 40; 47 mg, 0.19 mmol) in tetrahydrofuran (1 mL) was added. After the solution was stirred at −40° C., then at room temperature for overnight, it was distributed between pH 6 phosphate buffer (10 mL) and ethyl acetate (20 mL). The aqueous layer was extracted with ethyl acetate and the combined organic layers were washed with brine, dried (MgSO$_4$), filtered and the volatiles were removed in vacuo. A solution of the residual material in a mixture of trifluoroacetic acid/dichloromethane (1:1; 2 mL) was stirred at room temperature. After 3 h the solvents were evaporated under reduced pressure and the crude material was partitioned between ethyl acetate was added and a 5% aqueous sodium bicarbonate solution. The separated organic extract was dried (MgSO$_4$), filtered and evaporated under reduced pressure and the resulting residue was chromatographed over silica gel (5% methanol/dichloromethane) to furnish [Z-(R)]-3-(1H-benzotriazol-5-yl)-2-[[2,6-dimethyl-4-[[1-(naphthalen-1-yl)ethylamino]carbonyl]benzoyl]amino]propenoic acid methyl ester (85 mg, 82% yield) as a colorless solid.

The following compound was prepared as described in Example 208:

| Example | Structure | Starting Materials | Comments |
|---|---|---|---|
| 209[a] | 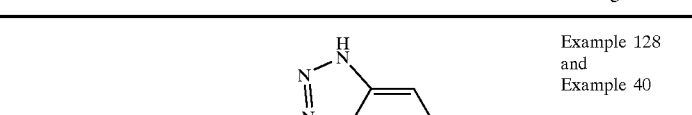 | Example 128 and Example 40 | Colorless solid, 38% yield |

[a]Horner Emmons reaction was run as in Example 208 except the room temperature phase of the procedure was reduced from overnight to 2 h.

Example 210

Preparation of (Z)-3-(1H-Benzotriazol-5-yl)-2-[[2-chloro-4-[[(3-hydroxybenzyl)amino]carbonyl]-6-methylbenzoyl]amino]propenoic Acid Methyl Ester

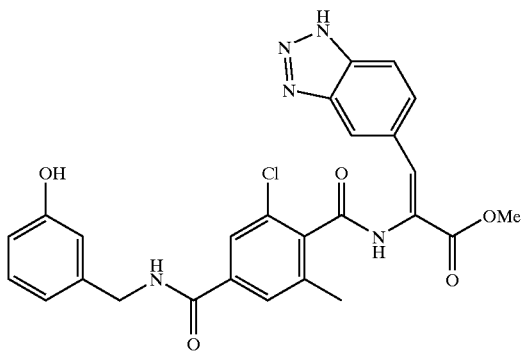

A. (Z)-2-[[2-Chloro-4-[[(3-hydroxybenzyl)amino]carbonyl]-6-methylbenzoyl]amino]-3-[1-(1,1-dimethylethoxycarbonyl)-1H-benzotriazol-5-yl]propenoic Acid Methyl Ester.

1,1,3,3-Tetramethylguanidine (60 μL, 0.48 mmol) was added to a solution of rac.-N-[2-chloro-4-[[(3-hydroxybenzyl)amino]carbonyl]-6-methylbenzoyl]-2-(dimethoxyphosphinyl)glycine methyl ester (Example 132; 109 mg, 0.22 mmol) in tetrahydrofuran (3 mL) at room temperature. 1-(1,1-dimethylethoxycarbonyl)-1H-benzotriazole-5-carboxaldehyde (Example 40; 55 mg, 0.22 mmol) was added and the solution was stirred at room temperature for 42 h. After the solvents were removed under reduced pressure, the residue was partitioned between ethyl acetate (10 mL) and pH 6 phosphate buffer (5 mL). The organic phase was washed with pH 6 phosphate buffer, brine, 10% aqueous sodium bicarbonate solution and brine. Each of the aqueous layers was extracted in turn with ethyl acetate. The combined organic layers were dried (Na$_2$SO$_4$), filtered and evaporated to give crude (Z)-2-[[2-chloro-4-[[(3-hydroxybenzyl)amino]carbonyl]-6-methylbenzoyl]amino]-3-[1-(1,1-dimethylethoxycarbonyl)-1H-benzotriazol-5-yl] propenoic acid methyl ester (120 mg) which was used directly in the next step.

B. (Z)-3-(1H-Benzotriazol-5-yl)-2-[[2-chloro-4-[[(3-hydroxybenzyl)amino]carbonyl]-6-methylbenzoyl]amino] propenoic Acid Methyl Ester.

A mixture of crude (Z)-2-[[2-chloro-4-[[(3-hydroxybenzyl)amino]carbonyl]-6-methylbenzoyl]amino]-3-[1-(1,1-dimethylethoxycarbonyl)-1H-benzotriazol-5-yl] propenoic acid methyl ester (120 mg) in a 4N solution of hydrogen chloride in dioxane (5 mL) was stirred at room temperature for 2.5 h. The solvent was evaporated and the residue was chromatographed over silica gel using in turn, chloroform, chloroform/methanol/water/acetic acid (300:30:10:6) and then chloroform/methanol/water/acetic acid (150:30:10:6) to elute the column. The material obtained was further purified by reverse phase HPLC (gradient elution using increasing concentrations of acetonitrile in water containing 0.1% trifluoroacetic acid). The appropriate fractions were combined, evaporated and lyophilized to give (Z)-3-(1H-benzotriazol-5-yl)-2-[[2-chloro-4-[[(3-hydroxybenzyl)amino]carbonyl]-6-methylbenzoyl] amino]propenoic acid methyl ester trifluoroacetate salt as a colorless solid (18 mg, 13% yield over two steps).

Example 211

Preparation of (Z)-2-[[2-Chloro-4-[[(3-hydroxybenzyl)amino]carbonyl]-6-methylbenzoyl] amino]-3-(quinolin-3-yl) propenoic Acid Methyl Ester

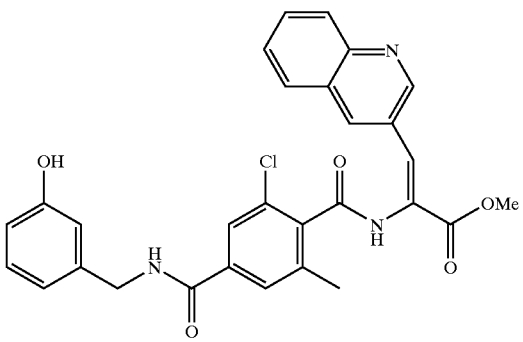

1,1,3,3-Tetramethylguanidine (30 μL, 0.24 mmol) was added to a solution of rac.-N-[2-chloro-4-[[(3-hydroxybenzyl)amino]carbonyl]-6-methylbenzoyl]-2-(dimethoxyphosphinyl)glycine methyl ester (Example 132; 55 mg, 0.11 mmol) in tetrahydrofuran (2 mL) at room temperature. After 5 min, quinoline-3-carboxaldehyde (18 mg, 0.114 mmol) was added and the solution was stirred at room temperature for 16 h. The reaction mixture was evaporated to dryness and the residue was dissolved in a solvent mixture of chloroform/methanol/water/acetic acid (150:30:10:6) and evaporated to dryness. A solution of the residue in a minimum amount of chloroform/methanol/water/acetic acid (150:30:10:6) was applied to a column of three piggy-backed SepPak Plus® silica gel cartridges that had been pre-washed with chloroform. The column was eluted with chloroform, then with a mixture of chloroform/methanol/water/acetic acid (300:30:10:6). Evaporation of the appropriate fractions gave (Z)-2-[[2-chloro-4-[[(3-hydroxybenzyl)amino]carbonyl]-6-methylbenzoyl]amino]-3-(quinolin-3-yl)propenoic acid methyl ester (32.7 mg, 55% yield) as a colorless powder.

Example 212

Preparation of (Z)-2-[[2-Chloro-4-[[(3-hydroxybenzyl)amino]carbonyl]-6-methylbenzoyl]amino]-3-phenylpropenoic Acid Methyl Ester

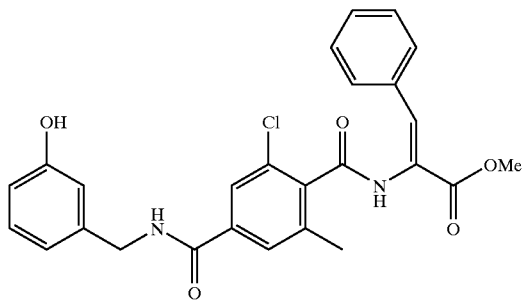

1,1,3,3-Tetramethylguanidine (20 µL, 0.16 mmol) was added to a solution of rac.-N-[2-chloro-4-[[(3-hydroxybenzyl)amino]carbonyl]-6-methylbenzoyl]-2-(dimethoxyphosphinyl)glycine methyl ester (Example 132; 33 mg, 0.066 mmol) in tetrahydrofuran (1 mL) at room temperature. After 5 min, benzaldehyde (7 µL, 0.068 mmol) was added and the solution was stirred at room temperature for 16 h. The solvent was evaporated and the residue was purified by chromatography over silica gel. The column was eluted sequentially with chloroform, chloroform/methanol/water/acetic acid (600:30:10:6), chloroform/methanol/water/acetic acid (300:30:10:6) and chloroform/methanol/water/acetic acid (150:30:10:6). The appropriate fractions were combined and lyophilized to fuirnish (Z)-2-[[2-chloro-4-[[(3-hydroxybenzyl)amino]carbonyl]-6-methylbenzoyl]amino]-3-phenylpropenoic acid methyl ester (23 mg, 73% yield).

Example 213

Preparation of (Z)-2-[[4-[[(3-Hydroxybenzyl)amino]carbonyl]-2-methylbenzoyl]amino]-3-phenylpropenoic Acid Methyl Ester

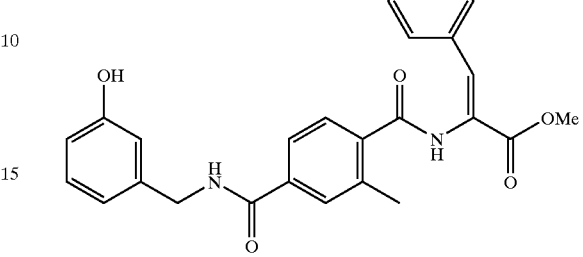

1,1,3,3-Tetramethylguanidine (0.20 g, 1.7 inmol) was added to a solution of rac.-N-[4-[[(3-hydroxybenzyl)anlino]carbonyl]-2-methylbenzoyl]-2-(dimethoxyphosphinyl)glycine methyl ester (Example 140; 0.40 g, 0.9 mmol) and benzaldehyde (0.10 g, 0.9 mmol) in dichloromethane (50 mL) at room temperature and the reaction was stirred at ambient temperature over the weekend. The solution was diluted with dichloromethane (200 mL) and washed in turn with 1N hydrochloric acid solution, water and brine (200 mL each), dried (MgSO$_4$) and evaporated to give (Z)-2-[[4-[[(3-hydroxybenzyl)amino]carbonyl]-2-methylbenzoyl]amino]-3-phenylpropenoic acid methyl ester (300 mg, 78% yield) which was used directly in a subsequent step.

Also prepared by this procedure were:

| Example | Structure | Starting Materials | Yield |
|---|---|---|---|
| 214 | 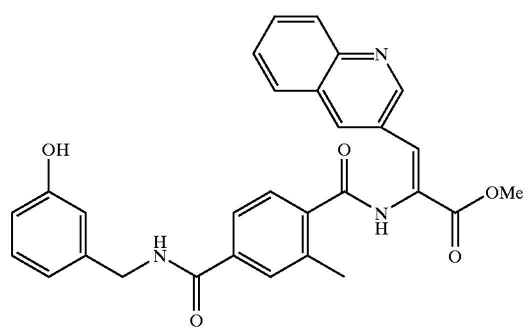 | Example 140 and quinoline-3-carboxaldehyde | 54% |
| 215 | 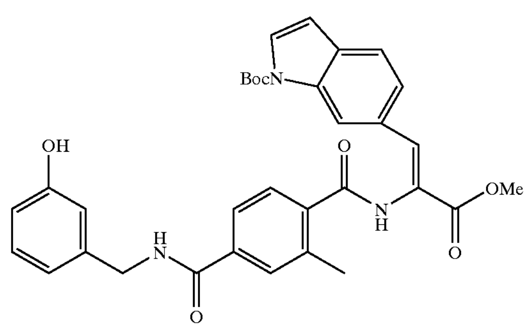 | Example 140 and Example 64 | 16% |

Example 216

Preparation of (Z)-2-[[2-Chloro-4-[[(3-hydroxybenzyl)amino]carbonyl]benzoyl]amino]-3-(2-ethyl-4-methylthiazole-5-yl)propenoic Acid Methyl Ester

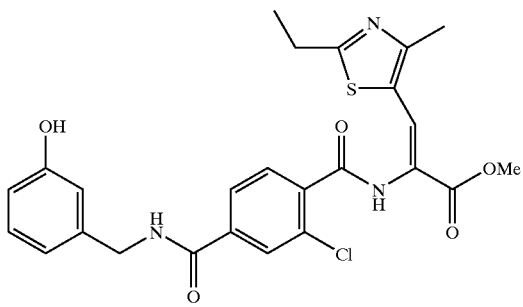

1,1,3,3-Tetramethylguanidine (107 mg, 0.9 mmol) was added to a solution of rac.-N-[2-chloro-4-[[(3-hydroxybenzyl)amino]carbonyl]benzoyl]-2-(dimethoxyphosphinyl)glycine methyl ester (Example 141; 300 mg, 0.6 mmol) in dichloromethane (10 mL) at ~5° C. The solution was stirred at ~5° C. for 30 min and then 2-ethyl-4-methylthiazole-5-carboxaldehyde (Example 60; 192 mg, 1.2 mmol) was added. The solution was stirred overnight at room temperature, then silica gel was added and the solvent was evaporated. The residue was applied to a column of silica gel and unreacted 2-ethyl-4-methylthiazole-5-carboxaldehyde was eluted with 50% ethyl acetate/hexanes. Evaporation of the appropriate fractions eluted with 5% methanol/dichloromethane gave (Z)-2-[[2-chloro-4-[[(3-hydroxybenzyl)amino]carbonyl]benzoyl]amino]-3-(2-ethyl-4-methylthiazole-5-yl)propenoic acid methyl ester (110 mg, 35% yield) as a colorless solid, mp>200° C.

Also prepared by this procedure were:

| Example | Structure | Starting Materials | Yield |
|---|---|---|---|
| 217 | 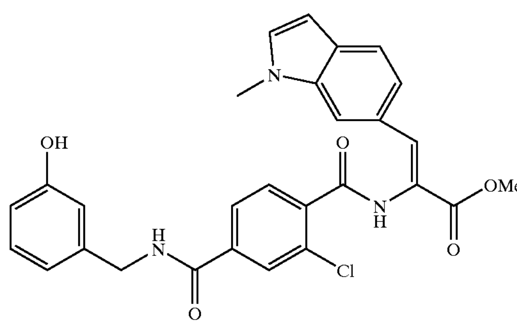 | Example 141 and Example 63 | 59% |
| 218 | 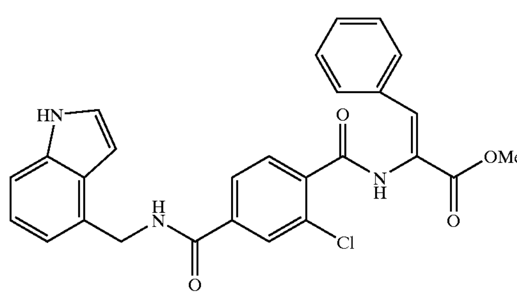 | Example 138 and benzaldehyde | 33% |
| 219 | 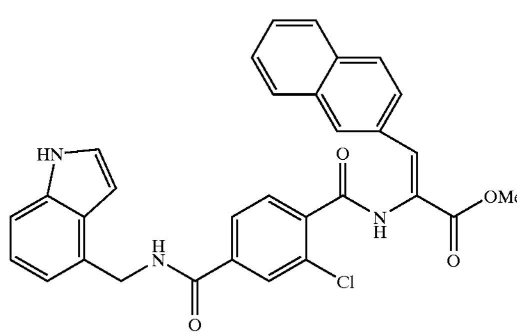 | Example 138 and naphthalene-3-carboxaldehyde | 41% |

| Example | Structure | Starting Materials | Yield |
|---|---|---|---|
| 220 | 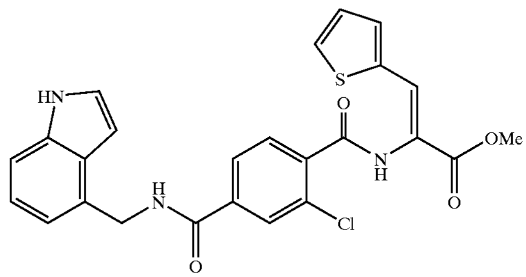 | Example 138 and thiophene-2-carboxaldehyde | 27% |
| 221 | 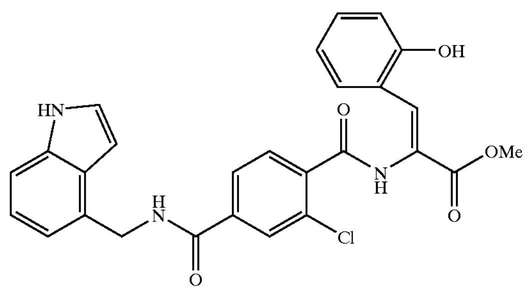 | Example 138 and salicylaldehyde | 17% |
| 222 | 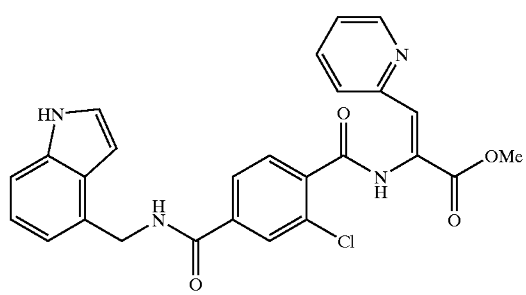 | Example 138 and pyridine-2-carboxaldehyde | 24% |

Example 223

Preparation of (Z)-2-[[2-Chloro-4-[[(3-hydroxybenzyl)amino]carbonyl]benzoyl]amino]3-[2-ethyl-4-(1-methylethyl)thiazole-5-yl]Propenoic Acid Methyl Ester

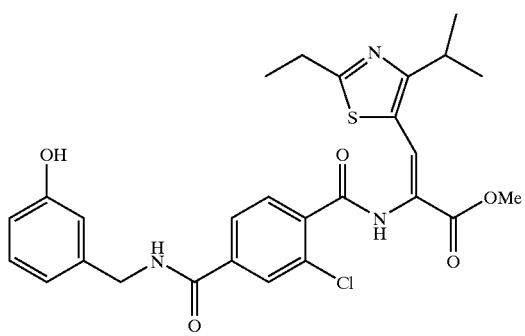

1,1,3,3-Tetramethylguanidine (107 mg, 0.93 mmol) was added to a solution of rac.-N-[2-chloro-4-[[(3-hydroxybenzyl)amino]carbonyl]benzoyl]-2-(dimethoxyphosphinyl)glycine methyl ester (Example 141; 300 mg, 0.62 mmol) in dichloromethane (10 mL) at ~5° C. The solution was stirred at ~5° C. for 30 min and then 2-ethyl-4-(1-methylethyl)thiazole-5-carboxaldehyde (Example 61; 224 mg, 1.24 mmol) was added. The solution was stirred over a weekend at room temperature, then water was added and the layers were separated. The aqueous layer was extracted with two portions of dichloromethane then the combined organic layers were washed in turn with brine, 0.5N hydrochloric acid solution, water and brine. The dried (MgSO$_4$) organic extracts were evaporated and the resulting oil was purified by chromatography over silica gel. Evaporation of the appropriate fractions afforded (Z)-2-[[2-chloro-4-[[(3-hydroxybenzyl)amino]carbonyl]benzoyl]amino]3-[2-ethyl-4-(1-methylethyl)thiazole-5-yl]propenoic acid methyl ester (220 mg, 65% yield).

Example 224

Preparation of (Z)-3-(4-Bromophenyl)-2-[[2-chloro-4-[[(3-hydroxybenzyl)amino]carbonyl]benzoylamino]Propenoic Acid Methyl Ester

Example 226

Preparation of (Z)-2-[[2-Chloro-4-[3-(3-hydroxyphenyl)-1-oxopropan-1-yl]benzoyl]amino]-3-(quinolin-3-yl)propenoic Acid Methyl Ester

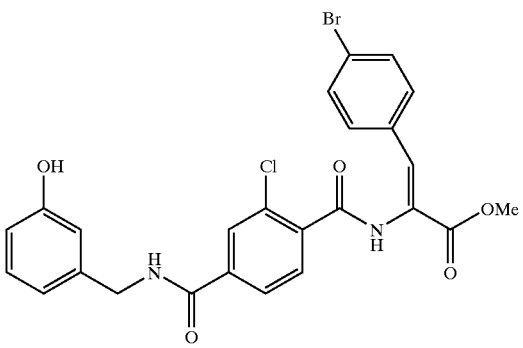

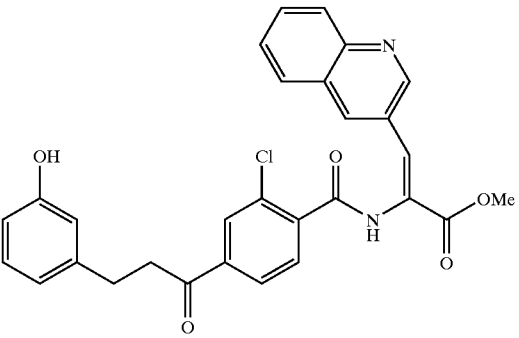

1,1,3,3-Tetramethylguanidine (0.047 g, 0.41 mmol) was added to a solution of rac.-N-[2-chloro-4-[[(3-hydroxybenzyl)amino]carbonyl]benzoyl]-2-(dimethoxyphosphinyl)glycine methyl ester (Example 141; 0.10 g, 0.21 mmol) and 4-bromobenzaldehyde (0.076 g, 0.412 mmol) in tetrahydrofuran (1.5 mL). Dioxane (1.5 mL) was added to bring everything into solution and the reaction mixture was stirred at room temperature for 15 h. The solution was then poured into 1N hydrochloric acid solution and the aqueous phase was extracted with ethyl acetate. The organic layer was concentrated in vacuo and the residual material was chromatographed over silica gel (45% ethyl acetate/hexanes) to give (Z)-3-(4-bromophenyl)-2-[[2-chloro-4-[[(3-hydroxybenzyl)amino]carbonyl]benzoyl]amino]propenoic acid methyl ester (69 mg, 62% yield).

Also prepared by this procedure was:

1,1,3,3-Tetramethylguanidine (94 μL, 0.75 mmol) was added to a solution of rac.-N-[2-chloro-4-[3-(3-hydroxyphenyl)-1-oxopropan-1-yl]benzoyl]-2-(dimethoxyphosphinyl)glycine methyl ester (Example 133; 244 mg, 0.5 mmol) in tetrahydrofuran (7 mL) at −20° C. After 30 min, quinoline-3-carboxaldehyde (82.5 mg, 0.525 mmol) was added and the solution was stirred at room temperature for 16 h. The solvent was evaporated and ethyl acetate (30 mL) was added. The solution was washed with saturated sodium bicarbonate solution (15 mL) and the aqueous layer was extracted with ethyl acetate (10 mL). Each organic layer was washed with brine. The combined organic layers were dried (MgSO$_4$), filtered, evaporated and chromatographed over silica gel (20–50% ethyl acetate/hexanes) to (Z)-2-[[2-chloro-4-[3-(3-hydroxyphenyl)-1-oxopropan-1-yl]benzoyl]amino]-3-(quinolin-3-yl)propenoic acid methyl ester (221 mg, 86% yield) as an orange-yellow solid.

| Example | Structure | Starting Materials | Yield |
|---|---|---|---|
| 225 | 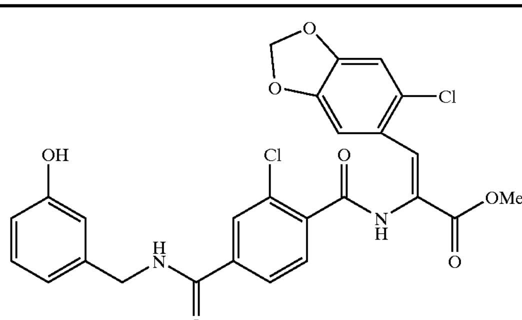 | Example 141 and 6-chlorobenzodioxole-5-carboxaldehyde | 47% |

Example 227

Preparation of (Z)-2-[[2-Chloro-4-[3-(3-hydroxyphenyl)-1-oxopropan-1-yl]benzoyl]amino]-3-(2,4-dimethylthiazol-5-yl)propenoic Acid Methyl Ester

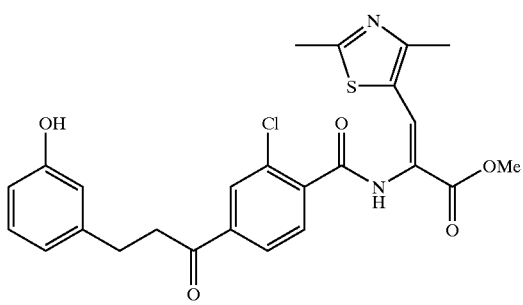

1,1,3,3-Tetramethylguanidine (60 μL, 0.48 mmol) was added to a solution of rac.-N-[2-chloro-4-[3-(3-hydroxyphenyl)-1-oxopropan-1-yl]benzoyl]-2-(dimethoxyphosphinyl)glycine methyl ester (Example 133; 116 mg, 0.24 mmol) in tetrahydrofuran (6 mL) at −20° C. After 15 min, 2,4-dimethylthiazole-5-carboxaldehyde (Example 43; 37 mg, 0.26 mmol) was added and the solution was stirred at room temperature for 16 h. The solvent was evaporated and ethyl acetate (15 mL) was added. The resulting solution was washed with saturated sodium bicarbonate solution (15 mL) and brine. The organic layer was dried (MgSO₄), filtered, evaporated, chromatographed over silica gel (60% ethyl acetate/hexanes) and crystallized from diethyl ether/hexanes to (Z)-2-[[2-chloro-4-[3-(3-hydroxyphenyl)-1-oxopropan-1-yl]benzoyl]amino]-3-(2,4-dimethylthiazol-5-yl)propenoic acid methyl ester (98 mg, 82% yield) as a colorless solid.

Example 228

Preparation of rac.-(Z)-2-[[2-Chloro-4-[1-hydroxy-3-(3-hydroxyphenyl)propan-1-yl]benzoyl]amino]-3-(quinolin-3-yl)propenoic Acid Methyl Ester

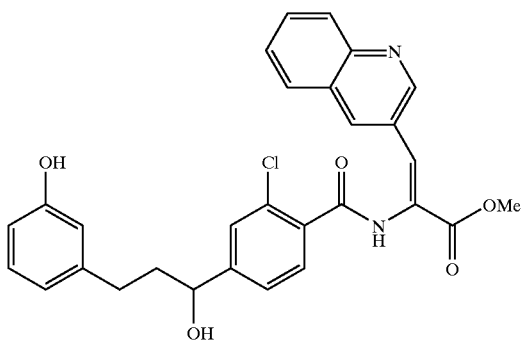

1,1,3,3-Tetramethylguanidine (60 μL, 0.48 mmol) was added to a solution of rac.-N-[2-chloro-4-[1-hydroxy-3-(3-hydroxyphenyl)propan-1-yl]benzoyl]-2-(dimethoxyphosphinyl)glycine methyl ester (Example 134; 120 mg, 0.24 mmol) in tetrahydrofuran (5 mL) at −20° C. After 10 min, quinoline-3-carboxaldehyde (39.3 mg, 0.25 mmol) was added and the solution was stirred at room temperature for 16 h. The solvent was evaporated and ethyl acetate (10 mL) was added. The solution was washed with saturated sodium bicarbonate solution (5 mL) and the aqueous layer was extracted with ethyl acetate. The combined organic layers were dried (MgSO₄), filtered, evaporated and chromatographed over silica gel (50% ethyl acetate/hexanes) to give rac.-(Z)-2-[[2-chloro-4-[1-hydroxy-3-(3-hydroxyphenyl)propan-1-yl]benzoyl]amino]-3-(quinolin-3-yl)propenoic acid methyl ester (93 mg, 75% yield) as an off-white solid.

Example 229

Preparation of rac.-(Z)-2-[[2-Chloro-4-[1-hydroxy-3-(3-hydroxyphenyl)propan-1-yl]benzoyl]amino]-3-(2,4-dimethylthiazol-5-yl)propenoic Acid Methyl Ester

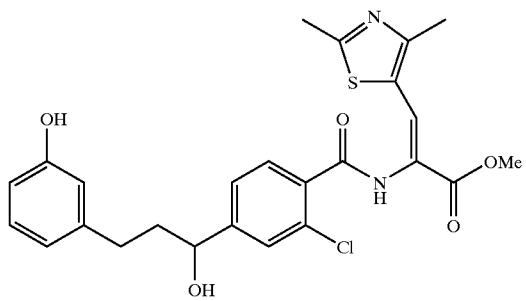

1,1,3,3-Tetramethylguanidine (60 μL, 0.48 mmol) was added to a solution of rac.-N-[2-chloro-4-[1-hydroxy-3-(3-hydroxyphenyl)propan-1-yl]benzoyl]-2-(dimethoxyphosphinyl)glycine methyl ester (Example 134; 120 mg, 0.24 mmol) in tetrahydrofuran (5 mL) at −20° C. After 10 min, 2,4-dimethylthiazole-5-carboxaldehyde (Example 43; 36 mg, 0.255 mmol) was added and the solution was stirred at room temperature for 16 h. After the volatiles were removed in vacuo, ethyl acetate (10 mL) was added. The resulting solution was washed with saturated sodium bicarbonate solution (5 μL) and the aqueous layer was extracted with ethyl acetate. The combined organic layers were dried (MgSO₄), filtered, evaporated and chromatographed over silica gel (3:2 ethyl acetate/hexanes). The appropriate fractions were combined, evaporated and the residue triturated with diethyl ether to yield rac.-(Z)-2-[[2-chloro-4-[1-hydroxy-3-(3-hydroxyphenyl)propan-1-yl]benzoyl]amino]-3-(2,4-dimethylthiazol-5-yl)propenoic acid methyl ester (88 mg, 75% yield) as a colorless solid.

Example 230

Preparation of rac.-(Z)-2-[[2-Chloro-4-[(E)-1-hydroxy-3-(3-hydroxyphenyl)prop-2-en-1-yl]benzoyl]amino]-3-(quinolin-3-yl)propenoic Acid Methyl Ester

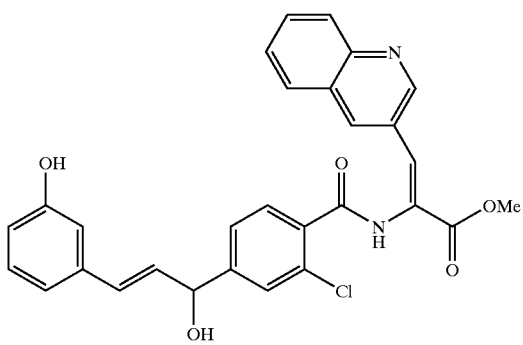

1,1,3,3-Tetramethylguanidine (60 µL, 0.48 mmol) was added to a solution of rac.-(E)-N-[2-chloro-4-[1-hydroxy-3-(3-hydroxyphenyl)prop-2-en-1-yl]benzoyl]-2-(dimethoxyphosphinyl)glycine methyl ester (Example 135; 116 mg, 0.24 mmol) in tetrahydrofuran (5 mL) at −20° C. After 10 min, quinoline-3-carboxaldehyde (40 mg, 0.255 mmol) was added and the solution was stirred at room temperature for 16 h. After the solvent was removed in vacuo, the residue was taken up in ethyl acetate (10 mL) and the solution was washed with saturated sodium bicarbonate solution (10 mL) and brine (10 mL). Each aqueous layer was back-extracted with ethyl acetate (10 mL). The combined organic extracts were dried, filtered, evaporated and chromatographed (50% ethyl acetate/hexanes) to give rac.-(Z)-2-[[2-chloro-4-[(E)-1-hydroxy-3-(3-hydroxyphenyl)prop-2-en-1-yl]benzoyl]amino]-3-(quinolin-3-yl)propenoic acid methyl ester (110 mg, 89% yield) as a colorless solid.

Example 231

Preparation of rac.-(Z)-2-[[2-Chloro-4-[(E)-1-hydroxy-3-(3-hydroxyphenyl)prop-2-en-1-yl]benzoyl]amino]-3-(2,4-dimethylthiazol-5-yl)propenoic Acid Methyl Ester

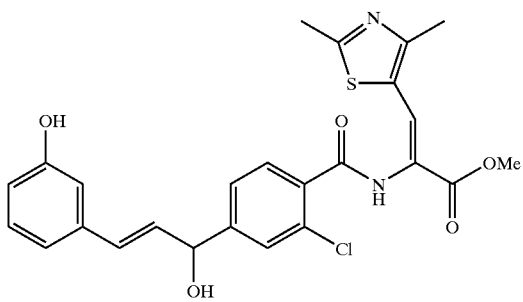

1,1,3,3-Tetramethylguanidine (60 µL, 0.48 mmol) was added to a solution of rac.-(E)-N-[2-chloro-4-[1-hydroxy-3-(3-hydroxyphenyl)prop-2-en-1-yl]benzoyl]-2-(dimethoxyphosphinyl)glycine methyl ester (Example 135; 116 mg, 0.24 mmol) in tetrahydrofuran (5 mL) at −20° C. After 10 min, 2,4-dimethylthiazole-5-carboxaldehyde (Example 43; 36 mg, 0.255 mmol) was added and the solution was stirred at room temperature for 16 h. The solvent was evaporated and ethyl acetate (10 mL) was added. The solution was washed with saturated sodium bicarbonate solution (10 mL) and brine (10 mL). Each aqueous layer was extracted with ethyl acetate (10 mL). The combined organic layers were dried, filtered, evaporated and chromatographed (60% ethyl acetate/hexanes) to give rac.-(Z)-2-[[2-chloro-4-[(E)-1-hydroxy-3-(3-hydroxyphenyl)prop-2-en-1-yl]benzoyl]amino]-3-(2,4-dimethylthiazol-5-yl)propenoic acid methyl ester (101 mg, 84% yield) as a colorless oil.

Example 232

Preparation of (Z)-2-[[2-Chloro-4-[[(3-hydroxybenzyl)amino]carbonyl]benzoyl]amino]-3-[4-(1-methylethyl)thiazol-5-yl]propenoic Acid Methyl Ester

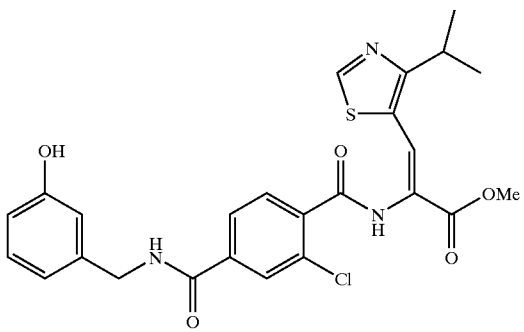

1,1,3,3-Tetramethylguanidine (41 µL, 0.33 mmol) was added to a solution of rac.-N-[2-chloro-4-[[(3-hydroxybenzyl)amino]carbonyl]benzoyl]-2-(dimethoxyphosphinyl)glycine methyl ester (Example 141; 75 mg, 0.15 mmol) in tetrahydrofuran (2 mL) at about −25° C. After 5 min, a solution of 4-(1-methylethyl)thiazole-5-carboxaldehyde (Example 56; 26 mg, 0.168 mmol) in tetrahydrofuran (1 mL) was added. The cooling bath was removed and the solution was stirred at room temperature for 17 h. The solvent was evaporated and the residue was partitioned between ethyl acetate (10 mL) and 10% aqueous acetic acid (5 mL). The ethyl acetate layer was washed with brine and each of the aqueous layers was extracted with ethyl acetate (10 mL). The combined organic extracts were dried (Na$_2$SO$_4$), filtered and evaporated to give a colorless foam which was triturated with diethyl ether (5 mL). The resulting solids were recovered by filtration to furnish (Z)-2-[[2-chloro-4-[[(3-hydroxybenzyl)amino]carbonyl]benzoyl]amino]-3-[4-(1-methylethyl)thiazol-5-yl]propenoic acid methyl ester (76 mg, 99% yield).

Example 233

Preparation of (Z)-2-[[2-Chloro-4-[[(3-hydroxybenzyl)amino]carbonyl]benzoyl]amino]-3-[2-(1-methylethyl)-4-methylthiazol-5-yl]propenoic Acid Methyl Ester

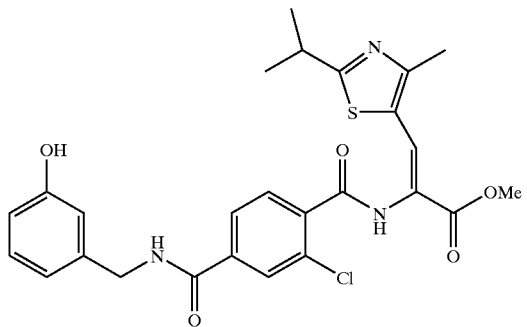

1,1,3,3-Tetramethylguanidine (55 μL, 0.44 mmol) was added to a solution of rac.-N-[2-chloro-4-[[(3-hydroxybenzyl)amino]carbonyl]benzoyl]-2-(dimethoxyphosphinyl)glycine methyl ester (Example 141; 100 mg, 0.20 mmol) in tetrahydrofuran (4 mL) at about −20° C. After 5 min, a solution of 2-(1-methylethyl)-4-methylthiazole-5-carboxaldehyde (Example 57; 38 mg, 0.225 mmol) in tetrahydrofuran (1 mL) was added. After 2 min, the cooling bath was removed and the solution was stirred at room temperature for 66 h. The solvent was evaporated and ethyl acetate (10 mL) and 10% aqueous acetic acid (5 mL) were added to the residue. The mixture was filtered to give (Z)-2-[[2-chloro-4-[[(3-hydroxybenzyl)amino]carbonyl]benzoyl]amino]-3-[2-(1-methylethyl)-4-methylthiazol-5-yl]propenoic acid methyl ester (65 mg, 62% yield) as a colorless solid.

Example 234

Preparation of (Z)-3-(2-Amino-4-trifluoromethylthiazol-5-yl)-2-[[2-chloro-4-[[(3-hydroxybenzyl)amino]carbonyl]benzoyl]amino]propenoic Acid Methyl Ester

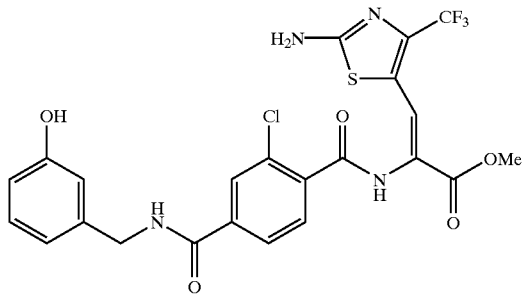

A. (Z)-2-[[2-Chloro-4-[[(3-hydroxybenzyl)amino]carbonyl]benzoyl]amino]-3-[2-(1,1-dimethylethoxycarbonyl)amino-4-trifluoromethylthiazol-5-yl]propenoic Acid Methyl Ester.

1,1,3,3-Tetramethylguanidine (0.1 mL, 0.80 mmol) was added to a solution of rac.-N-[2-chloro-4-[[(3-hydroxybenzyl)aminolcarbonyl]benzoyl]-2-(dimethoxyphosphinyl)glycine methyl ester (Example 141; 160 mg, 0.33 mmol) in tetrahydrofuran (5 mL) at about −20° C. After 5 min, a solution of an approximately 2:1 mixture of (5-formyl-4-trifluoromethylthiazol-2-yl)carbamic acid, 1,1-dimethylethyl ester and (5-ethoxycarbonyl-4-trifluoromethylthiazol-2-yl)carbamic acid, 1,1-dimethylethyl ester (Example 59; 200 mg) was added. The cooling bath was removed and the solution was stirred at ambient temperature for 16 h. The solvent was evaporated and the residue was partitioned between dichloromethane (25 mL) and 10% aqueous acetic acid (2×15 mL). The organic layer was washed in turn with saturated sodium bicarbonate solution and brine, then was dried (Na₂SO₄), filtered and evaporated. The residue was chromatographed over silica gel (10–70% ethyl acetate/hexanes) to give (Z)-2-[[2-chloro-4-[[(3-hydroxybenzyl)amino]carbonyl]benzoyl]amino]-3-[2-(1,1-dimethylethoxycarbonyl)amino-4-trifluoromethylthiazol-5-yl]propenoic acid methyl ester (130 mg).

B. (Z)-3-(2-Amino-4-trifluoromethylthiazol-5-yl)-2-[[2-chloro-4-[[(3-hydroxybenzyl)amino]carbonyl]benzoyl]amino]propenoic Acid Methyl Ester Triethylsilane (0.15 mL, 0.94 mmol) was added to a solution of (Z)-2-[[2-chloro-4-[[(3-hydroxybenzyl)amino]carbonyl]benzoyl]amino]-3-[2-(1,1-dimethylethoxycarbonyl)amino-4-trifluoromethylthiazol-5-yl]propenoic acid methyl ester (130 mg, 0.198 mmol) in dichloromethane (1 mL). Trifluoroacetic acid (1 mL, 13.0 mmol) was added and the solution was stirred at room temperature for 2 h and then the solvents were removed under reduced pressure. NMR indicated that the reaction had not gone to completion, so the crude residue was re-dissolved in dichloromethane and treated with triethylsilane and trifluoroacetic acid as before. After the solution was stirred at room temperature for 3 h, the solvents were removed in vacuo and the residue was partitioned between ethyl acetate and saturated sodium bicarbonate solution. The organic phase was dried (Na₂SO₄), filtered and evaporated to give (Z)-3-(2-amino-4-trifluoromethylthiazol-5-yl)-2-[[2-chloro-4-[[(3-hydroxybenzyl)amino]carbonyl]benzoyl]amino]propenoic acid methyl ester (100 mg, 91% yield) as a yellow foam.

Example 235

Preparation of (Z)-2-[[2-Bromo-4-[[(3-hydroxybenzyl)amino]carbonyl]benzoyl]amino]-3-(2-methylthiazol-4-yl)propenoic Acid

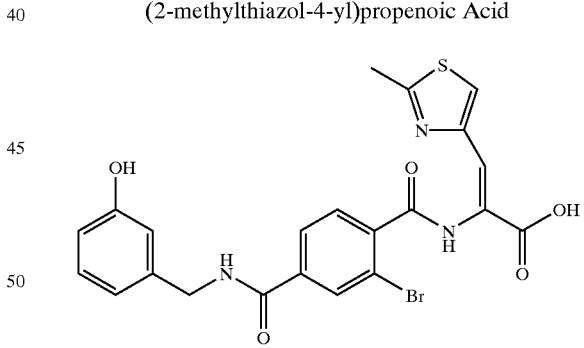

To a solution of (Z)-2-[[2-bromo-4-[[(3-hydroxybenzyl)amino]carbonyl]benzoyl]amino]-3-(2-methylthiazol-3-yl)-2-propenoic acid methyl ester (Example 167; 0.085 g, 0.160 mmol) in methanol (2 mL) was added sodium hydroxide (1N, 0.641 mL, 0.64 mmol) at room temperature. The reaction mixture was then stirred at 50° C. for 24 h. The volatiles were evaporated using a rotary evaporator (water aspirator) and at then high vacuum. The residue was purified by reverse phase HPLC (20–45% acetonitrile in water containing 0.075% TFA). The appropriate fractions were combined, concentrated and the purified acid was freeze dried to give (Z)-2-[[2-bromo-4-[[(3-hydroxyenzyl)amino]carbonyl]benzoyl]amino]-3-(2-methylthiazol-4-yl)propenoic acid (14 mg, 17% yield) as a colorless solid.

The following compounds were prepared, isolated and purified using the method described in Example 235:

| Example | Structure | Starting Material | Comments |
|---------|-----------|-------------------|----------|
| 236 | 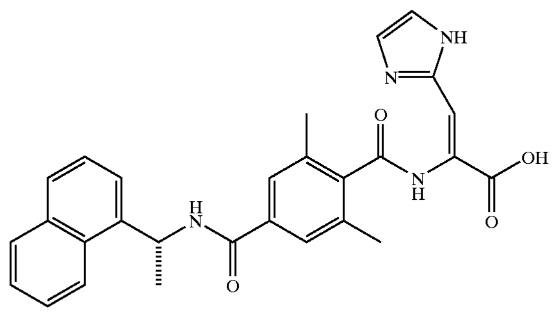 | Example 170 | 5 Equiv. of NaOH used. After 4 days at RT, heated at 60° C. for 3 h. HPLC: 20–80% acetonitrile in water with 0.075% TFA. Off-white solid. |
| 237 | 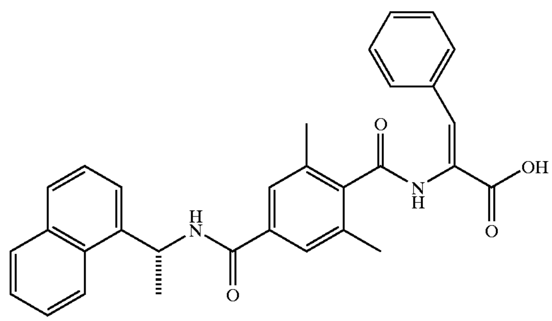 | Example 171 | 5 Equiv. of NaOH used. Run for 4 days at RT. HPLC: 20–80% acetonitrile in water with 0.075% TFA. Colorless solid. |
| 238 | 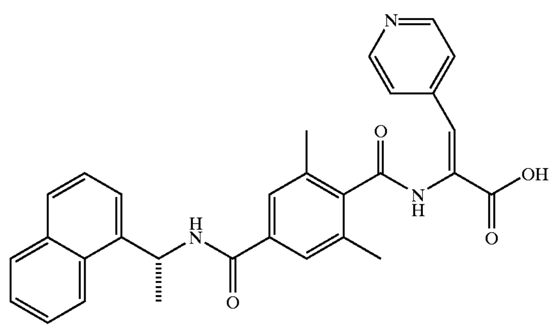 | Example 204 | 5 Equiv. of NaOH used. Run for 3 days at RT. HPLC: 10–50% acetonitrile in water with 0.075% TFA. Off-white solid. |
| 239 | 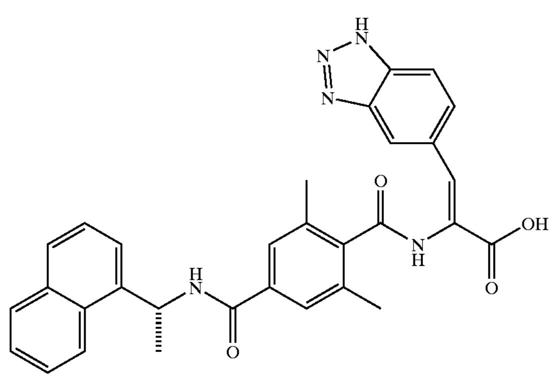 | Example 208 | 3 Equiv. of NaOH used. Run for 6 days at RT. HPLC: 10–50% acetonitrile in water with 0.075% TFA. Colorless solid. |

-continued

| Example | Structure | Starting Material | Comments |
|---|---|---|---|
| 240 | 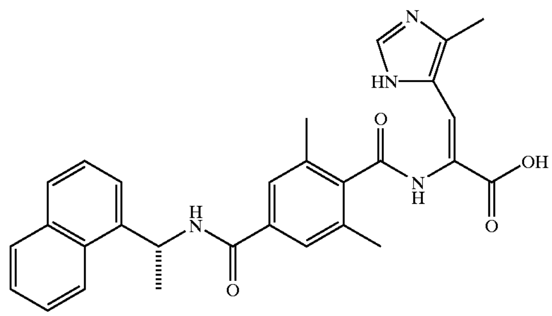 | Example 172 | 3 Equiv. of NaOH used. Run for 6 days at RT. HPLC: 10–50% acetonitrile in water with 0.075% TFA. Colorless solid. |
| 241 | 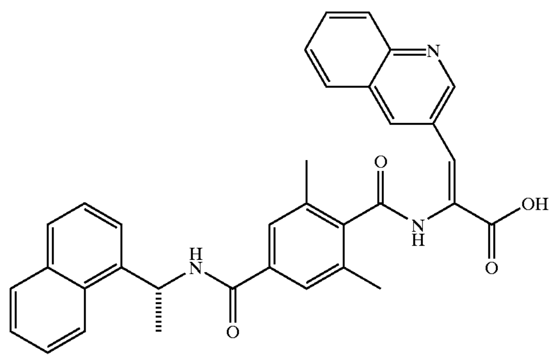 | Example 169 | 5 Equiv. of NaOH used. Run for 4 days at RT. HPLC: 20–80% acetonitrile in water with 0.075% TFA. Colorless solid. 55% yield. |
| 242 | 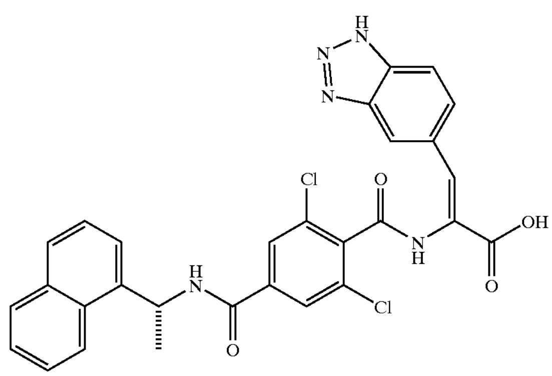 | Example 209 | 4 Equiv. of NaOH used. Run for 4 days at RT. HPLC: 20–70% acetonitrile in water with 0.075% TFA. Colorless solid. |
| 243 | 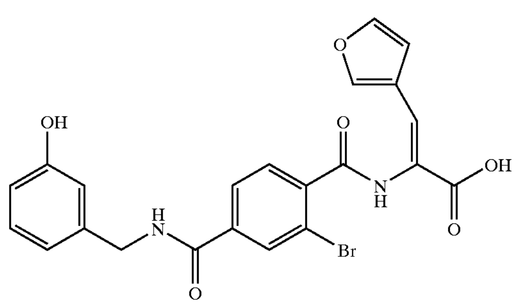 | Example 177 | 3 Equiv. of NaOH used. Run for 3 days at RT. HPLC: 10–60% acetonitrile in water with 0.075% TFA. Off-white solid. |

-continued

| Example | Structure | Starting Material | Comments |
|---|---|---|---|
| 244 | 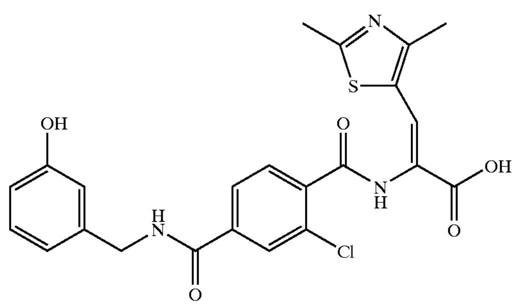 | Example 188 | 4 Equiv. of NaOH used. Run for 24 h at 50° C. HPLC: 20–70% acetonitrile in water with 0.075% TFA. Colorless solid. |
| 245 | 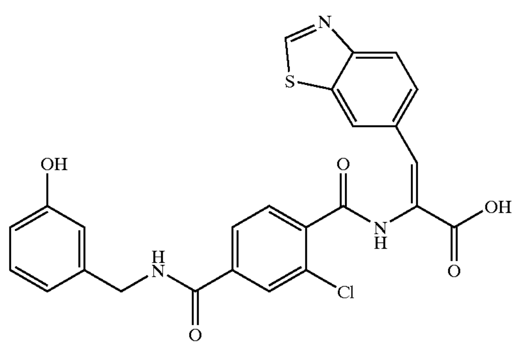 | Example 189 | 4 Equiv. of NaOH used. Run for 24 h at 50° C. HPLC: 20–60% acetonitrile in water with 0.075% TFA. Off-white solid; 57% yield |
| 246 | 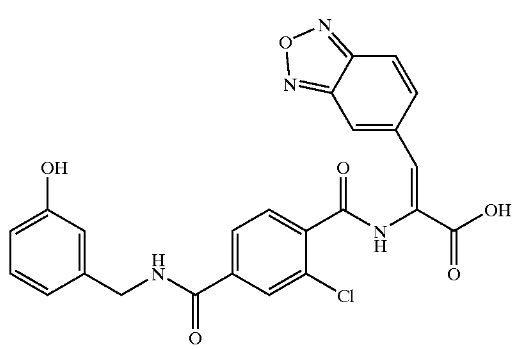 | Example 192 | 4 Equiv. of NaOH used. Run for 24 h at RT, then at 50° C. for 4 h. HPLC: 20–70% acetonitrile in water with 0.075% TFA. Colorless solid. (60% yield) |
| 247 | 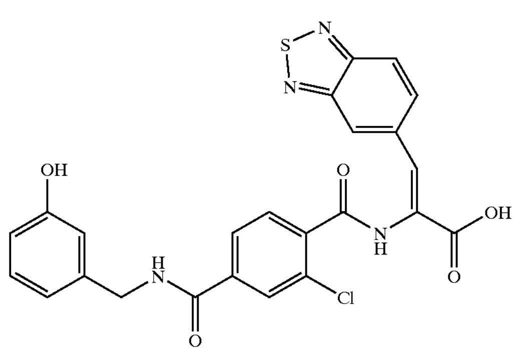 | Example 190 | 4 Equiv. of NaOH used. Run for 24 h RT, then at 50° C. for 4 h. HPLC: 20–70% acetonitrile in water with 0.075% TFA. Colorless solid. |

| Example | Structure | Starting Material | Comments |
|---|---|---|---|
| 248 | 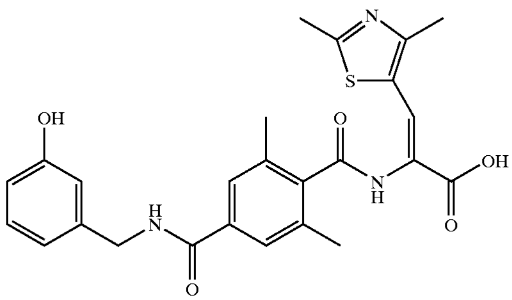 | Example 203 | 4 Equiv. of NaOH used. Run for 24 h at RT, then at 50° C. for 24 h. HPLC: 20–60% acetonitrile in water with 0.075% TFA. Colorless solid. (46% yield) |
| 249 | 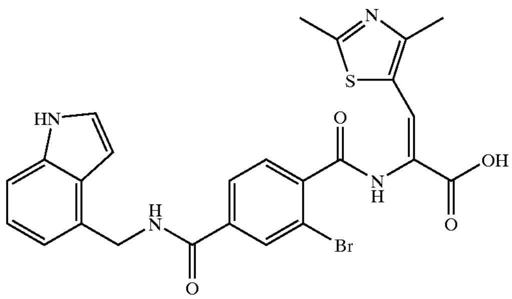 | Example 185 | 2 Equiv. of NaOH used. Run for 24 h RT, then at 50° C. for 24 h, followed by RT for 3 days HPLC: 20–70% acetonitrile in water with 0.075% TFA. Colorless solid. (93% yield) |

Example 250

Preparation of (Z)-2-[[4-[[(3,5-Difluorobenzyl) amino]carbonyl]-2,6-dimethylbenzoyl]amino]-3-(4-methyl-1H-imidazol-5-yl)propenoic Acid

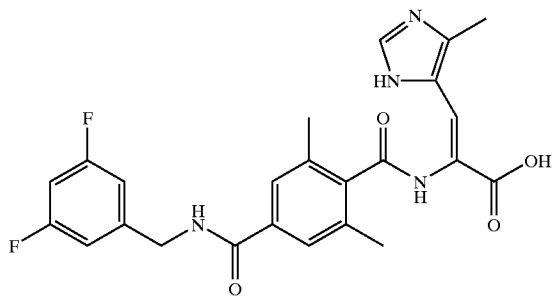

To a stirred solution of (Z)-2-[[4-[[(3,5-difluorobenzyl) amino]carbonyl]-2,6-dimethylbenzoyl]amino]-3-(4-methyl-1H-imidazol-5-yl)propenoic acid methyl ester (Example 174; 96.4 mg, 0.2 mmol) in methanol (2 mL) was added 1N sodium hydroxide solution (0.6 mL, 0.6 mmol) and the reaction was allowed to proceed at room temperature. After 24 h, a second portion of 1N sodium hydroxide solution 0.6 mL, 0.6 mmol) was added and the reaction was then stirred at 55° C. for 5 h. The reaction was concentrated to dryness and the resulting residue was purified by reverse phase HPLC (20–60% acetonitrile/water containing 0.075% trifluoroacetic acid). The appropriate fractions were combined and evaporated and the product was freeze dried to give (Z)-2-[[4-[[(3,5-difluorobenzyl)amino]carbonyl]-2,6-dimethylbenzoyl]amino]-3-(quinolin-3-yl)propenoic acid as a colorless solid (38 mg, 40.5% yield)

The following compounds were prepared, isolated and purified using the method described in Example 250:

| Example | Structure | Starting Material | Comments |
|---|---|---|---|
| 251 | 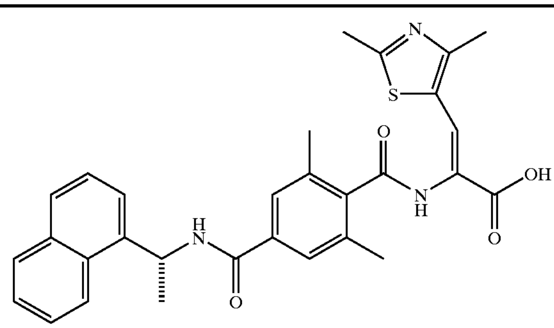 | Example 181 | Initially 2 equiv. of NaOH used. After 24 h at RT another 2 equiv. added and heated at 50° C. for 24 h. Then another 2 equiv. added and heated at 50° C. for 24 h. HPLC: 20–80% acetonitrile in water with 0.075% TFA. Colorless solid. |

| Example | Structure | Starting Material | Comments |
|---|---|---|---|
| 252 | 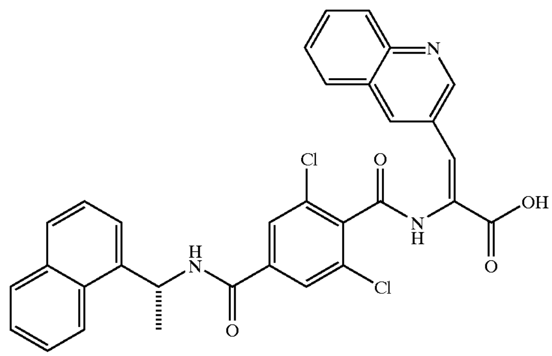 | Example 168 | Initially 2 equiv. of NaOH used. After 24 h at RT another 2 equiv. added and heated at 45° C. for 24 h. Then another 2 equiv. added and heated at 60° C. for 7 h.<br>HPLC: 20–80% acetonitrile in water with 0.075% TFA.<br>Yellow solid. |
| 253 | 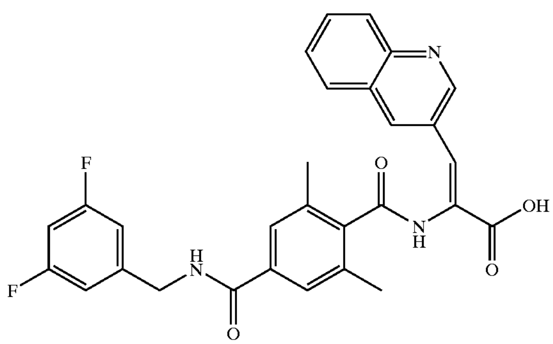 | Example 173 | Initially 4 equiv. of NaOH used. After 24 h at RT another 4 equiv. added and heated at 50° C. for 4 h.<br>HPLC: 10–60% acetonitrile in water with 0.075% TFA.<br>Colorless solid. |
| 254 | 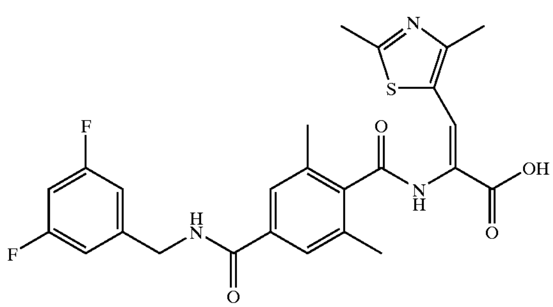 | Example 175 | Initially 2 equiv. of NaOH used. After 24 h at RT another 2 equiv. added and run at 50° C. for 24 h then 72 h at RT.<br>HPLC: 20–80% acetonitrile in water with 0.075% TFA.<br>Colorless solid. |
| 255 | 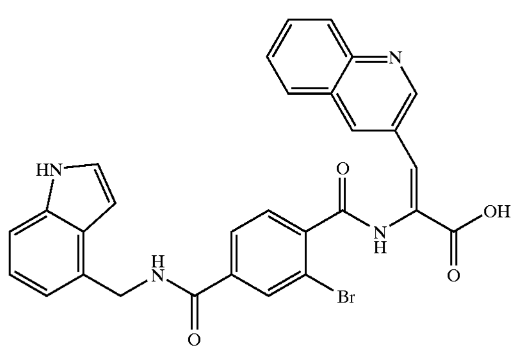 | Example 195 | 24 equiv. of NaOH used. Run for 24 h RT, then at 50° C. for 24 h followed by RT for 3 days<br>HPLC: 20–60% acetonitrile in water with 0.075% TFA.<br>Colorless solid. (2% yield). |

-continued

| Example | Structure | Starting Material | Comments |
|---|---|---|---|
| 256 | 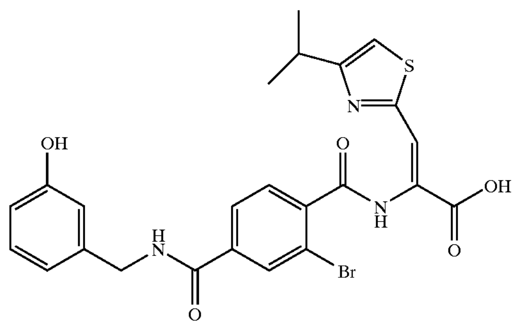 | Example 201 | Initially 3 equiv. of NaOH used. After 72 h at RT another 3 equiv. added and heated at 50° C. for 24 h.<br>HPLC: 30–60% acetonitrile in water with 0.075% TFA.<br>Freeze dried and obtained a colorless solid. |
| 257 | 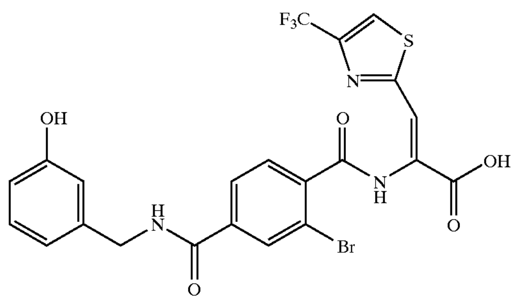 | Example 202 | Initially 3 equiv. of NaOH used. After 24 h at RT another 3 equiv. added and heated at 50° C. for 24 h.<br>HPLC: 20–70% acetonitrile in water with 0.075% TFA.<br>Off-white solid. |
| 258 | 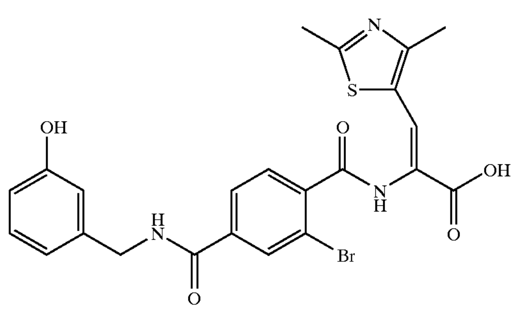 | Example 176 | Initially 4 equiv. of NaOH used. After 24 h at RT another 2 equiv. added and heated at 50° C. for 24 h.<br>HPLC: 20–50% acetonitrile in water with 0.075% TFA.<br>Colorless solid. |
| 259 | 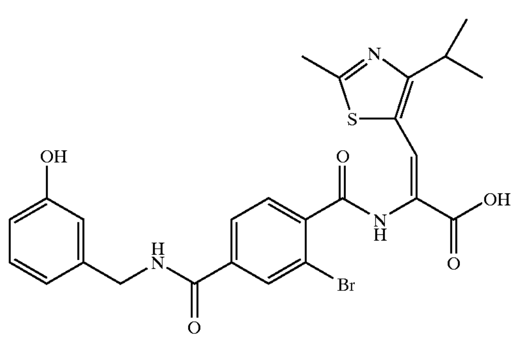 | Example 193 | Initially 2.5 equiv. of NaOH used. After 24 h at 50° C. another 1.5 equiv. added and heated at 50° C. for 24 h.<br>HPLC: 15–60% acetonitrile in water with 0.075% TFA.<br>Freeze dried and obtained a colorless solid. |

-continued

| Example | Structure | Starting Material | Comments |
|---|---|---|---|
| 260 | 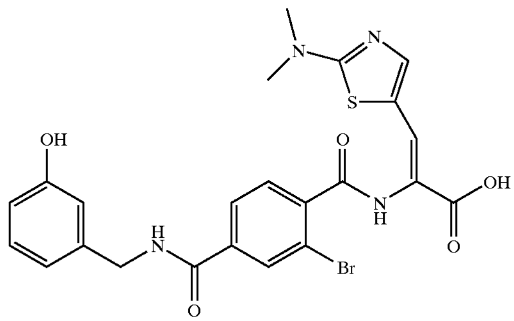 | Example 179 | Initially 3 equiv. of NaOH used. After 7 days at RT another 3 equiv. added and run at RT for another 72 h. HPLC: 20–70% acetonitrile in water with 0.075% TFA. Yellow solid. (49% yield) |
| 261 | 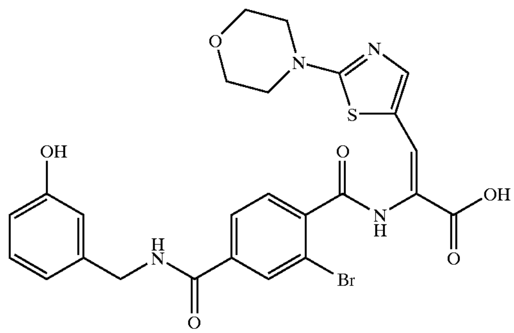 | Example 182 | Initially 4 equiv. of NaOH used. After 24 h at RT another 4 equiv. added and heated at 50° C. for 24 h. HPLC 20–50% acetonitrile in water with 0.075% TFA. Yellow solid |
| 262 | 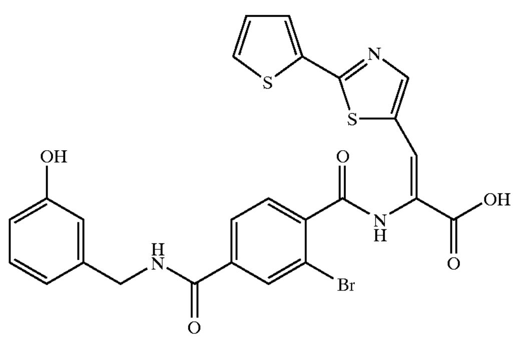 | Example 200 | Initially 3 equiv. of NaOH used. After 72 h at RT another 3 equiv. added and run at RT for another 72 h. HPLC: 20–50% acetonitrile in water with 0.075% TFA. Off-white solid. (49% yield) |
| 263 | 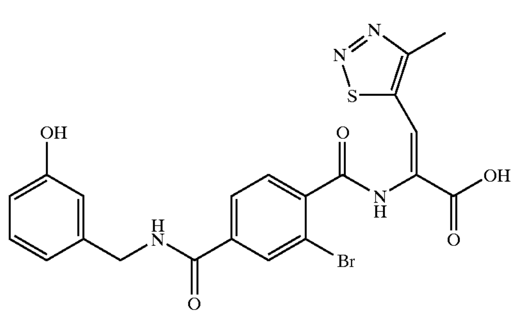 | Example 180 | Initially 4 equiv. of NaOH used. After 24 h at RT another 4 equiv. added and heated at 50° C. for 24 h. HPLC: acetonitrile in water with 0.075% TFA. Colorless solid. (74% yield) |

-continued

| Example | Structure | Starting Material | Comments |
|---|---|---|---|
| 264 | 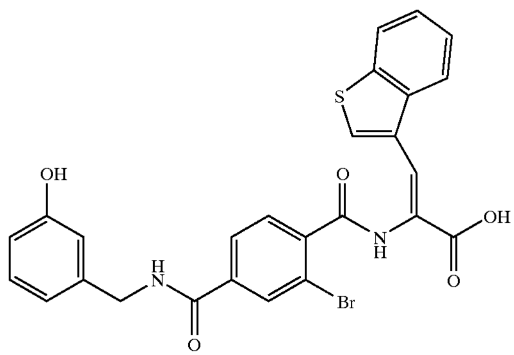 | Example 183 | Initially 4 equiv. of NaOH used. After 72 h at RT another 4 equiv. added and heated at 50° C. for 24 h then 24 h at RT. HPLC: 15–40% acetonitrile in water with 0.075% TFA. Colorless solid. (42% yield) |
| 265 | 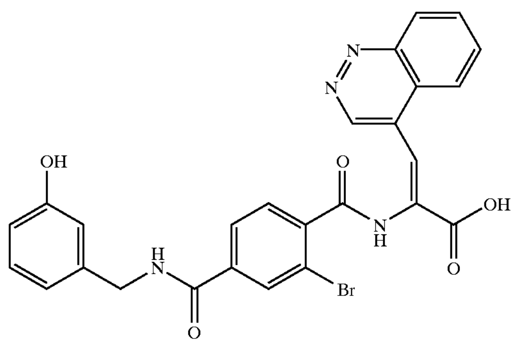 | Example 196 | Initially 2 equiv. of NaOH used. After 24 h at RT another 1 equiv. added and run at RT for another 72 h. HPLC: 20–60% acetonitrile in water with 0.075% TFA. Yellow solid. (31% yield) |
| 266 | 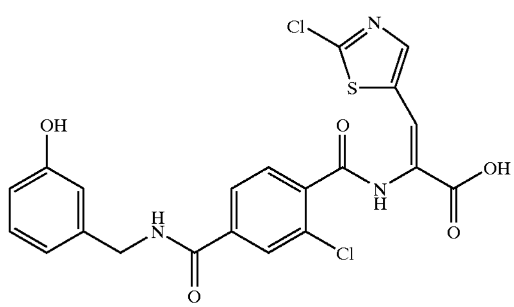 | Example 191 | Initially 4 equiv. of NaOH used. After 24 h at RT and 50° C. for 24 h, another 2 equiv. added and heated at 50° C. for 24 h. HPLC: 20–60% acetonitrile in water with 0.075% TFA. Colorless solid. (19% yield) |
| 267 | 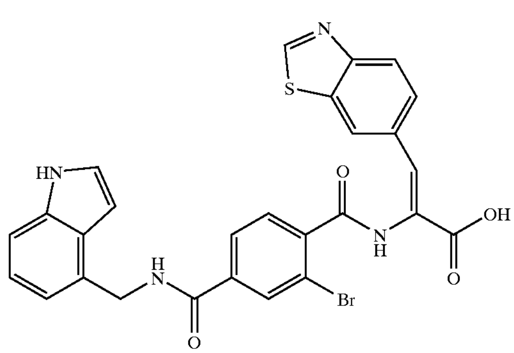 | Example 194 | Initially 2 equiv. of NaOH used. After 72 h at RT another 2 equiv. added and heated at 50° C. for 24 h. HPLC: 20–45% acetonitrile in water with 0.075% TFA. Pale pink solid. (45% yield) |

Example 268

Preparation of (Z)-2-[[2-Bromo-4-[[(3-hydroxybenzyl)amino]carbonyl]benzoyl]amino]-3-(thiazol-2-yl)propenoic Acid

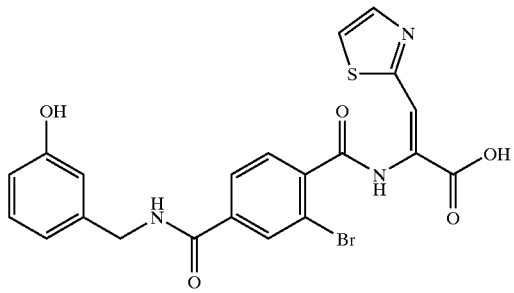

A solution of 1N sodium hydroxide (0.16 mL, 0.16 mmol) was added to a solution of (Z)-2-[[2-bromo-4-[[(3-hydroxybenzyl)amino]carbonyl]benzoyl]amino]-3-(thiazol-2-yl)propenoic acid methyl ester (Example 153; 39.3 mg, 0.076 mmol) in tetrahydrofuran/methanol (2:1; 0.25 mL). After the solution had been allowed to stir at room temperature for 16 h, a second portion of 1N sodium hydroxide solution (0.05 mL) was added and the reaction was allowed to proceed for another 24 h at ambient temperature. The solvent was evaporated using a rotary evaporator then high vacuum. The de-esterification had not gone to completion, so the residue was re-dissolved in tetrahydrofuran/methanol (2:1; 0.25 mL) and treated with a solution of 1N sodium hydroxide (0.16 mL, 0.16 mmol). The reaction mixture was stirred for 16 h and after the solvents were removed in vacuo, the residue was purified by HPLC to give (Z)-2-[[2-bromo-4-[[(3-hydroxybenzyl)amino]carbonyl]benzoyl]amino]-3-(thiazol-2-yl)propenoic acid (14.8 mg, 39%).

Also prepared by this procedure were:

| Example | Structure | Starting Material | Comments |
|---------|-----------|-------------------|----------|
| 269 | 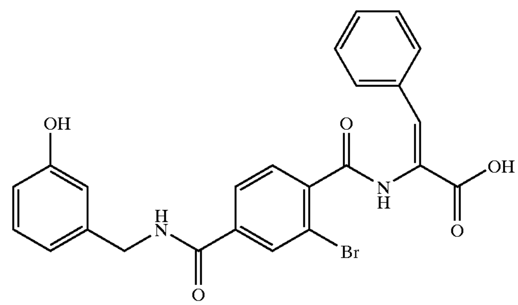 | Example 148 | |
| 270 | 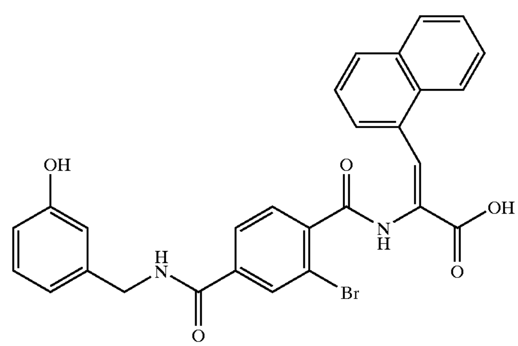 | Example 149 | |
| 271 | 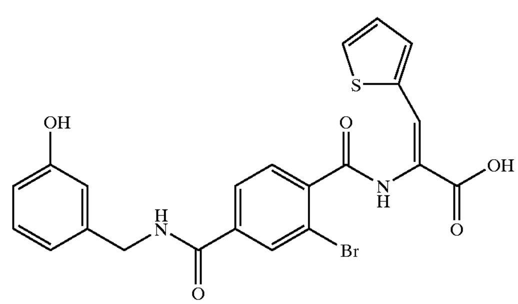 | Example 151 | |

-continued

| Example | Structure | Starting Material | Comments |
|---------|-----------|-------------------|----------|
| 272 | 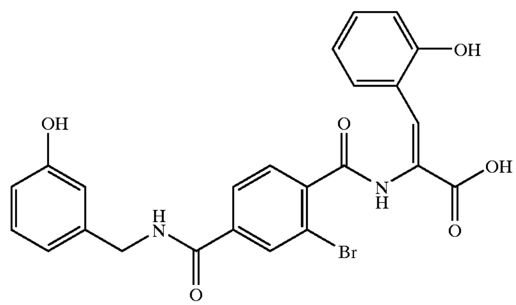 | Example 152 | |
| 273 | 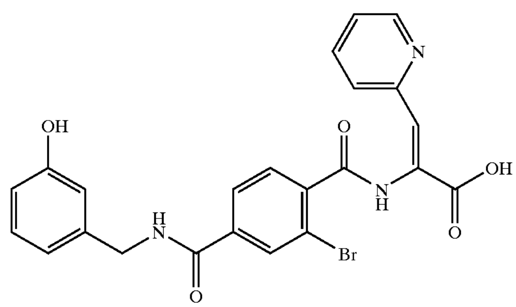 | Example 154 | |
| 274 | 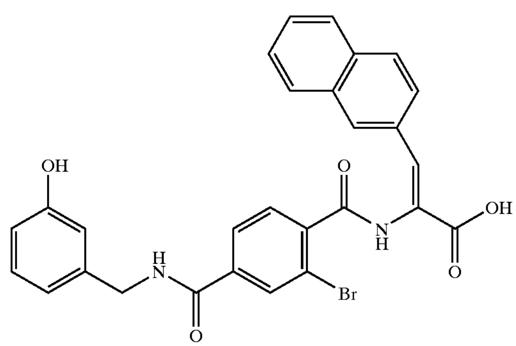 | Example 147 | 29% yield |
| 275 | 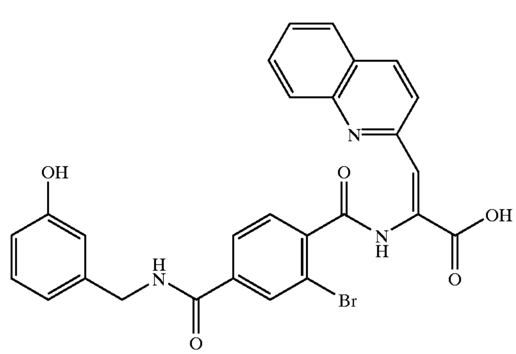 | Example 155 | 51% yield |

-continued

| Example | Structure | Starting Material | Comments |
|---------|-----------|-------------------|----------|
| 276 | 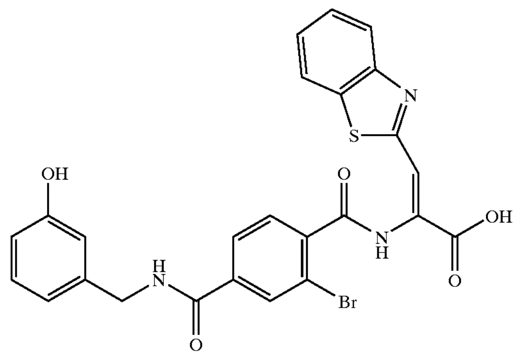 | Example 158 | |
| 277 | 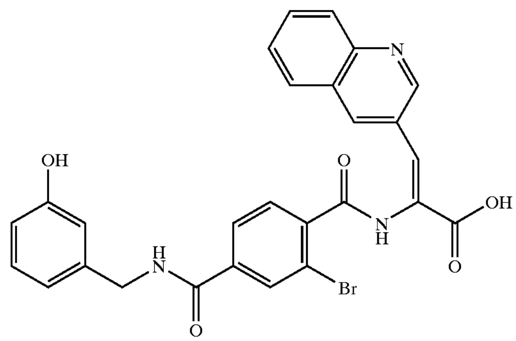 | Example 146 | 61% yield |
| 278 | 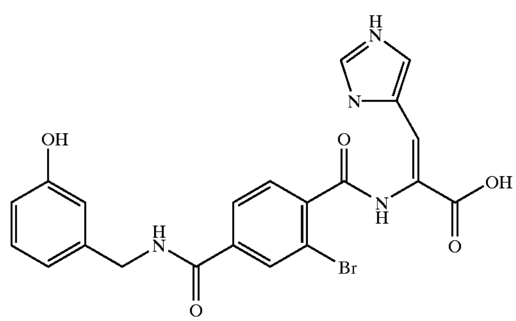 | Example 159 | 35% yield |
| 279 | 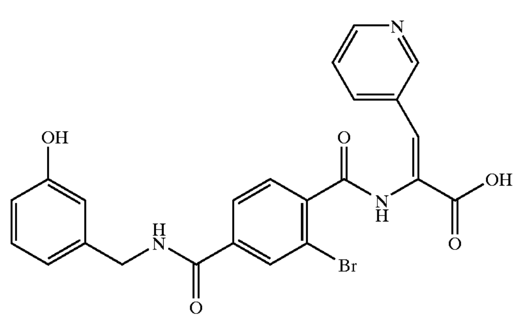 | Example 160 | |

-continued
| Example | Structure | Starting Material | Comments |
|---|---|---|---|
| 280 | 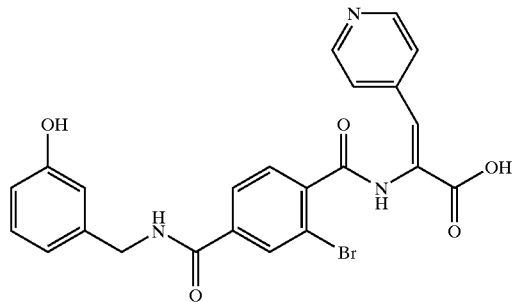 | Example 161 | |
| 281 | 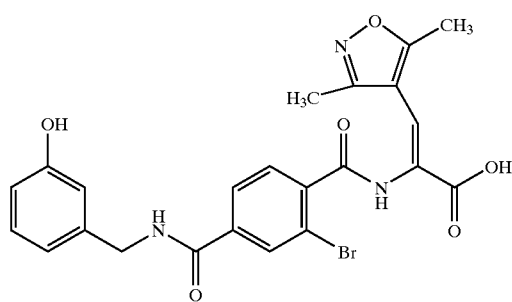 | Example 162 | 15% yield |
| 282 | 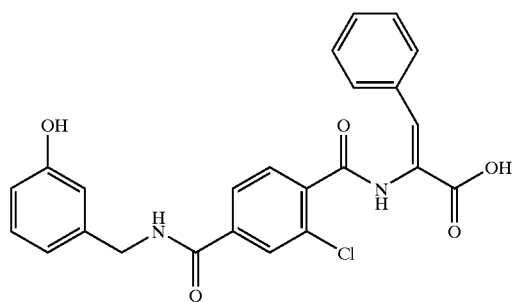 | Example 163 | |
| 283 | 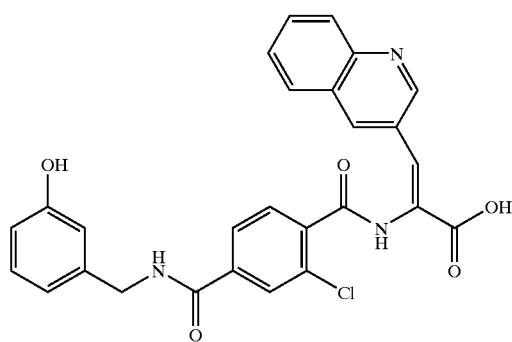 | Example 164 | |

-continued
| Example | Structure | Starting Material | Comments |
| --- | --- | --- | --- |
| 284 | 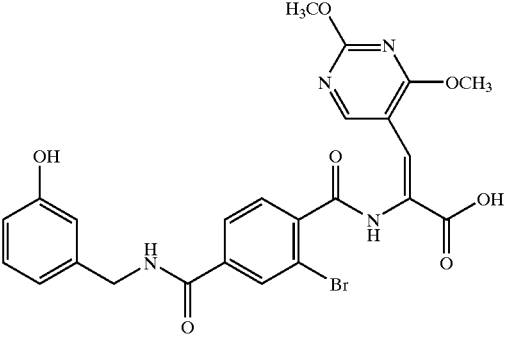 | Example 166 | |
| 285 | 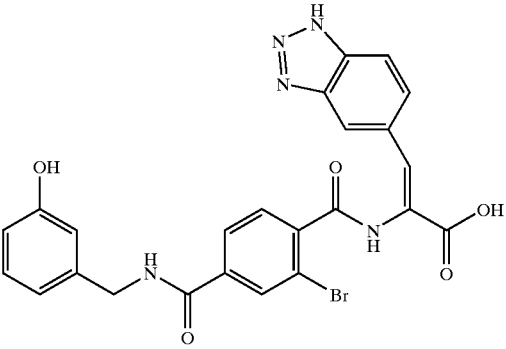 | Example 206 | |
| 286 | 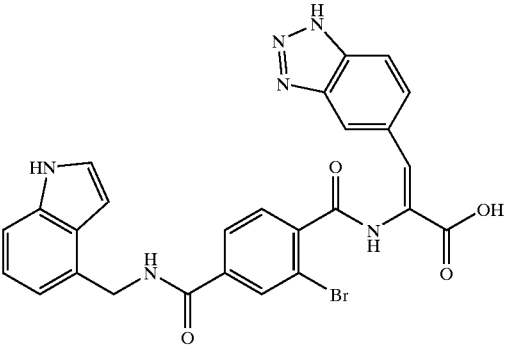 | Example 207 | >5% yield |
| 287 | 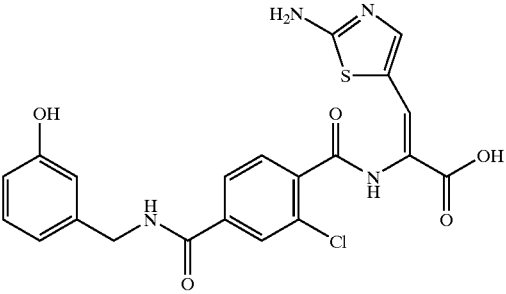 | Example 205 | 76% yield |

-continued

| Example | Structure | Starting Material | Comments |
|---|---|---|---|
| 288 | 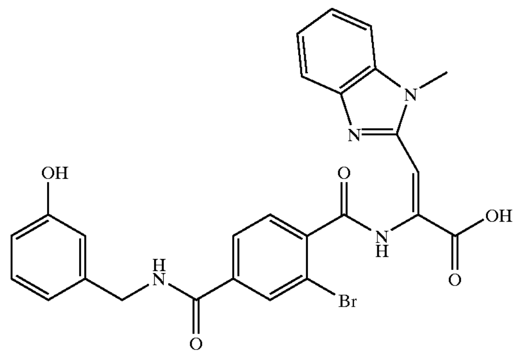 | Example 157 | Colorless powder |
| 289 | 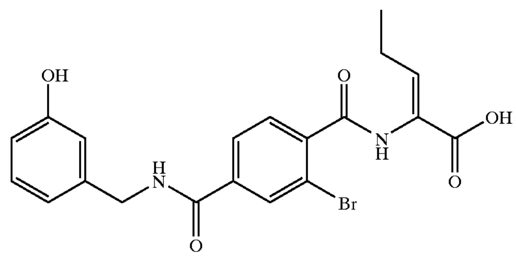 | Example 150 | Colorless powder |

Example 290

Preparation of (Z)-2-[[2-Bromo-4-[[(3-hydroxybenzyl)amino]carbonyl]benzoyl]amino]-3-(1,2,4triazol-3-yl)propenoic Acid A solution of 1N sodium hydroxide (0.24 mL, 0.24 mmol) was added to a solution of (Z)-2-[[2-bromo-4-[[(3-hydroxybenzyl)amino]carbonyl]benzoyl]amino]-3-[1-(triphenylmethyl)-1,2,4-triazol-3-yl]propenoic acid methyl ester (Example 165; 85 mg, 0.11 mmol) in tetrahydrofuran/methanol (2:1; 350 µL). The reaction was stirred at room temperature under argon for 2 days then the solvent was evaporated and the residue was with hexanes and then with dichloromethane to give crude (Z)-2-[[2-bromo-4-[[(3-hydroxybenzyl)aminolcarbonyl]benzoyl]amino]-3-[1-(triphenylmethyl)-1,2,4-triazol-3-yl]propenoic acid (83 mg). To this crude material was added in turn a solution of trifluoroacetic acid/dichloromethane (1:1; 0.5 mL) and triethylsilane (21.2 µL). The solution was allowed to stir at room temperature for 1 h, then the solvent was evaporated and the residue was co-evaporated with toluene (3×5 mL) to remove traces of trifluoroacetic acid. Purification of the crude product by HPLC gave (Z)-2-[[2-bromo-4-[[(3-hydroxybenzyl)amino]carbonyl]benzoyl]amino]-3-(1,2,4-triazol-3-yl)propenoic acid.

Example 291

Preparation of (Z)-3-(1H-Benzotriazol-5-yl)-2-[[2-chloro-4-[[(3-hydroxybenzyl)amino]carbonyl]-6-methylbenzoyl]amino]propenoic Acid A mixture of (Z)-3-(1H-benzotriazol-5-yl)-2-[[2-chloro-4-[[(3-hydroxybenzyl)amino]carbonyl]-6-methylbenzoyl]amino]propenoic acid methyl ester trifluoroacetate salt (Example 210; 18 mg, 0.028 mmol) and lithium hydroxide monohydrate (6 mg, 0.144 mmol) in methanol/tetrahydrofuran/water (2:2:1; 0.5 mL) was stirred at room temperature for 125 h. After the volatiles were removed under reduced pressure, the residue was taken up in a mixture of chloroform/methanol/water/acetic acid (150:30:10:6) (10 mL) and evaporated to dryness. The crude product was re-suspended in the same solvent mixture (1 mL) and applied to a column of two piggy-backed SepPak Plus® silica gel cartridges that had been pre-washed with chloroform. The column was eluted with in turn with chloroform, chloroform/methanol/water/acetic acid (600:30:10:6), chloroform/methanol/water/acetic acid (300:30:10:6 and chloroform/methanol/water/acetic acid (150:30:10:6). The appropriate fractions were combined, evaporated and lyophilized to furnish (Z)-3-(1H-benzotriazol-5-yl)-2-[[2-chloro-4-[[(3-hydroxybenzyl) amino]carbonyl]-6-methylbenzoyl]amino]propenoic acid (8.7 mg, 61% yield) as a colorless powder.

Example 292

Preparation of (Z)-2-[[2-Chloro-4-[[(3-hydroxybenzyl)amino]carbonyl]-6-methylbenzoyl] amino]-3-(quinolin-3-yl)propenoic Acid

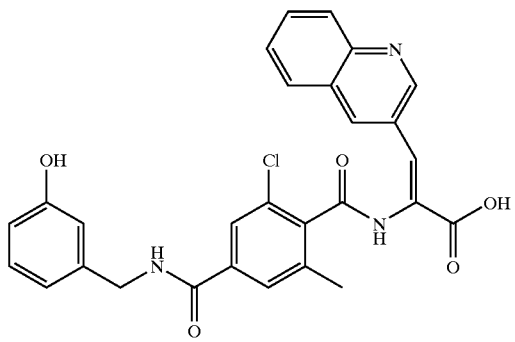

A mixture of (Z)-2-[[2-chloro-4-[[(3-hydroxybenzyl) amino]carbonyl]-6-methylbenzoyl]amino]-3-(quinolin-3-yl)propenoic acid methyl ester (Example 211; 32 mg, 0.06 mmol) and lithium hydroxide monohydrate (11 mg, 0.262 mmol) in methanol/tetrahydrofuran/water (2:2:1; 0.25 mL) was stirred at room temperature for 48 h. An additional portion of lithium hydroxide monohydrate (6 mg, 0.14 mmol) was added and the solution was stirred for an additional 4 h. The reaction mixture was concentrated under reduced pressure and the residue was dissolved in a mixture of chloroform/methanol/water/acetic acid (150:30:10:6) and re-evaporated. A solution of the residual material in the same solvent mixture (1 mL) was applied to a silica gel column. The column was eluted with in turn with chloroform, chloroform/methanol/water/acetic acid (600:30:10:6), chloroform/methanol/water/acetic acid (300:30:10:6 and chloroform/methanol/water/acetic acid (150:30:10:6). The appropriate homogeneous fractions were combined, evaporated and then lyophilized to give (Z)-2-[[2-chloro-4-[[(3-hydroxybenzyl)amino]carbonyl]-6-methylbenzoyl]amino]-3-(quinolin-3-yl)propenoic acid (18 mg, 58% yield).

Example 293

Preparation of (Z)-2-[[2-Chloro-4-[[(3-hydroxybenzyl)amino]carbonyl]-6-methylbenzoyl] amino]-3-phenylpropenoic Acid

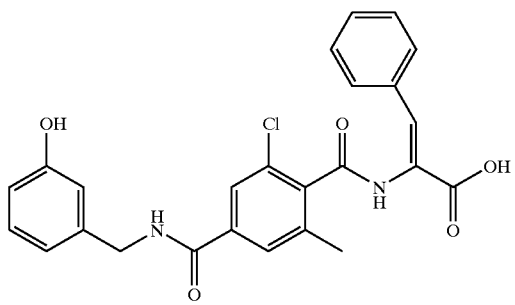

A mixture of (Z)-2-[[2-chloro-4-[[(3-hydroxybenzyl) amino]carbonyl]-6-methylbenzoyl]amino]-3-phenylpropenoic acid methyl ester (Example 212; 23 mg, 0.048 mmol) and lithium hydroxide monohydrate (6 mg, 0.144 mmol) in methanol/tetrahydrofuran/water (2:2:1; 0.25 mL) was stirred at room temperature for 17 h. An second portion of lithium hydroxide monohydrate (2 mg, 0.05 mmol) was added and the solution was stirred for an additional 4 h. The volatiles were removed in vacuo and the residue was taken up in a mixture of chloroform/methanol/water/acetic acid (150:30:10:6) and evaporated to dryness. The residue was re-dissolved in the same solvent mixture (1 mL) and applied to a silica gel column. The column was eluted with in turn with chloroform, chloroform/methanol/water/acetic acid (300:30:10:6) and chloroform/methanol/water/acetic acid (150:30:10:6). The appropriate fractions were combined, evaporated and then lyophilized to give (Z)-2-[[2-chloro-4-[[(3-hydroxybenzyl)amino]carbonyl]-6-methylbenzoyl] amino]-3-phenylpropenoic acid (9.5 mg, 43% yield) as a colorless powder.

Example 294

Preparation of (Z)-2-[[2-Chloro-4-[3-(3-hydroxyphenyl)-1-oxopropan-1-yl]benzoyl]amino]-3-(quinolin-3-yl)propenoic Acid

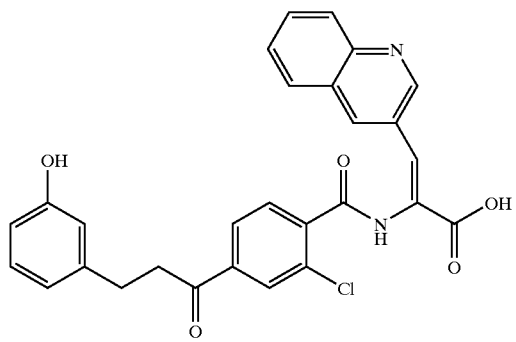

An aqueous 1N solution of sodium hydroxide (0.9 mL, 0.9 mmol) was added to a solution of (Z)-2-[[2-chloro-4-[3-(3-hydroxyphenyl)-1-oxopropan-1-yl]benzoyl]amino]-3-(quinolin-3-yl)propenoic acid methyl ester (Example 226; 140 mg, 0.272 mmol) in methanol/tetrahydrofuran (1:1; 3.6 mL). The solution was stirred at room temperature for 16 h and the solvent was evaporated. Water (7 mL) was added and the mixture was extracted with diethyl ether. The diethyl ether extract was discarded and the water layer was filtered through Celite® and then acidified with 1N hydrochloric acid solution (1 mL). The resulting solid was filtered off, washed with water, dried and crystallized from tetrahydrofuran/methanol/water to give (Z)-2-[[2-chloro-4-[3-(3-hydroxyphenyl)-1-oxopropan-1-yl]benzoyl]amino]-3-(quinolin-3-yl)propenoic acid (96 mg, 70% yield) as a colorless solid.

Example 295

Preparation of (Z)-2-[[2-chloro-4-[3-(3-hydroxyphenyl)-1-oxopropan-1-yl]benzoyl]benzoyl]amino]-3-(2,4-dimethylthiazol-5-yl)propenoic Acid

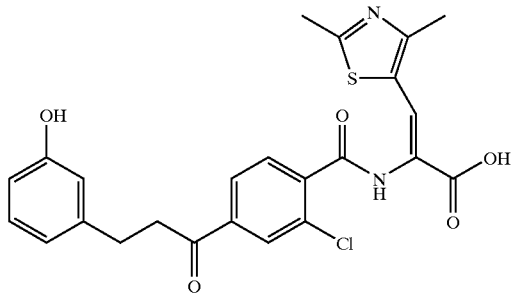

An aqueous 1N solution of sodium hydroxide (0.6 mL, 0.6 mmol) was added to a solution of (Z)-2-[[2-chloro-4-[3-(3-hydroxyphenyl)-1-oxopropan-1-yl]benzoyl]amino]-3-(2,4-dimethylthiazol-5-yl)propenoic acid methyl ester (Example 227; 95 mg, 0.19 mmol) in methanol/tetrahydrofuran (1:1; 2.4 mL). The solution was stirred at room temperature for 6 h and the solvent was evaporated. Water (5 mL) was added and the mixture was extracted with diethyl ether. The organic extract was discarded and the aqueous layer was acidified with 1N hydrochloric acid solution (0.6 mL) and stirred for 30 min at room temperature. The resulting precipitate was filtered off, washed with water, dried and crystallized from tetrahydrofuran/methanol/water to furnish (Z)-2-[[2-chloro-4-[3-(3-hydroxyphenyl)-1-oxopropan-1-yl]benzoyl]amino]-3-(2,4-dimethylthiazol-5-yl)propenoic acid (65 mg, 71% yield) as a colorless solid.

Example 296

Preparation of rac.-(Z)-2-[[2-Chloro-4-[1-hydroxy-3-(3-hydroxyphenyl)propan-1-yl]benzoyl]amino]-3-(quinolin-3-yl)propenoic Acid

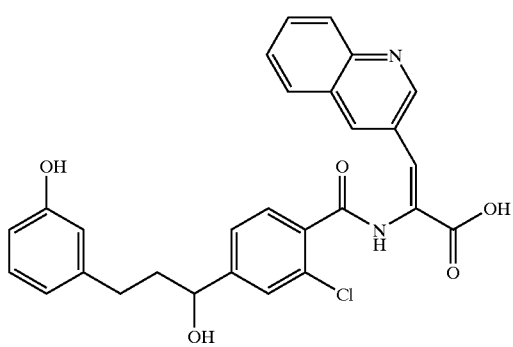

An aqueous solution of sodium hydroxide (1N; 0.5 mL, 0.5 mmol) was added to a solution of rac.-(Z)-2-[[2-chloro-4-[1-hydroxy-3-(3-hydroxyphenyl)propan-1-yl]benzoyl]amino]-3-(quinolin-3-yl)propenoic acid methyl ester (Example 228; 82 mg, 0.16 mmol) in methanol/tetrahydrofuran (1:1; 2 mL). The solution was stirred at room temperature for 16 h and the solvent was evaporated. Water (3 mL) was added and the mixture was acidified with 1N hydrochloric acid solution (0.25 mL). The precipitated solids were recovered by filtration, washed with water, dried and crystallized from tetrahydrofuran/methanol/water to give rac.-(Z)-2-[[2-chloro-4-[1-hydroxy-3-(3-hydroxyphenyl)propan-1-yl]benzoyl]amino]-3-(quinolin-3-yl)propenoic acid (53 mg, 66% yield) as a colorless solid.

Example 297

Preparation of rac.-(Z)-2-[[2-Chloro-4-[1-hydroxy-3-(3-hydroxyphenyl)propan-1-yl]benzoyl]amino]-3-(2,4-dimethylthiazol-5-yl)propenoic Acid

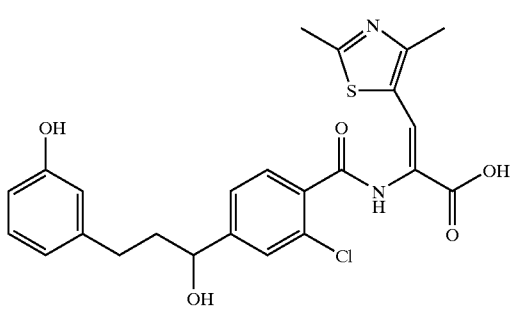

An aqueous 1N solution of sodium hydroxide (0.5 mL, 0.5 mmol) was added to a solution of rac.-(Z)-2-[[2-chloro-4-[1-hydroxy-3-(3-hydroxyphenyl)propan-1-yl]benzoyl]amino]-3-(2,4-dimethylthiazol-5-yl)propenoic acid methyl ester (Example 229; 70 mg, 0.14 mmol) in methanol/tetrahydrofuran (1:1; 2 mL). After the solution was stirred at room temperature for 5 h and the solvents were removed under reduced pressure. Water (5 mL) was added and the mixture was filtered through Celite®. The filter pad was washed with water (2 mL) and the combined filtrates were acidified with 1N hydrochloric acid solution (0.5 mL). The mixture was stirred for 1 h, then the solids were filtered off, washed with water, dried and crystallized from tetrahydrofuran/methanol/water to give rac.-(Z)-2-[[2-chloro-4-[1-hydroxy-3-(3-hydroxyphenyl)propan-1-yl]benzoyl]amino]-3-(2,4-dimethylthiazol-5-yl)propenoic acid (39.3 mg, 58% yield) as a colorless solid.

Example 298

Preparation of rac.-(Z)-2-[[2-Chloro-4-[(E)-1-hydroxy-3-(3-hydroxyphenyl)prop-2-en-1-yl]benzoyl]amino]-3-(quinolin-3-yl)propenoic Acid

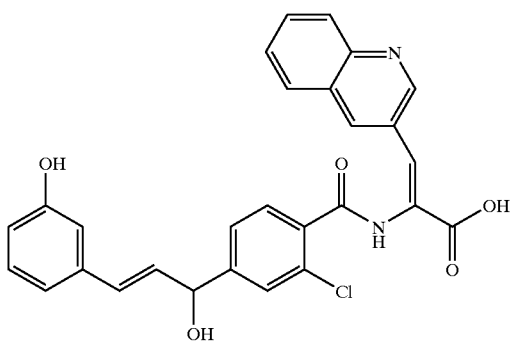

An aqueous 1N solution of sodium hydroxide (0.6 mL, 0.6 mmol) was added to a suspension of rac.-(Z)-2-[[2-chloro-4-[(E)-1-hydroxy-3-(3-hydroxyphenyl)prop-2-en-1-yl]benzoyl]amino]-3-(quinolin-3-yl)propenoic acid methyl ester (Example 230; 95 mg, 0.184 mmol) in water (2 mL). The reaction mixture was stirred at room temperature for 16 h and then acidified with 1N hydrochloric acid solution (0.6 mL). The mixture was stirred for 1 h, then the solid was filtered off, washed with water, dried and purified by reverse phase HPLC and lyophilized to give rac.-(Z)-2-[[2-chloro-4-[(E)-1-hydroxy-3-(3-hydroxyphenyl)prop-2-en-1-yl]benzoyl]amino]-3-(quinolin-3-yl)propenoic acid (57 mg, 62% yield) as a colorless solid.

Example 299

Preparation of rac.-(Z)-2-[[2-Chloro-4-[(E)-1-hydroxy-3-(3-hydroxyphenyl)prop-2-en-1-yl]benzoyl]amino]-3-(2,4-dimethylthiazol-5-yl)propenoic Acid

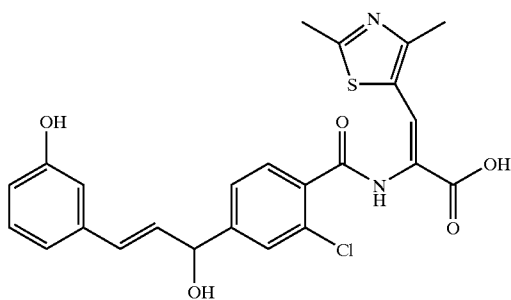

An aqueous 1N solution of sodium hydroxide (0.55 mL, 0.55 mmol) was added to a suspension of rac.-(Z)-2-[[2-chloro-4-[(E)-hydroxy-3-(3-hydroxyphenyl)prop-2-en-1-yl]benzoyl]amino]-3-(2,4-dimethylthiazol-5-yl)propenoic acid methyl ester (Example 231; 90 mg, 0.175 mmol) in water (3 mL). The reaction mixture was stirred at room temperature for 5 h and then acidified with 1N hydrochloric acid solution (0.55 mL). The mixture was stirred for 30 min, then the solid was filtered off, washed with water, dried and evaporated. The crude acid was purified by reverse phase HPLC and lyophilized to give rac.-(Z)-2-[[2-chloro-4-[(E)-1-hydroxy-3-(3-hydroxyphenyl)prop-2-en-1-yl]benzoyl]amino]-3-(2,4-dimethylthiazol-5-yl)propenoic acid (43 mg, 51% yield) as a colorless solid.

Example 300

Preparation of (Z)-2-[[2-Chloro-4-[[(3-hydroxybenzyl)amino]carbonyl]benzoyl]amino]-3-[4-(1-methylethyl)thiazol-5-yl]propenoic Acid

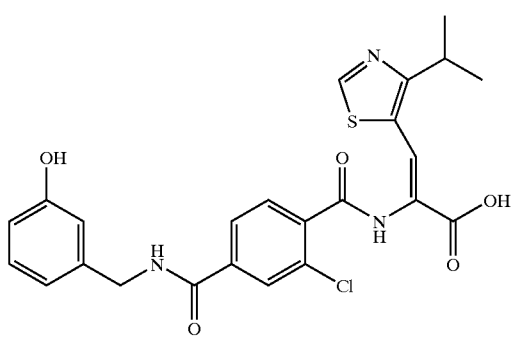

A mixture of (Z)-2-[[2-chloro-4-[[(3-hydroxybenzyl)amino]carbonyl]benzoyl]amino]-3-[4-(1-methylethyl)thiazol-5-yl]propenoic acid methyl ester (Example 232; 75 mg, 0.146 mmol) and lithium hydroxide monohydrate (24 mg, 0.572 mmol) in methanol/tetrahydrofuran/water (2:2:1; 1.25 mL) was stirred at room temperature for 90 min. A further potion of lithium hydroxide monohydrate (6 mg, 0.143 mmol) was added and the reaction mixture was allowed to stir at room temperature for 65 h. After the reaction mixture was evaporated to dryness, water was added, followed by 1N hydrochloric acid solution (0.72 mL). The resulting colorless precipitate was filtered off, then was purified by reverse phase HPLC and lyophilized to afford (Z)-2-[[2-chloro-4-[[(3-hydroxybenzyl)amino]carbonyl]benzoyl]amino]-3-[4-(1-methylethyl)thiazol-5-yl]propenoic acid (42 mg, 58% yield) as a colorless powder.

Example 301

Preparation of 2-[[2-Chloro-4-[[(3-hydroxybenzyl)amino]carbonyl]benzoyl]amino]-3-[2-(1-methylethyl)-4-methylthiazol-5-yl]propenoic Acid

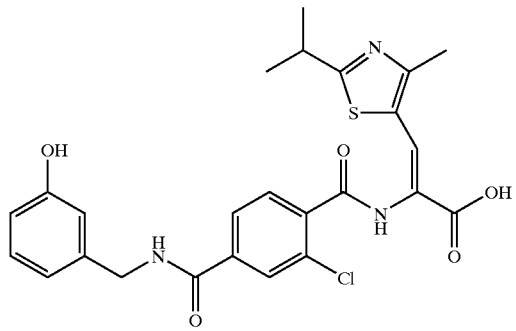

An aqueous 1N solution of sodium hydroxide (1 mL, 1 mmol) was added to a solution of (Z)-2-[[2-chloro-4-[[(3-hydroxybenzyl)amino]carbonyl]benzoyl]amino]-3-[2-(1-methylethyl)-4-methylthiazol-5-yl)]propenoic acid methyl ester (Example 233; 65 mg, 0.123 mmol) in methanol/tetrahydrofuran (1:1; 2 mL). The solution was stirred at room temperature for 18 h, then at 50° C. for 6 h and finally at room temperature for 16 h. The reaction mixture was evaporated to dryness and after the addition of water the solution was acidified with 1N hydrochloric acid solution. The gelatinous colorless solid that precipitated was recovered by filtration and washed thoroughly with water. It was re-suspended in water and lyophilized. The obtained tacky material was dissolved in methanol (0.25 mL) and treated to constant turbidity with water. The resulting off-white solid was filtered off, washed with water/methanol (9:1) and dried in vacuo (45° C., 66 h) to give (Z)-2-[[2-chloro-4-[[(3-hydroxybenzyl)amino]carbonyl]benzoyl]amino]-3-[2-(1-methylethyl)-4-methylthiazol-5-yl]propenoic acid (41 mg, 65% yield) as an off-white powder.

Example 302
Preparation of (Z)-3-(2-Amino-4-trifluoromethylthiazol-5-yl)-2-[[2-chloro-4-[[(3-hydroxybenzyl)amino]carbonyl]benzoyl]amino] propenoic acid and (Z)-2-[[2-chloro-4-[[(3-hydroxybenzyl)amino]carbonyl]benzoyl]amino]-3-(2-methylamino-4-trifluoromethylthiazol-5-yl) propenoic Acid

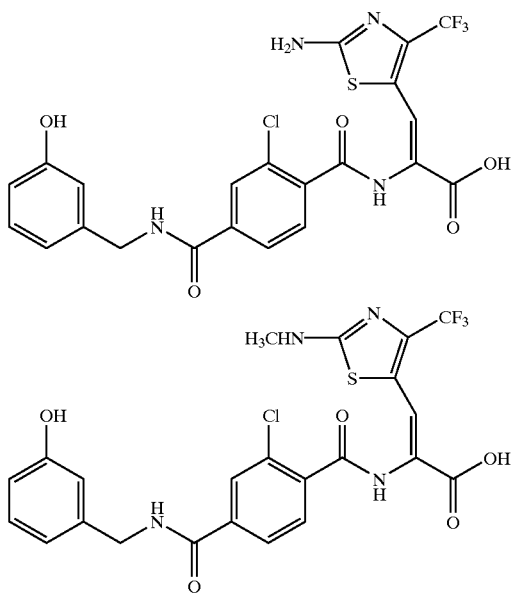

An aqueous 3N solution of sodium hydroxide (0.5 mL, 1.5 mmol) was added to a solution of (Z)-3-(2-amino-4-trifluoromethylthiazol-5-yl)-2-[[2-chloro-4-[[(3-hydroxybenzyl)amino]carbonyl]benzoyl]amino]propenoic acid methyl ester (Example 234; 90 mg, 0.16 mmol) in methanol (0.5 mL). The solution was stirred at room temperature for 16 h and then at 50° C. for 2 h. The reaction mixture was evaporated to dryness and the residue was dissolved in water (2 mL). 1N Hydrochloric acid solution (1.5 mL) was added and the resulting yellow solid was filtered off and washed well with water. The mixture of crude acids was purified by reverse phase HPLC and lyophilized to give (Z)-3-(2-amino-4-trifluoromethylthiazol-5-yl)-2-[[2-chloro-4-[[(3-hydroxybenzyl)amino]carbonyl]benzoyl]amino]propenoic acid (15 mg) and (Z)-2-[[2-chloro-4-[[(3-hydroxybenzyl)amino]carbonyl]benzoyl]amino]-3-(2-methylamino-4-trifluoromethylthiazol-5-yl)propenoic acid (15 mg).

Example 303
Preparation of (Z)-2-[[2-Chloro-4-[[3-(3-hydroxybenzyl)amino]carbonyl]benzoyl]amino]-3-[2-ethyl-4-(1-methylethyl)thiazol-5-yl]propenoic Acid

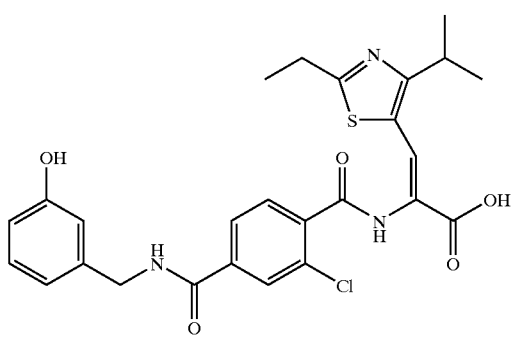

A solution of (Z)-2-[[2-chloro4-[[(3-hydroxybenzyl)amino]carbonyl]benzoyl]amino]-3-[2-ethyl-4-(1-methylethyl)thiazol-5-yl]propenoic acid methyl ester (Example 223; 220 mg, 0.41 mmol) in methanol/tetrahydrofuran (1:3; 4 mL) was added to a solution of lithium hydroxide monohydrate (52 mg, 1.23 mmol) in water (2 mL). After the reaction mixture was stirred at room temperature overnight, it was concentrated in vacuo to remove the organic solvents. Water (5 mL) was added and acidification the solution with 1N hydrochloric acid solution resulted in the precipitation of an off-white solid. On the addition of ethyl acetate, the solids dissolved. The layers were separated and the aqueous phase was extracted with ethyl acetate. The combined extracts were washed with brine, dried (MgSO$_4$) and evaporated under reduced pressure to give a light yellow glass. Trituration of the residue with diethyl ether furnished (Z)-2-[[2-chloro-4-[[3-(3-hydroxybenzyl)amino]carbonyl]benzoyl]amino]-3-[2-ethyl-4-(1-methylethyl)thiazol-5-yl]propenoic acid (20.2 mg, 9.4% yield) as an off-white solid.

Example 304

Preparation of (Z)-2-[[2-Chloro-4-[[(3-hydroxybenzyl)amino]carbonyl]benzoyl]amino]-3-(2-ethyl-4-methylthiazole-5-yl)propenoic Acid

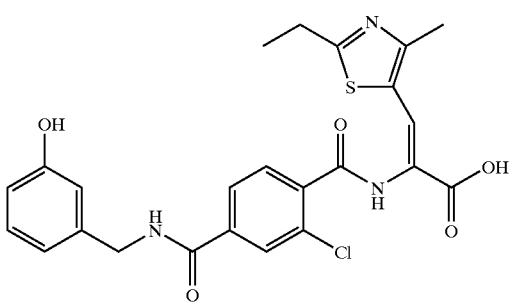

A solution of lithium hydroxide monohydrate (100 mg, 2.4 mmol) in water (3 mL) was added to a solution of (Z)-3-(2-ethyl-4-methylthiazole-5-yl)-2-[[4-[[(3-hydroxybenzyl)amino]carbonyl]-2-methylbenzoyl]amino]propenoic acid methyl ester (Example 216; 120 mg, 0.2 mmol) in tetrahydrofuran/methanol (3:1; 12 mL) and the reaction was allowed to stir at room temperature overnight. Water (50 mL) and 1N hydrochloric acid solution (3 mL) were added and the mixture was extracted with ethyl acetate (2×50 mL). The ethyl acetate layers were concentrated and purified by HPLC to give (Z)-2-[[2-chloro-4-[[(3-hydroxybenzyl)amino]carbonyl]benzoyl]amino]-3-(2-ethyl-4-methylthiazole-5-yl)propenoic acid (105 mg, 90% yield) as a colorless solid, mp>200° C.

Also prepared by this procedure were:

| Example | Structure | Starting Material | Comments |
|---|---|---|---|
| 305 | (structure) | Example 217 | 47% |
| 306 | (structure) | Example 218 | 65% |
| 307 | (structure) | Example 219 | 64% yield |
| 308 | (structure) | Example 220 | 53% yield |
| 309 | (structure) | Example 221 | 55% yield |

-continued

| Example | Structure | Starting Material | Comments |
|---|---|---|---|
| 310 | 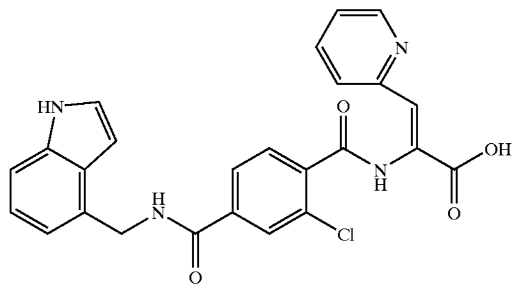 | Example 222 | 60% yield |
| 311 | 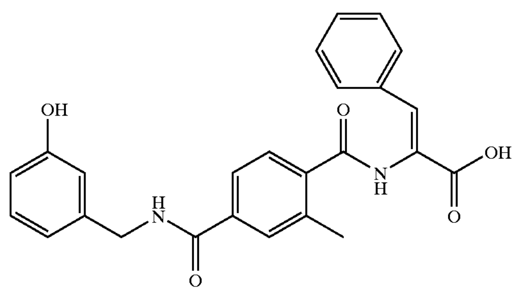 | Example 213 | 7% yield |
| 312 | 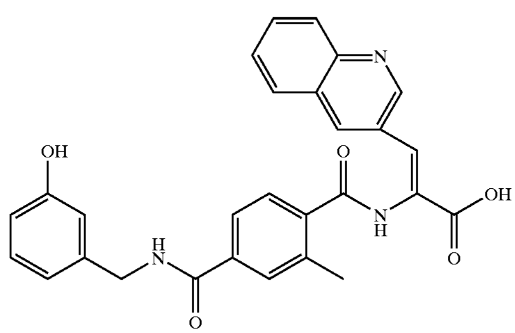 | Example 214 | 6% yield |
| 313 | 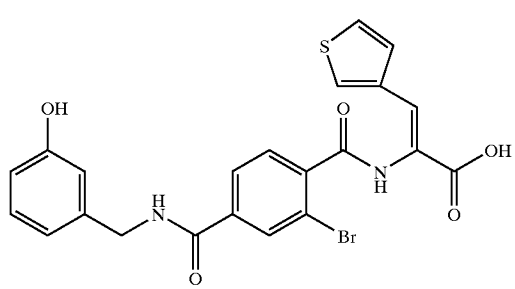 | Example 178 | colorless powder, 41% yield |

Example 314

Preparation of (Z)-3-(4-Bromophenyl)-2-[[2-chloro-4-[[(3-hydroxybenzyl)amino]carbonyl]benzoyl]amino]propenoic Acid

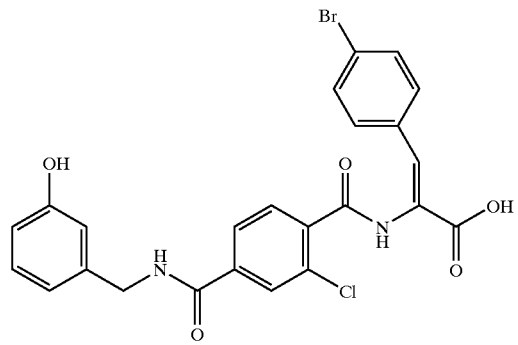

A solution of lithium hydroxide monohydrate (10.6 mg, 0.25 mmol) in water (1 mL) was added to a solution of (Z)-3-(4-bromophenyl)-2-[[2-chloro-4-[[(3-hydroxybenzyl)amino]carbonyl]benzoyl]amino]propenoic acid methyl ester (Example 224; 69 mg, 0.13 mmol) in tetrahydrofuran/methanol/water (3:1:1; 1.5 ml). The mixture was stirred for 4 h at room temperature and then acidified. The product was filtered off and purified by HPLC (Waters system) to give (Z)-3-(4-bromophenyl)-2-[[2-chloro-4-[[(3-hydroxybenzyl)amino]carbonyl]benzoyl]amino]propenoic acid (33 mg, 49% yield).

Also prepared by this procedure was:

| Example | Structure | Starting Material | Comments |
|---|---|---|---|
| 315 | 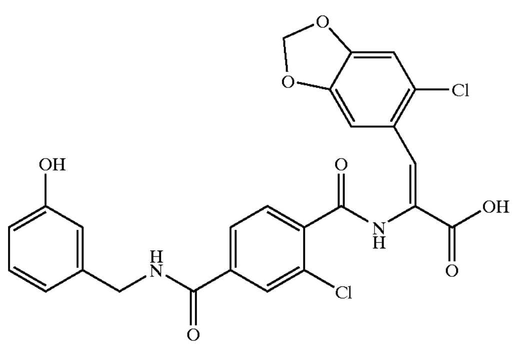 | Example 225 | 50% Yield |

Example 316

Preparation of (Z)-2-[[4-[[(3-Hydroxybenzyl)amino]carbonyl]-2-methylbenzoyl]amino]-3-(1N-indol-6-yl)propenoic Acid

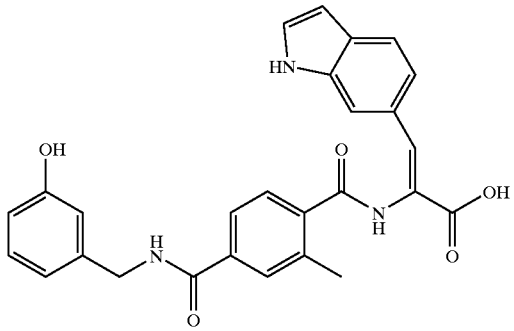

A solution of (Z)-3-[1-(1,1-dimethylethoxy)carbonyl]-1N-indol-6-yl]-2-[[4-[[(3-hydroxybenzyl)amino/carbonyl]-2-methylbenzoyl]amino]propenoic acid methyl ester (Example 215; 0.08 g, 0.14 mmol), trifluoroacetic acid (1 mL) and triethylsilane (1 mL) in dichloromethane (20 mL) was stirred at room temperature overnight. After the solvent was removed under reduced pressure, toluene (20 mL) was added and the volatiles were evaporated again. Tetrahydrofuran (30 mL), methanol (10 mL) and a solution of lithium hydroxide monohydrate (0.50 g, 11.9 mmol) in water (10 mL) were added and the resulting mixture was stirred for 6 h at room temperature. The mixture was acidified to pH 2 using 1N hydrochloric acid solution and extracted with ethyl acetate (2×50 mL). The combined ethyl acetate layers were washed with brine (100 mL), dried (MgSO$_4$), filtered and evaporated. The resulting material was purified in two batches by reverse phase HPLC (5–95% acetonitrile/water with 0.1% trifluoroacetic acid). The appropriate fractions were combined and evaporated and the purified acid was lyophilized to furnish (Z)-3-(1N-indol-6-yl)-2-[[4-[[(3-hydroxybenzyl)amino]carbonyl]-2-methylbenzoyl]amino]propenoic acid (27.2 mg, 42% yield) as a cream colored solid.

Example 317

Preparation of (Z)-2-[[2-Bromo-4-[[(3-hydroxybenzyl)amino]carbonyl]benzoyl]amino]-3-[2-(piperazin-1-yl)thiazol-4-yl]propenoic Acid

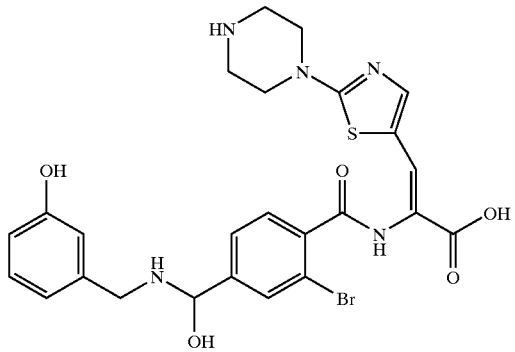

A solution of (Z)-3-[2-[[4-(1,1-dimethylethoxy)carbonyl]piperazin-1-yl]thiazol-4-yl]-2-[[2-bromo-4-[[(3-hydroxybenzyl)amino]carbonyl]benzoyl]amino]propenoic acid methyl ester (Example 184; 162 mg, 0.231 mmol) in methanol (2 mL) was treated with 1N sodium hydroxide solution (0.924 mL, 0.924 mmol). The reaction mixture was stirred at room temperature for 2 days, then at 50° C. for 24 h and finally at room temperature for 3 days. The solution was concentrated to dryness in vacuo and the resulting brown solid was suspended in dichloromethane (2 mL) and, in an atmosphere of argon, trifluoroacetic acid (2 mL) was added. After stirring for 5 h at room temperature, the solution was evaporated to dryness and the resulting residue was purified by reverse phase HPLC (10–50% acetonitrile in water containing 0.075% TFA). The appropriate fractions were combined, evaporated and freeze dried to give (Z)-2-[[2-bromo-4-[[(3-hydroxybenzyl)amino]carbonyl]benzoyl]amino]-3-[2-(piperazin-1-yl)thiazol-4-yl]propenoic acid as a yellow solid (84 mg, 82% yield for the 2 steps).

The following compounds were prepared in the manner described in Example 310:

| Example | Structure | Starting Material | Comments |
|---|---|---|---|
| 318[a] | 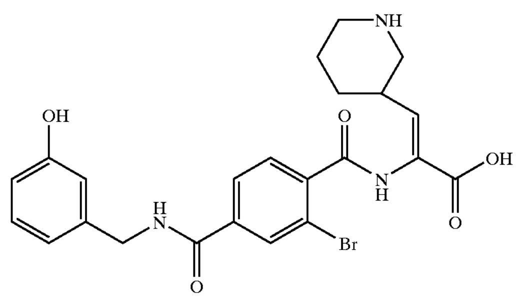 | Example 198 | Saponification: 2 equiv. NaOH; 48 h at RT. N-deprotection: 3 h at RT off-white solid (50% yield) |
| 319 | 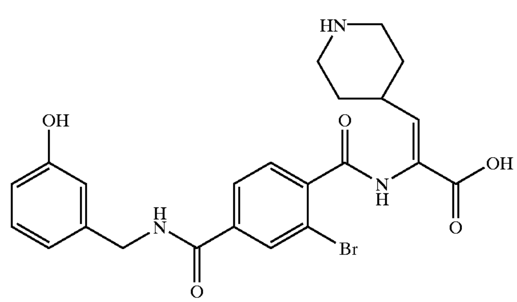 | Example 197 | Saponification: 2 equiv. NaOH; 48 h at RT. N-deprotection: 3 h at RT Colorless solid, (26% yield) |
| 320[a] | 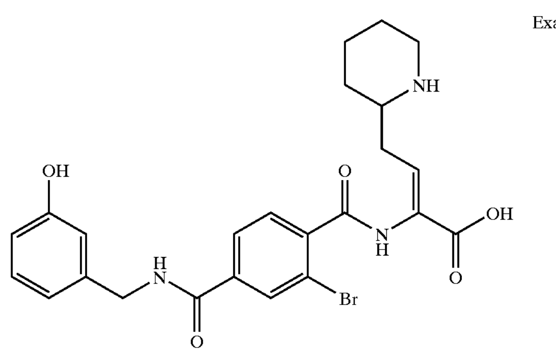 | Example 199 | Saponification: 4 equiv. NaOH; 24 h at RT. N-deprotection: 1.5 h at RT Colorless solid, (44% yield) |

-continued

| Example | Structure | Starting Material | Comments |
|---|---|---|---|
| 321 | 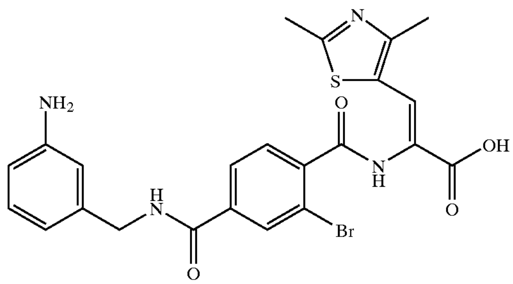 | Example 186 | Saponification: 3 equiv. NaOH; 3 d at 50° C. N-deprotection: 3.5 h at RT Colorless solid, (55% yield) |
| 322 | 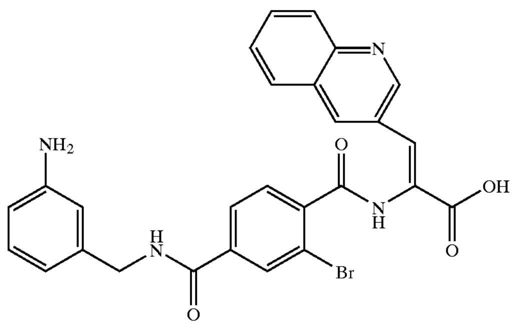 | Example 187 | Saponification: 3 equiv. NaOH; 3 d at 50° C. N-deprotection: 3.5 h at RT Colorless solid, (78% yield) |

[a]racemic

Example 323

Preparation of (Z)-3-(4-Aminosulfonylphenyl)-2-[[2-chloro-4-[[(3-hydroxybenzyl)amino]carbonyl]benzoyl]amino]propenoic Acid

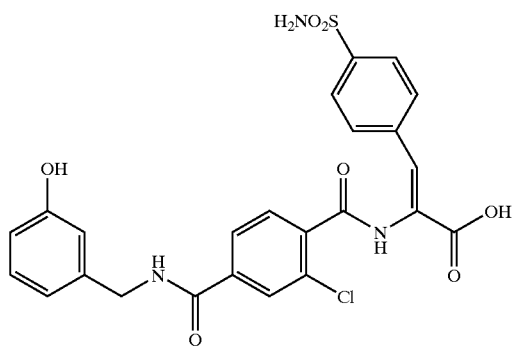

1,1,3,3-Tetramethylguanidine (0.046 g, 0.40 mmol) was added to a solution of rac.-N-[2-chloro-4-[[(3-methoxymethoxybenzyl)amino]carbonyl]benzoyl]-2-(dimethoxyphosphinyl)glycine methyl ester (Example 142; 0.047 g, 0.10 mmol) and 4-15 formylbenzenesulfonamide (lit.: Van Es, T.; Staskun, B. *Organic Syntheses* 1971, 51, 20–23; 0.019 g, 0.10 mmol) in DME (4 mL). The solution was stirred at room temperature for 20 h and then was poured into water (25 mL). The aqueous layer was extracted with ethyl acetate and the organic layers were dried ($Na_2SO_4$), filtered and evaporated to give crude (Z)-3-(4-aminosulfonylphenyl)-2-[[2-chloro-4-[[(3-methoxymethoxybenzyl)amino]carbonyl]benzoyl]amino]propenoic acid methyl ester. A solution of tetrahydrofuran/methanol/water (3:1:1; 4 mL) was added, followed by lithium hydroxide monohydrate (7 mg, 0.17 mmol). The mixture was stirred at room temperature for 24 h, neutralized with 1N hydrochloric acid solution and extracted with ethyl acetate. The solvent was evaporated to give (Z)-3-(4-aminosulfonylphenyl)-2-[[2-chloro-4-[[(3-methoxymethoxybenzyl)amino]carbonyl]benzoyl]amino]propenoic acid as a light brown oil. A solution of trifluoroacetic acid/dichloromethane (1:1) was added and the solution was stirred at room temperature overnight. The solvent was evaporated and the residue purified by HPLC (Waters system) to give (Z)-3-(4-aminosulfonylphenyl)-2-[[2-chloro-4-[[(3-hydroxybenzyl)amino]carbonyl]benzoyl/amino]propenoic acid.

Example 324

Preparation of (Z)-2-[[2-Chloro-4-[[[(1N-indol-6-yl)methyl]amino]carbonyl]benzoyl]amino]-3-(quinolin-3-yl)propenoic Acid

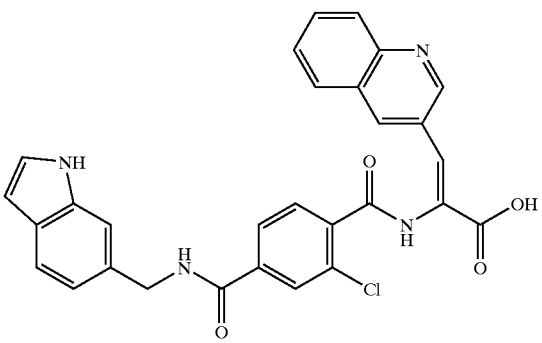

1,1,3,3-Tetramethylguanidine (102 mg, 0.9 mmol) was added to a solution of rac.-N-[2-chloro-4-[[[(1H-indol-6-yl)

methyl]amino]carbonyl]benzoyl]-2-(dimethoxyphosphinyl) glycine methyl ester (Example 136; 300 mg, 0.6 mmol) in dichloromethane (10 mL) at ~5° C. The solution was stirred at ~5° C. for 30 min and then quinoline-3-carboxaldehyde (186 mg, 1.2 mmol) was added. The solution was stirred overnight at room temperature, then it was washed with cold 1N hydrochloric acid solution and brine, dried, filtered and evaporated to give a mixture (230 mg) of (Z)-2-[[2-chloro-4-[[[(1H-indol-6-yl)methyl]amino]carbonyl]benzoyl] amino]-3-(quinolin-3-yl)propenoic acid methyl ester and unreacted quinoline-3-carboxaldehyde. This mixture was dissolved in tetrahydrofuran/methanol (3:1; 4 mL) and the solution was added to a solution of lithium hydroxide monohydrate (28 mg, 0.7 mmol) in water (1 mL). The solution was allowed to stir at room temperature for 5 days and then concentrated to remove tetrahydrofuran and methanol. The remaining solution was diluted with water and acidified with 1N hydrochloric acid solution. The resulting mixture was extracted with ethyl acetate and the organic extracts were washed with brine, dried (MgSO$_4$), filtered, concentrated and purified by reverse phase HPLC (5–95% acetonitrile/water with 0.1% trifluoroacetic acid). The appropriate fractions were combined and evaporated and the purified acid was lyophilized to give (Z)-2-[[2-chloro-4-[[[(1H-indol-6-yl)methyl]amino]carbonyl]benzoyl]amino]-3-(quinolin-3-yl)propenoic acid (37 mg, 12% yield).

Also prepared by this procedure was:

A. (Z)-3-[1-(1,1-Dimethylethoxycarbonyl)-1H-benzotriazol-5-yl]-2-[[4-[[[3-[[(1,1-dimethylethyl)dimethylsilyl] oxy]benzyl]amino]carbonyl]-2,6-dimethylbenzoyl]amino] propenoic Acid Methyl Ester and (Z)-3-(1H-Benzotriazole-5-yl)-2-[[4-[[[3-[[(1,1-dimethylethyl)dimethylsilyl]oxy] benzyl]amino]carbonyl]-2,6-dimethylbenzoyl]amino] propenoic Acid Methyl Ester 1,1,3,3-Tetramethylguanidine (32 µL, 0.254 mmol) was added to a solution of rac.-2-(dimethoxyphosphinyl)-N-[4-[[[3-[[(1,1-dimethylethyl)dimethylsilyl]oxy]benzyl]amino] carbonyl]-2,6-dimethylbenzoyl] glycine methyl ester (Example 126; 100 mg, 0.169 mmol) in tetrahydrofuran (2 mL) at −40° C. The solution was stirred at −40° C. for 5 min and then 1-(1,1-dimethylethoxycarbonyl)-1H-benzotriazole-5-carboxaldehyde (Example 40; 41 mg, 0.169 mmol) was added. The solution was stirred at −40° C. for 2 h and then allowed to stir at room temperature for 24 h. The solution was quenched with pH 6 phosphate buffer, diluted with ethyl acetate (25 mL) and the organic layer was washed with pH 6 phosphate buffer (5 mL) and brine (15 mL). The organic layer was dried (MgSO$_4$), filtered and evaporated. The residue was flash chromatographed (silica gel, 60% ethyl acetate in petroleum ether −100% ethyl acetate) to yield two compounds, the less polar (Z)-3-[1-(1,1-dimethylethoxycarbonyl)-1H-benzotriazol-5-yl]-2-[[4-[[[3-[[(1,1-dimethylethyl)dimethylsilyl]oxy]benzyl]amino] carbonyl]-2,6-dimethylbenzoyl]amino]propenoic acid methyl ester (21 mg) as well as the more polar

| Example | Structure | Starting Materials | Yield |
|---|---|---|---|
| 325 | 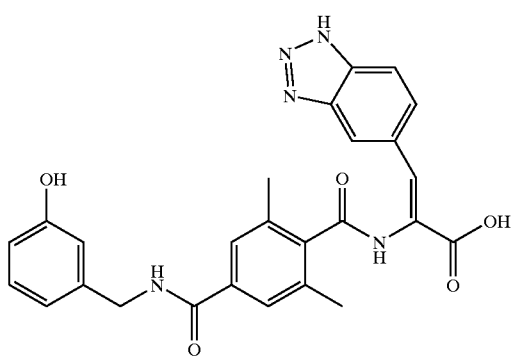 | Example 137 and quinoline-3-carboxaldehyde | 49% |

Example 326

Preparation of (Z)-3-(1H-Benzotriazol-5-yl)-2-[[4-[[[(3-hydroxybenzyl)amino]carbonyl]-2,6-dimethylbenzoyl]amino]propenoic Acid N-deprotected product (Z)-3-(1H-benzotriazol-5-yl)-2-[[4-[[[3-[[(1,1-dimethylethyl)dimethylsilyl]oxy]benzyl]amino] carbonyl]-2,6-dimethylbenzoyl]amino]propenoic acid methyl ester (40 mg).

B. Mixture of (Z)-3-[1-(1,1-Dimethylethoxycarbonyl)-1H-benzotriazol-5-yl]-2-[[4-[[[(3-hydroxybenzyl)amino] carbonyl]-2,6-dimethylbenzoyl]amino]propenoic Acid Methyl Ester and (Z)-3-(1H-Benzotriazole-5-yl)-2-[[4-[[[(3-hydroxybenzyl)amino]carbonyl]-2,6-dimethylbenzoyl] amino]propenoic Acid Methyl Ester A solution of the above recombined materials (61 mg) in tetrahydrofuran (2 mL) was treated with a 1M solution of tetrabutylammonium fluoride in tetrahydrofuran (103 µL, 0.103 mmol) and the reaction was allowed to stir at room temperature for 6 h. The solution was partitioned between saturated aqueous ammonium chloride solution and ethyl acetate, then the dried (MgSO$_4$), organic phase was evaporated. The residual desilylated material was used per se in the next step.

C. (Z)-3-(1H-Benzotriazole-5-yl)-2-[[4-[[(3-hydroxybenzyl)amino]carbonyl]-2,6-dimethylbenzoyl]amino]propenoic Acid Methyl Ester A solution of the crude mixture from step B in dichloromethane (1 ml) and trifluoroacetic acid (1 mL) was stirred at room temperature for 3 h, then the volatiles were removed in vacuo and the resulting material was partitioned between ethyl acetate and 5% aqueous sodium bicarbonate solution. The organic layer was dried (MgSO$_4$), filtered and evaporated to constant weight under reduced pressure. The crude ester was used in the next step without further purification.

D. (Z)-3-(1H-Benzotriazole-5-yl)-2-[[4-[[(3-hydroxybenzyl)amino]carbonyl]-2,6-dimethylbenzoyl]amino]propenoic Acid To a solution of the crude ester from step C (54 mg, 0.098 mmol) in methanol (1 mL) was added 1N sodium hydroxide (294 μL, 0.294 mmol,) and the solution was stirred at room temperature for 6 days. The solvents were removed under reduced pressure and the crude product was purified by reverse phase HPLC (10–50% acetonitrile/water). The appropriate fractions were combined, evaporated and the residual material was lyophilized to afford (Z)-3-(1H-benzotriazole-5-yl)-2-[[4-[[(3-hydroxybenzyl)amino]carbonyl]-2,6-dimethylbenzoyl]amino]propenoic acid as a colorless solid (20 mg, 20% yield over 4 steps).

Example 327

Preparation of (Z)-2-[[2-Chloro-4-[[(1-(naphthalen-1-yl)ethylamino]carbonyl]benzoyl]amino]-3-(thiophen-2-yl)propenoic Acid

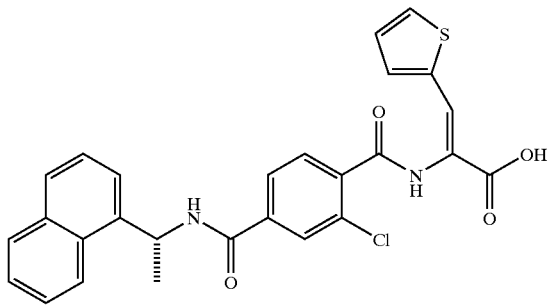

In a 6 mL polyethylene vial equipped with a coarse glass frit, (R,S)-N-[2-chloro-4-[[(R)-1-(naphthalen-1-yl) ethylamino]carbonyl]benzoyl]-2-(dimethoxyphosphinyl) glycine substituted Wang resin (Example 145; 100 mg) was treated with 1,1,3,3-tetramethylguanidine (83 μL, 0.685 mmol) in tetrahydrofuran (1 mL). The mixture was agitated for 10 min before thiophene-2-carboxaldehyde (57 mg, 0.51 mmol) was added and the resulting mixture was shaken for 2 h. The resin was filtered and washed with tetrahydrofuran, dichloromethane and methanol, then the dried resin was shaken with a solution of trifluoroacetic acid in dichloromethane (1:1) for 30 min. The mixture was filtered and the filtrate was evaporated to dryness under reduced pressure. The residue was purified by reverse phase HPLC (5–95% acetonitrile/water containing 0.1% trifluoroacetic acid). The appropriate fractions were combined and evaporated to furnish of (Z)-2-[[2-chloro-4-[[(1-(naphthalen-1-yl) ethylamino]carbonyl]benzoyl]amino]-3-(thiophen-2-yl) propenoic acid.

Example 328

Preparation of (Z)-2-[[2-Bromo-4-[[(3-hydroxybenzyl)amino]carbonyl]benzoyl]amino]-3-(2,4-dimethylthiazol-5-yl)propenoic Acid Monosodium Salt

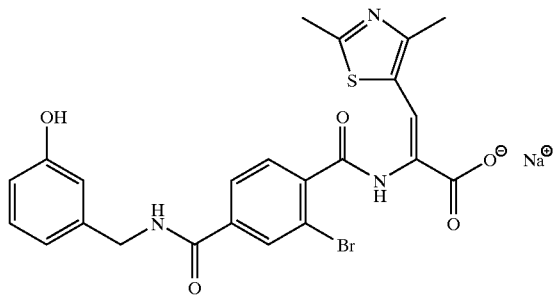

A solution of (Z)-2-[[2-bromo-4-[[(3-hydroxybenzyl) amino]carbonyl]benzoyl]amino]-3-(2,4-dimethylthiazol-5-yl)propenoic acid (Example 258; 700 mg, 1.28 mmol) in methanol (3 mL) was treated with 1N sodium hydroxide solution (2.7 mL, 2.7 mmol) and the reaction mixture was stirred at 50° C. overnight and then was left at room temperature for three days. The solution was concentrated to dryness in vacuo and the residue was placed on a reverse phase silica gel column made up in deionized water. The column was eluted with increasing concentrations (5–10%) of methanol in water and the appropriate fractions were combined and evaporated. The residual material was lyophilized to yield 0.745 g of a colorless solid shown to be the desired monosodium salt along with a small amount of silica. The contaminant was removed by passing a suspension of the above solid in deionized water through a 0.45 micron filter. The filtrate was concentrated and lyophilized to furnish (Z)-2-[[2-bromo-4-[[(3-hydroxybenzyl)amino] carbonyl]benzoyl]amino]-3-(2,4-dimethylthiazol-5-yl) propenoic acid as its mono sodium salt.

Example 329

Preparation of 2,6-Dimethyl-4-[5-[(1H-indol-4-yl) methylamino]tetrazol-1-yl]benzoic Acid

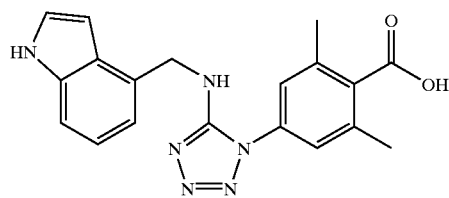

A. 3,5-Dimethyl-4-hydroxybenzoic Acid Methyl Ester.
In a flask fitted with a Soxhlet extractor filled with 3A molecular sieves is added a solution of 3,5-dimethyl-4- hydroxybenzoic (8.3 g, 50 mmol) acid in methanol (50 mL) containing p-toluenesulfonic acid (0.1 g) After heating at gentle reflux overnight, the reaction is cooled to room temperature and treated with solid sodium bicarbonate. The volatiles are removed under reduced pressure and a solution of the residue in dichloromethane is washed with a 5% aqueous sodium bicarbonate solution and with brine. The dichloromethane layer is dried ($MgSO_4$), filtered and evaporated in vacuo to give 3,5-dimethyl-4-hydroxybenzoic acid methyl ester.

B. Trifluoromethanesulfonic Acid, 2,6-Dimethyl-4-(methoxycarbonyl)phenyl Ester

To a solution of 3,5-dimethyl-4-hydroxybenzoic acid methyl ester (4.5 g, 25 mmol) in dry dichloromethane (175 mL) is cooled to −78° C. is added triethylamine (13.9 mL, 100 mmol) followed by the dropwise addition of trifluoromethanesulfonic anhydride (4.25 mL, 30 mmol). After the solution is stirred for 2 h at −78° C., the reaction is quenched with saturated aqueous ammonium chloride (15 mL). The mixture is warmed to room temperature, then is diluted with ethyl acetate (70 mL) and is washed with 1N hydrochloric acid solution (1–250 mL), saturated aqueous sodium bicarbonate solution (1–250 mL), water (250 mL) and brine (250 mL). The organic layer is then dried ($MgSO_4$), filtered, evaporated under reduced pressure and is quickly passed over a short column of silica gel (increasing concentrations of ethyl acetate in hexane). The appropriate fractions are combined and evaporated to give trifluoromethanesulfonic acid, 4-(methoxycarbonyl)-2,6-dimethylphenylester.

C. 4-(Methoxycarbonyl)-2,6-dimethylbenzoic Acid

To a solution of trifluoromethanesulfonic acid, 4-(methoxycarbonyl)-2,6-dimethylphenyl ester (3.12 g, 10 mmol) in acetonitrile (80 mL) and water (10 mL) at 25° C. is added palladium (II) acetate (224.5 mg, 1.0 mmol), 1,3-bis(diphenylphosphino)propane (412.5 mg, 10 mmol), followed by triethylamine (2.79 mL, 20 mmol). The reaction is then pressurized to 40 psi with carbon monoxide and heated to 80° C. for 4 h. The mixture is diluted with ethyl acetate (500 mL) and is washed with water (250 mL) containing 5 mL of triethylamine. The separated aqueous layer is re-extracted with ethyl acetate (2×250 mL) and the combined organic layers are discarded. The aqueous phase is then adjusted with 1N hydrochloric acid solution to pH 2 and is extracted with ethyl acetate (500 mL). The organic extract is washed with water (250 mL) and brine (250 mL), then is dried ($MgSO_4$), filtered and evaporated in vacuo to yield 2,6-dimethyl-4-(methoxycarbonyl)benzoic acid.

D. 4-(Methoxycarbonyl)-3,5-dimethylbenzoic Acid

A solution of 4-(methoxycarbonyl)-2,6-dimethylbenzoic acid (2.08 g: 10 mmol) in methanol (25 mL) is treated with ethereal diazomethane until the yellow color persists and the solution is left at room temperature overnight. The solution is concentrated in vacuo to remove the remaining diethyl ether, then tetrahydrofuran (25 mL) is added. The solution is stirred in an ice-water bath as a solution of lithium hydroxide monohydrate (0.462 g, 11 mmol) in water (25 mL) is added. After the cooling bath is removed, the reaction is allowed to proceed at room temperature overnight. The volatiles are removed under reduced pressure on a rotary evaporator (bath temperature <30° C.), then the concentrate is diluted with brine and extracted with dichloromethane to remove residual 2,6-dimethylterephthalic acid dimethyl ester. The aqueous phase is acidified to pH 2 using 3N hydrochloric acid (4 mL), then is extracted with dichloromethane (2×25 mL). The combined organic extracts are washed with brine, then are dried ($MgSO_4$), filtered and evaporated in vacuo to yield 3,5-dimethyl-4-(methoxycarbonyl)benzoic acid.

E. 4-[[(1H-Indol-4-yl)methylamino]carbonyl]amino-2,6-dimethylbenzoic Acid, Methyl Ester In an inert atmosphere, a solution of 4-(methoxycarbonyl)-3,5-dimethylbenzoic acid (2.08 g, 10 mmol), diphenylphosphoryl azide (2.8 g, 10.17 mmol) and diisopropylethylamine (1.92 mL, 11 mmol) in benzene (25 mL) is stirred at room temperature for 1 h, then the reaction temperature is slowly raised to 75° C. The reaction is held at that temperature until the evolution of gas ($CO_2$) is no longer evident and the reaction solution containing 3,5-dimethyl-4-(methoxycarbonyl)phenylisocyanate is cooled to 40° C. Another portion of diisopropylethylamine (1.92 mL, 11 mmol) is added, followed by 1H-indole-4-methanamine hydrochloride salt (Example 68; 2.95 g, 11 mmol) and the solution is stirred and heated at reflux under argon overnight. The reaction mixture is cooled, diluted with benzene (50 mL) and washed in turn with 1N hydrochloric acid (50 mL) and dilute brine. The aqueous layers are re-extracted with benzene and the combined extracts are dried ($MgSO_4$) and evaporated under reduced pressure. The product is purified if necessary by crystallization or by chromatography over silica gel using increasing concentrations of ethyl acetate in hexane to furnish the urea, 4-[[(1H-indol-4-yl)methylamino]carbonyl]amino-2,6-dimethylbenzoic acid, methyl ester.

F. 2,6-Dimethyl-4-[5-[(1H-indol-4-yl)methylamino]tetrazol-1-yl]benzoic Acid.

In a dry argon atmosphere, a solution of triphenylphosphine (2.62 g, 10 mmol), diethyl azodicarboxylate (1.74 g, 10 mmol) 4-[[(1H-indol-4-yl)methylamino]carbonyl]amino-2,6-dimethylbenzoic acid, methyl ester (1.76 g, 5 mmol) in dry tetrahydrofuran (50 mL) is treated with trimethylsilyl azide (1.34 mL, 10 mmol) and is stirred at room temperature for 24 h. If examination of the reaction mixture by tlc suggests that a significant percentage of starting urea persists, a second portion of each of triphenylphosphine (1.31 g, 5 mmol), diethyl azodicarboxylate (0.87 g, 5 mmol) and trimethylsilyl azide (0.67 mL, 5 mmol) are added. The reaction is stirred at room temperature until the reaction is completed. The solvents are removed under reduced pressure and the residue is taken up in dichloromethane (150 mL) and washed with water (2×75 mL). The aqueous layers are back-extracted in turn with dichloromethane (75 mL) and the combined organic phases are dried ($MgSO_4$), filtered and evaporated in vacuo. The residue is dissolved in a mixture of methanol (20 mL), tetrahydrofuran (20 mL) and 1 N aqueous lithium hydroxide solution (10 mL) and the mixture is stirred at 50° C. for 5 h. Most of the volatiles are removed under reduced pressure, then the basic solution is diluted with water (30 mL) and is washed with dichloromethane (2×50 mL). The aqueous layer is then acidified with 1N hydrochloric acid (11 mL) and extracted with ethyl acetate (2×50 mL) are dried ($MgSO_4$) and evaporated under reduced pressure. The product is purified if necessary by crystallization or by chromatography over silica gel using increasing concentrations of ethyl acetate in hexane to give 2,6-dimethyl-4-[5-[(1H-indol-4-yl)methylamino]tetrazol-1-yl]benzoic acid.

Example 330

Preparation of rac.-N-[2,6-Dimethyl-4-[5-[(1H-indol-4-yl)methylamino]tetrazol-1-yl]benzoyl]-2-(dimethoxyphosphinyl)glycine Methyl Ester

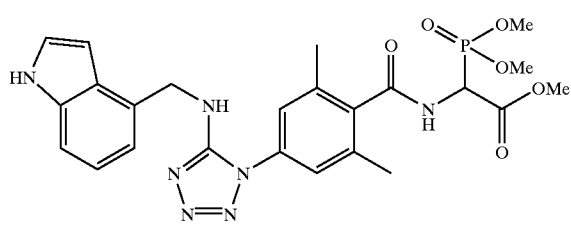

Triphenylphosphine (1.31 g, 5 mmol) is added to a suspension of give 2,6-dimethyl-4-[5-[(1H-indol-4-yl)methylamino]tetrazol-1-yl]benzoic acid (Example 329; 1.81 g, 5 mmol) in dichloromethane (25 mL) at 25° C. The mixture is cooled to 0° C. and N-chlorosuccinimide (0.668 g, 5 mmol) is added. After stirring 15 min at 0° C., the mixture is stirred for an additional 15 min at 25° C. and then a solution of rac.-2-(dimethoxyphosphinyl)glycine methyl ester (Example 125) freshly prepared from rac.-N-(benzyloxycarbonyl)-2-(dimethoxyphosphinyl)glycine methyl ester (3.01 g, 10 mmol) in dichloromethane (5 mL) is added in one portion. The reaction is stirred for 5 h, then the precipitated amine hydrochloride is filtered off, washed with dichloromethane and discarded. The filtrate is washed with 1N hydrochloric acid solution (50 mL), saturated aqueous sodium bicarbonate solution (50 mL) and brine (50 mL), then is dried ($MgSO_4$) and concentrated under reduced pressure. The residue is chromatographed over silica gel (increasing percentages of ethyl acetate in petroleum ether) and the appropriate fractions are combined and evaporated to yield rac.-N-[2,6-dimethyl-4-[5-[(1H-indol-4-yl)methylamino]tetrazol-1-yl]benzoyl]-2-(dimethoxyphosphinyl) glycine methyl ester.

Prepared in the same manner is:

Example 332

Preparation of (Z)-2-[2,6-Dimethyl-4-[5-[(1H-indol-4-yl)methylamino]tetrazol-1-yl]benzoyl]amino]-3-(2,4-dimethylthiazol-5-yl)propenoic Acid Methyl Ester

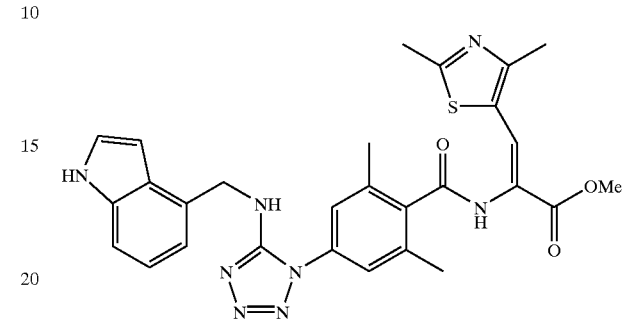

1,1,3,3-Tetramethylguanidine (53 μL, 0.42 mmol) is added to a solution of rac.-N-[2,6-dimethyl-4-[5-[(1H-indol-4-yl)methylamino]tetrazol-1-yl]benzoyl]-2-(dimethoxyphosphinyl)glycine methyl ester (Example 330; 108.3 mg, 0.2 mmol) in tetrahydrofuran (2 mL) at −40° C. The solution is stirred at −40° C. for 5 min and then 2,4-dimethylthiazole-4-carboxaldehyde (Example 43; 56.4 mg, 0.4 mmol) is added. The solution is stirred at −40° C. for 1 h and then allowed to stir at room temperature for 4 h. The solution is quenched with pH 6 phosphate buffer, diluted with ethyl acetate (15 mL) and the separated organic layer is washed with pH 6 phosphate buffer (10 mL) and brine (10 mL). The organic phase is dried ($MgSO_4$), filtered, evaporated under reduced pressure. The residue is chromatographed over silica gel (increasing percentages of ethyl acetate in petroleum ether) and the appropriate fractions are combined and evaporated to yield to give (Z)-2-[2,6-dimethyl-4-[5-[(1H-indol-4-yl)methylamino]tetrazol-1-yl]benzoyl]amino]-3-(2,4-dimethylthiazol-5-yl)propenoic acid methyl ester.

The following examples are prepared in the same manner:

| Example | Structure | Starting Material |
|---|---|---|
| 331 | ![structure] | Example 123 |

| Example | Structure | Starting Material |
|---|---|---|
| 333 | 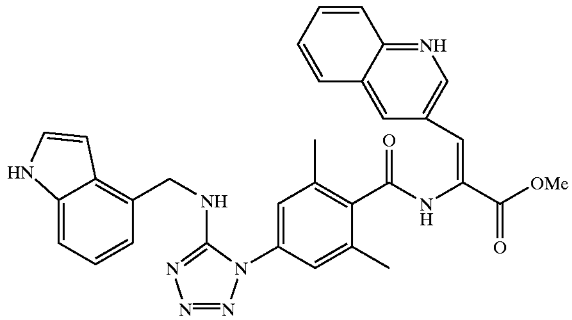 | Example 330 and quinoline 3-carboxaldehyde |
| 334 | 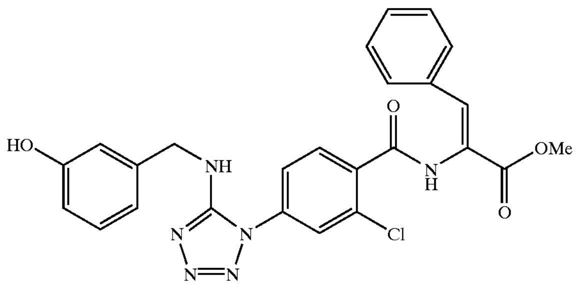 | Example 331 and benzaldehyde |

Example 335

Preparation of (Z)-2-[2,6-Dimethyl-4-[5-[(1H-indol-4-yl)methylamino]tetrazol-1-yl]benzoyl]amino]-3-(2,4-dimethylthiazol-5-yl)propenoic Acid

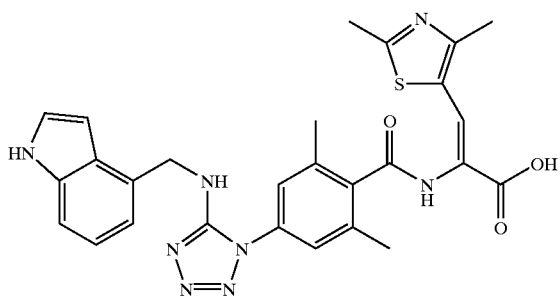

A solution of 1N lithium hydroxide (0.3 mL, 0.3 mmol) is added to a solution of (Z)-2-[[2-bromo-4-[[(3-hydroxybenzyl)amino]carbonyl]benzoyl]amino]-3-(thiazol-2-yl)propenoic acid methyl ester (Example 332; 55.6 mg, 0.1 mmol) in tetrahydrofuran/methanol (2:1; 1 mL). After the solution is allowed to stir at room temperature for 16 h, the volatiles are evaporated in vacuo and the residue is purified by reverse phase HPLC (increasing percentages of acetonitrile in water containing 0.1% trifluoroacetic acid). The appropriate fractions are combined and evaporated to yield to give (Z)-2-[2,6-dimethyl-4-[5-[(1H-indol-4-yl)methylamino]tetrazol-1-yl]benzoyl]amino]-3-(2,4-dimethylthiazol-5-yl)propenoic acid.

The following compounds are prepared in the same manner:

| Example | Structure | Starting Material |
|---|---|---|
| 336 | 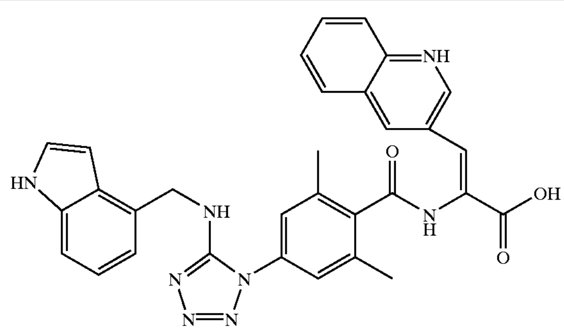 | Example 333 |

| Example | Structure | Starting Material |
|---|---|---|
| 337 | 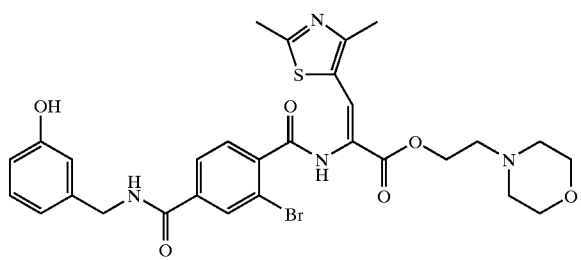 | Example 334 |

Example 338

Preparation of (Z)-2-[[2-Bromo-4-[[(3-hydroxybenzyl)amino]carbonyl]benzoyl]amino]-3-(2,4-dimethylthiazol-5-yl)propenoic Acid Morpholino Ethyl Ester To a suspension of (Z)-2-[[2-bromo-4-[[(3-hydroxybenzyl)amino]carbonyl]benzoyl]amino]-3-[2,4-dimethylthiazol-5-yl]propenoic acid, sodium salt (Example 328; 50 mg, 0.0905 mmol) in tetrahydrofuran (1 mL) at room temperature was added (3-dimethylaminopropyl)-3-ethylcarbodiimide (18 mg, 0.0935 mmol), followed by 4-dimethylaminopyridine (0.0085 mmol, 1 mg) and 2-(morpholin-4-yl)ethanol (0.203 mL, 1.7 mmol). After the mixture was stirred at room temperature 24 h, it was diluted with ethyl acetate (100 mL) and washed with water (3×10 mL) and brine (10 mL). The organic layer was dried with $MgSO_4$, filtered, concentrated and flash chromatographed (silica gel, 5–15% methanol in dichloromethane) to afford (Z)-2-[[2-bromo-4-[[(3-hydroxybenzyl)amino]carbonyl]benzoyl]amino]-3-[2,4-dimethylthiazol-5-yl]propenoic acid morpholino ethyl ester (15 mg, 26% yield) as a colorless solid.

Bioassays

LFA-1/ICAM-1 Protein-Protein Assay

LFA-1/ICAM-1 antagonist activity, defined as the ability to block LFA-1 binding to immobilized ICAM-1, was quantitated using a solid-phase ELISA. Typically, fusion protein consisting of the entire extracellular domain of human ICAM-1 and the Fc domain of human IgG (5dICAM-Ig) was coated onto 96-well microtiter plates (0.15 μg in 100 μL PBS) overnight at 4° C. The plates were then blocked with 150 μL of 1% BSA/1 mM $MnCl_2$/0.14 M NaCl/20 mM HEPES, pH 7.2 for 1 h at 37° C. and washed 3 times (150 μL each) with Wash Buffer (50 mM Tris, pH 7.4/100 mM NaCl/1 mM $MnCl_2$/0.05% Tween 20). Stock solutions (100 μM in 100% DMSO) of test compounds were diluted 50 fold with 150 μL of Binding Buffer (0.05% BSA/0.05% Tween 20/1 mM $MnCl_2$/0.14 M NaCl/20 mM HEPES, pH 7.2) plus 10% DMSO. A series of 1:4 dilutions were performed to achieve a concentration range of 0.12 nM–2 μM. Fifty μL per well of each dilution was added to the ICAM-1 coated plates, followed by 50 μL per well of membrane-bound LFA-1 (280 ng/mL in Binding Buffer) derived from transfected 293 cells. The plates were shaken vigorously for 1 min (room temperature) and gently for 2 h (37° C.). After incubation, the plates were washed 3 times (150 μL each) with Wash Buffer. Mouse anti-human integrin β2 monoclonal antibody was added (100 μL/well, 1 μg/ml in Binding Buffer) and allowed to incubate for 1 h (37° C.) with gentle agitation. The plates were then washed 3 times with Wash Buffer. HRP-conjugated goat anti-mouse IgG (100 μL/well, 1:1500 dilution in Binding Buffer) was added to each well, followed by incubation for 1 h (37° C.) and concluded by three washes (150 μL each) with Wash Buffer. TMB solution (100 μL per well) was added for color development (10 min). The reaction was stopped by the addition of 100 μL of 1M $H_3PO_4$ to each well. The plates were then read at 450 nm. The inhibitory activities of test compounds were determined by the $IC_{50}$s and are presented in the following table:

Mixed Lymphocyte Reaction (MLR)

Admixture of murine spleen cells from two different inbred strains of mice induces proliferation of T lymphocytes. The magnitude of T cell proliferation depends on the extent of disparity in the major histocompatibility antigens between the two strains. Splenic T lymphocytes from both strains proliferate due to alloantigen recognition, a process for which the interaction of ICAM-1 on antigen-presenting cells with LFA-1 on lymphocytes is necessary. The ability of antagonists to inhibit T lymphocyte proliferation following recognition of alloantigens was assessed in a one-way MLR, where cells from one strain were irradiated to permit measurement of the proliferative response of cells from the other strain. Spleen cells were washed three times in tissue culture medium (TCM; see below). Fifty microliters of a spleen cell suspension (prepared at $10 \times 10^6$ cells/ml in TCM) obtained from C57B1/6 mice were added to an equal number of lethally-irradiated (2000 rads) spleen cells obtained from BALB/c mice in a 96-well U-bottom tissue culture plate (Costar, 3799). One hundred microliters of serial dilutions of antagonists or TCM were added to the spleen cell mixture. The total volume in each well was 200 μL. TCM was RPMI1640 containing 10% heat-inactivated fetal bovine serum, 200 mM L-glutamine, 100 Units/ml each of penicillin and streptomycin and $5\times10^{-5}$ M 2-mercaptoethanol. Dilutions of antagonists were prepared in TCM. Plates were incubated in 5% $CO_2$ for 3 days. On the third day, 0.5 µCi of tritiated thymidine (10 µCi/mL) was added to all the wells. Cells were harvested 6 h later on a 96-well plate harvester and the amount of tritiated thymidine incorporated was assessed in a liquid scintillation counter. $IC_{50}$s were calculated and are presented in the following table.

Screening Results from Protein-protein and Cell-based Assays

| Example # | LFA-1/ICAM-1 Protein-Protein Assay $IC_{50}$ (nM) | MLR $IC_{50}$ (µM) |
| --- | --- | --- |
| 235 | 42.9 | 13.5 |
| 236[a] | 25.6 | 7.18 |
| 237 | 27.0 | 20 |
| 238[a] | 16.7 | |
| 239[a] | 2.15 | |
| 240[a] | 4.78 | 3.47 |
| 241[a] | 2.04 | 2.6 |
| 242[a] | 22.0 | |
| 243 | 13.2 | |
| 244 | 1.95 | 3.0 |
| 245 | 0.94 | 1.38 |
| 246 | 2.4 | 7.85 |
| 247 | 2.0 | 5.15 |
| 248 | 3.96 | 24.0 |
| 249 | 5.78 | 16.0 |
| 250[a] | 37.0 | |
| 251 | 20.5 | 20.0 |
| 252[a] | 2.68 | 2.5 |
| 253[a] | 6.54 | 8.1 |
| 254 | 110.1 | 95.0 |
| 255[a] | 5.82 | 14.8 |
| 256 | 278.8 | |
| 257 | 101.1 | |
| 258 | 2.33 | 2.05 |
| 258[b] | 2.01 | 2.74 |
| 259 | 8.14 | |
| 260[a] | 0.77 | 3.0 |
| 261[a] | 39.6 | 26.0 |
| 262 | 123.0 | |
| 263 | 6.86 | 2.85 |
| 264 | 4.2 | 13.0 |
| 265[a] | 123.7 | |
| 266 | 2.7 | 9.0 |
| 267 | 6.37 | 6.38 |
| 268 | 10.55 | 9.0 |
| 269 | 4.31 | 2.2 |
| 270 | 20.3 | 20.0 |
| 271 | 33 | |
| 272 | 1.4 | 1.5 |
| 273 | 5.4 | 1.4 |
| 274 | 0.62 | 1.65 |
| 275[a] | 42.5 | |
| 276 | 50.6 | |
| 277[a] | 0.53 | 0.356 |
| 278[a] | 2.0 | 1.45 |
| 279[a] | 6.2 | 1.3 |
| 280[a] | 5.0 | 0.86 |
| 281 | 243.9 | 14.5 |
| 282 | 4.46 | 1.9 |
| 283[a] | 0.79 | 0.37 |
| 284[a] | 12.6 | |
| 285[a] | 0.34 | 0.235 |
| 285[c] | 1.14 | 0.19 |
| 236[a] | 0.74 | 1.2 |
| 287[a] | 0.65 | 1.4 |
| 288[a] | 201 | |
| 289 | 40.9 | |
| 290[a] | 13.36 | 1.3 |
| 291[a] | 0.4 | 0.515 |
| 292 | 0.54 | 0.925 |
| 293 | 1.29 | 7.1 |
| 294 | 2.38 | 13.00 |
| 295 | 3.0 | 10.0 |
| 296 | 1.56 | 2.4 |
| 297 | 5.96 | 5.7 |
| 298 | 4.26 | 6.2 |
| 299 | 13.13 | 10.0 |
| 300 | 32.5 | 21.5 |
| 301 | 3.03 | 4.25 |
| 302[d] | 3.22 | |
| 302[e] | 3.76 | |
| 303 | 190.1 | |
| 304 | 3.0 | 2.1 |
| 305 | 4.13 | 7.25 |
| 306 | 10.38 | 13.75 |
| 307 | 18.65 | 27.0 |
| 308 | 56.26 | |
| 309 | 18.75 | 14.5 |
| 310 | 56.1 | |
| 311 | 11.84 | 10.5 |
| 312[a] | 4.7 | 0.99 |
| 313 | 8.2 | |
| 314 | 3.05 | 6.1 |
| 315 | 1.89 | 2.5 |
| 316 | 3.00 | 1.15 |
| 317[a] | 6.7 | 9.33 |
| 318[a] | 171.0 | |
| 319[a] | 72.0 | |
| 320[a] | 139.6 | |
| 321[a] | 7.52 | 11.5 |
| 322[a] | 1.74 | 4.45 |
| 323 | 0.84 | 0.23 |
| 324[a] | 50.82 | |
| 325[a] | 41.7 | |
| 326[a] | 1.12 | |
| 327 | 20.45 | |

[a] trifluoroacetate salt
[b] mono sodium salt
[c] disodium salt
[d] 2-amino-4-trifluoromethylthiazole derivative
[e] 2-methylamino-4-trifluoromethylthiazole derivative Croton Oil-Induced Dermatitis in Mice Adult female BALB/c mice (20–25 g) receive 10 µl of 20 mg/ml of croton oil in 80% acetone: 20% olive oil vehicle on each side of the right ear (total of 20 µl per mouse). All the mice receive a similar volume of the acetone/olive oil vehicle on the contralateral left ear. Negative control mice receive vehicle on both ears. Six hours thereafter, the ear swelling on both ears is measured with microcalipers. The ear swelling response is determined by subtraction of the swelling measurements of the left ear from that of the right ear for each individual mouse.

Inhibitors are administered to mice via 3 day Alzet osmotic minipumps. Pumps containing different concentrations of the inhibitors are implanted on the backs of anaesthetized mice 2 days prior to croton oil application. Additional mice receive an equal volume of distilled water in pumps. For mice receiving antibodies, anti-CD 18 antibody (HB226) or control rat IgG is administered i.p. at 200 µg per mouse 18 hours prior to croton oil application.

The results demonstrate in vivo inhibition of the ear swelling response in a dose-dependent manner in this acute model of inflammation. Measurement of circulating serum drug levels are made to show an efficacious concentration. In parallel studies, anti-CD18 antibody has been found to be effective in inhibiting the ear swelling response.

What is claimed is:

1. A compound of formula:

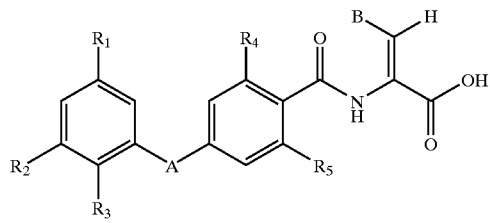

wherein $R_1$ is hydrogen, hydroxy, amino or halogen, $R_2$ is hydrogen, hydroxy, or halogen and $R_3$ is hydrogen;

A is

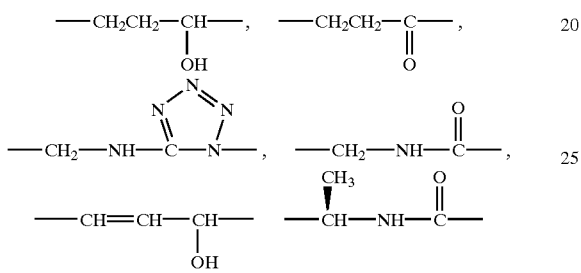

$R_4$ and $R_5$ are hydrogen, methyl, ethyl or halogen except that $R_4$ and $R_5$ cannot both be hydrogen; and 1) B is hydrogen, or lower alkyl; or
2) B is

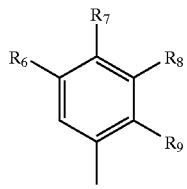

where $R_6$ $R_7$ $R_8$ and $R_9$ are independently hydrogen, hydroxy, aminosulfonyl, halogen, lower alkoxy, cyano, amino, lower alkyl, lower alkyl amino, or nitro; or 3) B is

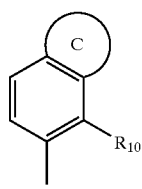

where $R_{10}$ is hydrogen, hydroxy, halogen, or lower alkyl and C is a five- or six-membered ring with 0 to 3 heteroatoms which heteroatoms are selected from nitrogen, oxygen, and sulfur, which ring may be unsubstituted or mono- or di-substituted with lower alkyl, cycloalkyl, amino, or substituted amino; or 4) B is

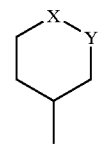

where X and Y are independently methylene or nitrogen; or

5) B is

where at least one of T, U, V, or W is nitrogen, and any of T, U, V or W which is carbon may be substituted with lower alkyl, lower alkyl amino, lower alkoxy, hydroxy, aminosulfonyl, halogen, cyano, amino, or nitro; or 6) B is

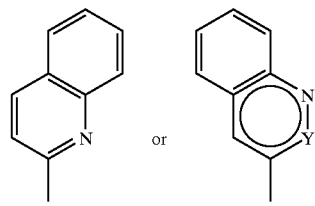

wherein Y is carbon or nitrogen; or

7) B is a five-membered aromatic ring with 1 to 3 heteroatoms selected from nitrogen, oxygen, and sulfur which ring may be unsubstituted or mono- or di-substituted with lower alkyl, cycloalkyl, trifluoroloweralkyl, amino, halogen, substituted amino, or which ring may be fused with a 5 or 6 membered aromatic ring containing 0 to 3 heteroatoms which heteroatoms are selected from nitrogen, oxygen, and sulfur;

or pharmaceutically acceptable salts thereof.

2. A compound of claim 1 wherein B is

where T, U, or W may be nitrogen or carbon, and any of T, U, or W which is carbon may be substituted with lower alkyl, lower alkyl amino, lower alkoxy, hydroxy, aminosulfonyl, halogen, cyano, amino, or nitro.

3. A compound of claim 1 wherein B is a five-membered aromatic ring with 1 to 3 heteroatoms selected from nitrogen, oxygen, and sulfur having one heteroatom two positions from the attachment point, and which ring may be unsubstituted or which ring may be fused at positions not adjacent to the attachment point with a 5 or 6 membered aromatic ring containing 0 to 3 heteroatoms which heteroatoms are selected from nitrogen, oxygen, and sulfur.

4. A compound of formula:

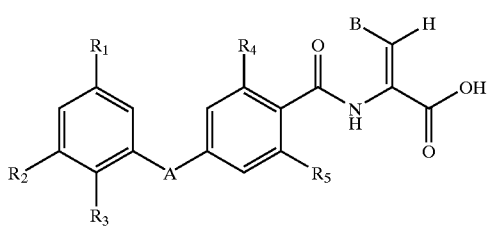

wherein $R_1$ is hydrogen and $R_2$ and $R_3$ taken together with the ethenylene group connecting them form phenyl, pyrrole, pyrroline, oxopyrroline, pyrazole, triazole, or imidazole;

A is

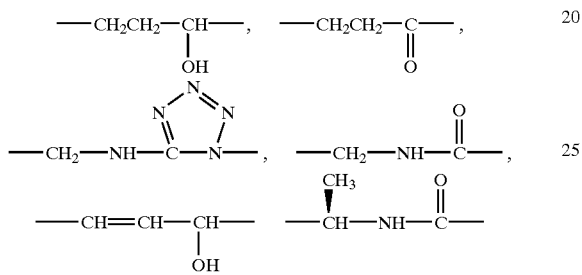

$R_4$ and $R_5$ are hydrogen, methyl, ethyl or halogen except that $R_4$ and $R_5$ cannot both be hydrogen; and
1) B is hydrogen, or lower alkyl; or
2) B is

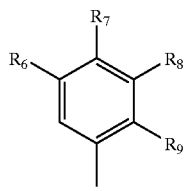

where $R_6$ $R_7$ $R_8$ and $R_9$ are independently hydrogen, hydroxy, aminosulfonyl, halogen, lower alkoxy, cyano, amino, lower alkyl, lower alkyl amino, or nitro; or
3) B is

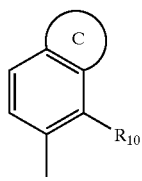

where $R_{10}$ is hydrogen, hydroxy, halogen, or lower alkyl and C is a five- or six-membered ring with 0 to 3 heteroatoms which heteroatoms are selected from nitrogen, oxygen, and sulfur, which ring may be unsubstituted or mono- or di-substituted with lower alkyl, cycloalkyl, amino, or substituted amino; or 4) B is

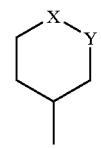

where X and Y are independently methylene or nitrogen; or
5) B is

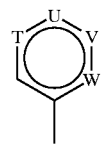

where at least one of T, U, V, or W is nitrogen, and any of T, U, V or W which is carbon may be substituted with lower alkyl, lower alkyl amino, lower alkoxy, hydroxy, aminosulfonyl, halogen, cyano, amino, or nitro; or
6) B is

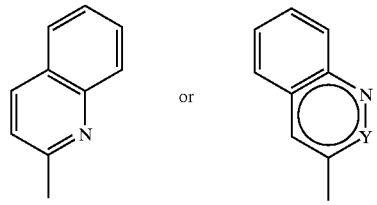

wherein Y is carbon or nitrogen; or
7) B is a five-membered aromatic ring with 1 to 3 heteroatoms selected from nitrogen, oxygen, and sulfur which ring may be unsubstituted or mono- or di-substituted with lower alkyl, cycloalkyl, trifluoroloweralkyl, amino, halogen, substituted amino, or which ring may be fused with a 5 or 6 membered aromatic ring containing 0 to 3 heteroatoms which heteroatoms are selected from nitrogen, oxygen, and sulfur;
or pharmaceutically acceptable salts thereof.

5. A compound of claim 4 wherein B is

where T, U, or W may be nitrogen or carbon, and any of T, U, or W which is carbon may be substituted with lower alkyl, lower alkylamino, lower alkoxy, hydroxy, aminosulfonyl, halogen, cyano, amino, or nitro.

6. A compound of claim 4 wherein B is a five-membered aromatic ring with 1 to 3 heteroatoms selected from nitrogen, oxygen, and sulfur having one heteroatom two positions from the attachment point, and which ring may be unsubstituted or which ring may be fused at positions not adjacent to the attachment point with a 5 or 6 membered aromatic ring containing 0 to 3 heteroatoms which heteroatoms are selected from nitrogen, oxygen, and sulfur.

7. A compound of claim 1 wherein $R_1$ is hydroxy or amino and $R_2$ and $R_3$ are hydrogen;

A is

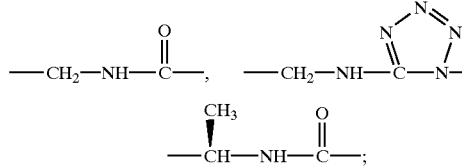

$R_4$ and $R_5$ are lower alkyl or halogen;

and B is

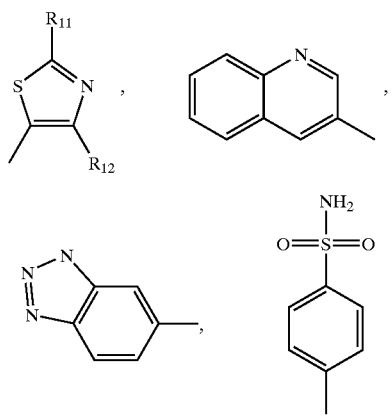

where $R_{11}$ is hydrogen, lower alkyl, substituted amino, or amino and $R_{12}$ is hydrogen, trifluoroloweralkyl, or lower alkyl.

8. A compound of claim 4 wherein $R_2$ and $R_3$ together with the ethenylene to which they are attached form phenyl, pyrazole or pyrrole;

A is

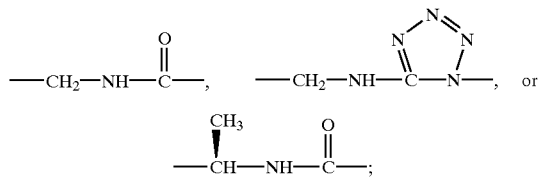

$R_4$ and $R_5$ are lower alkyl or halogen;

and B is

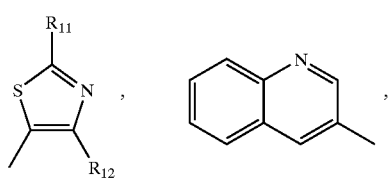

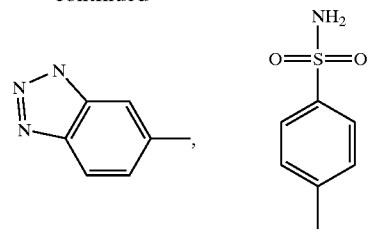

where $R_{11}$ is hydrogen, lower alkyl, substituted amino, or amino and $R_{12}$ is hydrogen, trifluoroloweralkyl, or lower alkyl.

9. A compound of claim 8 wherein $R_2$ and $R_3$ together with the ethenylene to which they are attached form pyrazole or pyrrole;

A is

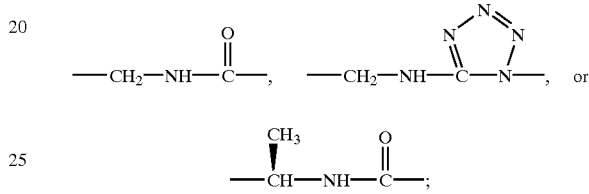

$R_4$ and $R_5$ are methyl or halogen; and B is

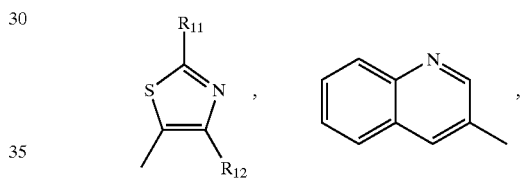

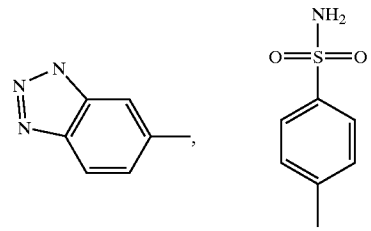

where $R_{11}$ is hydrogen, methyl, piperazinyl, or amino and $R_{12}$ is hydrogen, trifluoromethyl, methyl, or isopropyl.

10. A compound of claim 8 wherein A is

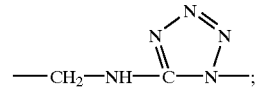

B is

and R₁₁ and R₁₂ are methyl.

11. A compound of claim 1 having the formula

1a wherein R₄ and R₅ are hydrogen, methyl, ethyl or halogen except that R₄ and R₅ cannot both be hydrogen; and
1) B is hydrogen, or lower alkyl; or
2) B is where R₆ R₇ R₈ and R₉ are independently hydrogen, hydroxy, aminosulfonyl, halogen, lower alkoxy, cyano, amino, lower alkyl, lower alkyl amino, or nitro; or
3) B is where R₁₀ is hydrogen, hydroxy, halogen, or lower alkyl and C is a five- or six-membered ring with 0 to 3 heteroatoms, which heteroatoms are selected from nitrogen, oxygen, and sulfur, which ring may be unsubstituted or mono- or di-substituted with lower alkyl, cycloalkyl, amino, or substituted amino; or
4) B is where X and Y are independently methylene or nitrogen; or 5) B is where at least one of T, U, V, or W is nitrogen, and any of T, U, V or W which is carbon may be substituted with lower alkyl, lower alkyl amino, lower alkoxy, hydroxy, aminosulfonyl, halogen, cyano, amino, or nitro; or
6) B is or wherein Y is carbon or nitrogen; or
7) B is a five-membered aromatic ring with 1 to 3 heteroatoms selected from nitrogen, oxygen, and sulfur which ring may be unsubstituted or mono- or di-substituted with lower alkyl, cycloalkyl, trifluoroloweralkyl, amino, halogen, substituted amino, or which ring may be fused with a 5 or 6 membered aromatic ring containing 0 to 3 heteroatoms which heteroatoms are selected from nitrogen, oxygen, and sulfur.

12. A compound of claim 11 wherein B is hydrogen or lower alkyl.

13. A compound of claim 11 which is (Z)-2-[[2-bromo-4-[[(3-hydroxybenzyl)amino]carbonyl]benzoyl]amino]pent-2-enoic acid, or 2-[[2-bromo-4-[[(3-hydroxybenzyl)amino]carbonyl]benzoyl]amino]propenoic acid.

14. A compound of claim 11 wherein B is and R₆, R₇, R₈ and R₉ are independently hydrogen, hydroxy, aminosulfonyl, halogen, lower alkoxy, cyano, lower alkyl, lower alkyl amino, amino, or nitro.

15. A compound of claim 14 wherein R₆, R₇, R₈, and R₉ are independently hydrogen, hydroxy, aminosulfonyl, or halogen.

16. A compound of claim 14 wherein any one of R₆, R₇, R₈, or R₉ is aminosulfonyl.

17. A compound of claim 16 which is (Z)-2-[[2-chloro-4-[[(3-hydroxybenzyl)amino]carbonyl]benzoyl]amino]-3-(4-sulfamoylphenyl)propenoic acid.

18. Compounds of claim 15 which are (Z)-2-[[2-bromo-4-[[(3-hydroxybenzyl) amino]carbonyl]benzoyl]amino]-3-(2-hydroxyphenyl)propenoic acid, and
 (Z)-3-(4-bromophenyl)-2-[[2-chloro-4-[[(3-hydroxybenzyl)amino]carbonyl]benzoyl]amino]propenoic acid.

19. A compound of claim 15 wherein $R_6$ $R_7$ $R_8$ and $R_9$ are hydrogen.

20. Compounds of claim 19 which are (Z)-2-[[2-chloro-4-[[(3-hydroxybenzyl)amino]carbonyl]-6-methylbenzoyl]amino]-3-phenylpropenoic acid,
(Z)-2-[[2-bromo-4-[[(3-hydroxybenzyl)amino]carbonyl]benzoyl]amino]-3-phenylpropenoic acid,
(Z)-2-[[2-chloro-4-[[(3-hydroxybenzyl)amino]carbonyl]benzoyl]amino]-3-phenylpropenoic acid, and (Z)-2-[[4-[[(3-hydroxybenzyl)amino]carbonyl]-2-methylbenzoyl]amino]-3-phenylpropenoic acid.

21. A compound of of claim 11 wherein B is

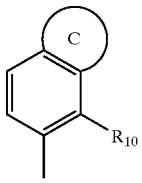

where $R_{10}$ is hydrogen, hydroxy, halogen, or lower alkyl and C is a five- or six-membered ring with 0 to 3 heteroatoms, which heteroatoms are selected from nitrogen, oxygen, and sulfur, which ring may be unsubstituted or mono- or di-substituted with lower alkyl, cycloalkyl, or substituted amino.

22. A compound of claim 21 wherein C is a six-membered ring.

23. A compound of claim 22 wherein C is a six-membered ring with 0 heteroatoms.

24. A compound of claim 23 which is (Z)-2-[[2-bromo-4-[[(3-hydroxybenzyl)amino]carbonyl]benzoyl]amino]-3-(naphthalen-2-yl)propenoic acid.

25. A compound of claim 21 wherein C is a five-membered heterocyclic ring.

26. Compounds of claim 25 which are (Z)-3-(6-chlorobenzo[1,3]dioxol-5-yl)-2-[[2-chloro-4-[[(3-hydroxybenzyl)amino]carbonyl]benzoyl]amino]propenoic acid,
(Z)-3-(benzothiazol-6-yl)-2-[[2-chloro-4-[[(3-hydroxybenzyl)amino]carbonyl]benzoyl]amino]propenoic acid,
(Z)-3-(2,1,3-benzoxadiazol-5-yl)-2-[[2-chloro-4-[[(3-hydroxybenzyl)amino]carbonyl]benzoyl]amino]propenoic acid, and
(Z)-3-(2,1,3-benzothiadiazol-5-yl)-2-[[2-chloro-4-[[(3-hydroxybenzyl)amino]carbonyl]benzoyl]amino]propenoic acid.

27. A compound of claim 25 wherein C is a heterocyclic ring with 1 to 3 nitrogens.

28. Compounds of claim 25 which are (Z)-3-(1H-benzotriazol-5-yl)-2-[[2-chloro-4-[[(3-hydroxybenzyl)amino]carbonyl]-6-methylbenzoyl]amino]propenoic acid,
(Z)-3-(1H-benzotriazol-5-yl)-2-[[2-bromo-4-[[(3-hydroxybenzyl)amino]carbonyl]benzoyl]amino]propenoic acid,
(Z)-3-(1H-benzotriazol-5-yl)-2-[[2,6-dimethyl-4-[[(3-hydroxybenzyl)amino]carbonyl]benzoyl]amino]propenoic acid,
(Z)-2-[[2-chloro-4-[[(3-hydroxybenzyl)amino]carbonyl]benzoyl]amino]-3-(1-methyl-1H-indol-6-yl)propenoic acid and
(Z)-2-[[4-[[(3-hydroxybenzyl)amino]carbonyl]-2-methylbenzoyl]amino]-3-(1H-indol-6-yl)propenoic acid.

29. A compound of claim 11 wherein B is

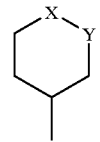

where X and Y are independently methylene or nitrogen.

30. A compound of claim 29 which is (Z)-2-[[bromo-4-[[(3-hydroxybenzyl)amino]carbonyl]benzoyl]amino]-3-(piperidin-4-yl)propenoic acid.

31. A compound of claim 11 wherein B is

where at least one of T, U, V, or W is nitrogen, and any of T, U, V or W which is carbon may be substituted with lower alkyl, lower alkylamino, lower alkoxy, hydroxy, aminosulfonyl, halogen, cyano, amino, or nitro.

32. A compound of claim 31 wherein B is unsubstituted or substituted with lower alkoxy.

33. Compounds of claim 31 which are (Z)-2-[[2-bromo-4-[[(3-hydroxybenzyl)amino]carbonyl]benzoyl]amino]-3-(pyridin-2-yl)propenoic acid,
(Z)-2-[[2-bromo-4-[[(3-hydroxybenzyl)amino]carbonyl]benzoyl]amino]-3-(2,4-dimethoxypyrimidin-5-yl)propenoic acid,
(Z)-2-[[2-bromo-4-[[(3-hydroxybenzyl)amino]carbonyl]benzoyl]amino]-3-(pyridin-3-yl)propenoic acid, and
(Z)-2-[[2-bromo-4-[[(3-hydroxybenzyl)amino]carbonyl]benzoyl]amino]-3-(pyridin-4-yl)propenoic acid.

34. A compound of claim 11 wherein B is

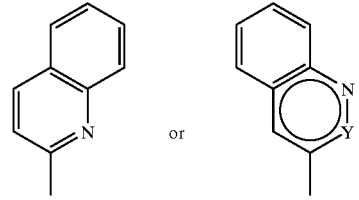

and Y is carbon or nitrogen.

35. Compounds of claim 34 which are (Z)-2-[[2-bromo-4-[[(3-hydroxybenzyl)amino]carbonyl]benzoyl]amino]-3-(quinolin-3-yl)propenoic acid,
(Z)-2-[[2-chloro-4-[[3-hydroxybenzyl)amino]carbonyl]benzoyl]amino]-3-(quinolin-3-yl)propenoic acid,
(Z)-2-[[2-chloro-4-[[(3-hydroxybenzyl)amino]carbonyl]-6-methylbenzoyl]amino]-3-(quinolin-3-yl)propenoic acid,
(Z)-2-[[4-[[(3-hydroxybenzyl)amino]carbonyl]-2-methylbenzoyl]amino]-3-(quinolin-3-yl)propenoic acid, and (Z)-2-[[2-bromo-4-[[(3-hydroxybenzyl)amino]carbonyl]benzoyl]amino]-3-(quinolin-2-yl)propenoic acid.

36. A compound of claim 11 wherein B is a five-membered aromatic ring with 1 to 3 heteroatoms selected from nitrogen, oxygen, and sulfur which ring may be unsubstituted or mono- or di-substituted with lower alkyl, cycloalkyl, trifluoroloweralkyl, amino, halogen, substituted amino, or which ring may be fused with a 5 or 6 membered aromatic ring containing 0 to 3 heteroatoms which heteroatoms are selected from nitrogen, oxygen, and sulfur.

37. A compound of claim 34 wherein B is thiadiazole.

38. A compound of claim 35 which is (Z)-2-[[2-bromo-4-[[(3-hydroxybenzyl)amino]carbonyl]benzoyl]amino]-3-(4-methyl-[1,2,3]thiadiazol-5-yl)propenoic acid.

39. A compound of claim 34 wherein B is an unsubstituted five-membered aromatic ring with 1 heteroatom selected from nitrogen, oxygen, and sulfur or with 1 to 3 nitrogen heteroatoms.

40. Compounds of claim 37 which are (Z)-2-[[2-bromo-4-[[(3-hydroxybenzyl)amino]carbonyl]benzoyl]amino]-3-(thien-2-yl)propenoic acid, (Z)-2-[[2-bromo-4-[[(3-hydroxybenzyl)amino]carbonyl]benzoyl]amino]-3-(thien-3-yl)propenoic acid, (Z)-2-[[2-bromo-4-[[(3-hydroxybenzyl)amino]carbonyl]benzoyl]amino]-3-(furan-3-yl)propenoic acid, (Z)-2-[[2-bromo-4-[[(3-hydroxybenzyl)amino]carbonyl]benzoyl]amino]-3-(1H-imidazol-4-yl)propenoic acid, and (Z)-2-[[2-bromo-4-[[(3-hydroxybenzyl)amino]carbonyl]benzoyl]amino]-3-(1-[1,2,4]triazol-3-yl)propenoic acid.

41. A compound of claim 36 wherein B is a five-membered aromatic ring fused with phenyl.

42. Compounds of claim 41 which are (Z)-3-(benzo[b]thiophen-3-yl)-2-[[2-bromo-4-[[(3-hydroxybenzyl)amino]carbonyl]benzoyl]amino]propenoic acid, (Z)-3-(benzothiazol-2-yl)-2-[[2-bromo-4-[[(3-hydroxybenzyl)amino]carbonyl]benzoyl]amino]propenoic acid, and (Z)-2-[[2-bromo-4-[[(3-hydroxybenzyl)amino]carbonyl]benzoyl]amino]-3-(1-methyl-1H-benzodiazol-2-yl)propenoic acid.

43. A compound of claim 36 wherein B is thiazole which is unsubstituted or is mono or di-substituted with amino, lower alkyl, trifluoromethyl, substituted amino or halogen.

44. Compounds of claim 43 which are (Z)-2-[[2-bromo-4-[[(3-hydroxybenzyl)amino]carbonyl]benzoyl]amino]-3-(thiazol-2-yl)propenoic acid, (Z)-3-(2-aminothiazol-5-yl)-2-[[2-bromo-4-[[(3-hydroxybenzyl)amino]carbonyl]benzoyl]amino]propenoic acid, (Z)-2-[[2-bromo-4-[[(3-hydroxybenzyl)amino]carbonyl]benzoyl]amino]-3-(2,4-dimethylthiazol-5-yl)propenoic acid, (Z)-2-[[2-chloro-4-[[(3-hydroxybenzyl)amino]carbonyl]benzoyl]amino]-3-(2-ethyl-4-methylthiazol-5-yl)propenoic acid, (Z)-2-[[2-bromo-4-[[(3-hydroxybenzyl)amino]carbonyl]benzoyl]amino]-3-(2-dimethylamino-thiazol-5-yl)propenoic acid, (Z)-2-[[2-bromo-4-[[(3-hydroxybenzyl)amino]carbonyl]benzoyl]amino]-3-(2-methylthiazol-4-yl)propenoic acid, (Z)-2-[[2-chloro-4-[[(3-hydroxybenzyl)amino]carbonyl]benzoyl]amino]-3-[4-methyl-2-(1-methylethyl)thiazol-5-yl]propenoic acid, (Z)-2-[[2-bromo-4-[[(3-hydroxybenzyl)amino]carbonyl]benzoyl]amino]-3-[2-(morpholin-4-yl)thiazol-5-yl]propenoic acid, (Z)-2-[[2-bromo-4-[[(3-hydroxybenzyl)amino]carbonyl]benzoyl]amino]-3-[2-(piperazin-1-yl)thiazol-5-yl]propenoic acid, (Z)-2-[[2-bromo-4-[[(3-hydroxybenzyl)amino]carbonyl]benzoyl]amino]-3-(2,4-dimethylthiazol-5-yl)propenoic acid sodium salt, (Z)-3-(2-amino-4-trifluoromethylthiazol-5-yl)-2-[[2-chloro-4-[[(3-hydroxybenzyl)amino]carbonyl]benzoyl]amino]propenoic acid, (Z)-2-[[2-chloro-4-[[(3-hydroxybenzyl)amino]carbonyl]benzoyl]amino]-3-(2-chlorothiazol-5-yl)propenoic acid, (Z)-2-[[2-chloro-4-[[(3-hydroxybenzyl)amino]carbonyl]benzoyl]amino]-3-(2,4-dimethylthiazol-5-yl)propenoic acid, (Z)-2-[[2-chloro-4-[[(3-hydroxybenzyl)amino]carbonyl]benzoyl]amino]-3-(2-methylamino-4-trifluoromethylthiazol-5-yl)propenoic acid, (Z)-2-[[2,6-dimethyl-4-[[(3-hydroxybenzyl]amino]carbonyl]benzoyl]amino]-3-(2,4-dimethylthiazol-5-yl)propenoic acid, (Z)-2-[[2-chloro-4-[[(3-hydroxybenzyl)amino]carbonyl]benzoyl]amino]-3-[4-(1-methylethyl)thiazol-5-yl]propenoic acid and (Z)-2-[[2-bromo-4-[[(3-hydroxybenzyl)amino]carbonyl]benzoyl]amino]-3-[2-methyl-4-(1-methylethyl)thiazol-5-yl]propenoic acid (Z)-2-[[2-bromo-4-[[3-hydroxybenzyl) amino]carbonyl]benzoyl]amino]-3-[4-(trifluoromethyl)thiazol-2-yl]propenoic acid; and (Z)-2-[[2-bromo-4-[[3-hydroxybenzyl) amino]carbonyl]benzoyl]amino]-3-[4-(1-methylethyl)thiazol-2-yl]propenoic acid.

45. A compound of claim 1 having the formula

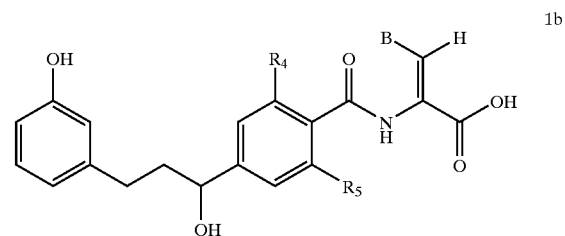

1b wherein $R_4$ and $R_5$ are hydrogen, methyl, ethyl or halogen, except that $R_4$ and $R_5$ cannot both be hydrogen;

1) B is hydrogen or lower alkyl; or
2) B is

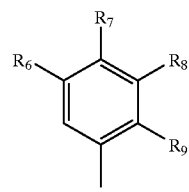

where $R_6$ $R_7$ $R_8$ and $R_9$ are independently hydrogen, hydroxy, aminosulfonyl, halogen, lower alkoxy, cyano, amino, lower alkyl, lower alkyl amino, or nitro); or 3) B is

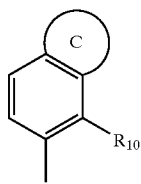

where $R_{10}$ is hydrogen, hydroxy, halogen, or lower alkyl and C is a five- or six-membered ring with 0 to 3 heteroatoms which heteroatoms are selected from nitrogen, oxygen, and sulfur, which ring may be unsubstituted or mono- or di-substituted with lower alkyl, cycloalkyl, amino, or substituted amino; or 4) B is

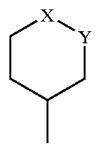

where X and Y are independently methylene or nitrogen; or

5) B is

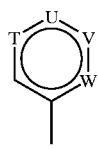

where at least one of T, U, V, or W is nitrogen, and any of T, U, V or W which is carbon may be substituted with lower alkyl, lower alkyl amino, lower alkoxy, hydroxy, aminosulfonyl, halogen, cyano, amino, or nitro; or 6) B is

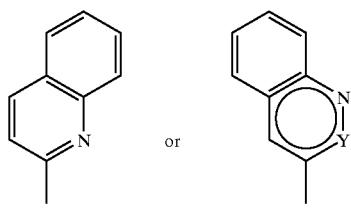

wherein Y is carbon or nitrogen; or

7) B is a five-membered aromatic ring with 1 to 3 heteroatoms selected from nitrogen, oxygen, and sulfur which ring may be unsubstituted or mono- or di-substituted with lower alkyl, cycloalkyl, trifluoroloweralkyl, amino, halogen, substituted amino, or which ring may be fused with a 5 or 6 membered aromatic ring containing 0 to 3 heteroatoms which heteroatoms are selected from nitrogen, oxygen, and sulfur.

46. A compound of claim 45 wherein $R_4$ is halogen and $R_5$ is hydrogen.

47. A compound of claim 46 wherein B is a five-membered aromatic ring with 1 to 3 heteroatoms selected from nitrogen, oxygen, and sulfur, which ring may be unsubstituted or mono- or di-substituted at any position with lower alkyl, cycloalkyl, trifluoroloweralkyl, amino, halogen, substituted amino, or which ring may be fused at positions not adjacent to the attachment point with a 5 or 6 membered aromatic ring containing 0 to 3 heteroatoms, which heteroatoms are selected from nitrogen, oxygen, and sulfur.

48. A compound of claim 47 wherein B is thiazole.

49. A compound of claim 48 which is rac.-(Z)-2-[[2-chloro-4-[1-hydroxy-3-(3-hydroxyphenyl)propan-1-yl]benzoyl]amino]-3-(2,4-dimethylthiazol-5-yl)propenoic acid.

50. A compound of claim 46 wherein B is

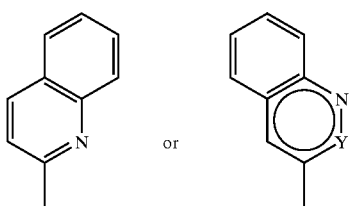

wherein Y is carbon or nitrogen.

51. A compound of claim 50 which is rac.-(Z)-2-[[2-chloro-4-[1-hydroxy-3-(3-hydroxyphenyl)propan-1-yl]benzoyl]amino]-3-(quinolin-3-yl)propenoic acid.

52. A compound of claim 1 having the formula

1c

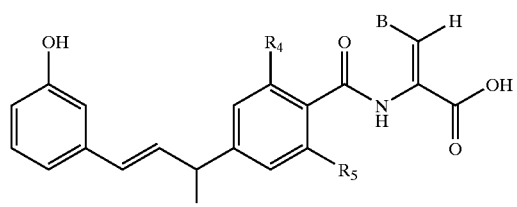

wherein $R_4$ and $R_5$ are hydrogen, methyl, ethyl or halogen, except that $R_4$ and $R_5$ cannot both be hydrogen; and 1) B is hydrogen, or lower alkyl; or
2) B is

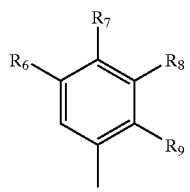

where $R_6$ $R_7$ $R_8$ and $R_9$ are independently hydrogen, hydroxy, aminosulfonyl, halogen, lower alkoxy, cyano, amino, lower alkyl, lower alkyl amino, or nitro; or 3) B is

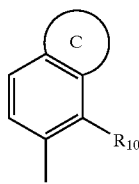

where $R_{10}$ is hydrogen, hydroxy, halogen, or lower alkyl and C is a five- or six-membered ring with 0 to 3 heteroatoms, which heteroatoms are selected from nitrogen, oxygen, and sulfur, which ring may be unsubstituted or mono- or di-substituted with lower alkyl, cycloalkyl, amino, or substituted amino; or 4) B is

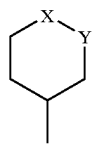

where X and Y are independently methylene or nitrogen; or

5) B is

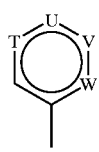

where at least one of T, U, V, or W is nitrogen, and any of T, U, V or W which is carbon may be substituted with lower alkyl, lower alkyl amino, lower alkoxy, hydroxy, aminosulfonyl, halogen, cyano, amino, or nitro; or 6) B is

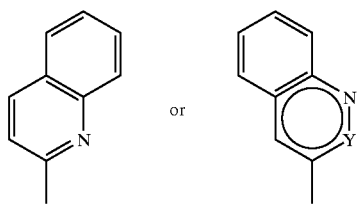

wherein Y is carbon or nitrogen; or

7) B is a five-membered aromatic ring with 1 to 3 heteroatoms selected from nitrogen, oxygen, and sulfur which ring may be unsubstituted or mono- or di-substituted with lower alkyl, cycloalkyl, trifluoroloweralkyl, amino, halogen, substituted amino, or which ring may be fused with a 5 or 6 membered aromatic ring containing 0 to 3 heteroatoms which heteroatoms are selected from nitrogen, oxygen, and sulfur.

53. A compound of claim 52 wherein $R_4$ is halogen and $R_5$ is hydrogen.

54. A compound of claim 53 wherein B is a five-membered aromatic ring with 1 to 3 heteroatoms selected from nitrogen, oxygen, and sulfur, which ring may be unsubstituted or mono- or di-substituted at any position with lower alkyl, cycloalkyl, trifluoroloweralkyl, amino, halogen, substituted amino, or which ring may be fused at positions not adjacent to the attachment point with a 5 or 6 membered aromatic ring containing 0 to 3 heteroatoms, which heteroatoms are selected from nitrogen, oxygen, and sulfur.

55. A compound of claim 54 wherein B is thiazole.

56. A compound of claim 55 which is rac.-(Z)-2-[[2-chloro-4-[(E)-1-hydroxy-3-(3-hydroxyphenyl)prop-2-en-1-yl]benzoyl]amino]-3-(2,4-dimethylthiazol-5-yl)propenoic acid.

57. A compound of claim 53 wherein B is

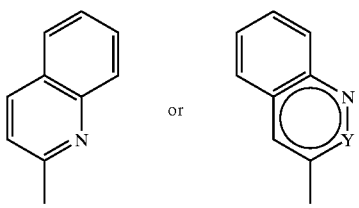

wherein Y is carbon or nitrogen.

58. A compound of claim 57 which is rac.-(Z)-2-[[2-chloro-4-[(E)-1-hydroxy-3-(3-hydroxyphenyl)prop-2-en-1-yl]benzoyl]amino]-3-(quinolin-3-yl)propenoic acid.

59. A compound of claim 1 having the formula

1d

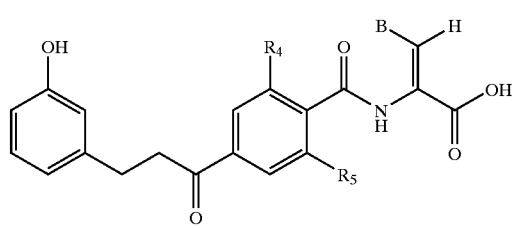

wherein $R_4$ and $R_5$ are hydrogen, methyl, ethyl or halogen, except that $R_4$ and $R_5$ cannot both be hydrogen; and 1) B is hydrogen, or lower alkyl; or
2) B is

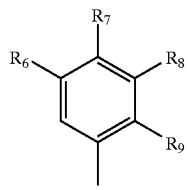

where $R_6$ $R_7$ $R_8$ and $R_9$ are independently hydrogen, hydroxy, aminosulfonyl, halogen, lower alkoxy, cyano, amino, lower alkyl, lower alkyl amino, or nitro; or 3) B is

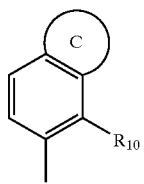

where R$_{10}$ is hydrogen, hydroxy, halogen, or lower alkyl and C is a five- or six-membered ring with 0 to 3 heteroatoms, which heteroatoms are selected from nitrogen, oxygen, and sulfur, which ring may be unsubstituted or mono- or di-substituted with lower alkyl, cycloalkyl, amino, or substituted amino; or 4) B is

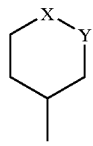

where X and Y are independently methylene or nitrogen; or

5) B is

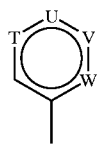

where at least one of T, U, V, or W is nitrogen, and any of T, U, V or W which is carbon may be substituted with lower alkyl, lower alkyl amino, lower alkoxy, hydroxy, aminosulfonyl, halogen, cyano, amino, or nitro; or 6) B is

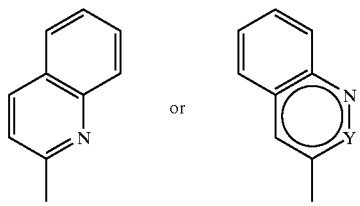

wherein Y is carbon or nitrogen; or

7) B is a five-membered aromatic ring with 1 to 3 heteroatoms selected from nitrogen, oxygen, and sulfur which ring may be unsubstituted or mono- or di-substituted with lower alkyl, cycloalkyl, trifluoroloweralkyl, amino, halogen, substituted amino, or which ring may be fused with a 5 or 6 membered aromatic ring containing 0 to 3 heteroatoms which heteroatoms are selected from nitrogen, oxygen, and sulfur.

60. A compound of claim 59 wherein R$_4$ is halogen and R$_5$ is hydrogen.

61. A compound of claim 60 wherein B is a five-membered aromatic ring with 1 to 3 heteroatoms selected from nitrogen, oxygen, and sulfur which may be unsubstituted or mono- or di-substituted at any position with lower alkyl, cycloalkyl, trifluoroloweralkyl, amino, halogen, substituted amino, or which may be fused at positions not adjacent to the attachment point with a 5 or 6 membered aromatic ring containing 0 to 3 heteroatoms, which heteroatoms are selected from nitrogen, oxygen, and sulfur.

62. A compound of claim 61 which is (Z)-2-[[2-chloro-4-[3-(3-hydroxyphenyl)-1-oxopropan-1-yl]benzoyl]amino]-3-(2,4-dimethylthiazol-5-yl)propenoic acid.

63. A compound of claim 60 wherein B is

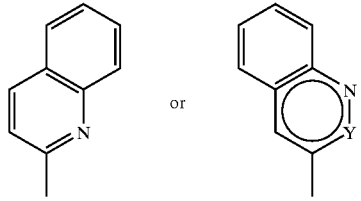

and Y is carbon or nitrogen.

64. A compound of claim 63 which is (Z)-2-[[2-chloro-4-[3-(3-hydroxyphenyl)-1-oxopropan-1-yl]benzoyl]amino]-3-(quinolin-3-yl)propenoic acid.

65. A compound of claim 1 having formula

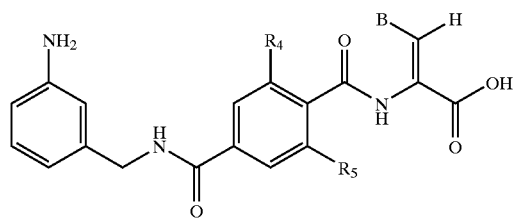

R$_4$ and R$_5$ are hydrogen, methyl, ethyl or halogen except that R$_4$ and R$_5$ cannot both be hydrogen;
1) B is hydrogen, or lower alkyl; or
2) B is

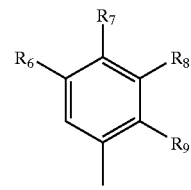

where R$_6$ R$_7$ R$_8$ and R$_9$ are independently hydrogen, hydroxy, aminosulfonyl, halogen, lower alkoxy, cyano, amino, lower alkyl, lower alkyl amino, or nitro; or 3) B is

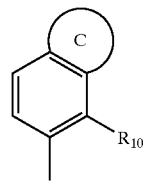

where R$_{10}$ is hydrogen, hydroxy, halogen, or lower alkyl and C is a five- or six-membered ring with 0 to 3 heteroatoms, which heteroatoms are selected from nitrogen, oxygen, and sulfur, which ring may be unsubstituted or mono- or di-substituted with lower alkyl, cycloalkyl, amino, or substituted amino; or 4) B is

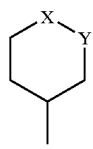

where X and Y are independently methylene or nitrogen; or

5) B is

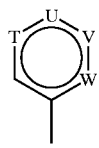

where at least one of T, U, V, or W is nitrogen, and any of T, U, V or W which is carbon may be substituted with lower alkyl, lower alkyl amino, lower alkoxy, hydroxy, aminosulfonyl, halogen, cyano, amino, or nitro; or 6) B is

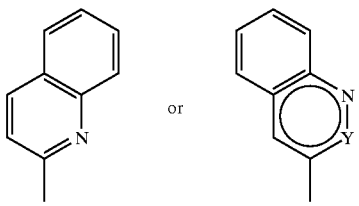

wherein Y is carbon or nitrogen; or

7) B is a five-membered aromatic ring with 1 to 3 heteroatoms selected from nitrogen, oxygen, and sulfur which ring may be unsubstituted or mono- or di-substituted with lower alkyl, cycloalkyl, trifluoroloweralkyl, amino, halogen, substituted amino, or which ring may be fused with a 5 or 6 membered aromatic ring containing 0 to 3 heteroatoms which heteroatoms are selected from nitrogen, oxygen, and sulfur.

66. A compound of claim 65 wherein $R_4$ is hydrogen and $R_5$ is halogen.

67. A compound of claim 66 wherein B is

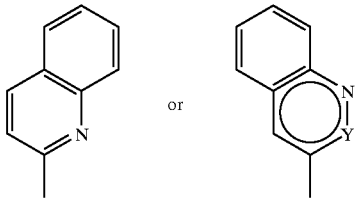

and Y is carbon or nitrogen.

68. A compound of claim 67 which (Z)-2-[[4-[[(3-aminobenzyl)amino]carbonyl]-2-bromobenzoyl]amino]-3-(quinolin-3-yl)propenoic acid.

69. A compound of claim 66 wherein B is a five-membered aromatic ring with 1 to 3 heteroatoms selected from nitrogen, oxygen, and sulfur which ring may be unsubstituted or mono- or di-substituted at any position with lower alkyl, cycloalkyl, trifluoroloweralkyl, amino, halogen, substituted amino, or which ring may be fused at positions not adjacent to the attachment point with a 5 or 6 membered aromatic ring containing 0 to 3 heteroatoms, which heteroatoms are selected from nitrogen, oxygen, and sulfur.

70. A compound of claim 69 which is (Z)-2-[[4-[[(3-aminobenzyl)amino]carbonyl]-2-bromobenzoyl]amino]-3-(2,4-dimethylthiazol-5-yl)propenoic acid.

71. A compound of claim 1 having the formula

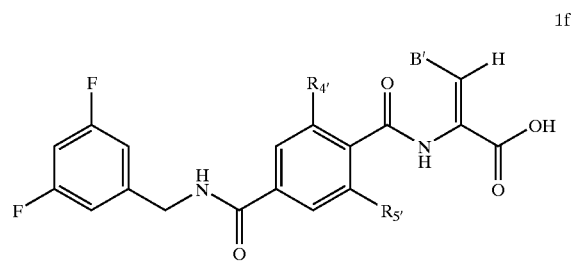

1f wherein $R_4$ and $R_5$ are hydrogen, methyl, ethyl or halogen except that $R_4$ and $R_5$ cannot both be hydrogen; and 1) B' is hydrogen, or lower alkyl; or 2) B' is

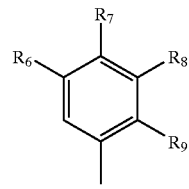

where $R_6$ $R_7$ $R_8$ and $R_9$ are independently hydrogen, hydroxy, aminosulfonyl, halogen, lower alkoxy, cyano, amino, lower alkyl, lower alkyl amino, or nitro; or 3) B' is

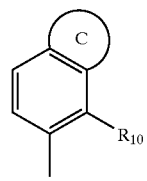

where $R_{10}$ is hydrogen, hydroxy, halogen, or lower alkyl and C is a five- or six-membered ring with 0 to 3 heteroatoms, which heteroatoms are selected from nitrogen, oxygen, and sulfur, which ring may be unsubstituted or mono- or di-substituted with lower alkyl, cycloalkyl, amino, or substituted amino; or 4) B' is

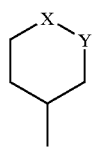

where X and Y are independently methylene or nitrogen; or

5) B' is

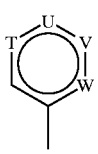

where at least one of T, U, V, or W is nitrogen, and any of T, U, V or W which is carbon may be substituted with lower alkyl, lower alkyl amino, lower alkoxy, hydroxy, aminosulfonyl, halogen, cyano, amino, or nitro; or 6) B' is

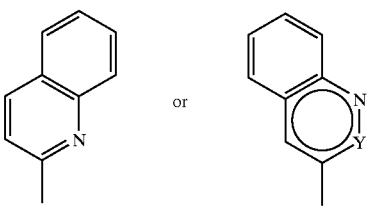

wherein Y is carbon or nitrogen; or

7) B' is a five-membered aromatic ring with 1 to 3 heteroatoms selected from nitrogen, oxygen, and sulfur which ring may be unsubstituted or mono- or di-substituted with lower alkyl, cycloalkyl, trifluoroloweralkyl, amino, halogen, substituted amino, or which ring may be fused with a 5 or 6 membered aromatic ring containing 0 to 3 heteroatoms which heteroatoms are selected from nitrogen, oxygen, and sulfur.

72. A compound of claim 71 wherein $R^4$ and $R^5$ are methyl.

73. A compound of claim 72 wherein B is a five-membered aromatic ring with 1 to 3 heteroatoms selected from nitrogen, oxygen, and sulfur which ring may be unsubstituted or mono- or di-substituted at any position with lower alkyl, cycloalkyl, trifluoroloweralkyl, amino, halogen, substituted amino, or which ring may be fused at positions not adjacent to the attachment point with a 5 or 6 membered aromatic ring containing 0 to 3 heteroatoms, which heteroatoms are selected from nitrogen, oxygen, and sulfur.

74. Compounds of claim 73 which are (Z)-2-[[4-[[(3,5-difluorobenzyl) amino]carbonyl]-2,6-dimethylbenzoyl] amino]-3-(4-methyl-1H-imidazol-5-yl)propenoic acid, and (Z)-2-[[4-[[(3,5-difluorobenzyl)amino]carbonyl]-2,6-dimethylbenzoyl]amino]-3-(2,4-dimethylthiazol-5-yl) propenoic acid.

75. A compound of claim 72 wherein B is

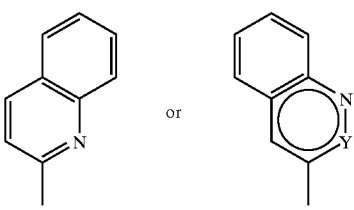

and Y is carbon or nitrogen.

76. A compound of claim 75 which is (Z)-2-[[4-[[(3,5-difluorobenzyl]amino]carbonyl]-2,6-dimethylbenzoyl] amino]-3-(quinolin-3-yl)propenoic acid.

77. A compound of claim 4 having the formula

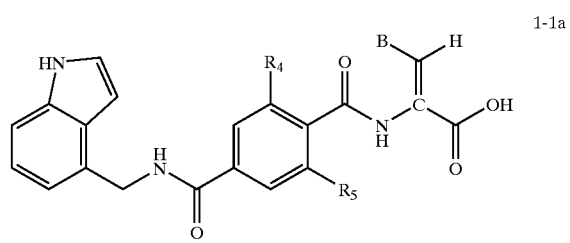

1-1a wherein $R_4$ and $R_5$ are hydrogen, methyl, ethyl or halogen, except that $R_4$ and $R_5$ cannot both be hydrogen; and 1) B is hydrogen, or lower alkyl; or
2) B is

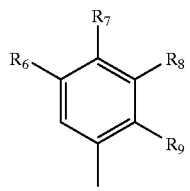

where $R_6$ $R_7$ $R_8$ and $R_9$ are independently hydrogen, hydroxy, aminosulfonyl, halogen, lower alkoxy, cyano, amino, lower alkyl, lower alkyl amino, or nitro; or 3) B is

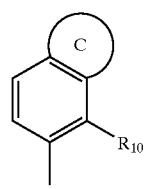

where $R_{10}$ is hydrogen, hydroxy, halogen, or lower alkyl and C is a five- or six-membered ring with 0 to 3 heteroatoms which heteroatoms are selected from nitrogen, oxygen, and sulfur, which ring may be unsubstituted or mono- or di-substituted with lower alkyl, cycloalkyl, amino, or substituted amino; or 4) B is

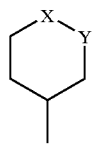

where X and Y are independently methylene or nitrogen; or

5) B is

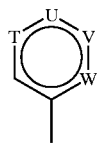

where at least one of T, U, V, or W is nitrogen, and any of T, U, V or W which is carbon may be substituted with lower alkyl, lower alkylamino, lower alkoxy, hydroxy, aminosulfonyl, halogen, cyano, amino, or nitro; or 6) B is

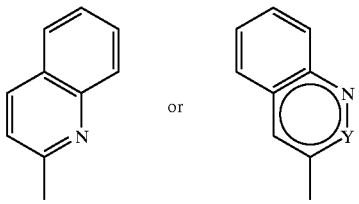

wherein Y is carbon or nitrogen; or

7) B is a five-membered aromatic ring with 1 to 3 heteroatoms selected from nitrogen, oxygen, and sulfur which ring may be unsubstituted or mono- or di-substituted with lower alkyl, cycloalkyl, trifluoroloweralkyl, amino, halogen, substituted amino, or which ring may be fused with a 5 or 6 membered aromatic ring containing 0 to 3 heteroatoms which heteroatoms are selected from nitrogen, oxygen, and sulfur.

78. A compound of claim 77 wherein B is a five-membered aromatic ring with 1 to 2 heteroatoms selected from nitrogen and sulfur, which ring may be unsubstituted, or mono- or di-substituted with lower alkyl, trifluoroloweralkyl, amino, halogen, or substituted amino.

79. A compound of claim 78 wherein B may be unsubstituted or di-substituted with lower alkyl.

80. Compounds of claim 79 which are (Z)-2-[[2-bromo-4-[[[(1H-indol-4-yl)methylamino]carbonyl]benzoyl]amino]-3-(2,4-dimethylthiazol-5-yl)propenoic acid and (Z)-2-[[2-chloro-4-[[[(1H-indol-4-yl)methyl]amino] carbonyl]benzoyl]amino]-3-(thien-2-yl)propenoic acid.

81. A compound of claim 77 wherein B is

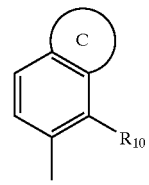

where $R_{10}$ is hydrogen, hydroxy, halogen, or lower alkyl and C is a five- or six-membered ring with 0 to 3 heteroatoms, which heteroatoms are selected from nitrogen, oxygen, and sulfur, which ring may be unsubstituted or mono- or di-substituted with lower alkyl, cycloalkyl, or substituted amino.

82. Compounds of claim 81 which are (Z)-3-(3H-benzotriazol-5-yl)-2-[[2-bromo-4-[[[(1H-indol-4-yl)methyl] amino]carbonyl]benzoyl]amino]propenoic acid, (Z)-3-(benzothiazol-6-yl)-2-[[2-bromo-4-[[[(1H-indol-4-yl)methyl]amino]carbonyl]benzoyl]amino]propenoic acid, and (Z)-2-[[2-chloro-4-[[[(1H-indol-4-yl)methyl]amino] carbonyl]benzoyl]amino]-3-(naphthalen-2-yl) propenoic acid.

83. A compound of claim 77 wherein B is

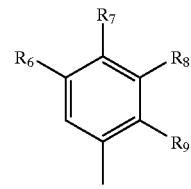

where $R_6$ $R_7$ $R_8$ and $R_9$ are independently hydrogen, hydroxy, aminosulfonyl, halogen, lower alkoxy, cyano, amino, or nitro.

84. Compounds of claim 83 which are (Z)-2-[[2-chloro-4-[[[(1H-indol-4-yl)methyl]amino]carbonyl]benzoyl] amino]-3-phenylpropenoic acid and (Z)-2-[[2-chloro-4-[[[(1H-indol-4-yl)methyl]amino] carbonyl]benzoyl]amino]-3-(2-hydroxyphenyl) propenoic acid.

85. A compound of claim 77 wherein B is

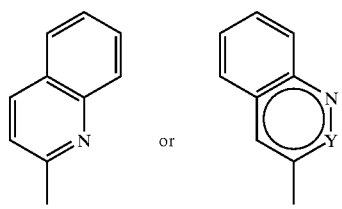

and Y is carbon or nitrogen.

86. A compound of claim 85 which is (Z)-2-[[2-bromo-4-[[[(1H-indol-4-yl)methyl]amino]carbonyl]benzoyl] amino]-3-(quinolin-3-yl)propenoic acid.

87. A compound of claim 77 wherein B is

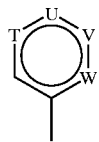

where at least one of T, U, V, or W is nitrogen, and any of T, U, V, or W which are carbon may be substituted with lower alkyl, lower alkyl amino, lower alkoxy, hydroxy, aminosulfonyl, halogen, cyano, amino, or nitro.

88. A compound of claim 87 which is (Z)-2-[[2-chloro-4-[[[(1H-indol-4-yl)methyl]amino]carbonyl]benzoyl]amino]-3-(pyridin-2-yl)propenoic acid.

89. A compound of claim 4 having the formula

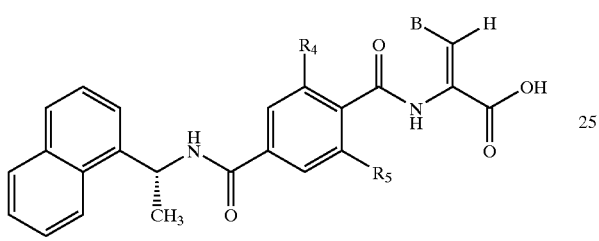

1-1b wherein $R_4$ and $R_5$ are hydrogen, methyl, ethyl or halogen, except that $R_4$ and $R_5$ cannot both be hydrogen; and
1) B is hydrogen, or lower alkyl; or
2) B is

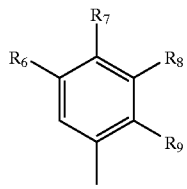

where $R_6$ $R_7$ $R_8$ and $R_9$ are independently hydrogen, hydroxy, aminosulfonyl, halogen, lower alkoxy, cyano, amino, lower alkyl, lower alkyl amino, or nitro; or
3) B is where $R_{10}$ is hydrogen, hydroxy, halogen, or lower alkyl and C is a five- or six-membered ring with 0 to 3 heteroatoms, which heteroatoms are selected from nitrogen, oxygen, and sulfur, which ring may be unsubstituted or mono- or di-substituted with lower alkyl, cycloalkyl, amino, or substituted amino; or 4) B is where X and Y are independently methylene or nitrogen; or
5) B is

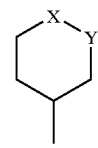

where at least one of T, U, V, or W is nitrogen, and any of T, U, V or W which is carbon may be substituted with lower alkyl, lower alkyl amino, lower alkoxy, hydroxy, aminosulfonyl, halogen, cyano, amino, or nitro; or
6) B is wherein Y is carbon or nitrogen; or
7) B is a five-membered aromatic ring with 1 to 3 heteroatoms selected from nitrogen, oxygen, and sulfur which ring may be unsubstituted or mono- or di-substituted with lower alkyl, cycloalkyl, trifluoroloweralkyl, amino, halogen, substituted amino, or which ring may be fused with a 5 or 6 membered aromatic ring containing 0 to 3 heteroatoms which heteroatoms are selected from nitrogen, oxygen, and sulfur.

90. A compound of claim 89 wherein
B is

And $R_6$, $R_7$, $R_8$, and $R_9$ are hydrogen.

91. A compound of claim 90 which is [Z, (R)]-2-[2,6-dimethyl-4-[[[1-naphthalen-1-yl)ethyl]amino]carbonyl]benzoyl]amino]-3-phenylpropenoic acid.

92. A compound of claim 89 wherein B is

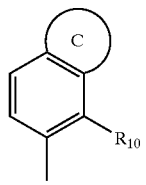

R₁₀ is hydrogen and C is triazole.

93. Compounds of claim 92 which are [Z, (R)]-3-(1H-benzotriazol-5-yl)-2-[[2,6-dimethyl-4-[[[1-naphthalen1-yl)ethyl]amino]carbonyl]benzoyl]amino]propenoic acid and
[Z, (R)]-3-(1H-benzotriazol-5-yl)-2-[[2,6-dichloro-4-[[[1-naphthalen-1-yl)ethyl]amino]carbonyl]benzoyl]amino]propenoic acid.

94. A compound of claim 89 wherein B is

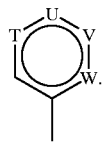

95. A compound of claim 94 which is [Z,(R)]-2-[[2,6-dimethyl-4-[[[(1-(naphthalen-1-yl)ethyl]amino]carbonyl]benzoyl]amino]-3-(pyridin-4-yl)propenoic acid.

96. A compound of claim 89 wherein B is a five-membered aromatic ring with one to two heteroatoms selected from N and S which ring may be unsubstituted, or monosubstituted or disubstituted with lower alkyl.

97. Compounds of claim 96 which are [Z, (R)]-2-[[2,6-dimethyl-4-[[[1-naphthalen-1-yl)ethyl]amino]carbonyl]benzoyl]amino]-3-(4-methyl-1H-imidazol-5-yl)propenoic acid,
[Z, (R)]-2-[[2-chloro-4-[[[1-naphthalen-1-yl)ethyl]amino]carbonyl]benzoyl]amino]-3(thien-2-yl)propenoic acid,
[Z, (R)]-2-[[2,6-dimethyl-4-[[[1-naphthalen-1-yl)ethyl]amino]carbonyl]benzoyl]amino]-3-(2,4-dimethyl-thiazol-5-yl)propenoic acid and
[Z, (R)]-2-[[2,6-dimethyl-4-[[[1-naphthalen-1-yl)ethyl]amino]carbonyl]benzoyl]amino]-3-(1H-imidazol-2-yl)propenoic acid.

98. A compound of claim 89 wherein B is

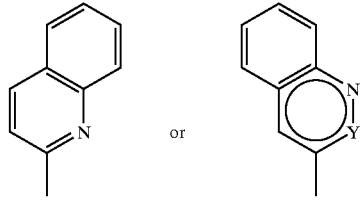

and Y is carbon or nitrogen.

99. Compounds of claim 98 which are [Z,(R)]-2-[[2,6-dichloro-4-[[[(1-(naphthalen-1-yl)ethyl]amino]carbonyl]benzoyl]amino]-3-(quinolin-3-yl)propenoic acid and [Z,(R)]-2-[[2,6-dimethyl-4-[[[(1-(naphthalen-1-yl)ethyl]amino]carbonyl]benzoyl]amino]-3-(quinolin-3-yl)propenoic acid.

100. A compound of claim 1 having the formula

1g

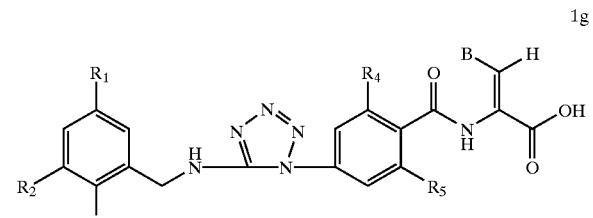

wherein $R_1$ is hydrogen, hydroxy, amino or halogen, $R_2$ is hydrogen, hydroxy, or halogen and $R_3$ is hydrogen; $R_4$ and $R_5$ are hydrogen, methyl, ethyl, or halogen except that $R_4$ and $R_5$ cannot both be hydrogen, and 1) B is hydrogen, or lower alkyl; or
2) B is

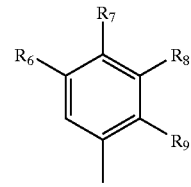

where $R_6$ $R_7$ $R_8$ and $R_9$ are independently hydrogen, hydroxy, aminosulfonyl, halogen, lower alkoxy, cyano, amino, lower alkyl, lower alkyl amino, or nitro; or 3) B is

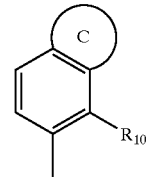

where $R_{10}$ is hydrogen, hydroxy, halogen, or lower alkyl and C is a five- or six-membered ring with 0 to 3 heteroatoms, which heteroatoms are selected from nitrogen, oxygen, and sulfur, which ring may be unsubstituted or mono- or di-substituted with lower alkyl, cycloalkyl, amino, or substituted amino; or 4) B is

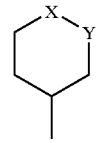

where X and Y are independently methylene or nitrogen; or

5) B is

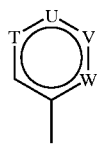

where at least one of T, U, V, or W is nitrogen, and any of T, U, V or W which is carbon may be substituted with lower alkyl, lower alkyl amino, lower alkoxy, hydroxy, aminosulfonyl, halogen, cyano, amino, or nitro; or 6) B is

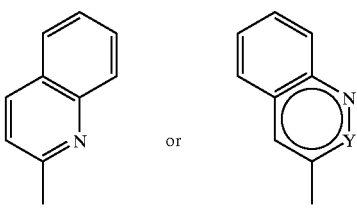

wherein Y is carbon or nitrogen; or

7) B is a five-membered aromatic ring with 1 to 3 heteroatoms selected from nitrogen, oxygen, and sulfur which ring may be unsubstituted or mono- or di-substituted with lower alkyl, cycloalkyl, trifluoroloweralkyl, amino, halogen, substituted amino, or which ring may be fused with a 5 or 6 membered aromatic ring containing 0 to 3 heteroatoms which heteroatoms are selected from nitrogen, oxygen, and sulfur.

101. A compound of claim 1 having the formula

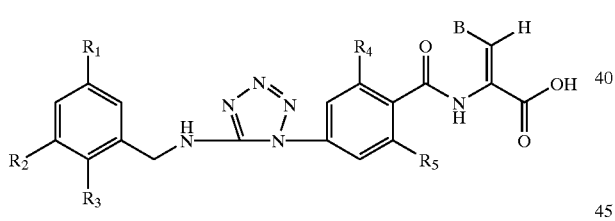

1-1c wherein $R_1$ is hydrogen and $R_2$ and $R_3$ taken together with the ethenylene group connecting them form phenyl, pyrrole, pyrroline, oxopyrroline, pyrazole, triazole, or imidazole; $R_4$ and $R_5$ are hydrogen, methyl, ethyl, or halogen except that $R_4$ and $R_5$ cannot both be hydrogen, and
1) B is hydrogen, or lower alkyl; or
2) B is

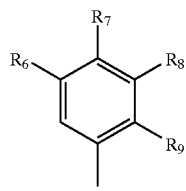

where $R_6$ $R_7$ $R_8$ and $R_9$ are independently hydrogen, hydroxy, aminosulfonyl, halogen, lower alkoxy, cyano, amino, lower alkyl, lower alkyl amino, or nitro; or 3) B is

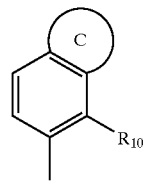

where $R_{10}$ is hydrogen, hydroxy, halogen, or lower alkyl and C is a five- or six-membered ring with 0 to 3 heteroatoms, which heteroatoms are selected from nitrogen, oxygen, and sulfur, which ring may be unsubstituted or mono- or di-substituted with lower alkyl, cycloalkyl, amino, or substituted amino; or 4) B is

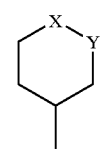

where X and Y are independently methylene or nitrogen; or

5) B is

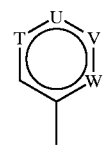

where at least one of T, U, V, or W is nitrogen, and any of T, U, V or W which is carbon may be substituted with lower alkyl, lower alkyl amino, lower alkoxy, hydroxy, aminosulfonyl, halogen, cyano, amino, or nitro; or 6) B is

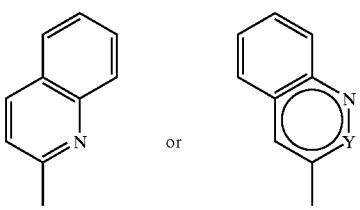

wherein Y is carbon or nitrogen; or

7) B is a five-membered aromatic ring with 1 to 3 heteroatoms selected from nitrogen, oxygen, and sulfur which ring may be unsubstituted or mono- or di-substituted with lower alkyl, cycloalkyl, trifluoroloweralkyl, amino, halogen, substituted amino, or which ring may be fused with a 5 or 6 membered aromatic ring containing 0 to 3 heteroatoms which heteroatoms are selected from nitrogen, oxygen, and sulfur.

102. A compound of formula:

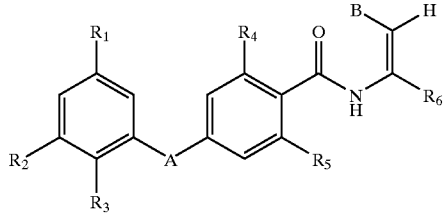

wherein $R_2$ and $R_3$ taken together with the ethenylene group connecting them form phenyl, pyrroline, pyrrole, oxopyrroline, pyrazole, triazole, or imidazole; $R_4$ and $R_5$ are hydrogen, methyl, ethyl, or halogen except that $R_4$ and $R_5$ cannot both be hydrogen, and
$R^6$ is

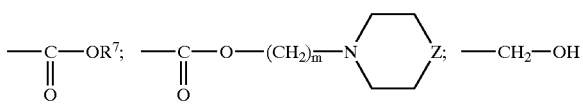

where $R^7$ is lower alkyl,

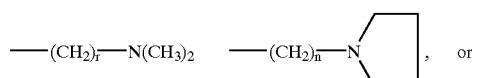

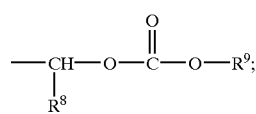

Z is oxygen or NH, $R^8$ is hydrogen or methyl and $R^9$ is lower alkyl or cycloalkyl and m, n, and r are 1 to 5;
A is

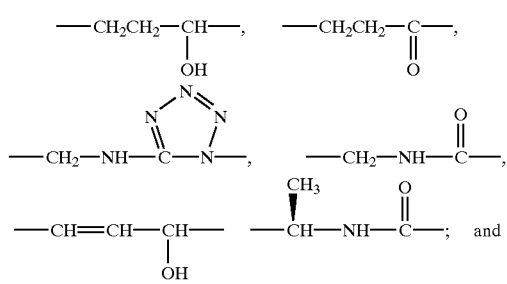

1) B is hydrogen, or lower alkyl; or
2) B is

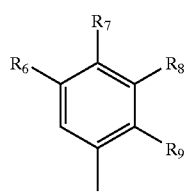

where $R^6$ $R_7$ $R_8$ and $R_9$ are independently hydrogen, hydroxy, aminosulfonyl, halogen, lower alkoxy, cyano, amino, lower alkyl, lower alkyl amino, or nitro; or 3) B is

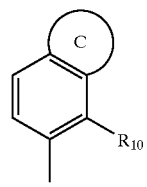

where $R_{10}$ is hydrogen, hydroxy, halogen, or lower alkyl and C is a five- or six-membered ring with 0 to 3 heteroatoms, which heteroatoms are selected from nitrogen, oxygen, and sulfur, which ring may be unsubstituted or mono- or di-substituted with lower alkyl, cycloalkyl, amino, or substituted amino; or 4) B is

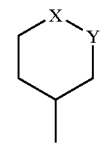

where X and Y are independently methylene or nitrogen; or

5) B is

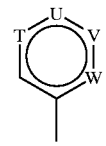

where at least one of T, U, V, or W is nitrogen, and any of T, U, V or W which is carbon may be substituted with lower alkyl, lower alky amino, lower alkoxy, hydroxy, aminosulfonyl, halogen, cyano, amino, or nitro; or 6) B is

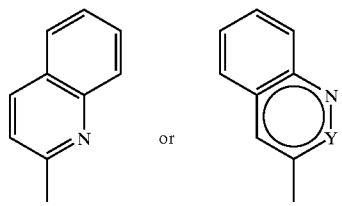

wherein Y is carbon or nitrogen; or
7) B is a five-membered aromatic ring with 1 to 3 heteroatoms selected from nitrogen, oxygen, and sulfur which ring may be unsubstituted or mono- or di-substituted with lower alkyl, cycloalkyl, trifluoroloweralkyl, amino, halogen, substituted amino, or which ring may be fused with a 5 or 6 membered aromatic ring containing 0 to 3 heteroatoms which heteroatoms are selected from nitrogen, oxygen, and sulfur;or pharmaceutically acceptable salts thereof.

103. A compound of claim 102 wherein wherein $R^{6'}$ is

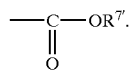

104. A compound of claim 103 wherein $R^{7'}$ is ethyl.
105. A compound of claim 102 wherein m, n, and r are 2.
106. A compound of claim 105 wherein $R^{6'}$ is —C(O)—O—$(CH_2)_r$—$N(CH_2)_2$,

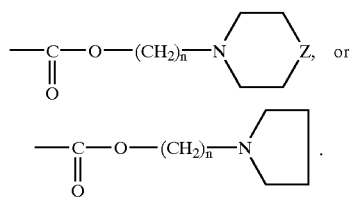

107. A compound of claim 102 wherein $R^6$ is

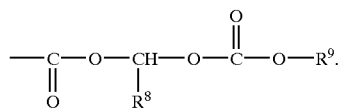

108. A compound of claim 107 wherein $R^8$ is hydrogen or methyl and $R^9$ is ethyl or cyclohexyl.
109. A compound of claim 102 wherein $R^6$ is

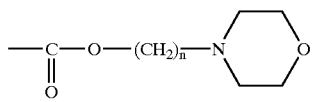

and n is 2.

110. A compound of formula:

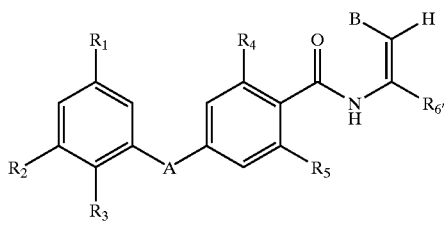

wherein $R_1$ is hydrogen, hydroxy, amino or halogen, $R_2$ is hydrogen, hydroxy or halogen and $R_3$ is hydrogen, $R_4$ and $R_5$ are hydrogen, methyl, ethyl, or halogen except that $R_4$ and $R_5$ cannot both be hydrogen, and $R^{6'}$ is

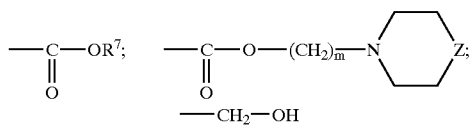

where $R^7$ is lower alkyl, —$(CH_2)_r$—$N(CH_3)_2$,

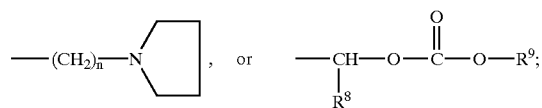

Z is oxygen or NH, $R^{8'}$ is hydrogen or methyl and $R^9$ is lower alkyl or cycloalkyl and m, n, and r are 1 to 5;
A is

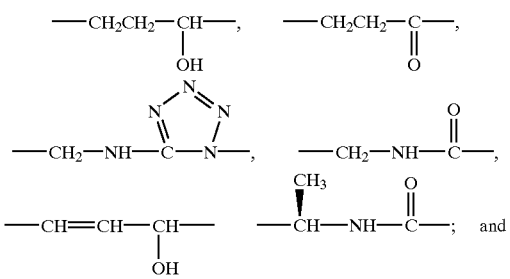

1) B is hydrogen, or lower alkyl; or
2) B is

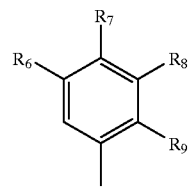

where $R_6$ $R_7$ $R_8$ and $R_9$ are independently hydrogen, hydroxy, aminosulfonyl, halogen, lower alkoxy, cyano, amino, lower alkyl, lower alkyl amino, or nitro; or
3) B is

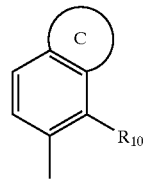

where $R_{10}$ is hydrogen, hydroxy, halogen, or lower alkyl and C is a five- or six-membered ring with 0 to 3 heteroatoms, which heteroatoms are selected from nitrogen, oxygen, and sulfur, which ring may be unsubstituted or mono- or di-substituted with lower alkyl, cycloalkyl, amino, or substituted amino; or
4) B is

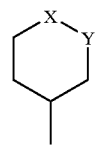

where X and Y are independently methylene or nitrogen; or

5) B is

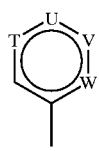

where at least one of T, U, V, or W is nitrogen, and any of T, U, V or W which is carbon may be substituted with lower alkyl, lower alkyl amino, lower alkoxy, hydroxy, aminosulfonyl, halogen, cyano, amino, or nitro; or 6) B is

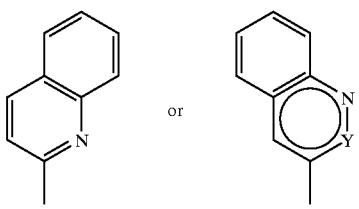

wherein Y is carbon or nitrogen; or

7) B is a five-membered aromatic ring with 1 to 3 heteroatoms selected from nitrogen, oxygen, and sulfur which ring may be unsubstituted or mono- or di-substituted with lower alkyl, cycloalkyl, trifluoroloweralkyl, amino, halogen, substituted amino, or which ring may be fused with a 5 or 6 membered aromatic ring containing 0 to 3 heteroatoms which heteroatoms are selected from nitrogen, oxygen, and sulfur; or pharmaceutically acceptable salts thereof.

111. A compound of claim 110 wherein $R^6$ is

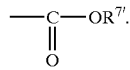

112. A compound of claim 111 wherein $R^7$ is ethyl.

113. A compound of claim 110 wherein m, n and r are 2.

114. A compound of claim 113 wherein $R^6$ is —C(O)—O—(CH$_2$)$_n$—N(CH$_2$)$_2$,

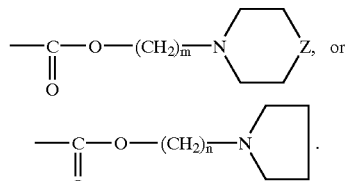

115. A compound of claim 110 wherein $R^6$ is

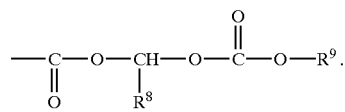

116. A compound of claim 115 wherein $R^8$ is hydrogen or methyl and $R^9$ is ethyl or cyclohexyl.

117. A compound of claim 110 wherein $R^6$ is

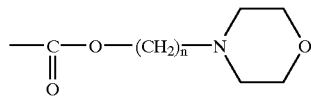

and n is 2.

118. A compound of claim 117 which is (Z)-2-[[2-bromo-4-[[(3-hydroxy-benzyl]amino]carbonyl]benzoyl]amino]-3-(2,4-dimethylthiazol-5-yl)propenoic acid 2-(morpholin-4-yl)ethyl ester.

* * * * *